(12) United States Patent
Habashita et al.

(10) Patent No.: US 8,575,134 B2
(45) Date of Patent: Nov. 5, 2013

(54) AMINOCARBOXYLIC ACID DERIVATIVE AND MEDICINAL USE THEREOF

(75) Inventors: Hiromu Habashita, Osaka (JP); Haruto Kurata, Osaka (JP); Shinji Nakade, Tsukuba (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 92 days.

(21) Appl. No.: 12/986,760

(22) Filed: Jan. 7, 2011

(65) Prior Publication Data

US 2011/0105432 A1 May 5, 2011

Related U.S. Application Data

(63) Continuation of application No. 11/721,601, filed as application No. PCT/JP2005/022765 on Dec. 12, 2005, now Pat. No. 7,906,549.

(30) Foreign Application Priority Data

| Dec. 13, 2004 | (JP) | 2004-360539 |
| Apr. 22, 2005 | (JP) | 2005-125740 |
| Aug. 11, 2005 | (JP) | 2005-233790 |

(51) Int. Cl.
*A01N 55/08* (2006.01)
*C07D 205/00* (2006.01)

(52) U.S. Cl.
USPC .......................................... 514/64; 548/950

(58) Field of Classification Search
None
See application file for complete search history.

(56) References Cited

U.S. PATENT DOCUMENTS

| 5,618,843 | A | 4/1997 | Fisher et al. |
| 5,789,595 | A | 8/1998 | Kohama et al. |
| 6,818,774 | B2 | 11/2004 | Cesura et al. |
| 7,060,697 | B2 | 6/2006 | Marsilje et al. |
| 7,351,725 | B2 | 4/2008 | Doherty et al. |
| 7,381,719 | B2 | 6/2008 | Blanco-Pillado et al. |
| 7,825,109 | B2 * | 11/2010 | Nakade et al. ........... 514/210.17 |
| 2002/0072518 | A1 | 6/2002 | Khanna et al. |
| 2003/0139597 | A1 | 7/2003 | Xue et al. |
| 2004/0058894 | A1 | 3/2004 | Doherty et al. |
| 2004/0224941 | A1 | 11/2004 | Seko et al. |
| 2007/0167425 | A1 | 7/2007 | Nakade et al. |

FOREIGN PATENT DOCUMENTS

| CA | 2 420 869 | | 3/2002 |
| CA | 2 446 593 | | 11/2002 |
| CA | 2 424 540 | | 4/2003 |
| CA | 2 472 715 | A1 | 7/2003 |
| CA | 2 483 461 | | 11/2003 |
| CA | 2 509 218 | | 7/2004 |
| CA | 2 534 473 | | 2/2005 |
| EP | 0635492 | A1 | 1/1995 |
| EP | 0 790 247 | A1 | 8/1997 |
| EP | 1391199 | A1 | 2/2004 |
| WO | 96/13497 | A1 | 5/1996 |
| WO | 98/38156 | A1 | 9/1998 |
| WO | 01/21577 | A2 | 3/2001 |
| WO | 02/18377 | A1 | 3/2002 |
| WO | 02/092068 | A1 | 11/2002 |
| WO | 03/061567 | A2 | 7/2003 |
| WO | 03/062248 | A2 | 7/2003 |
| WO | 03/062252 | A1 | 7/2003 |
| WO | 03/091219 | A1 | 11/2003 |
| WO | 2004/026305 | A1 | 4/2004 |
| WO | 2004/113330 | A | 12/2004 |
| WO | 2005/020882 | A2 | 3/2005 |

OTHER PUBLICATIONS

Haerter et al., caplus an 2004:515469.*
Bugianesi et al., caplus an 2003:591193.*
European Patent Office, Communication dated Nov. 3, 2011 issued in counterpart European Application No. 11168698.6.
U.S. Office Action issued on May 3, 2010 in the U.S. Appl. No. 11/721,601.
Warrener, et. al. "Preparation of (-)-(7R)-7-Acetyl-7-hydroxy-4,4-dimethoxy-5,6,7,8-tetrahydro-naphthalen-1(4H)-one, a Chiral AB-Synthon for Anthracyckine Synthesis", J.C.S. Chem. Comm., 1981, pp. 1100-1101.
Wu, K. et. al. "Regulatory perspectives of Type II prodrug development and time-dependent toxicity management: Nonclinical Pharm/Tox analysis and the role of comparative toxicology", Toxicology, vol. 236, 2007, pp. 1-6.
European Patent Office, Office Action dated Apr. 9, 2013, issued in European Application No. 04 772 717.7 corresponding co-pending U.S. Appl. No. 12/879,158.

(Continued)

*Primary Examiner* — Sun Jae Loewe
(74) *Attorney, Agent, or Firm* — Sughrue Mion, PLLC

(57) ABSTRACT

The present invention relates to a compound represented by the formula (I), a salt thereof, an N-oxide form thereof, a solvate thereof, or a prodrug thereof, and a medicament containing the same. The compound represented by the formula (I) has an ability to bind to an S1P receptor (particularly, EDG-1, EDG-6, and/or EDG-8) and is useful for preventing and/or treating for rejection to transplantation, graft-versus-host disease, autoimmune diseases, allergic diseases, neurodegenerating diseases, and the like.

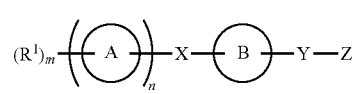

(I)

wherein all symbols are described in the specification.

4 Claims, 10 Drawing Sheets

(56) References Cited

OTHER PUBLICATIONS

Kurata, Haruto et al. "Structure-activity relationship studies of S1P agonists with a dihydronaphthalene scaffold," Bioorganic & Medicinal Chemistry Letters, Pergamon, Elsevier Science, GB, vol. 22, No. 1, Nov. 14, 2011, pp. 144-148, XP028352291.
Matthew J. Fisher et al., "Dihydroisoquinolone RGD Mimics. Exploration of the Aspartate Isostere", Bioorganic & Medicinal Chemistry Letters, 1997, pp. 2537-2542, vol. 7, No. 19.
Ai Yu Shen et al., "Cytotoxicity and Antimicrobial Activity of Some Naphthol Derivatives", Arch. Pharm., 1995, pp. 197-201, 328.
Examination Report dated Aug. 17, 2010, issued by the Intellectual Property Office of New Zealand in counterpart New Zealand Application No. 555810.
Canadian Office Action issued on Nov. 18, 2010 in the corresponding Canadian Patent Application No. 2537093 of co-pending U.S. Appl. No. 12/879,158.
Nakade et al, caplus an 2005:216595.
Office Action from the Australian Government IP dated Aug. 31, 2010, issued in counterpart Australian Patent Application No. 2005314938.
Chawla et al., "Challenges in Polymorphism of Pharmaceuticals", CRIPS vol. 5, No. 1, Jan.-Mar. 2004 (4 pgs).
Newman et al., "Solid-state analysis of hte active pharmaceutical ingredient in drug products", DDT vol. 8, No. 19, Oct. 2003, pp. 898-905.
Anthony R. West., "Solid State Chemistry and Its Applications", 1988, pp. 358 and 365, Wiley, New York.
Russian Office Action dated Oct. 9, 2009 in Application No. 2007126654.
M.D. Mashkovsky, "Lekarstvennie Sredstva," Moskva, vol. 1, p. 8 (1993).
"Khimicheskii Enciklopedicheskii Slovar," Moskva, "Sovetskaya Enciklopediya," pp. 130-131 (1983).
Chinese Office Action issued in counterpart Application No. 200580048066.7, dated May 27, 2010.
Russian Office Action issued in counterpart Application No. 2007126654, dated May 27, 2010.

* cited by examiner

AMINOCARBOXYLIC ACID DERIVATIVE AND MEDICINAL USE THEREOF

CROSS REFERENCE TO RELATED APPLICATIONS

This is a continuation of U.S. application Ser. No. 11/721,601 filed Jun. 13, 2007, which is a national stage under 35 U.S.C. §371 of PCT/JP2005/022765 filed on Dec. 12, 2005, which claims priority from Japanese patent applications 2004-360539 filed Dec. 13, 2004, 2005-125740 filed on Apr. 22, 2005, and 2005-233790 filed Aug. 11, 2005. The entire disclosures of all of the prior applications are incorporated herein by reference.

TECHNICAL FIELD

The present invention relates to a compound capable of binding sphingosine-1-phosphate (hereinafter, abbreviated as "S1P") receptor which is useful as a medicament and a medicament containing the same as an active ingredient.

More specifically, the present invention relates to:
(1) a compound represented by a formula (I):

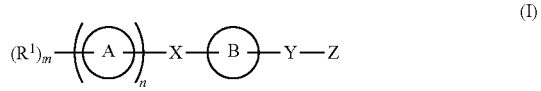

wherein all symbols have the same meanings as described below; a salt thereof, an N-oxide form thereof, a solvate thereof, or a prodrug thereof; and
(2) a medicament containing the compound represented by the formula (I), a salt thereof, an N-oxide form thereof, a solvate thereof, or a prodrug thereof as an active ingredient.

BACKGROUND ART

Sphingosine-1-phosphate (S1P) represented by the formula (A) is a lipid that is synthesized by the intracellular metabolic turnover of sphingolipids or the extracellular action of secretory sphingosine kinase. It is pointed out that S1P acts as an intercellular and intracellular messenger (*Biochem. Pharm.*, 58, 201 (1999)).

As receptors of S1P, EDG-1 which is a G-protein-coupled receptor and its analogous molecules, EDG-3, EDG-5, EDG-6, and EDG-8 (also called $S1P_1$, $S1P_3$, $S1P_2$, $S1P_4$, and $S1P_5$, respectively) are known. They are called EDG family together with EDG-2, EDG-4, and EDG-7 which are lysophosphatidic acid (LPA) receptors. S1P receptors bind to S1P and deliver signals into cells via G-protein coupled with the receptors. Gs, Gi, Gq, and $G_{12/13}$ etc. are known as G-proteins to which S1P receptor can couple, and it is considered that the receptor is involved in responses such as increase of cell proliferation, suppression of cell proliferation, induction of cell chemotaxis, and inhibition of cell chemotaxis.

As biological action of S1P, inhibition of migration of smooth muscle cells or cancer cells, platelet aggregation, induction of cell chemotaxis, inhibition of cell chemotaxis, and the like are known in vitro experiments, and as the results of in vitro experiments, it is known that S1P shows effects of controlling blood pressure, promoting angiogenesis, reducing renal blood flow, inhibiting lung fibrosis, promoting the lymphocyte homing into lymphatic organs, and the like. It is considered that those various physiological effects are mediated by S1P receptors existing in cell membrane. However, it has been scarcely clarified excluding some cases which subtypes of S1P receptors mediate these effects in practice.

Recently, from the study for EDG-1 knock-out mice, it is strongly indicated that S1P induced angiogenesis via EDG-1 (J. Clin. Invest., 106, 951 (2000)). Therefore, it is suggested that an EDG-1 agonist is used as an agonist for treating diseases caused by anangioplasia. For example, it is used as an agent for prevention and/or treatment of peripheral arterial disease such as arteriosclerosis obliterans, thromboangiitis obliterans, Buerger's disease, or diabetic neuropathy; varicose vein such as hemorrhoid, anal fissure, or anal fistula; dissecting aneurysm of the aorta, sepsis, inflammatory disease such as angiitis, nephritis, or pneumonia, various edematous disease involved in ischemia of various organ and increase of the blood permeability, for example, myocardial infarction, cerebral infarction, angina, disseminated intravascular coagulation (DIC), pleuritis, congestive heart failure, multiple organ failure, shock with blood incompatibility during blood transfusion, and the like. In addition, the EDG-1 agonist can also be used as an agent for enhancing wound healing of cornea, skin, digestive organs, or the like, or, for example, as an agent for prevention and/or treatment of bedsore, burn, ulcerative colitis, Crohon's disease, or the like. Further, the EDG-1 agonist can also be used as a preoperative, postoperative, and/or prognostic activator for blood vessel accompanying transplantation of various organs, for example, as an adhesion activator of transplanted organs such as heart transplantation, renal transplantation, dermal transplantation or liver transplantation.

On the other hand, EDG-6 is localized and strongly expressed in cells of the lymphatic and hematopoietic systems including spleen, leukocytes, lymph gland, thymus, bone marrow, lung and the like, which suggests the possibility that the EDG-6 is closely related to the effects of S1P in the

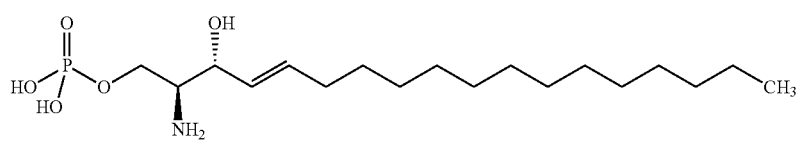

(A)

course of inflammation or in the immune system (Biochem. Biophys. Res. Commun., 268, 583 (2000)).

Moreover, it is known that the EDG-6 polypeptide or its homolog is involved in immunomodulation, antiinflammation and the like in a similar manner as EDG-1, which brings about the potential usability of those substances in treating autoimmune diseases (e.g., systemic lupus erythematosus, rheumatoid arthritis, multiple sclerosis, myasthenia gravis, muscular dystrophy, and the like), allergic diseases (e.g., atopic dermatitis, pollen disease, food allergy, and allergy of chemical drug (e.g., anesthetic such as lidocaine), and the like) allergy, and the like), asthma, inflammatory diseases, infection, ulcer, lymphoma, malignant tumor (e.g., cancer and the like), leukemia, arteriosclerosis, diseases involving lymphocyte infiltration into a tissue, such as multiple organ failure and reperfusion injury after ischemia, shock with blood incompatibility during blood transfusion, and the like.

Meanwhile, it has been known that EDG-8 is mainly expressed in neuronal cells, so EDG-8 can be used for treating various neurodegenerating diseases (e.g., Parkinson's disease, parkinsonian syndrome, Alzheimer's disease, and amyotrophic lateral sclerosis).

Thus, it has been considered that a drug that acts on EDG-1, EDG-6, and/or EDG-8 is useful as a preventive drug and/or a therapeutic drug for rejection to transplantation, transplanted organ abolition, graft-versus-host disease (e.g., acute graft-versus-host disease during bone-marrow transplantation and the like), autoimmune diseases (e.g., systemic lupus erythematosus, rheumatoid arthritis, myasthenia gravis, and muscular dystrophy), allergic diseases (e.g., atopic dermatitis, pollen disease, food allergy, and allergy of chemical drug (e.g., anesthetic such as lidocaine), and the like), asthma, inflammatory diseases, infection, ulcer, lymphoma, malignant tumor (e.g., cancer), leukemia, arteriosclerosis, diseases involving lymphocyte infiltration into a tissue, such as multiple organ failure and reperfusion injury after ischemia, shock with blood incompatibility during blood transfusion, and neurodegenerating diseases (e.g., Parkinson's disease, parkinsonian syndrome, Alzheimer's disease, and amyotrophic lateral sclerosis), and the like.

In recent years, it has been reported that EDG-1 agonist is useful as an immunosuppressant. However, there is no description that EDG-6 agonist or antagonist is useful as an immunosuppressant (see Patent Document 1: WO 03/061567).

On the other hand, it is disclosed that a compound represented by the formula (S):

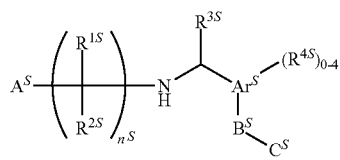

wherein $Ar^S$ represents phenyl or naphthyl; $A^S$ represents carboxy, or the like; $n^S$ represents 2, 3, or 4; $R^{1S}$ and $R^{2S}$ each independently represent a hydrogen atom, a halogen atom, hydroxy, carboxy, C1-6 alkyl which may be substituted by 1 to 3 halogen atoms, or phenyl which may be substituted by 1 to 3 halogen atoms; $R^{3S}$ represents a hydrogen atom or C1-4 alkyl which may be substituted by 1 to 3 hydroxy or halogen atoms; $R^{4S}$'s each independently represent hydroxy, a halogen atom, carboxy, or the like; $C^S$ represents C1-8 alkyl, C1-8 alkoxy, phenyl, or the like or $C^S$ is nil; and $B^S$ represents phenyl, C5-16 alkyl, or the like (only necessary parts of the definitions of the symbols are extracted);

a pharmaceutically acceptable salt thereof and a hydrate thereof, and a compound represented by the formula (T):

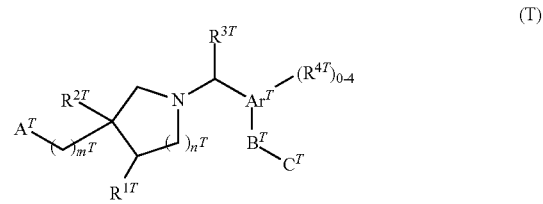

wherein $Ar^T$ represents phenyl or naphthyl; $A^T$ represents carboxy, or the like; $m^T$ represents 0 or 1; $n^T$ represents 0 or 1; $R^{1T}$ and $R^{2T}$ each independently represent a hydrogen atom, a halogen atom, hydroxy, carboxy, C1-4 alkyl or phenyl which may be substituted by a halogen atom, or the like; $R^{3T}$ represents a hydrogen atom, C1-4 alkyl which may be substituted by hydroxy or a halogen atom, or the like; $R^{4T}$'s each independently represent a halogen atom, C1-4 alkyl, C1-3 alkoxy, or the like; $C^T$ represents C1-8 alkyl, C1-8 alkoxy, phenyl, or the like or $C^T$ is nil; and $B^T$ represents phenyl, C5-16 alkyl, or the like (only necessary parts of the definitions of the symbols are extracted);

a pharmaceutically acceptable salt thereof, and a hydrate thereof are useful as EDG-1 agonists (see Patent Document 2: WO 03/062248 and Patent Document 3: WO 03/062252).

On the other hand, it is disclosed that a carboxylic acid derivative represented by the formula (Z):

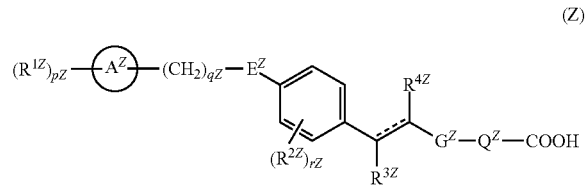

wherein $R^{1Z}$ represents C1-8 alkyl, C1-8 alkoxy, a halogen atom, nitro, or trifluoromethyl; ring $A^Z$ represents a C5-7 monocyclic carbocyclic ring or a 5- to 7-membered monocyclic heterocyclic ring containing one or two nitrogen atoms, one oxygen atom and/or one sulfur atom; $E^Z$ represents $-CH_2-$, $-O-$, $-S-$ or $-NR^{6Z}-$, in which $R^{6Z}$ represents a hydrogen atom or C1-8 alkyl; $R^{2Z}$ represents C1-8 alkyl, C1-8 alkoxy, a halogen atom, nitro or trifluoromethyl; $R^{3Z}$ represents a hydrogen atom or C1-8 alkyl; $R^{4Z}$ represents a hydrogen atom or C1-8 alkyl, or $R^{2Z}$ and $R^{4Z}$ may be taken together to form $-CH_2CH_2-$ or $-CH=CH-$; $G^Z$ represents $-CONR^{7Z}-$, $-NR^{7Z}CO-$, $-SO_2NR^{7Z}-$, $-NR^{7Z}SO_2-$, $-CH_2NR^{7Z}-$ or $-NR^{7Z}CH_2-$, in which $R^{7Z}$ represents a hydrogen atom, C1-8 alkyl, or the like; $Q^Z$ represents C1-4 alkylene or the like; $p^Z$ represents 0 or an integer of 1 to 5; $q^Z$ represents an integer of 4 to 6; $r^Z$ represents 0 or an integer of 1 to 4; and ----- represents a single bond or a double bond, a prodrug thereof, or a non-toxic salt thereof is known as an EDG-1 agonist (see Patent Document 4: WO 02/092068).

Moreover, it is disclosed that a compound represented by the formula (Y):

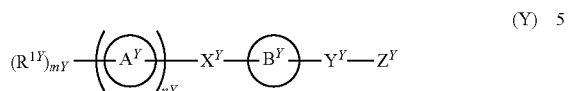 (Y)

wherein ring $A^Y$ represents a cyclic group; ring $B^Y$ represents a cyclic group which may further have a substituent(s); $X^Y$ represents a bond or a spacer which has a main chain having 1 to 8 atoms in which one atom in the spacer may be taken together with a substituent on ring $B^Y$ to form a ring group which may have a substituent(s); $Y^Y$ represents a bond or a spacer which has a main chain having 1 to 10 atoms in which one atom in the spacer may be taken together with a substituent on ring $B^Y$ to form a ring group which may have a substituent(s); $Z^Y$ represents an acidic group which may be protected; nY represents 0 or 1, wherein when nY is 0, mY represents 1 and $R^{1Y}$ represents a hydrogen atom or a substituent, and when nY is 1, mY is 0 or an integer of 1 to 7 and $R^{1Y}$ represents a substituent in which when mY is 2 or more, a plurality of $R^{1Y}$s are the same or different from each other, a salt thereof, a solvate thereof, or a prodrug thereof has an S1P receptor binding ability (see Patent Document 5: WO 2005/020882).

Patent Document 1: WO 03/061567
Patent Document 2: WO 2003/062248
Patent Document 3: WO 2003/062252
Patent Document 4: WO 2002/092068
Patent Document 5: WO 2005/020882

DISCLOSURE OF THE INVENTION

Problems to be Solved by the Invention

An immunosuppressant is useful for preventing and/or treating inflammatory diseases, autoimmune diseases, allergic diseases, and/or rejection to transplantation. However, an immunosuppressant and a therapeutic drug for autoimmune diseases, which are currently used, cause severe side effects at a considerable frequency. In addition, many of the existing immunosuppressants have an insufficient lasting effect. Thus, a novel drug that is safe, has no effect on a metabolic enzyme, and has a sufficient long-lasting and less side-effects as an immunosuppressant and a therapeutic drug for autoimmune diseases, is desired.

Means for Solving the Problems

The inventors of the present invention have made extensive studies on compounds having an ability of binding to sphingosine-1-phosphate (S1P) receptor useful as a medical drug. As a result, unexpectedly, they found that the compounds of the present invention indicated a strong agonist effect with respect to an S1P receptor, particularly, EDG-1 and/or EDG-6. In addition, they also found that: a part of the compounds of the present invention had an agonist effect with respect to EDG-8; those compounds of the present invention reduced the number of lymphocytes in the peripheral blood and expressed an immunodepressive effect; and the immunodepressive effect of the compounds of the present invention continued even after 24 hours, but this cannot be expected at all from in vitro activity thereof. Further, surprisingly, it was found that those compounds of the present invention had no side-effect and was safe for multiple species of animals. Thus, the present invention has been completed.

That is, the present invention relates to:

[1] a compound represented by the formula (I)

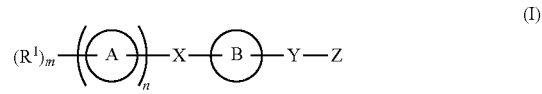 (I)

wherein a ring A represents a cyclic group,
a ring B represents a cyclic group which may further have a substituent(s),
X represents a bond or a spacer which has a main chain having 1 to 8 atoms and one atom of which may be taken together with a substituent of the ring B to form a ring which may have a substituent(s),
Y represents a bond or a spacer which has a main chain having 1 to 10 atoms and one atom of which may be taken together with a substituent of the ring B to form a ring which may have a substituent(s),
Z represents an acid group which may be protected, and
n represents 0 or 1, with proviso that when n is 0, m represents 1 and $R^1$ represents a hydrogen atom or a substituent, and when n is 1, m represents 0 or an integer of 1 to 7 and $R^1$ represents a substituent, when m is 2 or more, a plurality of $R^1$s may be the same or different,
a salt thereof, an N-oxide form thereof, a solvate thereof, or a prodrug thereof;

[2] the compound according to above item [1], a salt thereof, an N-oxide form thereof, a solvate thereof, or a prodrug thereof, wherein Z represents (1) a carboxyl group which may be protected; (2) a hydroxy group which may be protected, (3) a hydroxamic acid group which may be protected, (4) a sulfonic acid group which may be protected, (5) a boronic acid group which may be protected, (6) a carbamoyl group which may be protected, (7) a sulfamoyl group which may be protected, (8) a —P(=O)(OR$^2$) (OR$^3$) group, wherein $R^2$ and $R^3$ each independently represent a hydrogen atom and a C1-8 alkyl group, or $R^2$ and $R^3$ join together to represent a C2-4 alkylene group, or (9) a tetrazolyl group;

[3] the compound according to above item [1], a salt thereof, an N-oxide form thereof, a solvate thereof, or a prodrug thereof, wherein Y represents

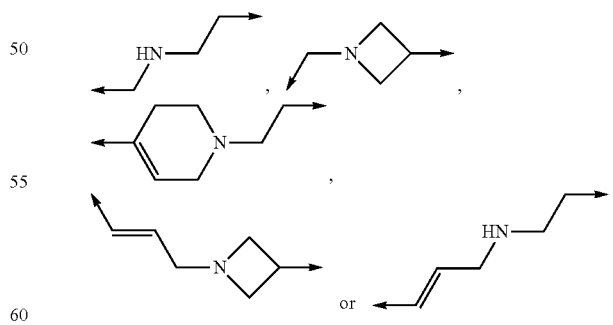

wherein a carbon atom or a nitrogen atom may be substituted by an arbitrary number of substituents on its arbitrary positions where the substituents can be placed, and a right arrow binds to Z;

[4] the compound according to above item [1], a salt thereof, an N-oxide form thereof, a solvate thereof, or a prodrug thereof, in which a ring B is a benzene ring which may have a substituent(s), or a dihydronaphthalene ring which may have a substituent(s); [5] the compound according to above item [1], a salt thereof, an N-oxide form thereof, a solvate thereof, or a prodrug thereof, wherein

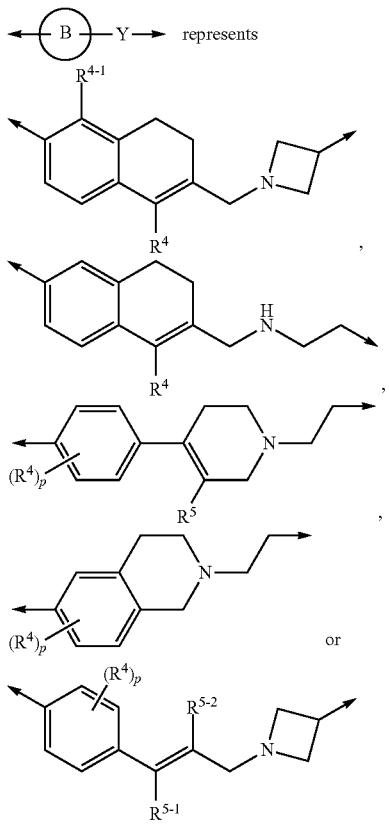 represents

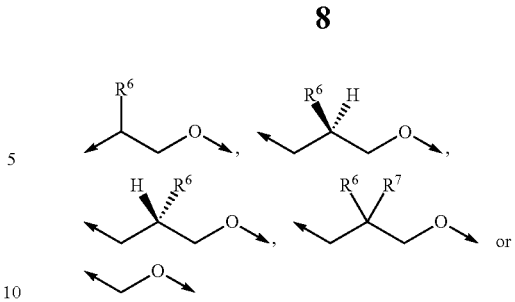

wherein $R^6$ and $R^7$ each independently represent a hydrogen atom, a halogen atom, hydroxy which may be protected, amino which may be protected, C1-8 alkyl, or C1-8 alkyl substituted by hydroxy which may be protected; or $R^6$ and $R^7$ may be taken together with a carbon atom to which they are bound to form a ring which may have a substituent(s); a symbol represents an α-configuration; a symbol represents a β-configuration; and a right arrow binds to ring B;

[8] the compound according to above item [7], a salt thereof, an N-oxide form thereof, a solvate thereof, or a prodrug thereof, in which X represents

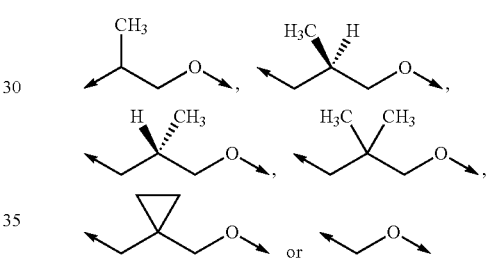

wherein all symbols have the same meanings as described in above item [7];

[9] the compound according to above item [8], a salt thereof, an N-oxide form thereof, a solvate thereof, or a prodrug thereof, in which X represents

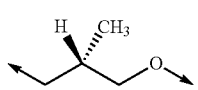

wherein all symbols have the same meanings as described in above item [7];

wherein $R^4$, $R^{4-1}$, $R^5$, $R^{5-1}$, and $R^{5-2}$ each independently represent a hydrogen atom, a halogen atom, trifluoromethyl, trifluoromethoxy, C1-8 alkoxy, or C1-8 alkyl; p represents an 0 or an integer of 1 to 4, in which when p is 2 or more, a plurality of $R^4$'s may be the same or different; and a right arrow binds to Z;

[6] the compound according to above items [1] and [5], a salt thereof, an N-oxide form thereof, a solvate thereof, or a prodrug thereof, wherein

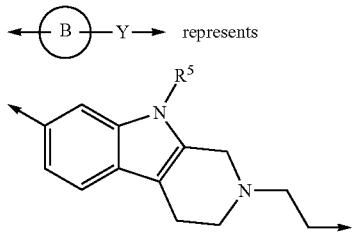 represents wherein all symbols have the same meanings as described in above items [1] and [5];

[7] the compound according to above item [1], a salt thereof, an N-oxide form thereof, a solvate thereof, or a prodrug thereof, in which X represents

[10] the compound according to above item [1], a salt thereof, an N-oxide form thereof, a solvate thereof, or a prodrug thereof, in which ring A is a benzene ring or a pyridine ring;

[11] the compound according to above item [1], a salt thereof, an N-oxide form thereof, a solvate thereof, or a prodrug thereof, in which $R^1$ represents a halogen atom, C1-8 alkyl, or C1-8 alkoxy;

[12] the compound according to above item [5], a salt thereof, an N-oxide form thereof, a solvate thereof, or a prodrug thereof, wherein

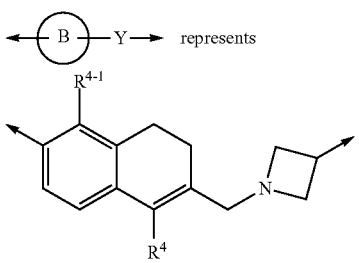 represents wherein all symbols have the same meanings as described in above items [1] and [5];

[13] the compound according to above item [12], a salt thereof, an N-oxide form thereof, a solvate thereof, or a prodrug thereof, in which Z is carboxyl which may be protected;

[14] the compound according to above item [12], a salt thereof, an N-oxide form thereof, a solvate thereof, or a prodrug thereof, wherein X represents

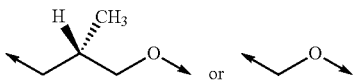

wherein a right arrow binds to a ring B and the other symbols have the same meanings as described in above item [7];

[15] the compound according to above item [12], a salt thereof, an N-oxide form thereof, a solvate thereof, or a prodrug thereof, wherein a ring A is a benzene ring or a pyridine ring;

[16] the compound according to above item [12], a salt thereof, an N-oxide form thereof, a solvate thereof, or a prodrug thereof, wherein $R^1$ represents a halogen atom, C1-8 alkyl which may have a substituent(s), or C1-8 alkoxy which may have a substituent(s);

[17] the compound according to above item [12], a salt thereof, an N-oxide form thereof, a solvate thereof, or a prodrug thereof, which is a compound represented by the formula (IC-2):

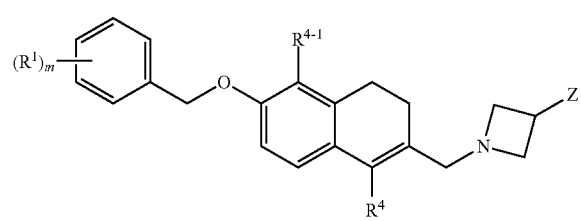

(IC-2)

wherein all symbols have the same meanings as described in above items [1] and [5];

[18] the compound according to above item [1], a salt thereof, an N-oxide form thereof, a solvate thereof, or a prodrug thereof, which is 1-({6-[(2-methoxy-4-propylbenzyl)oxy]-1-methyl-3,4-dihydro-2-naphthalenyl}methyl)-3-azetidinecarboxylic acid, 1-({6-[(4-isobutyl-2-methoxybenzyl)oxy]-1-methyl-3,4-dihydro-2-naphthalenyl}methyl)-3-azetidinecarboxylic acid, 1-({6-[(4-isobutyl-3-methoxybenzyl)oxy]-1-methyl-3,4-dihydro-2-naphthalenyl}methyl)-3-azetidinecarboxylic acid, 1-({6-[(2-ethoxy-4-isobutylbenzyl)oxy]-1-methyl-3,4-dihydro-2-naphthalenyl}methyl)-3-azetidinecarboxylic acid, 1-[(6-{[4-isopropoxy-2-(trifluoromethyl)benzyl]oxy}-1-methyl-3,4-dihydro-2-naphthalenyl)methyl]-3-azetidinecarboxylic acid, 1-[(6-{[2,4-bis(trifluoromethyl)benzyl]oxy}-1-methyl-3,4-dihydro-2-naphthalenyl)methyl]-3-azetidinecarboxylic acid, 1-({1-chloro-6-[(2-methoxy-4-propylbenzyl)oxy]-3,4-dihydro-2-naphthalenyl}methyl)-3-azetidinecarboxylic acid, 1-({1-chloro-6-[(4-isobutyl-2-methoxybenzyl)oxy]-3,4-dihydro-2-naphthalenyl}methyl)-3-azetidinecarboxylic acid, 1-[(1-chloro-6-{[(2S)-3-(2,4-difluorophenyl)-2-methylpropyl]oxy}-3,4-dihydro-2-naphthalenyl)methyl]-3-azetidinecarboxylic acid, 1-[(6-{[4-ethoxy-2-(trifluoromethyl)benzyl]oxy}-1-methyl-3,4-dihydro-2-naphthalenyl)methyl]-3-azetidinecarboxylic acid, 1-({6-[(4-ethyl-2-methoxybenzyl)oxy]-1-methyl-3,4-dihydro-2-naphthalenyl}methyl)-3-azetidinecarboxylic acid, 1-({6-[(2-methoxy-4-propylbenzyl)oxy]-1,5-dimethyl-3,4-dihydro-2-naphthalenyl}methyl)-3-azetidinecarboxylic acid, 1-[(6-{[2,4-bis(trifluoromethyl)benzyl]oxy}-1-chloro-3,4-dihydro-2-naphthalenyl)methyl]-3-azetidinecarboxylic acid, 1-[(6-{[2-(difluoromethoxy)-4-propylbenzyl]oxy}-1,5-dimethyl-3,4-dihydro-2-naphthalenyl)methyl]-3-azetidinecarboxylic acid, 1-[(6-{[4-ethoxy-3-(trifluoromethyl)benzyl]oxy}-1-methyl-3,4-dihydro-2-naphthalenyl)methyl]-3-azetidinecarboxylic acid, or 1-({6-[(2-methoxy-6-propyl-3-pyridinyl)methoxy]-1,5-dimethyl-3,4-dihydro-2-naphthalenyl}methyl)-3-azetidinecarboxylic acid;

[19] the compound according to above item [17], a salt thereof, an N-oxide form thereof, a solvate thereof, or a prodrug thereof, which is 1-({6-[(2-methoxy-4-propylbenzyl)oxy]-1-methyl-3,4-dihydro-2-naphthalenyl}methyl)-3-azetidinecarboxylic acid or 1-[(6-{[2,4-bis(trifluoromethyl)benzyl]oxy}-1-methyl-3,4-dihydro-2-naphthalenyl)methyl]-3-azetidinecarboxylic acid;

[20] a pharmaceutical composition which comprises the compound represented by the formula (I) according to above item [1], a salt thereof, an N-oxide form thereof, a solvate thereof, or a prodrug thereof;

[21] the pharmaceutical composition according to above item [20], which is an EDG-1 agonist, EDG-6 agonist, and/or EDG-8 agonist;

[22] the pharmaceutical composition according to above item [21], which is an EDG-1 agonist;

[23] the pharmaceutical composition according to above item [20], which is an agent for preventing and/or treating a disease related to EDG-1, EDG-6, and/or EDG-8;

[24] the pharmaceutical composition according to above item [23], wherein the disease related to EDG-1, EDG-6, and/or EDG-8 is rejection in transplantation of an organ, tissues, and/or cells, autoimmune disease, allergic disease, asthma, multiple organ failure, ischemia-reperfusion injury, malignant tumor, and/or neurodegenerative disease;

[25] the pharmaceutical composition according to above item [24], wherein the rejection in transplantation of an organ, tissues, and/or cells is a rejection in transplantation of kidney, liver, heart, lung, dermal graft, cornea, vascular, chordae, bone, bone marrow cells, neuronal cells, and/or pancreatic islet cells; the autoimmune disease is collagen disease, systemic lupus erythematosus, rheumatoid arthritis, multiple sclerosis, psoriasis, inflammatory bowel disease, autoimmune diabetes, lung fibrosis, and/or liver fibrosis, and the allergic disease is atopic dermatitis, pollen disease, and/or food allergy;

[26] the pharmaceutical composition according to above item [20], which is an immunosuppressant agent and/or an agent causing lymphopenia;

[27] an agent comprising the compound represented by the formula (I) described in above item [1], a salt thereof, an N-oxide form thereof, a solvate thereof, or a prodrug thereof in combination with one or at least two agent(s) selected from the group consisting of an antimetabolite, an alkylating agent, a T cell activation inhibitor, a calcineurin inhibitor, a proliferation signal inhibitor, a steroid, an immunosuppressant agent, an antibody used in immune suppression, an agent for treating rejection, an antibiotic, an antiviral agent, and an antifungal agent;

[28] a method for prevention and/or treatment of a disease related to EDG-1, EDG-6, and/or EDG-8 in a mammal, which comprises administering to a mammal an effective amount of the compound represented by the formula (I) described in above item [1], a salt thereof, an N-oxide form thereof, a solvate thereof, or a prodrug thereof;

[29] a method for immune suppression and/or lymphopenia in a mammal, which comprises administering to a mammal an effective amount of the compound represented by the formula (I) according to above item [1], a salt thereof, an N-oxide form thereof, a solvate thereof, or a prodrug thereof;

[30] use of the compound represented by the formula (I) described in above item [1], a salt thereof, an N-oxide form thereof, a solvate thereof, or a prodrug thereof for the manufacture of an agent for preventing and/or treating a disease related to EDG-1, EDG-6, and/or EDG-8;

[31] use of the compound represented by the formula (I) described in above item [1], a salt thereof, an N-oxide form thereof, a solvate thereof, or a prodrug thereof for the manufacture of an immunosuppressant agent and/or an agent causing lymphopenia;

[32] a method for preparation of the compound represented by the formula (I) according to above item [1], a salt thereof, an N-oxide form thereof, a solvate thereof, or a prodrug thereof.

In the present specification, S1P means sphingosine-1-phosphate ((2S,3R,4E)-2-amino-3-hydroxyoctadec-4-enyl-1-phosphate). EDG means endothelial differentiation gene which is a generic term including from EDG-1 to EDG-8. Among the EDGs, EDG-1, EDG-3, EDG-5, EDG-6, and EDG-8 (named $S1P_1$, $S1P_3$, $S1P_2$, $S1P_4$, and $S1P_5$, respectively) are regarded as S1P receptors.

In the present specification, a compound having an ability of binding to a receptor includes an agonist, an antagonist, and an inverse agonist. The agonist includes a full agonist and a partial agonist.

In the present invention, a preferable compound having an ability of binding to S1P receptor is an EDG-1 agonist which may have an agonistic activity against EDG-6 and/or an EDG-6 agonist which may have an agonistic activity against EDG-1.

In the present specification, examples of the disease related to EDG-1 and/or EDG-6 include rejection to transplantation, transplanted organ abolition, graft-versus-host disease (e.g., acute graft-versus-host disease during bone-marrow transplantation and the like), autoimmune diseases (e.g., systemic lupus erythematosus, rheumatoid arthritis, multiple sclerosis, myasthenia gravis, and muscular dystrophy), allergic diseases (e.g., atopic dermatitis, pollen disease, food allergy, and chemical drug (e.g., anesthetic such as lidocaine) allergy), asthma, inflammatory diseases, infection, ulcer, lymphoma, malignant tumor (e.g., cancer), leukemia, arteriosclerosis, diseases involving lymphocyte infiltration into a tissue, shock with blood incompatibility during blood transfusion, acute cardiac failure, angina, apoplexia cerebri, traumatism, genetic disease, peripheral arterial disease such as arteriosclerosis obliterans, thromboangiitis obliterans, Buerger's disease, diabetic neuropathy, sepsis, angiitis, nephritis, pneumonia, cerebral infarction, myocardial infarction, edematous disorder, varicose vein such as hemorrhoid, anal fissure, or anal fistula, dissecting aneurysm of the aorta, DIC, pleuritis, congestive heart failure, multiple organ failure, shock with blood incompatibility during blood transfusion, bedsore, burn, ulcerative colitis, Crohon's disease, osteoporosis, fibrosis (e.g., lung fibrosis and liver fibrosis), interstitial pneumonia, chronic hepatitis, cirrhosis, chronic renal failure, and renal glomerulus sclerosis. Further, the EDG-1 also relates to a preoperative, postoperative, and/or prognostic activator for blood vessel accompanying transplantation of various organs, tissues, and/or cells, for example, an adhesion activator of transplanted organs, tissues, and/or cells in heart transplantation, renal transplantation, dermal transplantation, liver transplantation, and the like.

In the present specification, examples of the disease related to the EDG-8 include neurodegenerating diseases. The neurodegenerating diseases include all diseases involving denaturation of nerve, and are not limited by causes of the diseases. The neurodegenerating diseases of the present invention also include a nervous disorder. Preferable examples of the neurodegenerating diseases include central neurologic diseases such as Parkinson's disease, parkinsonian syndrome, Alzheimer's disease, Down's syndrome, amyotrophic lateral sclerosis, familial amyotrophic lateral sclerosis, progressive supranuclear palsy, Huntington's disease, spinocerebellar ataxia, dentaterubral-pallidoluysian atrophy, olivopontocerebellar atrophy, cortico-basal degeneration, familial dementia, frontotemporal dementia, senile dementia, diffuse Lewy body disease, striato-nigral degeneration, chorea-athetosis, dystonia, Meige syndrome, late cortical cerebellar atrophy, familial spastic paraplegia, motor neuron disease, Machado-Joseph disease, Pick syndrome, neurologic dysfunction after cerebral embolism (e.g., cerebral hemorrhage such as hypertensive intracerebral hemorrhage, cerebral infarction such as cerebral thrombosis and cerebral embolization, transient ischemic attack, and subarachnoid hemorrhage), neurologic dysfunction after cerebrospinal trauma, demyelinating disease (e.g., multiple sclerosis, Guillain-Barre syndrome, acute disseminated encephalomyelitis, acute cerebellitis, and transverse myelitis), brain tumor (e.g., astrocytoma), brain and spinal cord disease accompanying infection (e.g., meningitis, brain abscess, CJD, and AIDS dementia), and mental disorder (e.g., integration disorder syndrome, bipolar disorder, nervous disease, psychosomatic disorder, and epilepsy). As the neurodegenerating diseases, for example, Parkinson's disease, parkinsonian syndrome, Alzheimer's disease, amyotrophic lateral sclerosis, and the like are more preferable. Further, the nervous disorders include all diseases with neuronal dysfunction. That is, the disorders generally include disorders recognized as symptoms in diseases. Examples of the disorder in Parkinson's disease or parkinsonian syndrome include tremor, muscle rigidity, slow movement, position reflex disturbance, autonomic disorder, rush phenomena, gait disorder, and neurologic manifestation. Alzheimer's disease includes dementia. amyotrophic lateral sclerosis and familial amyotrophic lateral sclerosis include atrophia musculorum, muscular weakness, dysfunctions of upper extremities, gait disorder, dysarthria, dysphagia, and breathing disorder.

In the present specification, the rejection includes an acute rejection occurring within 3 months, chronic rejection occurring thereafter, and graft-versus-host disease (e.g., acute graft-versus-host disease during bone-marrow transplantation and the like).

In the present specification, the graft means a transplanted organ (e.g., kidney, liver, heart, lung, and small intestine), a transplanted tissue (e.g., skin such as a full-thickness skin graft, an epidermal graft, a dermis graft, and a Davis graft; cornea; vessels; cord; bone; a fetal tissue; and the like), or transplanted cells (e.g., bone marrow cells, hematopoietic stem cells, peripheral blood stem cells, cord blood stem cells, pancreatic islet cells, Langerhans islet cells being part thereof, hepatocytes, neuronal cells, and intestinal epithelial cells). As preferable organs, kidney, liver, heart, and lung may be cited. As preferable tissues, skin, cornea, vessels, cord, and bones may be cited. As preferable cells, bone marrow cells, neurons, and pancreatic islet cells may be cited.

In the present specification, "T cell mediated" means that a T cell involves in any one of the processes of formation, exacerbation, and continuation of disorders.

In the present specification, the autoimmune disease includes collagenosis, systemic lupus erythematosus, Behcet's disease, rheumatoid arthritis, multiple sclerosis, nephrotic syndrome, lupus nephritis, Sjoegren's syndrome, scleroderma, multiple myositis, psoriasis, inflammatory bowel disease (e.g., ulcerative colitis, Crohn's disease, and the like), mixed connective tissue disease, primary myxedema, Addison's disease, hypolastic anemia, autoimmune hemolytic anemia, idiopathic thrombocytopenic purpura, autoimmune thrombopenia, autoimmune diabetes (e.g., type I diabetes), uveitis, antireceptor disease, myasthenia gravis, muscular dystrophythyrotoxicosis, thyroiditis, Hashimoto's disease and the like.

In the present specification, the allergic disease includes atopic dermatitis, rhinitis, conjunctivitis, pollen disease, food allergy, chemical drug (e.g., anesthetic such as lidocaine) allergy), and the like. As a preferable allergic disease, atopic dermatitis, pollen disease, and food allergy may be cited.

In the present specification, the immunosuppressant means a drug which is mainly used for preventing and/or treating rejection in transplantation. As such the drug, there may be used, for example, an antimetabolite, an alkylating agent, a T cell activation inhibitor (i.e., a T cell function suppressor), a calcineurin inhibitor, a proliferation signal inhibitor, a steroid, an antibody used in immune suppression, other remedies for rejection, and the like. Those drugs are clinically used for autoimmune diseases.

In the present specification, the agent causing lymphopenia means a drug having effects of reducing lymphocytes in the peripheral blood, reducing circulating lymphocytes, reducing the amount of permeated lymphocytes, promoting the lymphocytes homing into a secondary lymphatic tissue, suppressing the recirculation of lymphocytes from lymph nods into the blood, and the like.

In the present specification, the secondary lymphatic tissue includes lymph nods, Peyer's patch (e.g., an intestinal lymphatic tissue), spleen and the like.

In the present specification, the effect of promoting the lymphocytes homing into a secondary lymphatic tissue means promotion of the migration of lymphocytes into a secondary lymphatic tissue, enhancement of the separation of lymphocytes in a secondary lymphatic tissue, prolongation of the sustention of lymphocytes in a secondary lymphatic tissue, and the like. Owing to those effects, lymphocytes can be reduced in a site suffering from inflammation or rejection, or the like. Moreover, the effect of protecting lymphocytes in the peripheral blood during cancer therapy can be expected. The effect of protecting lymphocytes in the peripheral blood during cancer therapy means an effect of preliminarily homing lymphocytes in the peripheral blood into a secondary lymphatic tissue before a cancer therapy (in particular, chemotherapy, radiotherapy, etc.) to thereby protect the lymphocytes. This effect includes the protection of lymphocytes in pre-transplantation step of administering a large amount of an anticancer agent. It is known that the treatment of cancer by a chemotherapy, or the like with the use of an anticancer agent is accompanied by serious side effects such as the hypofunction of hematopoietic cells, thereby making a patient infectible. Such side effects can be lessened by the above-described function.

The compound of the present invention can be used as antirejection drug and the like with a preventing effect for bacterial infection, for example, because the compound having a lymphopenic effect cannot decrease all lymphocytes in the living body.

In the present specification, the side effect involved in the use of an immunosuppressant means renal disorder, liver disorder, infection, lymphoma, a circulatory disorder such as bradycardia or hypertension, diarrhea, emesis, alopecia, hirsutism, hyperlipidemia, a respiratory disorder, a central nervous system disorder, and an influence on an organ weight.

In the present specification, a "cyclic group" means a "carbocyclic ring" or a "heterocyclic ring".

In the present specification, a "carbocyclic ring" refers to a "C3-15 carbocyclic ring", for example. A "C3-15 carbocyclic ring" includes a C3-15 monocyclic ring or a polycyclic carbocyclic aryl ring, a carbocyclic ring saturated in a part or all thereof, a polycyclic carbocyclic ring subjected to a spiro bond, and a polycyclic carbocyclic ring subjected to a crosslinking. Examples thereof include cyclopropane, cyclobutane, cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, 6,7-dihydro-5H-benzo[7]annulene, 5H-benzo[7]annulene, heptalene, perhydroheptalene, biphenylene, as-indacene, s-indacene, acenaphthylene, acenaphthene, fluorene, phenalene, phenanthrene, anthracene, spiro[4.4]nonane, spiro[4.5]decane, spiro[5.5]undecane, bicyclo[2.2.1]heptane, bicyclo [2.2.1]hept-2-ene, bicyclo[3.1.1]heptane, bicyclo[3.1.1]hept-2-ene, bicyclo [2.2.2]octane, bicyclo[2.2.2]oct-2-ene, adamantane, and noradamantane rings.

In the present specification, a "C5-12 monocyclic ring or bicyclic carbocyclic ring" refers to a C5-12 monocyclic ring or bicyclic carbocyclic aryl ring or one obtained by partly or entirely saturating the ring. Examples thereof include cyclopentane, cyclohexane, cycloheptane, cyclooctane, cyclononane, cyclodecane, cycloundecane, cyclododecane, cyclotridecane, cyclotetradecane, cyclopentadecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene, perhydronaphthalene, 6,7-dihydro-5H-benzo[7]annulene, 5H-benzo[7] annulene, heptalene, and perhydroheptalene rings.

In the present specification, a "C3-7 monocyclic carbocyclic ring" refers to a C3-7 monocyclic carbocyclic aryl ring or one obtained by partly or entirely saturating the ring. Examples thereof include cyclopropane, cyclobutane, cyclopentane, cyclohexane, cycloheptane, cyclopentene, cyclohexene, cycloheptene, cyclopentadiene, cyclohexadiene, cycloheptadiene, and benzene ring.

In the present specification, examples of the "C3-7 monocyclic saturated carbocyclic ring" includes cyclopropane, cyclobutane, cyclopentane, cyclohexane, and cycloheptane.

In the present specification, a "heterocyclic ring" refers to a "3- to 15-membered heterocyclic ring including 1 to 5 hetero atoms each selected from an oxygen atom, a nitrogen atom, and a sulfur atom". A "3- to 15-membered heterocyclic ring including 1 to 5 hetero atoms each selected from an oxygen atom, a nitrogen atom, and a sulfur atom" includes a 3- to 15-membered monocyclic ring or a polycyclic heterocyclic aryl ring including 1 to 5 hetero atoms each selected from an oxygen atom, a nitrogen atom, and a sulfur atom and one obtained by partly or entirely saturating the ring, a polycyclic heterocyclic ring subjected to a spiro bond, and a polycyclic heterocyclic ring subjected to a crosslinking. Examples thereof include pyrrole, imidazole, triazole, tetrazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzoxepine, benzoxazepine, benzoxadiazepine, benzothiepine, benzothiazepine, benzothiadiazepine, benzazepine, benzodiazepine, benzofurazane, benzothiadiazole, benzotriazole, carbazole, β-carboline, acridine, phenazine, dibenzofuran, xanthene, dibenzothiophene, phenothiazine, phenoxazine, phenoxathiin, thianthrene, phenanthridine, phenanthroline, perimidine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepine, tetrahydrooxepine, perhydrooxepine, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxaythine, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, benzodioxepane, dihydrobenzoxazepine, tetrahydrobenzoxazepine, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, dioxaindan, benzodioxane, chromene, chroman, benzodithiolane, benzodithiane azaspiro[4.4]nonane, oxazaspiro[4.4]nonane, dioxaspiro[4.4]nonane, azaspiro[4.5]decane, thiaspiro[4.5]decane, dithiaspiro[4.5]decane, dioxaspiro[4.5]decane, oxazaspiro[4.5]decane, azaspiro[5.5]undecane, oxaspiro[5.5]undecane, dioxasprio[5.5]undecane, azabicyclo[2.2.1]heptane, oxabicyclo[2.2.1]heptane, azabicyclo[3.1.1]heptane, azabicyclo[3.2.1]octane, azabicyclo[2.2.2]octane diazabicyclo [2.2.2]octane, oxazaspiro[2.5]octane, 1,3,8-triazaspiro[4.5]decane, 2,7-diazaspiro[4.5]decane, 1,4,9-triazaspiro[5.5]undecane, and azabicyclo[2.1.1]hexane rings.

In the present specification, a "5- to 12-membered monocyclic or polycyclic heterocyclic ring including 1 to 3 hetero atoms each selected from an oxygen atom, a nitrogen atom, and a sulfur atom and one obtained by partly or entirely saturating the ring" refers to a "5- to 12-membered monocyclic ring or polycyclic heterocyclic aryl ring including 1 to 3 hetero atoms each selected from an oxygen atom, a nitrogen atom, and a sulfur atom, and one obtained by partly or entirely saturating the ring, a polycyclic heterocyclic ring subjected to a spiro bond, and a polycyclic heterocyclic ring subjected to a crosslinking". Examples thereof include pyrrole, imidazole, triazole, pyrazole, pyridine, pyrazine, pyrimidine, pyridazine, azepine, diazepine, furan, pyran, oxepine, thiophene, thiopyran, thiepine, oxazole, isoxazole, thiazole, isothiazole, furazane, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, phthalazine, naphthyridine, quinoxaline, quinazoline, cinnoline, benzoxazole, benzothiazole, benzimidazole, chromene, benzoxepine, dihydrobenzoxepin, benzoxazepine, benzoxadiazepine, benzothiepine, benzothiazepine, benzothiadiazepine, benzazepine, benzodiazepine, benzofurazane, benzothiadiazole, benzotriazole, pyrroline, pyrrolidine, imidazoline, imidazolidine, triazoline, triazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, bezoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, b enzodioxepane, dihydrobenzoxazepine, tetrahydrobenzoxazepine, dioxolane, dioxane, dithiolane, dithiane, dioxaindan, benzodioxane, chroman, benzodithiolane, benzodithiane, azaspiro[4.4]nonane, oxazaspiro[4.4]nonane, dioxaspro[4.4]nonane, azaspiro[4.5]decane, thiaspiro[4.5]decane, diazaspiro[4.5]decane, dioxaspiro[4.5]decane, oxazaspiro[4.5]decane, azaspiro[5.5]undecane, oxaspiro[5.5]undecane, dioxaspiro[5.5]undecane, azabicyclo[2.2.1]heptane, oxabicyclo[2.2.1]heptane, azabicyclo[3.1.1]heptane, azabicyclo[3.2.1]octane, azabicyclo[2.2.2]octane, diazabicyclo [2.2.2]octane, oxazaspiro[2.5]octane, 1,3,8-triazaspiro[4.5]decane, 2,7-diazaspiro[4.5]decane, 1,4,9-triazaspiro[5.5]undecane, and azabicyclo[2.1.1]hexane ring.

In the present specification, a "5- to 7-membered monocyclic heterocyclic ring including 1 to 2 nitrogen atoms, one oxygen atom, and/or one sulfur atom" is one obtained by saturating 5- to 7-membered monocyclic heterocyclic aryl ring including 1 to 2 nitrogen atoms, one oxygen atom, and/or one sulfur atom, or one obtained by partly or entirely saturating the ring. Examples thereof include pyrrole, imidazole, pyrazole, pyrroline, pyrrolidine, imidazoline, imidazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, tetrahydrooxazole, tetrahydroisoxazole, tetrahydrothiazole, tetrahydroisothiazole, dihydrooxadiazole, tetrahydrooxadiazole, dihydrothiodiazole, tetrahydrothiodiazole, tetrahydrooxadiazine, tetrahydrothiadiazine, tetrahydrooxadiazepine, perhydrooxazepine, perhydrooxadiazepine, tetrahydrothiadiazepine, perhydrothiazepine, perhydrothiadiazepine, morpholine, and thiomorpholine ring.

In the present specification, a "5- to 7-membered monocyclic heterocyclic ring including 1 to 2 nitrogen atoms, one oxygen atom, and/or one sulfur atom" of "be taken together with a nitrogen atom to which they are bound to form a 5- to 7-membered monocyclic heterocyclic ring containing 1 to 2 nitrogen atoms, one oxygen atom and/or one sulfur atom" represents the same as the above-mentioned "5- to 7-membered monocyclic heterocyclic ring including 1 to 2 nitrogen atoms, one oxygen atom, and/or one sulfur atom".

In the present specification, a "cyclic group" of a "cyclic group which may further have a substituent(s)", a "cyclic group which may be substituted", and "substituted by a cyclic group" represents the same as the above-mentioned "cyclic group".

In the present specification, the "substituent" in the phrase "which may have a substituent(s)" is not particularly limited, so long as it is a substituent. Examples of the substituent include (1) C1-20 alkyl which may be substituted, (2) C2-20 alkenyl which may be substituted, (3) C2-20 alkynyl which may be substituted, (4) C1-20 alkylidene which may be substituted, (5) a cyclic group which may be substituted, (6) oxo, (7) hydroxy, (8) C1-20 alkyloxy which may be substituted, (9) C2-20 alkenyloxy which may be substituted, (10) C2-20 alkynyloxy which may be substituted, (11) hydroxy which is protected by a cyclic group which may be substituted, (12) C1-20 acyloxy which may be substituted, (13) thioxo, (14) mercapto, (15) C1-20 alkylthio which may be substituted, (16) C2-20 alkenylthio which may be substituted, (17) C2-20 alkynylthio which may be substituted, (18) mercapto substituted with a cyclic group which may be substituted, (19) C1-20 alkylsulfinyl which may be substituted, (20) C2-20 alkenylsulfinyl which may be substituted, (21) C2-20 alkynylsulfinyl which may be substituted, (22) sulfinyl substituted with a cyclic group which may be substituted, (23) C1-20 alkylsulfonyl which may be substituted, (24) C2-20 alkenylsulfonyl which may be substituted, (25) C2-20 alkynylsulfonyl which may be substituted, (26) sulfonyl substituted with a cyclic group which may be substituted, (27) sulfino which may be substituted, (28) sulfo which may be substituted, (29) sulfamoyl which may be substituted (when the substituents are two, they may be taken together with a nitrogen atom to which they are bound to form a 5- to 7-membered monocyclic heterocyclic ring containing 1 to 2 nitrogen atoms, one oxygen atom and/or one sulfur atom (this heterocyclic ring may be substituted by C1-8 alkyl, hydroxy, or amino)), (30) carbonyl which may be substituted, (31) carboxy which may be substituted, (32) C1-20 acyl which may be substituted, (33) carbamoyl which may be substituted (when the substituents are two, they may be taken together with a nitrogen atom to which they are bound to form a 5- to 7-membered monocyclic heterocyclic ring containing 1 to 2 nitrogen atoms, one oxygen atom and/or one sulfur atom (this heterocyclic ring may be substituted by C1-8 alkyl, hydroxy, or amino)), (34) cyano, (35) amidino which may be substituted (when the substituents are two, they may be taken together with a nitrogen atom to which they are bound to form a 5- to 7-membered monocyclic heterocyclic ring containing 1 to 2 nitrogen atoms, one oxygen atom and/or one sulfur atom (this heterocyclic ring may be substituted by C1-8 alkyl, hydroxy, or amino)), (36) nitro, (37) nitroso, (38) imino which may be substituted, (39) amino which may be substituted (when the substituents are two, they may be taken together with a nitrogen atom to which they are bound to form a 5- to 7-membered monocyclic heterocyclic ring containing 1 to 2 nitrogen atoms, one oxygen atom and/or one sulfur atom (this heterocyclic ring may be substituted by C1-8 alkyl, hydroxy, or amino)), (40) trifluoromethyl, (41) trifluoromethoxy, and (42) a halogen atom, and the like.

In the present specification, the "substituent" in the phrase "which may be substituted" or the like is, for example, (1) C1-20 alkyl, (2) C2-20 alkenyl, (3) C2-20 alkynyl, (4) C1-20 alkylidene, (5) a cyclic group, (6) C1-20 alkyl substituted with a cyclic group, (7) oxo, (8) hydroxy, (9) C1-20 alkyloxy, (10) C2-20 alkenyloxy, (11) C2-20 alkynyloxy, (12) hydroxy protected by a cyclic group, (13) C1-20 acyloxy, (14) thioxo, (15) mercapto, (16) C1-20 alkylthio, (17) C2-20 alkenylthio, (18) C2-20 alkynylthio, (19) mercapto substituted with a cyclic group, (20) C1-20 alkylsulfinyl, (21) C2-20 alkenylsulfinyl, (22) C2-20 alkynylsulfinyl, (23) sulfinyl substituted with a cyclic group, (24) C1-20 alkylsulfonyl, (25) C2-20 alkenylsulfonyl, (26) C2-20 alkynylsulfonyl, (27) sulfonyl substituted with a cyclic group, (28) C1-20 alkylsulfonyl substituted with a cyclic group, (29) sulfino, (30) sulfo, (31) sulfamoyl, (32) carboxy, (33) C1-20 acyl, (34) C1-20 acyl substituted with a cyclic group, (35) carbonyl substituted with a cyclic group, (36) carbamoyl, (37) cyano, (38) amidino, (39) nitro, (40) nitroso, (41) imino, (42) amino, (43) mono(C1-8 alkyl)amino, (44) di(C1-8 alkyl)amino, (45) trifluoromethyl, (46) trifluoromethoxy, and (47) a halogen atom or the like. They may exist at any substitutable positions, any substitutable number of substituents may exist.

In the present specification, the "C1-20 alkyl" includes methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, and isomers thereof.

In the present specification, the "C1-8 alkyl" includes methyl, ethyl, propyl, butyl, pentyl, hexyl, heptyl, octyl, and isomers thereof.

In the present specification, the "C2-20 alkenyl" includes ethenyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, nonadecenyl, icosenyl, and isomers thereof.

In the present specification, the "C2-20 alkynyl" includes ethynyl, propynyl, butynyl, pentynyl, hexynyl, heptynyl, octynyl, nonynyl, decynyl, undecynyl, dodecynyl, tridecynyl, tetradecynyl, pentadecynyl, hexadecynyl, heptadecynyl, octadecynyl, nonadecynyl, icosynyl, and isomers thereof.

In the present specification, the "C1-20 alkylidene" includes methylidene, ethylidene, propylidene, butylidene, pentylidne, hexylidene, heptylidene, octylidene, nonylidene, decylidene, undecylidene, dodecylidene, tridecylidene, tetradecylidene, pentadecylidene, hexadecylidene, heptadecylidene, octadecylidene, nonadecylidene, icosylidene, and isomers thereof.

In the present specification, the "C1-20 alkyloxy" includes methoxy, ethoxy, propoxy, butoxy, pentyloxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy, icosyloxy, and isomers thereof.

In the present specification, the "C1-8 alkoxy" includes methoxy, ethoxy, propoxy, butoxy, pentyloxy, hexyloxy, heptyloxy, octyloxy, and isomers thereof.

In the present specification, the "C2-20 alkenyloxy" includes ethenyloxy, propenyloxy, butenyloxy, pentenyloxy, hexenyloxy, heptenyloxy, octenyloxy, nonenyloxy, decenyloxy, undecenyloxy, dodecenyloxy, tridecenyloxy, tetradecenyloxy, pentadecenyloxy, hexadecenyloxy, heptadecenyloxy, octadecenyloxy, nonadecenyloxy, icosenyloxy, and isomers thereof.

In the present specification, the "C2-20 alkynyloxy" includes ethynyloxy, propynyloxy, butynyloxy, pentynyloxy, hexynyloxy, heptynyloxy, octynyloxy, nonynyloxy, decynyloxy, undecynyloxy, dodecynyloxy, tridecynyloxy, tetradecynyloxy, pentadecynyloxy, hexadecynyloxy, heptadecynyloxy, octadecynyloxy, nonadecynyloxy, icosynyloxy, and isomers thereof.

In the present specification, the "C1-20 alkylthio" includes methylthio, ethylthio, propylthio, butylthio, pentylthio, hexylthio, heptylthio, octylthio, nonylthio, decylthio, undecylthio, dodecylthio, tridecylthio, tetradecylthio, pentadecylthio, hexadecylthio, heptadecylthio, octadecylthio, nonadecylthio, icosylthio, and isomers thereof.

In the present specification, the "C2-20 alkenylthio" includes ethenylthio, propenylthio, butenylthio, pentenylthio, hexenylthio, heptenylthio, octenylthio, nonenylthio, decenylthio, undecenylthio, dodecenylthio, tridecenylthio, tetradecenylthio, pentadecenylthio, hexadecenylthio, heptadecenylthio, octadecenylthio, nonadecenylthio, icosenylthio, and isomers thereof.

In the present specification, the "C2-20 alkynylthio" includes ethynylthio, propynylthio, butynylthio, pentynylthio, hexynylthio, heptynylthio, octynylthio, nonynylthio, decynylthio, undecynylthio, dodecynylthio, tridecynylthio, tetradecynylthio, pentadecynylthio, hexadecynylthio, heptadecynylthio, octadecynylthio, nonadecynylthio, icosynylthio, and isomers thereof.

In the present specification, the "C1-20 alkylsulfinyl" includes methylsulfinyl, ethylsulfinyl, propylsulfinyl, butylsulfinyl, pentylsulfinyl, hexylsulfinyl, heptylsulfinyl, octylsulfinyl, nonylsulfinyl, decylsulfinyl, undecylsulfinyl, dodecylsulfinyl, tridecylsulfinyl, tetradecylsulfinyl, pentadecylsulfinyl, hexadecylsulfinyl, heptadecylsulfinyl, octadecylsulfinyl, nonadecylsulfinyl, icosylsulfinyl, and isomers thereof.

In the present specification, the "C2-20 alkenylsulfinyl" includes ethenylsulfinyl, propenylsulfinyl, butenylsulfinyl, pentenylsulfinyl, hexenylsulfinyl, heptenylsulfinyl, octenylsulfinyl, nonenylsulfinyl, decenylsulfinyl, undecenylsulfinyl, dodecenylsulfinyl, tridecenylsulfinyl, tetradecenylsulfinyl, pentadecenylsulfinyl, hexadecenylsulfinyl, heptadecenylsulfinyl, octadecenylsulfinyl, nonadecenylsulfinyl, icosenylsulfinyl, and isomers thereof.

In the present specification, the "C2-20 alkynylsulfinyl" includes ethynylsulfinyl, propynylsulfinyl, butynylsulfinyl, pentynylsulfinyl, hexynylsulfinyl, heptynylsulfinyl, octynylsulfinyl, nonynylsulfinyl, decynylsulfinyl, undecynylsulfinyl, dodecynylsulfinyl, tridecynylsulfinyl, tetradecynylsulfinyl, pentadecynylsulfinyl, hexadecynylsulfinyl, heptadecynylsulfinyl, octadecynylsulfinyl, nonadecynylsulfinyl, icosynylsulfinyl, and isomers thereof.

In the present specification, the "C1-20 alkylsulfonyl" includes methylsulfonyl, ethylsulfonyl, propylsulfonyl, butylsulfonyl, pentylsulfonyl, hexylsulfonyl, heptylsulfonyl, octylsulfonyl, nonylsulfonyl, decylsulfonyl, undecylsulfonyl, dodecylsulfonyl, tridecylsulfonyl, tetradecylsulfonyl, pentadecylsulfonyl, hexadecylsulfonyl, heptadecylsulfonyl, octadecylsulfonyl, nonadecylsulfonyl, icosylsulfonyl, and isomers thereof.

In the present specification, the "C2-20 alkenylsulfonyl" includes ethenylsulfonyl, propenylsulfonyl, butenylsulfonyl, pentenylsulfonyl, hexenylsulfonyl, heptenylsulfonyl, octenylsulfonyl, nonenylsulfonyl, decenylsulfonyl, undecenylsulfonyl, dodecenylsulfonyl, trideceriylsulfonyl, tetradecenylsulfonyl, pentadecenylsulfonyl, hexadecenylsulfonyl, heptadecenylsulfonyl, octadecenylsulfonyl, nonadecenylsulfonyl, icosenylsulfonyl, and isomers thereof.

In the present specification, the "C2-20 alkynylsulfonyl" includes ethynylsulfonyl, propynylsulfonyl, butynylsulfonyl, pentynylsulfonyl, hexynylsulfonyl, heptynylsulfonyl, octynylsulfonyl, nonynylsulfonyl, decynylsulfonyl, undecynylsulfonyl, dodecynylsulfonyl, tridecynylsulfonyl, tetradecynylsulfonyl, pentadecynylsulfonyl, hexadecynylsulfonyl, heptadecynylsulfonyl, octadecynylsulfonyl, nonadecynylsulfonyl, icosynylsulfonyl, and isomers thereof.

In the present specification, the "C1-20 acyl" includes methanoyl, ethanoyl, propanoyl, butanoyl, pentanoyl, hexanoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, icosanoyl, and isomers thereof.

In the present specification, the "C1-20 acyloxy" includes methanoyloxy, ethanoyloxy, propanoyloxy, butanoyloxy, pentanoyloxy, hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, nonadecanoyloxy, icosanoyloxy, and isomers thereof.

In the present specification, the "mono(C1-8 alkyl)amino" includes methylamino, ethylamino, propylamino, butylamino, pentylamino, hexylamino, heptylamino, octylamino, and isomers thereof.

In the present specification, the "di(C1-8 alkyl)amino" includes dimethylamino, diethylamino, dipropylamino, dibutylamino, methylethylamino, methylpropylamino, ethylpropylamino and isomers thereof.

In the present specification, a "protective group" of an "acid group which may be protected", a "carboxyl group which may be protected", a "hydroxy group which may be protected", a "hydroxamic acid group which may be protected", a "sulfonic acid group which may be protected", a "boronic acid group which may be protected", a "carbamoyl group which may be protected", a "sulfamoyl group which may be protected", and an "amino group which may be protected" represents the same as the "substituent" of the abovementioned "which may be substituted (by substituent)".

In the present specification, the "halogen atom" includes fluorine, chlorine, bromine, and iodine.

In the present specification, the "bond" means that the atoms are directly bound without intermediation of any other atom.

In the present specification, the "spacer which has a main chain having 1 to 10 atoms" means spacing in which 1 to 10 atoms are continuously linked in its main chain. In this case, the "number of atoms as a main chain" should be counted such that the number of atoms in its main chain become minimum. For example, the number of atoms of 1,2-cyclopentylene is counted as 2, and the number of atoms of 1,3-cyclopentylene is counted as 3. The "spacer which has a main chain having 1 to 10 atoms" includes a divalent group having 1 to 10 atoms in its main chain which is composed of 1 to 4 combinations selected from the group consisting of C-10 alkylene which may be substituted, a C2-10 alkenylene which may be substituted, C2-10 alkynylene which may be substituted, an nitrogen atom (—NH—) which may be substituted, —CO—, —O—, —S—, —SO—, —SO$_2$—, -(carbocyclic ring which may be substituted)-, -(heterocyclic ring which may be substituted)-, and the like.

In the present specification, the "C1-10 alkylene" includes methylene, ethylene, trimethylene, tetramethylene, pentamethylene, hexamethylene, heptamethylene, octamethylene, nonamethylene, decamethylene and isomers thereof.

In the present specification, the "C2-4 alkylene" includes ethylene, trimethylene, tetramethylene, and isomers thereof.

In the present specification, the "C2-10 alkenylene" includes ethenylene, propenylene, butenylene, pentenylene, hexenylene, heptenylene, octenylene, nonenylene, decenylene, and isomers thereof.

In the present specification, the "C2-10 alkynylene" includes ethynylene, propynylene, bytynylene, pentynylene, hexynylene, heptynylene, octynylene, nonynylene, decynylene, and isomers thereof.

In the present specification, the "spacer which has a main chain having 1 to 9 atoms" means spacing in which 1 to 9 atoms are continuously linked in its main chain. In this case, the "number of atoms as a main chain" should be counted such that the number of atoms in its main chain become minimum. For example, the number of atoms of 1,2-cyclopentylene is counted as 2, and the number of atoms of 1,3-cyclopentylene is counted as 3. The "spacer which has a main chain having 1 to 9 atoms" includes a divalent group having 1 to 9 atoms in its main chain which is composed of 1 to 4 combinations selected from the group consisting of C1-9 alkylene which may be substituted, a C2-9 alkenylene which may be substituted, C2-9 alkynylene which may be substituted, an nitrogen atom (—NH—) which may be substituted, —CO—, —O—, —S—, —SO—, —SO$_2$—, -(carbocyclic ring which may be substituted)-, -(heterocyclic ring which may be substituted)-, and the like.

In the present specification, the "C1-9 alkylene" includes methylene, ethylene, trimethylene, tetramethylene, pentamethylene, hexamethylene, heptamethylene, octamethylene, nonamethylene, and isomers thereof.

In the present specification, the "C2-9 alkenylene" includes ethenylene, propenylene, butenylene, pentenylene, hexenylene, heptenylene, octenylene, nonenylene, and isomers thereof.

In the present specification, the "C2-9 alkynylene" includes ethynylene, propynylene, bytynylene, pentynylene, hexynylene, heptynylene, octynylene, nonynylene, and isomers thereof.

In the present specification, the "spacer which has a main chain having 1 to 8 atoms" means spacing in which 1 to 8 atoms are continuously linked in its main chain. In this case, the "number of atoms as a main chain" should be counted such that the number of atoms in its main chain become minimum. For example, the number of atoms of 1,2-cyclopentylene is counted as 2, and the number of atoms of 1,3-cyclopentylene is counted as 3. The "spacer which has a main chain having 1 to 8 atoms" includes a divalent group having 1 to 8 atoms in its main chain which is composed of 1 to 4 combinations selected from the group consisting of C1-8 alkylene which may be substituted, a C2-8 alkenylene which may be substituted, C2-8 alkynylene which may be substituted, an nitrogen atom (—NH—) which may be substituted, —CO—, —O—, —S—, —SO—, —SO$_2$—, -(carbocyclic ring which may be substituted)-, -(heterocyclic ring which may be substituted)-, 1,2,4-oxadiazole which may be substituted, and the like.

In the present specification, the "C1-8 alkylene" includes methylene, ethylene, trimethylene, tetramethylene, pentamethylene, hexamethylene, heptamethylene, octamethylene, and isomers thereof.

In the present specification, the "C2-8 alkenylene" includes ethenylene, propenylene, butenylene, pentenylene, hexenylene, heptenylene, octenylene, and isomers thereof.

In the present specification, the "C2-8 alkynylene" includes ethynylene, propynylene, bytynylene, pentynylene, hexynylene, heptynylene, octynylene, and isomers thereof.

In the present specification, the "spacer which has a main chain having 1 to 7 atoms" means spacing in which 1 to 7 atoms are continuously linked in its main chain. In this case, the "number of atoms as a main chain" should be counted such that the number of atoms in its main chain become minimum. For example, the number of atoms of 1,2-cyclopentylene is counted as 2, and the number of atoms of 1,3-cyclopentylene is counted as 3. The "spacer which has a main chain having 1 to 7 atoms" includes a divalent group having 1 to 7 atoms in its main chain which is composed of 1 to 4 combinations selected from the group consisting of C1-7 alkylene which may be substituted, a C2-7 alkenylene which may be substituted, C2-7 alkynylene which may be substituted, an nitrogen atom (—NH—) which may be substituted, —CO—, —O—, —S—, —SO—, —SO$_2$—, -(carbocyclic ring which may be substituted)-, -(heterocyclic ring which may be substituted)-, 1,2,4-oxadiazole which may be substituted, and the like.

In the present specification, the "C1-7 alkylene" includes methylene, ethylene, trimethylene, tetramethylene, pentamethylene, hexamethylene, heptamethylene, and isomers thereof.

In the present specification, the "C2-7 alkenylene" includes ethenylene, propenylene, butenylene, pentenylene, hexenylene, heptenylene, and isomers thereof.

In the present specification, the "C2-7 alkynylene" includes ethynylene, propynylene, bytynylene, pentynylene, hexynylene, heptynylene, and isomers thereof.

In the present specification, examples of an acid group include the following groups which may be protected: (1) a carboxyl group, (2) a hydroxy group producing an acid (e.g., phenolic hydroxy group), (3) a hydroxamic acid group, (4) a sulfonic acid group, (5) boronic acid group, (6) a carbamoyl group, (7) a sulfamoyl group, (8) a —P(=O)(OH)$_2$ group, (9) a —P(=O)(OR$^2$) (OR$^3$) group (in the group, R$^2$ and R$^3$ represent the same as those described above), and (10) a tetrazolyl group.

In the present specification, a "ring which may have a substituent(s)" represented by one spacer atom represented by X with the substituent of a ring B is a "ring which may have a substituent(s)" formed by one spacer atom represented by X together with one substituent of a ring B. The "ring which may have a substituent(s)" represents the same as the above-mentioned a "cyclic group which may further have substituent(s)".

In the present specification, a "ring which may have a substituent(s)" represented by one spacer atom represented by Y together with the substituent of a ring B is a "ring which may have a substituent(s)" formed by one spacer atom represented by Y with one substituent of a ring B. An example of the "ring which may have a substituent(s)" includes a "nitrogen-containing heterocyclic ring which may have a substituent(s)". An example of the "nitrogen-containing heterocyclic ring" of the "nitrogen-containing heterocyclic ring which may have a substituent(s)" includes a "3- to 15-membered heterocyclic ring including one nitrogen atom and which may further include 1 to 4 hetero atoms each selected from an oxygen atom, a nitrogen atom, and a sulfur atom". A "3- to 15-membered heterocyclic ring including one nitrogen atom and which may further include 1 to 4 hetero atoms each selected from an oxygen atom, a nitrogen atom, and a sulfur atom" includes 3- to 15-membered monocyclic ring or a polycyclic heterocyclic aryl ring including one nitrogen atom and which may further include 1 to 4 hetero atoms each selected from an oxygen atom, a nitrogen atom, and a sulfur atom and may be partly or entirely saturated, a polycyclic heterocyclic ring subjected to a spiro bond, and a polycyclic heterocyclic ring subjected to a crosslinking. Examples there of include pyrrole, imidazole, triazole, tetrazole, pyrazole, azepine, diazepine, indole, isoindole, indolizine, indazole, quinoline, isoquinoline, quinolizine, phthalazine, pteridine, naphthyridine, quinoxaline, quinazoline, cinnoline, purine, benzoxazole, benzothiazole, benzoxazepine, benzoxadiazepine, benzothiazepine, benzothiadiazepine, benzofurazane, benzothiadiazole, benzotriazole, pyrrolopyridine, benzimidazole, benzazepine, benzodiazepine, benzotriazole, carbazole, β-carboline, acridine, phenazine, phenothiazine, phenoxazine, phenanthridine, phenanthroline, perimidine, pyrazoloisoquinoline, pyrazolonaphthyridine, pyrimidoindole, indolizinoindole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazane, tetrahydrofurazane, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, tetrahydropyrrolopyridine, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydroacridine, tetrahydroacridine, perhydroacridine, tetrapyridonaphthyridine, dihydro-β-carboline, tetrahydro-β-carboline, dihydrodihydroazepinoindole, hexahydroazepinoindole, tetrahydropyrazoloisoquinoline, tetrahydropyrazolonaphthyridine, dihydroazepinoindazole, hexahydroazepinoindazole, dihydropyrazolopyridoazepine, hexahydropyrazolopyridoazepine, tetrahydropyrimidoindole, dihydrothiazinoindole, tetrahydrothiazinoindole, dihydrooxazinoindole, tetrahydrooxazinoindole, hexahydroindolizinoindole, dihydroindolobenzodiazepine, octahydroindoloquinolizine, hexahydroimidazopyridoindole, hexahydropyrrolothiazepinoindole, azaspiro[4.4]nonane, oxazaspiro[4.4]nonane, oxazaspiro[2.5]octane, azaspiro[4.5]decane, 1,3,8-triazaspiro[4.5]decane, 2,7-diazaspiro[4.5]decane, 1,4,9-triazaspiro[5.5]undecane, oxazaspiro[4.5]decane, azaspiro[5.5]undecane, azabicyclo[2.2.1]heptane, azabicyclo[3.1.1]heptane, azabicyclo[3.2.1]octane, azabicyclo[2.2.2]octane, azabicyclo[2.1.1]hexane.

In the present specification, "9- to 15-membered polycyclic heterocyclic ring including one nitrogen atom and which may further include 1 to 4 hetero atoms each selected from an oxygen atom, a nitrogen atom, and a sulfur atom" includes "9- to 15-membered polycyclic heterocyclic ring including one nitrogen atom and which may further include 1 to 4 hetero atoms each selected from an oxygen atom, a nitrogen atom, and a sulfur atom and may be partly or entirely saturated". Examples thereof include indole, isoindole, indolizine, indazole, quinoline, isoquinoline, quinolizine, purine, phthalazine, pteridine, naphthyridine, quinoxaline, quinazoline, cinnoline, benzoxazole, benzothiazole, benzoimidazole, benzoxazepine, benzoxadiazepine, benzothiazepine, benzothiadiazepine, benzoazepine, benzodiazepine, benzofurazane, benzothiadiazole, benzotriazole, carbazole, β-carboline, acridine, phenazine, phenothiazine, phenoxazine, phenanthridine, phenanthroline, perimidine, indoline, isoindoline, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dihydrobenzazepine, tetrahydrobenzazepine, dihydrobenzodiazepine, tetrahydrobenzodiazepine, dihydrobenzoxazepine, tetrahydrobenzoxazepine, dihydrocarbazole, tetrahydrocarbazole, perhydrocarbazole, dihydro-β-carboline, tetrahydro-β-carboline, dihydroacridine, tetrahydroacridine, perhydroacridine, azaspiro[4.4]nonane, oxazaspiro[4.4]nonane, azaspiro[4.5]decane, oxazaspiro[4.5]decane, azaspiro[5.5]undecane.

In the present specification, "substituent" represented by $R^1$ have the same meanings as the "substituent" in the above-mentioned "which may have a substituent(s)".

In the present specification, $R^4$ and $R^{4-1}$ have the same meanings as the "substituent" in the ring B "cyclic group which may have a substituent(s)".

In the present specification, $R^5$, $R^{5-1}$, and $R^{5-2}$ represents the same as a "substituent" of a "spacer which has a main chain having 1 to 10 atoms and one atom of which may form a ring that may have a substituent(s) together with a substituent of the ring B", which is represented by Y.

In the present specification, a "ring which may have a substituent(s)" represented by $R^6$ and $R^7$ together with a carbon atom bonding therewith represents the same as the above-mentioned "cyclic group which may further have a substituent(s)".

In the present invention, any of the ring, group, and atom represented by a ring A, a ring B, X, Y, Z, $R^1$, $R^2$, $R^3$, $R^4$, $R^{4-1}$, $R^5$, $R^{5-1}$, $R^{5-2}$, $R^6$, and $R^7$, respectively, is preferable. Hereinafter, a preferable group, ring, and atom are listed. It should be noted that all symbols used herein represent the same as the symbols described above.

In the present invention, a ring A is preferably a "C3-15 carbocyclic ring" or a "3- to 15-membered heterocyclic ring including 1 to 5 hetero atoms each selected from an oxygen atom, a nitrogen atom, and a sulfur atom", more preferably a "C3-7 monocyclic carbocyclic ring" or a "5- to 7-membered monocyclic heterocyclic ring including 1 to 2 nitrogen atoms, one oxygen atom, and/or one sulfur atom", or particularly preferably a benzene ring or a pyridine ring.

In the present invention, a "cyclic group" of a "cyclic group which may further have a substituent(s)" in a ring B is preferably a "C3-15 carbocyclic ring" or a "3- to 15-membered heterocyclic rings", more preferably a "C5-12 monocyclic or bicyclic carbocyclic ring" and a "5- to 12-membered monocyclic or polycyclic heterocyclic ring including 1 to 3 hetero atoms each selected from an oxygen atom, a nitrogen atom, and a sulfur atom and each of which may be partly or entirely saturated, or particularly preferably a benzene ring, a dihydronaphthalene ring, a pyrazole ring, a pyridine ring, and a benzothiophene ring.

In the present invention, a "ring" of a "ring which may have a substituent(s)" represented by one spacer atom represented by Y together with a substituent of the ring B is preferably a "3- to 15-membered heterocyclic ring including one nitrogen atom and which may further include 1 to 4 hetero atoms each selected from an oxygen atom, a nitrogen atom, and a sulfur atom, more preferably a "9- to 15-membered polycyclic heterocyclic ring including one nitrogen atom and which may further include 1 to 4 hetero atoms each selected from an oxygen atom, a nitrogen atom, and a sulfur atom, or particularly preferably a tetrahydroisoquinoline ring and a tetrahydro-β-carboline ring.

In the present invention, X is preferably a divalent group which has a main chain having 1 to 8 atoms and which is composed of a combination of 1 to 4 groups selected from a C1-8 alkylene group which may be substituted, a C2-8 alkenylene group which may be substituted, —CO—, —S—, —O—, and a 1,2,4-oxadiazole group which may be substituted, more preferably

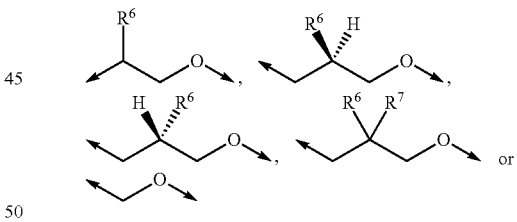

wherein all symbols represent the same as those described above; still more preferably

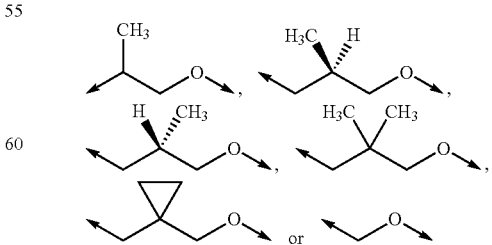

wherein all symbols represent the same as those described above; or particularly preferably

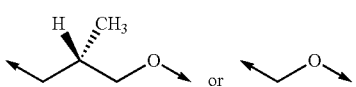

wherein all symbols represent the same as those described above.

In the present invention, Y is preferably a divalent group which has a main chain having 1 to 10 atoms and which is composed of a combination of 1 to 4 groups selected from a C1-10 alkylene group which may be substituted, a C2-10 alkenylene group which may be substituted, a nitrogen atom (—NH—) which may be substituted, —CO—, —O—, —S—, -(an aziridine which may be substituted)-, -(an azetidine which may be substituted)-, -(a pyrrolidine which may be substituted)-, -(a piperidine which may be substituted)-, -(a piperazine which may be substituted)-, and -(a tetrahydropyridine which may be substituted)-, more preferably —CH$_2$—NH—(CH$_2$)$_2$—, —CH$_2$— (azetidine)-, —CH$_2$—(piperidine)-(CH$_2$)$_2$—, -(tetrahydropyridine)-(CH$_2$)$_2$—, —CH=CH—CH$_2$—NH—(CH$_2$)$_2$—, and —CR$^{5-1}$=CR$^{5-2}$—CH$_2$—(azetidine)-(in groups, R$^{5-1}$ and R$^{5-2}$ represent the same as those described above), most preferably —CH$_2$— (azetidine)-.

In the present invention, Z is preferably an acid group which may be protected, more preferably a carboxyl group which may be protected, a hydroxy group which may be protected (e.g., —OP(=O)(OR$^2$)(OR$^3$) (in groups, R$^2$ and R$^3$ represent the same as those described above) is included), a hydroxamic acid group which may be protected, a sulfonic acid group which may be protected, a boronic acid group which may be protected, a carbamoyl group which may be protected, a sulfamoyl group which may be protected, —OP(=O)(OR$^2$) (OR$^3$) (in groups, R$^2$ and R$^3$ represent the same as those described above), or a tetrazolyl group, particularly preferably a carboxyl group which may be protected.

In the present invention, a "protective group" of an "acid group which may be protected (by protective group)" of Z is preferably a C1-20 alkyl group which may be substituted. In addition, a case wherein Z is not protected is also preferable.

In the present invention, R$^1$ preferably represents halogen atom, C1-8 alkyl which may be substituted, C1-8 alkoxy which may be substituted, and the like, and more preferably represents chlorine atom, fluorine atom, ethyl group, propyl group, isopropyl group, isobutyl group, sec-butyl group, trifluoromethyl group, methoxy group, difluoromethoxy group, isopropoxy group, or sec-butoxy group, and the like.

In the present invention, R$^2$ preferably represents hydrogen atom or C1-8 alkyl which may be substituted, and the like, and more preferably represents hydrogen atom or methyl group and the like.

In the present invention, R$^3$ preferably represents hydrogen atom or C1-8 alkyl which may be substituted, and the like, and more preferably represents hydrogen atom or methyl group, and the like.

In the present invention, R$^4$ and R$^{4-1}$ preferably represents a hydrogen atom, halogen atom, C1-8 alkyl, C1-8 alkoxy, trifluoromethyl group, trifluoromethoxy group, and the like, and more preferably represents a hydrogen atom, chlorine atom, methyl group, methoxy group, trifluoromethyl group, and the like.

In the present invention, R$^5$, R$^{5-1}$ and R$^{5-2}$ preferably represents a hydrogen atom, halogen atom, C1-8 alkyl, trifluoromethyl group, trifluoromethoxy group, and the like, and more preferably represents a hydrogen atom, chlorine atom, methyl group, trifluoromethyl group, and the like.

In the present invention, R$^6$ preferably represents a hydrogen atom, halogen atom, C1-8 alkyl, hydroxy which may be protected, amino which may be protected, C1-8 alkyl which is substituted by hydroxy which may be protected, and more preferably represents a hydrogen atom, methyl group, methoxy group, and the like.

In the present invention, R$^7$ preferably represents a hydrogen atom, halogen atom, C1-8 alkyl, hydroxy which may be protected, amino which may be protected, C1-8 alkyl which is substituted by hydroxy which may be protected, and more preferably represents a hydrogen atom, methyl group, methoxy group, and the like.

In the present invention, a "ring which may have a substituent(s)" represented by R$^6$ and R$^7$ together with a carbon atom bonding therewith is preferably a "C3-7 monocyclic carbocyclic ring", more preferably a "C3-7 monocyclic saturated carbocyclic ring", or particularly preferably a cyclopropane ring and a cyclobutane ring.

In the present invention, m preferably represents 0, 1 or 2, and more preferably represents 2.

In the present invention, n preferably represents 0 or 1, and more preferably represents 1.

In the present invention, p preferably represents 0, 1 or 2.

In the present invention, a compound represented by the formula (I) which contains the combinations listed above as preferable groups, preferable rings, and preferable atoms are preferable. A compound which is represented by any one of the following formulae, a salt thereof, an N-oxide form thereof, a solvate thereof, or a prodrug thereof is more preferable: the formula (IA-1):

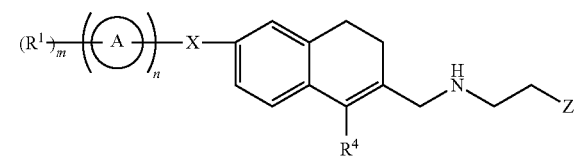

(IA-1)

wherein all symbols represent the same as those described above; the formula (IA-2):

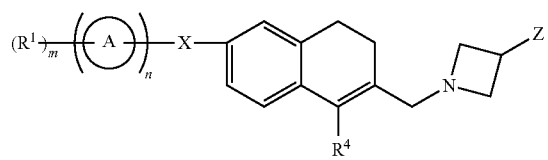

(IA-2)

wherein all symbols represent the same as those described above; the formula (IA-3):

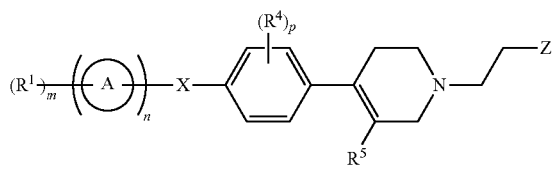

(IA-3)

wherein all symbols represent the same as those described above; the formula (IA-4):

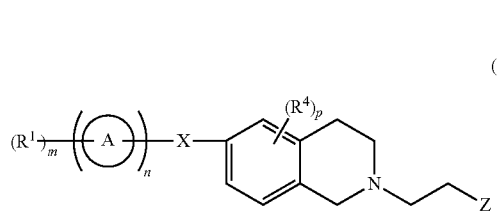
(IA-4)

wherein all symbols represent the same as those described above; the formula (IA-5):

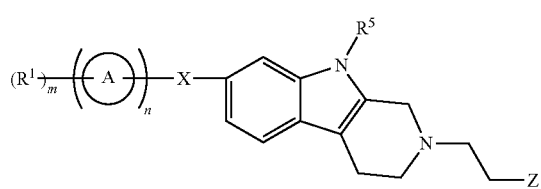
(IA-5)

wherein all symbols represent the same as those described above; and the formula (IA-6):

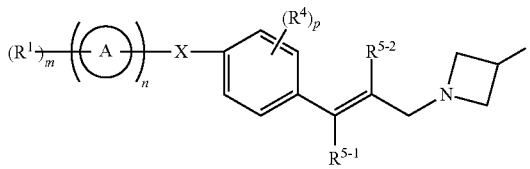
(IA-6)

wherein all symbols represent the same as those described above;

A compound which is represented by any one of the following formulae, a salt thereof, an N-oxide form thereof, a solvate thereof, or a prodrug thereof is particularly preferable: the formula (IB-1):

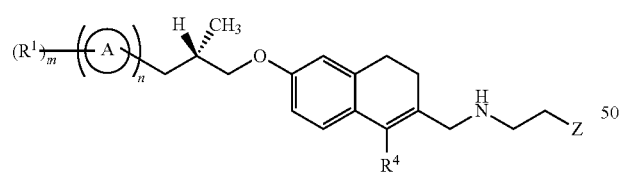
(IB-1)

wherein all symbols represent the same as those described above; the formula (IB-2):

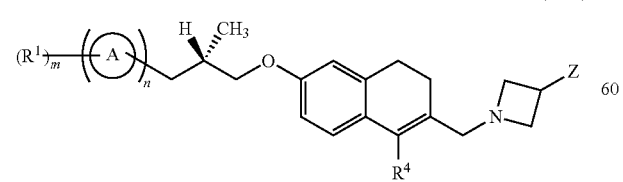
(IB-2)

wherein all symbols represent the same as those described above; the formula (IB-3):

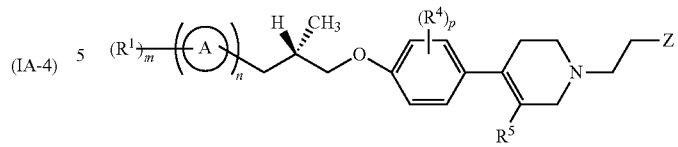
(IB-3)

wherein all symbols represent the same as those described above; the formula (IB-4):

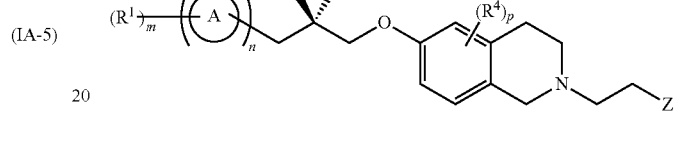
(IB-4)

wherein all symbols represent the same as those described above; the formula (IB-5):

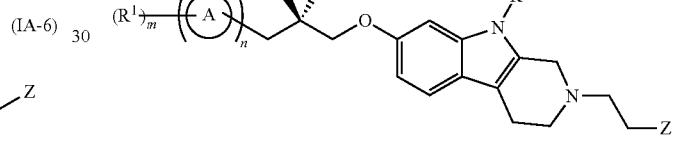
(IB-5)

wherein all symbols represent the same as those described above; and the formula (IB-6):

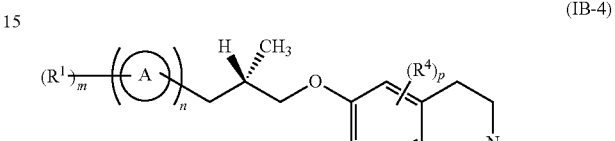
(IB-6)

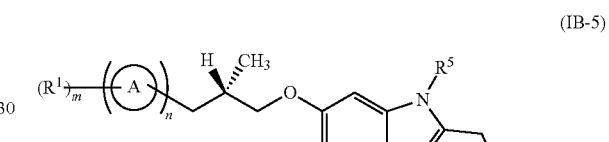
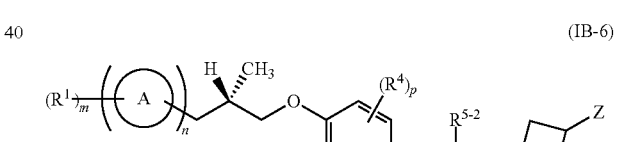

wherein all symbols represent the same as those described above.

A compound which is represented by any one of the following formulae, a salt thereof, an N-oxide form thereof, a solvate thereof, or a prodrug thereof is still particularly preferable: the formula (IC-1):

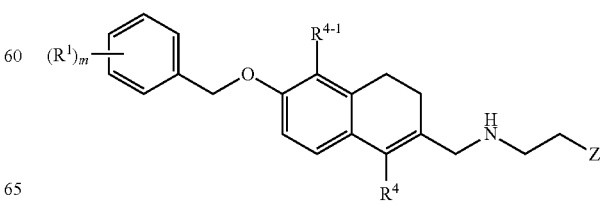
(IC-1)

wherein all symbols represent the same as those described above; the formula (IC-2):

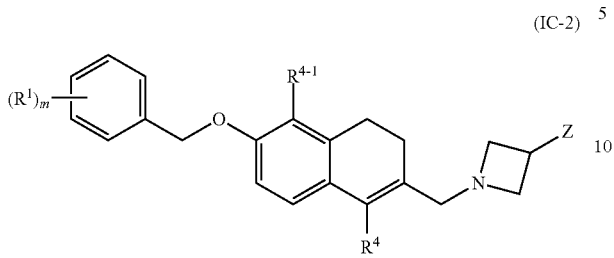
(IC-2)

wherein all symbols represent the same as those described above; the formula (ID-1):

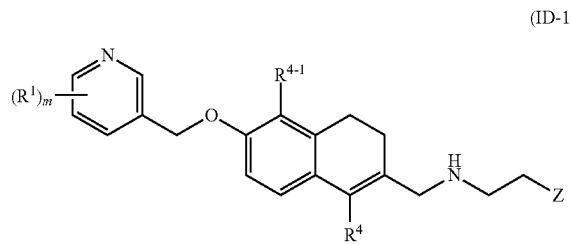
(ID-1)

wherein all symbols represent the same as those described above; and the formula (ID-2):

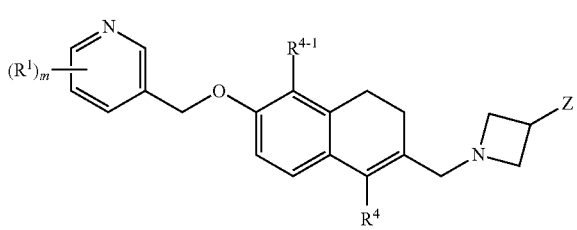
(ID-2)

wherein all symbols represent the same as those described above.

A compound which is represented by any one of the following formulae, a salt thereof, an N-oxide form thereof, a solvate thereof, or a prodrug thereof is most particularly preferable: the formula (IC-1-1):

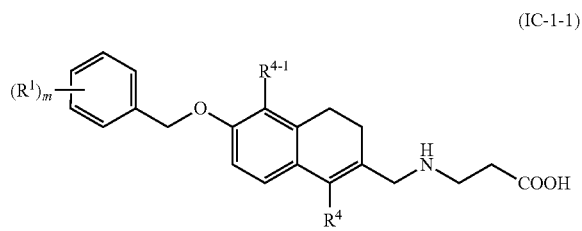
(IC-1-1)

wherein all symbols represent the same as those described above; the formula (IC-2-1):

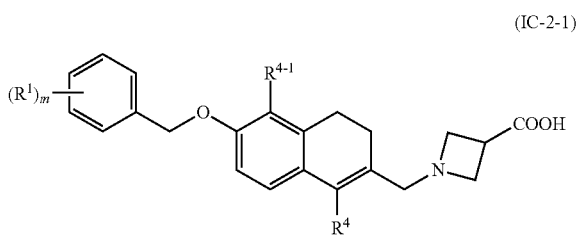
(IC-2-1)

wherein all symbols represent the same as those described above; and the formula (ID-2-1):

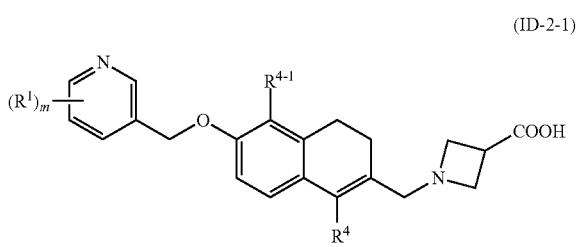
(ID-2-1)

wherein all symbols represent the same as those described above.

Further, in the above-mentioned formulae (IC-1), (IC-2), (IC-1-1) and (IC-2-1), m is preferably 2, and plurality of $R^1$s are the same or different. In addition, substitution positions are preferably 2- and 4-positions, 3- and 4-positions, and 3- and 5-positions, particularly preferably 2- and 4-positions.

Further, in the present invention, a compound described in Examples, a salt thereof, an N-oxide form thereof, a solvate thereof, and a prodrug thereof are all preferable. Particularly preferable examples thereof include 1-({6-[(2-methoxy-4-propylbenzyl)oxy]-1-methyl-3,4-dihydro-2-naphthalenyl}methyl)-3-azetidinecarboxylic acid, 1-({6-[(4-isobutyl-2-methoxybenzyl)oxy]-1-methyl-3,4-dihydro-2-naphthalenyl}methyl)-3-azetidinecarboxylic acid, 1-({6-[(4-isobutyl-3-methoxybenzyl)oxy]-1-methyl-3,4-dihydro-2-naphthalenyl}methyl)-3-azetidinecarboxylic acid, 1-({6-[(2-ethoxy-4-isobutylbenzyl)oxy]-1-methyl-3,4-dihydro-2-naphthalenyl}methyl)-3-azetidinecarboxylic acid, 1-[(6-{[4-isopropoxy-2-(trifluoromethyl)benzyl]oxy}-1-methyl-3,4-dihydro-2-naphthalenyl)methyl]-3-azetidinecarboxylic acid, 1-[(6-{[2,4-bis(trifluoromethyl)benzyl]oxy}-1-methyl-3,4-dihydro-2-naphthalenyl)methyl]-3-azetidinecarboxylic acid, 1-({1-chloro-6-[(2-methoxy-4-propylbenzyl)oxy]-3,4-dihydro-2-naphthalenyl}methyl)-3-azetidinecarboxylic acid, 1-({1-chloro-6-[(4-isobutyl-2-methoxybenzyl)oxy]-3,4-dihydro-2-naphthalenyl}methyl)-3-azetidinecarboxylic acid, 1-[(1-chloro-6-{[(2S)-3-(2,4-difluorophenyl)-2-methylpropyl]oxy}-3,4-dihydro-2-naphthalenyl)methyl]-3-azetidinecarboxylic acid, 1-[(6-{[4-ethoxy-2-(trifluoromethyl)benzyl]oxy}-1-methyl-3,4-dihydro-2-naphthalenyl)methyl]-3-azetidinecarboxylic acid, 1-({6-[(4-ethyl-2-methoxybenzyl)oxy]-1-methyl-3,4-dihydro-2-naphthalenyl}methyl)-3-azetidinecarboxylic acid, 1-({6-[(2-methoxy-4-propylbenzyl)oxy]-1,5-dimethyl-3,4-dihydro-2-naphthalenyl}methyl)-3-azetidinecarboxylic acid, 1-({6-[(2-difluoromethoxy-4-propylbenzyl)oxy]-1-methyl-3,4-dihydro-2-naphthalenyl}methyl)-3-azetidinecarboxylic acid, 1-[(6-{[2,4-bis(trifluoromethyl)benzyl]oxy}-1-chloro-3,4-dihydro-2-naphthalenyl)methyl]-3-azetidinecarboxylic acid, 1-[(6-{[2-(difluoromethoxy)-4-propylbenzyl]oxy}-1, 5-dimethyl-3,4-dihydro-2-naphthalenyl)methyl]-3-azetidinecarboxylic acid, 1-[(6-{[4-ethoxy-3-(trifluoromethyl)benzyl]oxy}-1-methyl-3,4-dihydro-2-naphthalenyl)methyl]-3-azetidinecarboxylic acid, and 1-({6-[(2-methoxy-6-propyl-3-pyridinyl)methoxy]-1,5-dimethyl-3,4-dihydro-2-naphthalenyl}methyl)-3-azetidinecarboxylic acid, a salt thereof, an N-oxide form thereof, a solvate thereof, and a prodrug thereof. Still particularly preferable examples thereof include 1-({6-[(2-methoxy-4-propylbenzyl)oxy]-1-methyl-3,4-dihydro-2-naphthalenyl}methyl)-3-azetidinecarboxylic acid, 1-[(6-{[2,4-bis(trifluoromethyl)benzyl]oxy}-1-methyl-3,4-dihydro-2-naphthalenyl)methyl]-3-azetidinecarboxylic acid, 1-({1-chloro-6-[(2-methoxy-4-propylbenzyl)oxy]-3,4-dihydro-2-naphthalenyl}methyl)-3-azetidinecarboxylic acid, 1-({1-chloro-6-[(4-isobutyl-2-methoxybenzyl)oxy]-3,4-dihydro-2-naphthalenyl}methyl)-3-azetidinecarboxylic acid, 1-[(6-{[2,4-bis(trifluoromethyl)benzyl]oxy}-1-chloro-3,4-dihydro-2-naphthalenyl)methyl]-3-azetidinecarboxylic acid, 1-[(6-{[2-(difluoromethoxy)-4-propylbenzyl]oxy}-1,5-dimethyl-3,4-dihydro-2-naphthalenyl)methyl]-3-azetidinecarboxylic acid, 1-[(6-{[4-ethoxy-3-(trifluoromethyl)benzyl]oxy}-1-methyl-3,4-dihydro-2-naphthalenyl)methyl]-3-azetidinecarboxylic acid, and 1-({6-[(2-methoxy-6-propyl-3-pyridinyl)methoxy]-1,5-dimethyl-3,4-dihydro-2-naphthalenyl}methyl)-3-azetidinecarboxylic acid, a salt thereof, an N-oxide form thereof, a solvate thereof, and a prodrug thereof. Most preferable examples thereof include 1-({6-[(2-methoxy-4-propylbenzyl)oxy]-1-methyl-3,4-dihydro-2-naphthalenyl}methyl)-3-azetidinecarboxylic acid, and 1-[(6-{[2,4-bis(trifluoromethyl)benzyl]oxy}-1-methyl-3,4-dihydro-2-naphthalenyl)methyl]-3-azetidinecarboxylic acid, a salt thereof, an N-oxide form thereof, a solvate thereof, and a prodrug thereof.

Isomers

Unless otherwise specifically mentioned, all isomers are included in the present invention. For example, alkyl, alkenyl, alkynyl, alkyloxy, alkoxy, alkenyloxy, alkynyloxy, alkylthio, alkylsulfinyl, alkylsulfonyl, alkylene, alkenylene, alkynylene, acyl, and acyloxy include straight chain and branched ones. Moreover, all of isomers due to double bond, ring, and fused ring (E-, Z-, cis- and trans-forms), isomers due to presence of asymmetric carbon or the like (R-, S-, α- and β-configuration, enantiomer, and diastereomer), optically active materials having optical rotation (D-, L-, d- and l-forms), polar compound by chromatographic separation (more polar compound and less polar compound), equilibrium compounds, rotamers, a mixture thereof in any proportion, and a racemic mixture are included in the present invention. All tautomers are also included in the present invention.

In the present invention, unless otherwise specified, as is clear to the person skilled in the art: a symbol ⟋ means an α-configuration; a symbol ⟋ means a β-configuration; and the symbol ⟋ means a mixture of α-configuration and β-configuration by an arbitrary ratio. Note that, in the present invention, a compound having each configuration as described above is not limited to one which is substantially pure and homogeneous as long as the compound includes the configuration in predominance.

Salt, N-oxide Form and Solvate

The salts of the compound of the present invention represented by the formula (I) include all pharmaceutically acceptable salts. The salts each preferably have nontoxicity and water-solubility. The salt of the compound of the present invention represented by the formula (I) preferably includes salts of alkali metal (such as potassium, sodium, and lithium), salts of alkaline earth metal (such as calcium and magnesium), ammonium salts (such as tetramethylammonium salt and tetrabutylammonium salt), salts of organic amine (such as triethylamine, methylamine, dimethylamine, cyclopentylamine, benzylamine, phenethylamine, piperidine, monoethanolamine, diethanolamine, tris(hydroxymethyl)methylamine, lysine, arginine, and N-methyl-D-glucamine), and acid addition salts (such as inorganic acid salts (e.g., hydrochloride, hydrobromide, hydroiodide, sulfate, phosphate, and nitrate), and organic acid salts (e.g., acetate, trifluoroacetate, lactate, tartrate, oxalate, fumarate, maleate, benzoate, citrate, methanesulfonate, ethanesulfonate, benzenesulfonate, toluenesulfonate, isethionate, glucuronate, and gluconate), or the like). Among them, sodium salt, potassium salt, calcium salt, or hydrochloride is preferable.

The salts further include a quaternary ammonium salt. The quaternary ammonium salt means the compound represented by the formula (I) which nitrogen atom is quaterinized by an $R^0$ group. $R^0$ group represents C1-8 alkyl which may be substituted by phenyl.

An N-oxide form of the compound represented by the formula (I) represents one in which the nitrogen atom of the compound represented by the formula (I) is oxidized. In addition, the N-oxide form of the present invention may be an alkali (earth) metal salt, an ammonium salt, organic amine salts, and acid addition salts.

Examples of an appropriate solvate of the compound represented by the formula (I) include solvates such as hydrate and alcoholate (such as methanolate and ethanolate). The solvates each preferably have nontoxicity and water-solubility, for example, is preferably monohydrate. In addition, the solvates of the compound of the present invention include solvates of alkali metal salts, alkali earth metal salts, ammonium salts, organic amine salts, acid addition salts, and N-oxide forms of the above-mentioned compound of the present invention.

The compound represented by the formula (I) may be converted into any one of the above-mentioned salts and solvates by a conventionally known method.

Prodrugs

A prodrug of the compound represented by the formula (I), a salt thereof, N-oxide form thereof, or a solvate thereof means a compound which is converted to the compound represented by the formula (I) by reaction with an enzyme, gastric acid, or the like in the living body. For example, with regard to a prodrug of the compound represented by the formula (I), when the compound represented by the formula (I) has amino, compounds in which amino is, for example, acylated, alkylated, or phosphorylated (e.g., compounds in which amino of the compound represented by the formula (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, acetoxymethylated, or tert-butylated); when the compound represented by the formula (I) has hydroxy, compounds where the hydroxy is, for example, acylated, alkylated, phosphorylated, or borated (e.g., compounds in which the hydroxy of the compound represented by the formula (I) is acetylated, palmitoylated, propanoylated, pivaloylated, succinylated, fumarylated, alanylated, or dimethylaminomethylcarbonylated); and when the compound represented by the formula (I) has carboxy, compounds where carboxy of the compound represented by the formula (I) is, for example, esterified or amidated (e.g., compounds in which carboxy of the compound represented by the formula (I) is made into ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, or methylamide). Those compounds may be prepared by a conventionally known method per se. The prodrug of the compound represented by the formula (I) may be either a hydrate or a non-hydrate. A prodrug of the compound represented by the formula (I) may also be a compound which is converted to the compound represented by the formula (I) under physiologic condition as described in "Iyakuhin no kaihatsu", Vol. 7 "Bunshi-sekkei", pp. 163-198 (Hirokawa-Shoten), 1990. Further, the compound represented by the formula (I) may also be labeled by a radio isotope (such as $^3$H, $^{14}$C, $^{35}$S, $^{125}$I, etc,).

The compounds of the present invention represented by the formula (I), a salt thereof, an N-oxide form thereof, a solvate thereof, or a prodrug thereof (hereinafter, also abbreviated as "the compounds of the present invention") are excellent in solubility and oral absorbability, exhibit a prolonged pharmacological action (e.g., promoting activity of lymphocyte homing and immunosuppressive action of lymphocyte), are hardly affected by drug-metabolic enzymes and have low toxicity. Those characteristics are the most important physical, chemical, and pharmaceutical properties required in developing drugs. Fulfilling those requirements, the compounds of the present invention are likely to be highly excellent drugs (see The Merck Manual of Diagnosis and Therapy, 17th Ed., Merck & Co.).

The fact that the compound of the present invention which is excellent in solubility and oral absorbability, exhibits a prolonged pharmacological action, is excellent in safety, and exhibits high safety index (SI) is useful as a medicinal drug can be evaluated by a method described in the following various experimental systems or biological examples or a method which can be carried out by appropriately improving the method. It can be also easily assessed that the compound of the present invention is excellent in terms of a length of serum half-life, a stability in the gastrointestinal tract, an absorption of oral preparations, bioavailability, or the like by conventionally known methods, for example, a method described in "Yakubutsu bioavailability (Hyouka to kaizen no kagaku)", Jul. 6, 1998, Gendaiiryou-sha, or the like.

(I) Experiments for Evaluating the Properties of Compound
Evaluation of the Solubility of the Present Invention Compound
[Experimental Method]

About 3 to 5 mg of a test compound having been heated to 37° C. (measured with a thermometer in practice) is sampled into a test tube. Then, a solvent (Official Solution I as specified in The Japanese Pharmacopoeia, Official Solution II as specified in The Japanese Pharmacopoeia and Official Solution II added by bovine bile acid in artificial bile juice (0.5% (w/w), SIGMA)), a pH 7.4 buffer solution (prepared by diluting 4-fold McIlvaine buffer), a pH 4.0 buffer solution (prepared by diluting 4-fold McIlvaine buffer), purified water and saline, having been heated to 37° C. in a water bath, are added thereto to respectively give concentrations of 1.5 mg/mL. After stirring at a constant temperature of 37° C. for 30 minutes, the mixture is filtered through a filter (in general, DISMIC-13 cp, cellulose acetate, hydrophilic, 0.20 μm, Advantec). Immediately thereafter, the filtrate is diluted 2-fold with an organic solvent in which the test compound is highly soluble (acetonitrile or methanol) and stirred. The solubility of the test compound can be evaluated by calculating its concentration by the external standard method with the use of HPLC.

Absorption test of the present invention compound in oral administration to dog

[Experimental Method]

To fasted adult beagle dogs, pentagastrin (10 μg/kg) is intramuscularly (i.m.) injected. Fifteen minutes thereafter, each test compound is orally administered (100 mg/body) with water (20 mL). Fifteen minutes thereafter, pentagastrin (10 μg/kg) is intramuscularly (i.m.) injected. Next, 15 and 30 minutes and 1, 2, 3, 4, 6, 8 and 10 hours after the administration of the test compound, the blood of the animal is collected and extracted with acetonitrile. Then, the concentration of the compound in the plasma is measured by high-performance liquid chromatography (the internal standard method). By using the concentrations of the blood in the plasma thus obtained, it is possible to determine the area under the plasma concentration curve (AUC, μg min/mL) and the maximum concentration in the plasma ($C_{max}$, ng/mL).

(II) Experimental System for Evaluating the Compound of the Present Invention for Validity (Pathologic Model)

The fact that the compound of the present invention has an immunosuppressive action can be confirmed with the following system. For example, the fact that the compound has a therapeutic effect on rejection to transplantation can be confirmed with a transplantation model for a heart, kidney, liver, pancreas, lung, bone marrow, skin, or the like. Description will be given below of a model for heart transplantation as an example.

Rat Ectopic Heart Transplantation Model
[Experimental Method]

Using rats, the heart is taken out from a donor rat and transplanted into the abdomen of a recipient rat. By orally administering a test compound for a preventive purpose, the heart transplantation survival days are estimated and the therapeutic effect can be thus evaluated.

The fact that the compound of the present invention has a preventive and/or a therapeutic effect on an autoimmune disease can be confirmed with the following experiments. For example, the fact that the compound has a preventive and/or a therapeutic effect on a neuropathy (such as multiple sclerosis) can be confirmed with the following experiment.

Experimental Allergic Encephalomyelitis (EAE) Model
[Experimental Method]

Using Lewis rats, experimental allergic encephalomyelitis is induced by using various antigens such as spinal cord or MOG (myelin oligodendrocyte elycoprotein). By comparing a group to which a test compound is orally administered with a non-administered group, a therapeutic or preventive effect can be evaluated.

(III) Experiments for Evaluating the Toxicity of the Present Invention Compound
Evaluation of the Activity of the Compound of the Present Invention Against hERG $I_{Kr}$ Current
[Experimental Method]

According to the report by Zou, et al. (Biophys. J., 74, 230-241 (1998)), using HEK293 cell overexpressed of human ether-a-go-go-related gene (hERG), max tale current of HERG $I_{Kr}$ current induced by depolarization pulse, followed by repolarization pulse is measured by patch-clamp recording. Rate of change (inhibition ratio) is calculated by comparison max tale current between before addition of the test compound and 10 minutes after. The influence of the test compound against hERG $I_{Kr}$ current can be evaluated by the inhibition ratio.

The compound of the present invention was named by using an ACD/NAME™ manufactured by Advanced Chemistry Development as a computer program for mechanically producing an IUPAC name. For example, the following compound was named 1-{[1-chloro-6-(3-cyclohexylpropoxy)-3,4-dihydronaphthalen-2-yl]methyl}azetidine-3-carboxylic acid.

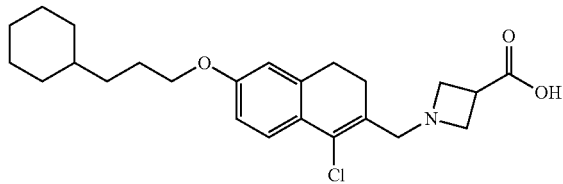 [SMILES: O=C(O)C1CN(CC2=C(Cl)c3ccc(OCCCC4CCCCC4)cc3CC2)C1]

[Processes for the Preparation of the Compound of the Present Invention]

The compound of the present invention can be prepared by appropriately modifying and combining a known method such as a method described in WO 02/092068, Synth. Commun., vol. 33(19), 3347 (2003), or in Comprehensive Organic Transformations: A Guide to Functional Group Preparations, 2nd Ed. (by Richard C. Larock, John Wiley & Sons Inc. (1999)), the following method and/or a method in accordance with the following method, and a method described in an example. It should be noted that a starting material compound may be used as a salt in each of the following methods. The salt of the compound represented by the formula (I) described hereinbefore is used as such salt.

The compounds of the present invention can be prepared by methods described in the following (A) to (H).

(A) Among the compounds of the present invention, a compound in which X binds to a ring B through an oxygen, that is, the compound represented by the formula (I-1-A):

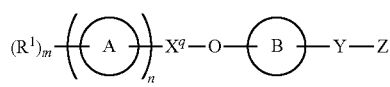 (I-1-A)

wherein $X^q$ represents a bond or a spacer which has a main chain having 1 to 7 atoms, and other symbols represent the same as those described above,
can be prepared by the methods of the following (A-1) or (A-2).

(A-1) The compound represented by the formula (2):

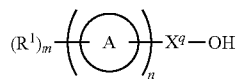 (2)

wherein all symbols represent the same as those described above;
and the compound represented by the formula (3):

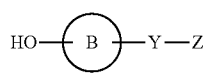 (3)

wherein all symbols represent the same as those described above;
is subjected to Mitsunobu reaction and then deprotection of the protective groups is performed, if required, to thereby produce the compound represented by the formula (I-1-A).

The Mitsunobu reaction is known in the art, and performed, for example, in an organic solvent (such as dichlromethane, dimethylether, tetrahydrofuran, acetonitrile, benzene, or toluene), in the presence of an azo compound (such as diethyl azodicarboxylate (DEAD), diisopropyl azodicarboxylate, 1,1'-(azodicarbonyl)dipiperidine, or 1,1'-azobis(N,N-dimethylformamide)) and a phosphine compound (such as triphenylphosphine, tributylphosphine, trimethylphosphine, or polymer-supported triphenylphosphine), at temperature of about 0 to 60° C. In addition, the deprotection reaction of the protective groups of a carboxyl group, a hydroxy group, hydroxamic acid, sulfonic acid, boronic acid, a carbamoyl group, a sulfamoyl group, phosphonic acid, phosphoric acid, and a tetrazolyl group can be performed by a known method, for example, a method described in WO 02/092068, a method conformed thereto and/or a method described in Protective Groups in Organic Synthesis (T. W. Greene, John Wiley & Sons Inc. (1999)). A protective group is not limited as long as the group can be deprotected easily and selectivity.

(A-2) The compound represented by the formula (2) and the compound represented by the formula (4):

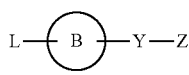 (4)

wherein L represents leaving groups such as a halogen atom, a methanesulfonyloxy group (OMs group), a toluenesulfonyloxy group (OTs group), a trifluoromethanesulfonyloxy group (OTf group), an alkylthio group, an alkylsulfinyl group, an alkylsulfonyl group, and a hydroxysulfonyl group, and other symbols represent the same as those described above, or the compound represented by the formula (5):

 (5)

wherein all symbols represent the same as those described above,
and the compound represented by the formula (3) are subjected to etherification reaction and then deprotection of the protective groups is performed, if required, to thereby produce the compound represented by the formula (I-1-A).

The etherification is known in the art, and performed, for example, in an organic solvent (such as N,N-dimethylformamide, dimethylsulfoxide, chloroform, dichlromethane, diethyl ether, tetrahydrofuran, or tert-butyl methyl ether), in the presence of a hydroxide of alkali metal (such as sodium hydroxide, potassium hydroxide, or lithium hydroxide), a hydroxide of alkali earth metal (such as barium hydroxide or calcium hydroxide), a carbonate (such as sodium carbonate, potassium carbonate, or cesium carbonate), aqueous solutions thereof, or mixtures thereof, at temperature of about 0 to 100° C. The deprotection of protecting groups can be performed in accordance with the method described above.

(B) Among the compounds of the present invention, a compound, in which Y is represented

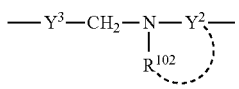

wherein $Y^2$ and $Y^3$ each independently represents a bond or a spacer which has a main chain with 1 to 8 atoms (provided that the total number of atom of a main chain in $Y^2$ and $Y^3$ dose not exceed 8), and $R^{102}$ represents a hydrogen atom or a substituent, or a heterocyclic ring containing at least one nitrogen atom which may have a substituent(s) may be formed by an atom of the spacer represented by $Y^2$ together with $R^{102}$, that is, the compound represented by the formula (I-1-B)

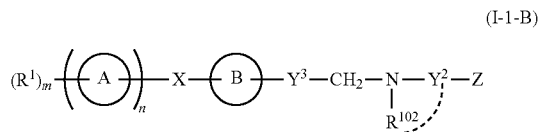

(I-1-B)

wherein all symbols represent the same as those described above, can be prepared as follows.

The compound represented by the formula (6):

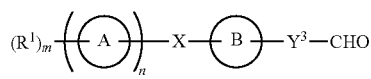

(6)

wherein all symbols represent the same as those described above, and the compound represented by the formula (7):

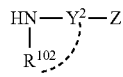

(7)

wherein all symbols represent the same as those described above, are subjected to reductive amination and then deprotection of the protective groups is performed, if required.

The reductive amination is known in the art, and performed, for example, in an organic solvent (such as N,N-dimethylformamide, dichlromethane, methanol by itself, or mixed solvent comprising any parts of these solvents), in the presence or absence of a dehydration agent (such as trimethoxymethane, or triethoxymethane), in the presence or absence of an organic acid (such as acetic acid), in the presence or absence of a base (such as triethylamine, sodium hydrogen carbonate, or sodium hydroxide), using a reducing agent (such as triacetoxy sodium borohydride, cyano sodium borohydride, tetrabutylammonium borohydride, or sodium borohydride) at temperature of about 0 to 100° C. The deprotection of protecting groups can be performed in accordance with the method as described above.

(C) Among the compounds of the present invention, a compound in which Y is represented

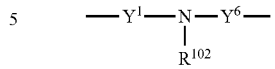

wherein $Y^1$ and $Y^6$ each independently represents a bond or a spacer which has a main chain with 1 to 9 atoms (provided that the total atomic number of a main chain in $Y^1$ and $Y^6$ dose not exceed 9), and all symbols represent the same as those described above, that is, the compound represented by the formula (I-1-C):

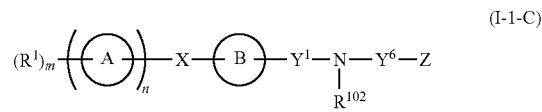

(I-1-C)

wherein all symbols represent the same as those described above, can be prepared as follows.

The compound represented by the formula (8):

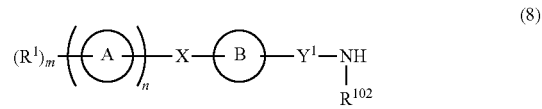

(8)

wherein all symbols represent the same as those described above, and the compound represented by the formula (9):

(9)

wherein all symbols represent the same as those described above, or the compound represented by the formula (10):

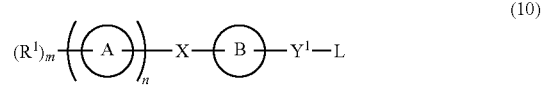

(10)

wherein all symbols represent the same as those described above, and the compound represented by the formula (11)

(11)

wherein all symbols represent the same as those described above, are subjected to alkylation, respectively and then deprotection of the protective groups is performed, if required.

The alkylation is known in the art, and performed, for example, in an organic solvent (such as N,N-dimethylformamide, dimethylsulfoxide, chloroform, dichloromethane, diethyl ether, tetrahydrofuran, or tert-butyl methyl ether), in the presence of a hydroxide of alkali metal (such as sodium hydroxide, potassium hydroxide, or lithium hydroxide), a hydroxide of alkali earth metal (such as barium hydroxide or calcium hydroxide), a carbonate (such as sodium carbonate, potassium carbonate, or cesium carbonate), aqueous solutions thereof, or mixtures thereof, at temperature of about 0 to 100° C. The deprotection of protecting groups can be performed in accordance with the method as described above.

(D) Among the compounds of the present invention, a compound in which Y is represented by

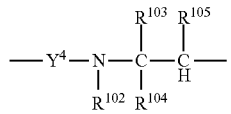

wherein $Y^4$ represents a bond or a spacer which has a main chain with 1 to 7 atoms, $R^{103}$, $R^{104}$, and $R^{105}$ each independently represents a hydrogen atom or a substituent, and other symbols represent the same as those described above,
that is, the compound represented by the formula (I-1-D):

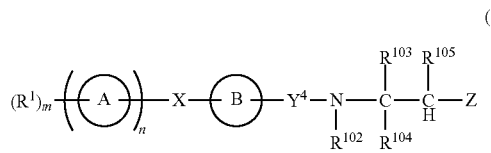
(I-1-D)

wherein all symbols represent the same as those described above,
can be prepared as follows.

The compound represented by the formula (12):

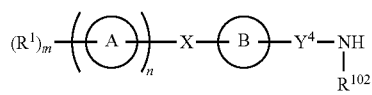
(12)

wherein all symbols represent the same as those described above,
and the compound represented by the formula (13):

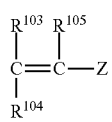
(13)

wherein all symbols represent the same as those described above,
are subjected to addition reaction of the amine and then deprotection of the protective groups is performed, if required.

The addition reaction of the amine is known, and is performed in, for example, an organic solvent (such as methanol, ethanol, propanol, benzene, toluene, diethyl ether, tetrahydrofuran, or dimethoxyethane) or no solvent in the presence or absence of a base (such as diisopropylethylamine) at about −78° C. to a reflux temperature. The deprotection of protecting groups can be performed in accordance with the method as described above.

(E) Among the compounds of the present invention, a compound in which Z represents a hydroxy group which may be protected, and Y represents

—$Y^5$—$CH_2$— wherein $Y^5$ represents a bond or a spacer which has a main chain having 1 to 9 atoms, that is, a compound represented by a formula (I-2-E):

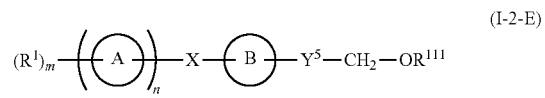
(I-2-E)

wherein all symbols represent the same as those described above,
is prepared by subjecting a compound, which can be prepared by the above-mentioned method, in which Z represents a carboxyl group which may be protected, that is, a compound represented by a formula (I-1):

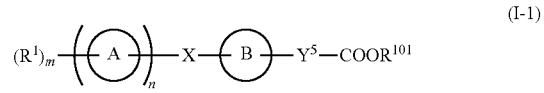
(I-1)

wherein $R^{101}$ represents a hydrogen atom or a protective group which represents the same as the "protective group" in the "carboxyl group which may be protected" represented by the Z group, and other symbols represent the same as those described above to a reduction reaction; and introducing a protective group as required.

The reduction reaction is known and is performed in an organic solvent (such as methanol, ethanol, tetrahydrofuran, or diethyl ether) in the presence of a reducing agent (such as lithium aluminum hydride, lithium borohydride, sodium borohydride, a borane-pyridine complex, or a borane-tetrahydrofuran complex) at about −10° C. to a reflux temperature. The reaction for introducing a protective group into a hydroxy group can be performed by employing a method described in Protective Groups in Organic Synthesis (by T. W. Greene, John Wiley & Sons Inc, (1999)).

(F) Among the compounds of the present invention, a compound in which Z represents a hydroxamic acid group which may be protected, that is, a compound represented by a formula (I-3-F):

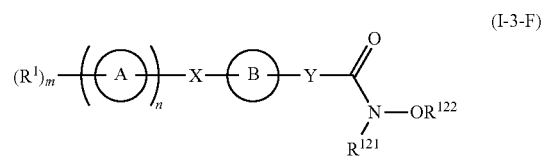
(I-3-F)

wherein $R^{121}$ and $R^{122}$ each independently represent a hydrogen atom or a protective group which represents the same as the "protective group" in the "hydroxamic acid group which may be protected" represented by the Z group, and other symbols represent the same as those described above,
is prepared by subjecting a compound, which can be prepared by the above-mentioned method, in which Z represents a carboxyl group, that is, a compound represented by a formula (I-1-1):

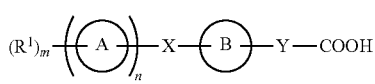 (I-1-1)

wherein all symbols represent the same as those described above and a compound represented by a formula (14)

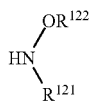 (14)

wherein all symbols represent the same as those described above to an amidation reaction; and deprotecting a protective group as required.

The amidation reaction is known, and examples of a method for the reaction include (1) a method involving the use of an acid halide, (2) a method involving the use of a mixed acid anhydride, and (3) a method involving the use of a condensation agent. Those methods will be specifically described. For example, (1) the method involving the use of an acid halide is performed by: causing a carboxylic acid to react with an acid-halogenating agent (such as oxalyl chloride or thionyl chloride) in an organic solvent (such as chloroform, dichloromethane, diethyl ether, or tetrahydrofuran) or no solvent at about −20° C. to a reflux temperature; and causing the resultant acid halide to react with an amine in the presence of a base (such as pyridine, triethylamine, dimethylaniline, dimethylaminopyridine, or diisopropylethylamine) in an organic solvent (such as chloroform, dichloromethane, diethyl ether, or tetrahydrofuran) at a temperature of about 0 to 40° C. Alternatively, the method can also be performed by causing the resultant acid halide to react with an amine in an organic solvent (such as dioxane or tetrahydrofuran) by using an alkali aqueous solution (such as solution of sodium hydrogen carbonate or a solution of sodium hydroxide) at about 0 to 40° C. For example, (2) the method involving the use of a mixed acid anhydride is performed by: causing a carboxylic acid to react with an acid halide (such as pivaloyl chloride, tosyl chloride, or mesyl chloride) or with an acid derivative (such as ethyl chloroformate or isobutyl chloroformate) in an organic solvent (such as chloroform, dichloromethane, diethyl ether, or tetrahydrofuran) or no solvent in the presence of a base (such as pyridine, triethylamine, dimethylaniline, dimethylaminopyridine, or diisopropylethylamine) at about 0 to 40° C.; and causing the resultant mixed acid anhydride to react with an amine in an organic solvent (such as chloroform, dichloromethane, diethyl ether, or tetrahydrofuran) at about 0 to 40° C. For example, (3) the method involving the use of a condensation agent is performed by causing a carboxylic acid and an amine to react with each other at about 0 to 40° C. in an organic solvent (such as chloroform, dichloromethane, dimethylformamide, diethyl ether, or tetrahydrofuran) or no solvent in the presence or absence of a base (such as pyridine, triethylamine, dimethylaniline, or dimethylaminopyridine) by using a condensation agent (such as 1,3-dicyclohexylcarbodiimide (DCC), 1-ethyl-3-[3-(dimethylamino)propyl]carbodiimide (EDC), 1,1′-carbonyldiimidazole (CDI), 2-chloro-1-methylpyridiniumiodine, or 1-propanephosphonic acid cyclic anhydride (PPA)) and by using or without using 1-hydroxybenzotriazole (HOBt). Each of those reactions (1), (2), and (3) is desirably performed under an inert gas (such as argon or nitrogen) atmosphere under unhydrous condition. The deprotection of protecting groups can be performed in accordance with the method as described above.

(G) Among the compounds of the present invention, a compound in which Z represents a tetrazolyl group, that is, a compound represented by a formula (T-4-G):

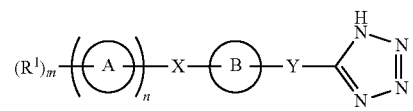 (I-4-G)

wherein all symbols represent the same as those described above,
can be prepared by subjecting a compound represented by a formula (15):

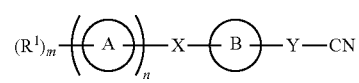 (15)

wherein all symbols represent the same as those described above,
to a tetrazole ring formation reaction.

The tetrazole ring formation reaction is known and is performed in, for example, an organic solvent (such as dimethylformamide, dioxane, or tetrahydrofuran) in the presence of an azide compound (such as sodium azide, trimethylsilyl azide, or tributyltin azide) at about −10 to 150° C.

(H) Among the compounds of the present invention, a compound in which Z represents —OP(=O)(OR$^2$)(OR$^3$) wherein R$^2$ and R$^3$ represent the same as those described above, that is, a compound represented by a formula (I-5-H):

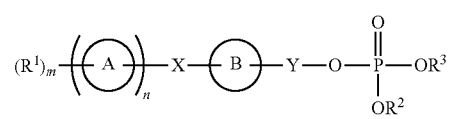 (I-5-H)

wherein all symbols represent the same as those described above,
can be prepared by any one of the following methods [H-2] and [H-2].

(H-1) Among the compounds each represented by the formula (I-5-H), a compound in which R$^2$ and R$^3$ each represent a hydrogen atom, that is, a compound represented by a formula (I-5-H-1):

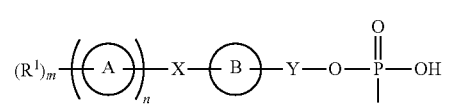 (I-5-H-1)

wherein all symbols represent the same as those described above,
is prepared by subjecting a compound, which can be prepared by the above-mentioned method, in which Z represents a hydroxy group, that is, a compound represented by a formula (I-1-2):

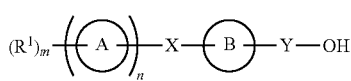 (I-1-2)

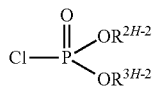 (16)

and a dialkylphosphoroamidite compound to a reaction; and subjecting the resultant to an oxidation reaction and then a reduction reaction.

The reaction between the alcohol compound and the dialkylphosphoroamidite compound, and the oxidation reaction are known. The reaction between the alcohol compound and the dialkylphosphoroamidite compound is performed by causing the alcohol compound to react with the dialkylphosphoroamidite compound (such as dibenzylphosphoroamidite, or N,N-diethyl-1,5-dihydro-2,4,3-benzodioxaphosphepine-3-amine) in an organic solvent (such as methylene chloride, toluene, or tetrahydrofuran) in the presence of tetrazole. The oxidation reaction is subsequently performed with an oxidant (such as m-chloroperbenzoic acid, iodine, or hydrogen peroxide). The reduction reaction is also known and is performed in a solvent [such as an ether (such as tetrahydrofuran, dioxane, dimethoxyethane, or diethyl ether), an alcohol (such as methanol or ethanol), a benzene (such as benzene or toluene), a ketone (such as acetone or methyl ethyl ketone), a nitrile (such as acetonitrile), an amide (such as dimethylformamide), water, ethyl acetate, acetic acid, or a mixed solvent containing two or more kinds of them] in the presence of a hydrogenation catalyst (such as palladium-carbon, palladium black, palladium, palladium hydroxide, platinum dioxide, platinum-carbon, nickel, Raney nickel, ruthenium chloride, or an ASCA-2 catalyst (manufactured by N.E. CHEMCAT CORPORATION, a 4.5% palladium-0.5% platinum catalyst carrying activated carbon, see Fine Chemical, Oct. 1, 2002, p.p. 5 to 14)) in the presence or absence of an acid (such as hydrochloric acid, sulfuric acid, hypochlorous acid, boric acid, tetrafluoroboric acid, acetic acid, p-toluenesulfonic acid, oxalic acid, trifluoroacetic acid, or formic acid) under a hydrogen atmosphere under normal pressure or increased pressure in the presence of ammonium formate or hydrazine at a temperature of about 0 to 200° C. Each of the reaction between the alcohol compound and the dialkylphosphoroamidite compound, the oxidation reaction, and the reduction reaction can also be performed by a method described in "Guide to *Organic Chemistry Experiment* 3-Synthesis Reaction [I]-" (edited by Toshio Goto, Tetsuo Shiba, and Teruo Matsuura, Kagaku-dojin Publishing Company, INC, 1990) in addition to the above-mentioned method.

(H-2) Among the compounds each represented by the formula (I-5-H), a compound in which $R^2$ and $R^3$ each represent one except a hydrogen atom, that is, a compound represented by a formula (I-5-H-2):

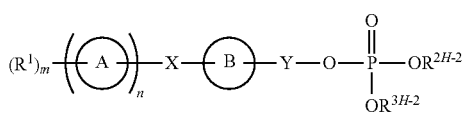 (I-5-H-2)

wherein $R^{2H-2}$ and $R^{3H-2}$ represent the same as those of $R^2$ and $R^3$ provided that none of them represents a hydrogen atom,
can be prepared by subjecting the compound represented by the formula (I-1-2) and a compound represented by a formula (16):

wherein all symbols represent the same as those described above to a reaction.

The reaction is known and is performed in an organic solvent (such as tetrahydrofuran or methylene chloride) in the presence of a base (such as pyridine, triethylamine, or butyllithium) at about −78° C. to 40° C.

In the present invention, compounds which are used as starting materials and represented by formulae (1) to (16) are conventionally known themselves, or can be prepared by any conventionally known method.

In each reaction of the present specification, a solid phase reagent which is supported by polymer (for example, polystyrene, polyacrylamide, polypropylene or polyethyleneglycol) may be used.

In each reaction of the present specification, the obtained products may be purified by conventional purification techniques. For example, the purification may be carried out by distillation under atmospheric or reduced pressure, by high performance liquid chromatography by using silica gel or magnesium silicate, by thin layer chromatography, by ion-exchange resin, by scavenger resin, by column chromatography, by washing or by recrystallization. The purification may be done each reaction or after several reactions.

In each reaction of the present specification, as is well known to those skilled in the art, reaction with heating can be performed by using a water bath, an oil bath, a sand bath, or microwave.

Toxicity:

The compounds of the present invention have sufficiently low toxicities and, therefore, they are considered to be sufficiently safe when used as drugs.

Application for Pharmaceutical Preparations:

The compound of the present invention has an ability to bind S1P receptor (particularly, EDG-1, EDG-6, and/or EDG-8, preferably EDG-1 and/or EDG-6). Therefore, in mammals (e.g., human and animals other than human such as a monkey, sheep, cow, horse, dog, cat, rabbit, rat, and mouse), the compound is useful as a preventive and/or therapeutic drug for rejection to transplantation, transplanted organ abolition, graft-versus-host disease (e.g., acute graft-versus-host disease during bone-marrow transplantation and the like), autoimmune diseases (e.g., systemic lupus erythematosus, Behcet's syndrome, scleroderma, nephrotic syndrome, rheumatoid arthritis, ulcerative colitis, Crohn's disease, autoimmune hemolytic anemia, idiopathic thrombocytopenic purpura, myasthenia gravis, muscular dystrophy, and multiple sclerosis), allergic diseases (e.g., atopic dermatitis, pollen disease, food allergy, psora, and drug (e.g., anesthetic such as lidocaine) allergy), inflammatory diseases (e.g., varicose vein such as hemorrhoid, anal fissure, or anal fistula, dissecting aneurysm of the aorta or sepsis, angiitis, nephritis, pneumonia, and chronic active hepatitis), respiratory disease (e.g., pulmonary fibrosis, asthma, and interstitial pneumonia), metabolic disease and endocrine disease (e.g., diabetes type-I), circulatory system disease (e.g., ischemia reperfusion disorders, arteriosclerosis, arteriosclerosis obliterans, thromboangiitis obliterans, diabetic neuropathy, acute cardiac failure, and angina), various edematous disorders developed from blood hyperpermeability (e.g., myocardial infarction, cerebral infarction, DIC, pleuritis, congestive heart failure, and multiple organ failure), traumatism (e.g., bedsore and burn), osteoporosis, chronic hepatitis, fibrosis such as liver fibrosis, chronic renal failure, renal glomerulus sclerosis, infection, ulcer, lymphoma, malignant tumor (e.g., cancer), leukemia, cerebral embolism, ischemic abnormality of various organs, shock with blood incompatibility during blood transfusion, genetic disease, neurodegenerating diseases (e.g., Parkinson's disease, parkinsonian syndrome, Alzheimer's disease, and amyotrophic lateral sclerosis), and the like. In addition, the compound of the present invention is useful, not only in vivo but also in vitro, as an adjusting agent such as a differentiation activator of cells or the like.

When the compound of the present invention or a combination preparation of the compound of the present invention and other drug is used for the above-described purpose, it is normally administered systemically or locally, by oral or parenteral administration. The doses to be administered are determined depending upon, for example, age, body weight, symptom, the desired therapeutic effect, the route of administration, and the duration of the treatment. In the human adult, the doses per person are generally from 1 ng to 100 mg, by oral administration, from once up to several times per day, from 0.1 ng to 10 mg, by parenteral administration, from once up to several times per day, or continuous infusion for 1 to 24 hours per day from vein. As described above, the doses to be administered depend upon various conditions. Therefore, there are cases in which doses lower than or greater than the above-described ranges are required to be administered.

When the compound of the present invention or a combination preparation of the compound of the present invention and other drug is administered, it is used in the form of solid for oral administration, liquid forms for oral administration, injections, liniments, suppositories, eye drops, inhalant, or the like for parenteral administration.

Solid forms for oral administration include tablets, pills, capsules, powder medicine, and granules. Capsules include hard capsules and soft capsules. Tablets include sublingual tablets, buccal adhesive tablets, oral rapid disintegrating tablets, and the like. Also, in such the solid forms for oral administration, one or more active material may be directly used or be admixed with a vehicle (such as lactose, mannitol, glucose, microcrystalline cellulose, or starch), a binder (such as hydroxypropylcellulose, polyvinylpyrrolidone, or magnesium metasilicate aluminate), a disintegrant (such as cellulose calcium glycolate), lubricants (such as magnesium stearate), a stabilizing agent, and a solubilizing agent (such as glutamic acid or aspartic acid) and prepared according to methods well known in the art. The solid forms may, if necessary, be coated with a coating agent (such as sucrose, gelatin, hydroxypropylcellulose, or hydroxypropylmethylcellulose phthalate), or be coated with two or more layers. Furthermore, coating may include capsules made of absorbable materials such as gelatin.

The sublingual tablets are prepared in accordance with a conventionally known method. For example, one or more active substance are used after being made into pharmaceutical preparations according to methods well known in the art by mixing with an vehicle (such as lactose, mannitol, glucose, microcrystalline cellulose, colloidal silica, or starch), a binder (such as hydroxypropylcellulose, polyvinylpyrrolidone, or magnesium aluminometasilicate), a disintegrant (such as starch, L-hydroxypropylcellulose, carboxymethylcellulose, croscarmellose sodium, or cellulose calcium glycolate), a lubricant (such as magnesium stearate), a swelling agent (such as hydroxypropylcellulose, hydroxypropylmethylcellulose, carbopol, carboxymethylcellulose, polyvinyl alcohol, xanthan gum, or guar gum), a swelling adjuvant (such as glucose, fructose, mannitol, xylitol, erythritol, maltose, trehalose, phosphate, citrate, silicate, glycine, glutamic acid, or arginine), a stabilizing agent, a solubilizing agent (such as polyethylene glycol, propylene glycol, glutamic acid, or aspartic acid), a flavoring agent (such as orange, strawberry, mint, lemon, or vanilla), and the like. Also, if necessary, they may be coated with a coating agent (such as sucrose, gelatin, hydroxypropylcellulose, or hydroxypropylmethylcellulose phthalate), or coated with two or more layers. In addition, if necessary, additive agents generally used such as an antispetic, an antioxidant, a colorant, and a sweetening agent can also be added thereto. The buccal adhesive tablets are produced or prepared in accordance with a conventionally known method. For example, one or more active substance are used after being made into pharmaceutical preparations according to methods well known in the art by mixing with an vehicle (such as lactose, mannitol, glucose, microcrystalline cellulose, colloidal silica, or starch), a binder (such as hydroxypropylcellulose, polyvinylpyrrolidone, or magnesium aluminometasilicate), a disintegrant (such as starch, L-hydroxypropylcellulose, carboxymethylcellulose, croscarmellose sodium, or cellulose calcium glycolate), a lubricant (such as magnesium stearate), a adhesion agent (such as hydroxypropylcellulose, hydroxypropylmethylcellulose, carbopol, carboxymethylcellulose, polyvinyl alcohol, xanthan gum, or guar gum), a adhesion adjuvant (such as glucose, fructose, mannitol, xylitol, erythritol, maltose, trehalose, phosphate, citrate, silicate, glycine, glutamic acid, or arginine), a stabilizing agent, a solubilizing agent (such as polyethylene glycol, propylene glycol, glutamic acid, or aspartic acid), a flavoring agent (such as orange, strawberry, mint, lemon, or vanilla) and the like. Also, if necessary, they may be coated with a coating agent (such as sucrose, gelatin, hydroxypropylcellulose, or hydroxypropylmethylcellulose phthalate), or coated with two or more layers. In addition, if necessary, additive agents generally used such as an antispetic, an antioxidant, a colorant, and a sweetening agent can also be added thereto. The oral rapid disintegrating tablets are produced in accordance with a conventionally known method. For example, one or more active substance are used as such or after being made into pharmaceutical preparations according to methods well known in the art by mixing the active substances, prepared by coating the material powder or granulated material particles with an appropriate coating agent (such as ethyl cellulose, hydroxypropylcellulose, hydroxypropylmethylcellulose, or acrylate-methacrylate copolymer) and a plasticizer (such as polyethylene glycol, or triethyl citrate), with an vehicle (such as lactose, mannitol, glucose, microcrystalline cellulose, colloidal silica, or starch), a binder (such as hydroxypropylcellulose, polyvinylpyrrolidone, or magnesium aluminometasilicate), a disintegrant (such as starch, L-hydroxypropylcellulose, carboxymethylcellulose, croscarmellose sodium, or cellulose calcium glycolate), a lubricant (such as magnesium stearate), a dispersing adjuvant (such as glucose, fructose, mannitol, xylitol, erythritol, maltose, trehalose, phosphate, citrate, silicate, glycine, glutamic acid, or arginine), a stabilizing agent, a solubilizing agent (such as polyethylene glycol, propylene glycol, glutamic acid, or aspartic acid), a flavoring agent (such as orange, strawberry, mint, lemon, or vanilla) and the like. Also, if necessary, they may be coated with a coating agent (such as sucrose, gelatin, hydroxypropylcellulose, or hydroxypropylmethylcellulose phthalate), or coated with two or more layers. In addition, if necessary, additive agents generally used such as a preservative, an antioxidant, a colorant, and a sweetening agent can also be added thereto.

Liquid forms for oral administration include pharmaceutically acceptable solutions, suspensions, emulsions, syrups, and elixirs. In the liquid forms, one or more active material may be dissolved, suspended, or emulized into diluent commonly used in the art (such as purified water, ethanol, or a mixture thereof). Further, the liquid forms may also include wetting agents, suspending agents, emulsifying agents, sweetening agents, flavoring agents, aromatic agent, preservative, or buffering agent.

The agent for parenteral administration may be in the form of, e.g., an ointment, a gel, a cream, a wet compress, a paste, a liniment, a nebula, an inhalant, a spray, an aerosol, eye drops, a collunarium, or the like. These agents each contain one or more active materials and are prepared by conventionally known methods or commonly used formulations.

The ointment is prepared by known or commonly used formulations. For example, one or more active materials are titurated or dissolved in a base to prepare such the ointment. The ointment base is selected from known or commonly used materials. For example, higher aliphatic acid or higher aliphatic acid ester (e.g., myristic acid, palmitic acid, stearic acid, oleic acid, myristic acid ester, palmitic acid ester, stearic acid ester, and oleic acid ester), wax (e.g., beeswax, whale wax, and ceresin), surface active agent (e.g., polyoxyethylenealkyletherphosphoric acid ester), higher alcohol (e.g., cetanol, stearyl alcohol, and setostearyl alcohol), silicon oil (e.g., dimethyl polysiloxane), hydrocarbons (e.g., hydrophilic petrolatum, white petrolatum, purified lanolin, and liquid paraffin), glycols (e.g., ethylene glycol, diethylene glycol, propylene glycol, polyethylene glycol, and macrogol), vegetable oil (e.g., castor oil, olive oil, sesame oil, and turpentine oil), animal oil (e.g., mink oil, yolk oil, squalane oil, and squalene oil), water, absorption accelerator, or rash preventive may be used alone or in combination of two or more thereof. The base may further include a humectant, a preservative, a stabilizer, an antioxidant, a perfume, or the like.

The gel is prepared by known or commonly used formulations. For example, one or more active materials are dissolved in a base to prepare such the gel. The gel base is selected from known or commonly used materials. For example, lower alcohol (e.g., ethanol, isopropyl alcohol), a gelling agent (e.g., carboxymethylcellulose, hydroxyethylcellulose, hydroxypropylcellulose, and ethylcellulose), a neutralizing agent (e.g., triethanolamine, and diisopropanolamine), a surface active agent (e.g., polyethylene glycol monostearate), a gum, water, an absorption accelerator, or a rash preventive may be used alone or in combination of two or more thereof. The gel base may further include a preservative, an antioxidant, a perfume, or the like.

The cream is prepared by known or commonly used formulations. For example, one or more active materials are dissolved or emulsified in a base to produce or prepare such the cream. The cream base is selected from known or commonly used materials. For example, higher aliphatic acid ester, lower alcohol, hydrocarbons, polyvalent alcohol (e.g., propylene glycol, and 1,3-butylene glycol), higher alcohol (e.g., 2-hexyldecanol, and cetanol), an emulsifier (e.g., polyoxyethylene alkyl ether, and aliphatic acid ester), water, an absorption accelerator, or a rash preventive may be used alone or in combination of two or more thereof. The cream base may further include a preservative, an antioxidant, a perfume, or the like.

The wet compress is prepared by known or commonly used formulations. For example, one or more active materials are dissolved in a base and then a kneaded mixture is spread and applied on a support to prepare such the wet compress. The wet compress base is selected from known or commonly used materials. For example, a thickening agent (e.g., polyacrylic acid, polyvinyl pyrrolidone, gum arabic, starch, gelatin, and methylcellulose), a wetting agent (e.g., urea, glycerin, and propylene glycol), a filler (e.g., kaolin, zinc oxide, talc, calcium, and magnesium), water, a solubilizing agent, a tackifier, and a rash preventive may be used alone or in combination of two or more thereof. The wet compress base may further include a preservative, an antioxidant, a perfume, or the like.

The pasting agent is prepared by known or commonly used formulations. For example, one or more active materials are dissolved in a base and then is spread and applied on a support to prepare such the pasting agent. The pasting agent base is selected from known or commonly used materials. For example, polymer base, fat and oil, higher aliphatic acid, a tackifier, or a rash preventive may be used alone or in combination of two or more thereof. The pasting agent base may further include a preservative, an antioxidant, a perfume, or the like.

The liniment is prepared by known or commonly used formulations. For example, one or more active materials are dissolved, suspended or emulsified in one or combination of two or more selected from water, alcohol (e.g., ethanol and polyethylene glycol), higher aliphatic acid, glycerin, soap, an emulsifier, a suspending agent, and the like, to prepare such the liniment. The liniment may further include a preservative, an antioxidant, a perfume, or the like.

The nebula, inhalant, and spray each may include a stabilizer such as sodium hydrogensulfite and a buffer capable of providing isotonicity such as an isotonic agent (e.g., sodium chloride, sodium citrate, and citric acid).

The injection for parenteral administration may be in the form of solution, suspension, emulsion, or solid injection to be dissolved or suspended in a solvent in use. The injection is prepared by dissolving, suspending, or emulsifying one or more active materials in a solvent. As such the solvent, there may be used distilled water for injection, saline, vegetable oil, alcohols such as propylene glycol, polyethylene glycol, and ethanol, or the like, and the combination thereof. The injection may further include a stabilizer, a solubilizing agent (e.g., glutamic acid, aspartic acid, Polysolvate 80 (trade name)), a suspending agent, an emulsifier, a soothing agent, a buffer, an antispetic, or the like. The injection is sterilized at the final step or prepared by an aseptic process. Alternatively, an aseptic solid agent such as freeze-dried product may be used by being rendered aseptic or dissolved in an aseptic distilled water for injection or other solvent before use.

The eye drops for parenteral administration may be in the form of liquid, suspension, emulsion or ointment, or may be dissolved in a solvent in use. These eye drops are prepared by conventionally known methods. For example, one or more active materials are dissolved, suspended or emulsified in a solvent. As such the solvent for eye drops, there may be used sterilized purified water, saline, and other aqueous or non-aqueous solvents for injection (e.g., vegetable oil), and the combination thereof. The eye drops may include an isotonic agent (e.g., sodium chloride and concentrated glycerin), a buffering agent (e.g., sodium phosphate and sodium acetate), a surface active agent (e.g., Polysolvate 80 (trade name), polyoxyl stearate 40, polyoxyethylene-hardened castor oil), a stabilizer (e.g., sodium citrate and sodium edetate), an antispetic (e.g., benzalconium chloride and Paraben), or the like to be properly selected as necessary. The eye drops are sterilized or prepared by an aseptic process in the final step. Alternatively, an aseptic solid agent such as freeze-dried product may be used by being rendered aseptic or dissolved in an aseptic distilled water for injection or other solvent before use.

The inhalant for parenteral administration may be in the form of aerosol, powder for inhalation, or liquid for inhalation. The liquid for inhalation may be dissolved or suspended in water or other proper medium in use. These inhalants are prepared by a conventionally known method. For example, the liquid for inhalation is prepared from materials properly selected from antspetics (e.g., benzalconium chloride and Paraben), colorants, buffering agents (e.g., sodium phosphate and sodium acetate), isotonic agents (e.g., sodium chloride and concentrated glycerin), thickening agents (e.g., carboxyvinyl polymer), absorption accelerators, and the like if necessary.

The powder for inhalation is prepared from materials properly selected from lubricants (e.g., stearic acid and salts thereof), binders (e.g., starch and dextrin), vehicles (e.g., lactose and cellulose), colorants, antispetics (e.g., benzalconium chloride and Paraben), absorption accelerators, or the like, if necessary.

In order to administer the liquid for inhalation, a sprayer (e.g., atomizer and nebulizer) is normally used. In order to administer the powder for inhalation, a powder inhaler is normally used.

Other examples of the composition for oral administration include suppository for rectal administration and pessary for vaginal administration prepared by an ordinary formulation and including one or more active materials.

The compound of the present invention may be administered as a combination preparation by being combined with other pharmaceuticals for the purpose of:

1) supplement and/or enhancement of a prevention effect and/or a treatment effect of the compound;

2) improvement in pharmacokinetics and absorption and reduction of doses to be administered of the compound; and/or 3) reduction of side effects of the compound.

The combination preparation of the compound of the present invention with other pharmaceuticals may be administered in a form of a compounded agent in which both components are compounded in one preparation or may be in a form in which they are administered by means of separate preparations. The case of administration by means of separate preparations includes a simultaneous administration and administrations with time intervals. In the case of administrations with time intervals, the compound of the present invention may be firstly administered, followed by administering the other pharmaceutical or the other pharmaceutical may be administered firstly, followed by administering the compound of the present invention. Methods for each of the administrations may be the same or different.

The combination preparations with other pharmaceuticals which supplement and/or enhance the prevention and/or treatment effect of the compound of the present invention are not limited to those exemplified in the present specification. Also, the combination preparations with other pharmaceuticals which supplement and/or enhance the prevention and/or treatment effect of the compound of the present invention include not only the ones which have been found up to now but also ones which will be found in future on the basis of mechanisms described in the present specification.

The diseases against which the combined drugs as described above have preventive and/or therapeutic effects are not particularly restricted. Namely, they may be diseases with which the preventive and/or therapeutic effects of the compounds of the present invention can be complemented and/or enhanced. For example, other immunosuppressants, antibiotics, or the like may be cited as drugs to be used for complementing and/or enhancing preventive and/or therapeutic effects on rejection in transplantation, which is a disease related to EDG-1 and/or EDG-6. Steroids, nonsteroidal anti-inflammatory drugs (NSAIDs), disease modifying antirheumatic drugs (DMARDs, slow-acting antirheumatic drugs), other immunosuppressants, T cell inhibitors, anti-inflammatory enzyme preparations, cartilage protecting agents, prostaglandins, prostaglandin synthase inhibitors, IL-1 inhibitors, IL-6 inhibitors (including protein preparations such as an anti-IL-6 receptor antibody), TNF-α inhibitors (including protein preparations such as an anti-TNF-α antibody), interferon γ agonists, phosphodiesterase inhibitors, metalloproteinase inhibitors, and the like can be cited as drugs to be used for complementing and/or enhancing in preventing and/or treating autoimmune diseases. Concerning drugs to be used for complementing and/or enhancing the preventive and/or therapeutic effects on allergic diseases, examples of drugs to be used for complementing and/or enhancing the preventive and/or therapeutic effects on, for example, atopic dermatitis include immunosuppressants, steroids, nonsteroidal anti-inflammatory drugs, prostaglandins, antiallergic agents, mediator release inhibitors, antihistaminic drugs, forskolin preparations, phosphodiesterase inhibitors, and cannabinoid-2 receptor stimulants.

Examples of the immunosuppressants include azathioprine (trade name: IMULAN and AZANIN), mizoribine (trade name: BREDININ), methotrexate (trade name: METHOTREXATE, RHEUMATREX), mycophenolate mofetil (trade name: CELLCEPT), cyclophosphamide (trade name: ENDOXAN P), cyclosporin A (trade name: NEORAL, SANDIMMUN), tacrolimus (FK506, trade name: PROGRAF), sirolimus (RAPAMYCIN), everolimus (trade name: CERTICAN), prednisolone (trade name: PREDONIN), methylprednisolone (trade name: MEDROL), orthoclone OKT3 (trade name: MUROMONAB CD3), anti human lymphocyte globulin (ALG, trade name: ALBULIN), deoxyspergualin (DSG, gusperimus hydrochloride, and trade name: SPANIDIN).

Examples of the antibiotics include cefuroxime sodium, meropenem trihydrate, netilmicin sulfate, sisomicin sulfate, ceftibuten, PA-1806, IB-367, tobramycin, PA-1420, doxorubicin, astromicin sulfate, or cefetamet pivoxil hydrochloride. Examples of antibiotics as inhalants include PA-1806, IB-367, tobramycin, PA-1420, doxorubicin, astromicin sulfate, or cefetamet pivoxil hydrochloride.

Examples of the steroid, in the case of external preparations, include clobetasol propionate, diflorasone diacetate, fluocinonide, mometasone furancarbaxylate, betamethasone dipropionate, betamethasone butyrate propionate, betamethasone valerate, difluprednate, budesonide, diflucortolone valerate, amcinonide, halcinonide, dexamethasone, dexamethasone propianate, dexamethasone valerate, dexamethasone acetate, hydrocortisone acetate, hydrocortisone butyrate, hydrocortisone butyrate propionate, deprodone propionate, prednisolone valerate acetate, fluocinolone acetonide, beclomethasone propionate, triamcinolone acetonide, flumetasone pivalate, alclometasone dipropionate, clobetasone butyrate, prednisolone, beclomethasone propionate, and fludroxycortide. Examples of internal medicines and injections include cortisone acetate, hydrocortisone, hydrocortisone sodium phosphate, hydrocortisone sodium succinate, fludrocortisone acetate, prednisolone, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, triamcinolone acetonide, dexamethasone, dexamethasone acetate, dexamethasone sodium phosphate, dexamethasone palmitate, paramethasone acetate, and betamethasone. Examples of inhalants include beclomethasone propionate, fluticasone propionate, budesonide, flunisolide, triamcinolone, ST-126P, ciclesonide, dexamethasone palmitate, mometasone furancarbonate, prasterone sulfonate, deflazacort, methylprednisolone suleptanate, and methylprednisolone sodium succinate.

Examples of the nonsteroidal antiinflammatory drug (NSAID) include sasapyrine, sodium salicylate, aspirin, aspirin dialuminate formulation, diflunisal, indomethacin, suprofen, ufenamate, dimethylisopropyl azulen, bufexamac, felbinac, diclofenac, tolmetin sodium, Clinoril, fenbufen, nabumetone, proglumetacin, indomethacin farnesil, acemetacin, proglumetacin maleate, amfenac sodium, mofezolac, etodolac, ibuprofen, ibuprofen piconol, naproxen, flurbiprofen, flurbiprofen axetil, ketoprofen, fenoprofen calcium, tiaprofenen, oxaprozin, pranoprofen, loxoprofen sodium, aluminoprofen, zaltoprofen, mefenamic acid, aluminum mefenamate, tolfenamic acid, floctafenine, ketophenylbutazone, oxyfenbutazone, piroxicam, tenoxicaam, anpiroxicam, napageln cream, epirizole, tiaramide hydrochloride, tinoridine hydrochloride, emorfazone, sulpyrine, Migrenin, Saridon, Sedes G, Amipylo N, Sorbon, pyrine system antipyretics, acetaminophen, phenacetin, dimethothiazine mesylate, simetride formulation, and antipyrine system antipyretics.

Examples of the disease modifying anti-rheumatic drug (DMARDs, slow-acting anti-rheumatic drug) include aurothioglucose, aurothiomalate sodium, auranofin, actarit, D-penicillamine preparations, lobenzarit disodium, bucillamine, hydroxychloroquine, salazosulfapyridine, methotrexate, and leflunomide.

Examples of the antiinflammatory enzyme preparations include lysozyme chloride, bromelain, pronase, serrapeptase, or streptokinase-streptodornase formulation.

Examples of the cartilage protecting agents include hyaluronate sodium, glucosamine, chondroitin sulfate, and glucosaminoglycan polysulfate.

Examples of the prostaglandins (hereinafter abbreviated as "PG") include a PG receptor agonist, and a PG receptor antagonist. Examples of the PG receptor include PGE receptor (EP1, EP2, EP3, EP4), PGD receptor (DP, CRTH2), PGF receptor (FP), PGI receptor (IP), or TX receptor (TP).

Examples of the prostaglandin synthase inhibitor include salazosulfapyridine, mesalazine, olsalazine, 4-aminosalicylic acid, JTE-522, auranofin, carprofen, diphenpyramid, flunoxaprofen, flurbiprofen, indomethacin, ketoprofen, lornoxicam, loxoprofen, Meloxicam, oxaprozin, parsalmide, piproxen, piroxicam, piroxicam betadex, piroxicam cinnamate, tropine indomethacinate, zaltoprofen, and pranoprofen.

Examples of the IL-1 inhibitors (including protein preparations such as a human IL-1 receptor antagonist) include anakinra.

Examples of the IL-6 inhibitors (including protein preparations such as an anti-IL-6 receptor antibody) include MRA.

Examples of the TNF-α inhibitors (including protein preparations such as an anti-TNF-α antibody) include infliximab, adalimumab, and etanercept.

Examples of the phosphodiesterase inhibitor include rolipram, cilomilast (trade name: Ariflo), Bay 19-8004, NIK-616, roflumilast (BY-217), cipamfylline (BGL-61063), atizolam (CP-80633), SCH-351591, YM-976, V-11294A, PD-168787, D-4396, IC-485, or ONO-6126 as a PDE-4 inhibitor.

Examples of the mediator release inhibitor include tranilast, sodium cromoglicate, anlexanox, repirinast, ibudilast, tazanolast, and pemilolast potassium.

Examples of the antihistaminic drugs include ketotifen fumarate, mequitazine, azelastine hydrochloride, oxatomide, terfenadine, emedastine fumarate, epinastine hydrochloride, astemizole, ebastin, cetirizine hydrochloride, bepotastine, fexofenadine, lolatadine, deslolatadine, olopatadine hydrochloride, TAK-427, ZCR-2060, NIP-530, mometasone furoate, mizolastine, BP-294, andolast, auranofin, and acrivastine.

Effect of the Invention

The compound of the present invention has an ability to bind S1P receptor (particularly, EDG-1, EDG-6, and/or EDG-8). Therefore in mammals (e.g., human and animals other than human such as a monkey, sheep, cow, horse, dog, cat, rabbit, rat, and mouse), the compound is useful as a preventive and/or therapeutic drug for rejection to transplantation, transplanted organ abolition, graft-versus-host disease (e.g., acute graft-versus-host disease during bone-marrow transplantation and the like), autoimmune diseases (e.g., systemic lupus erythematosus, Behcet's syndrome, scleroderma, nephrotic syndrome, rheumatoid arthritis, ulcerative colitis, Crohn's disease, autoimmune hemolytic anemia, idiopathic thrombocytopenic purpura, myasthenia gravis, muscular dystrophy, and multiple sclerosis), allergic diseases (e.g., atopic dermatitis, pollen disease, psora, food allergy, and drug (e.g., anesthetic such as lidocaine)allergy), inflammatory diseases (e.g., varicose vein such as hemorrhoid, anal fissure, or anal fistula, dissecting aneurysm of the aorta or sepsis, angiitis, nephritis, pneumonia, and chronic active hepatitis), respiratory disease (e.g., pulmonary fibrosis, asthma, and interstitial pneumonia), metabolic disease and endocrine disease (e.g., diabetes type-I), circulatory system disease (e.g., ischemia reperfusion disorders, arteriosclerosis, arteriosclerosis obliterans, thromboangiitis obliterans, diabetic neuropathy, acute cardiac failure, and angina), various edematous disorders developed from blood hyperpermeability (e.g., myocardial infarction, cerebral infarction, disseminated intravascular coagulation (DIC), pleuritis, congestive heart failure, and multiple organ failure), traumatism (e.g., bedsore and burn), osteoporosis, chronic hepatitis, fibrosis such as liver fibrosis, chronic renal failure, renal glomerulus sclerosis, infection, ulcer, lymphoma, malignant tumor (e.g., cancer), leukemia, cerebral embolism, ischemic abnormality of various organs, shock with blood incompatibility during blood transfusion, genetic disease, and neurodegenerating diseases (e.g., Parkinson's disease, parkinsonian syndrome, Alzheimer's disease, and amyotrophic lateral sclerosis), and the like.

BEST MODE FOR CARRYING OUT THE INVENTION

The present invention will be described in greater detail by the following Examples. However, the present invention is not construed as being restricted thereto.

Concerning chromatographic separation or TLC, a solvent in parentheses corresponds to an eluting solvent or a developing solvent employed and a ratio is expressed in volume. Aqueous ammonia to be used is a commercially available 28% aqueous ammonia.

A solvent in parenthesis shown in NMR was used for measurement.

An X-ray powder diffractogram was measured under the following conditions: Device: BRUKER D8 DISCOVER with GADDS, manufactured by BRUKER axs; Target: Cu; Filter: None; Voltage: 40 kV; Electric current: 40 mA; Exposure time: 5 min.

The relative intensity shown in the tables is expressed as a percentage relative to the highest peak (set to 100%).

Differential scanning calorie (DSC) was measured under the following conditions: Device: DSC 822e, manufactured by METTLER TOLEDO; Sample cell: aluminium open cell; Argon gas flow rate: 40 mL/min; Heating rate: indicated in each Example.

EXAMPLE 1

6-(benzyloxy)-3,4-dihydronaphthalene-1(2H)-one

To a solution of 6-hydroxy-3,4-dihydronaphthalen-1(2H)-one (24.3 g) in acetone (160 mL), benzyl bromide (29.4 mL) and potassium carbonate (31.1 g) were added at room temperature, followed by stirring at 40° C. for 3.5 hours. After filtering off the insoluble matters and concentrating the filtrate, the resultant was washed with a mixed solvent of tert-butyl methyl ether-hexane (1:4), to thereby obtain the title compound (34.5 g) having the following physical properties.
TLC: Rf 0.38 (hexane:ethyl acetate=3:1)

EXAMPLE 2

7-(benzyloxy)-4-methyl-1,2-dihydronaphthalene

To a solution of the compound (34.5 g) prepared in Example 1 in tetrahydrofuran (300 mL), methylmagnesiumbromide (3 mol/L diethyl ether solution, 55 mL) was added at 0° C., followed stirring at room temperature for 1 hours. The reaction mixture was cooled to 0° C. and poured into ice-saturated aqueous ammonium chloride solution. After adding 2 mol/L hydrochloric acid, the mixture was stirred at room temperature for 3 hours. Then, the resultant was extracted with ethyl acetate and the organic layer was successively washed with water and a brine, dried and concentrated. The obtained residue was purified by silica gel column chromatography (hexane:ethyl acetate=10:1), to thereby obtain the title compound (24.8 g) having the following physical properties.
TLC: Rf 0.57 (hexane:ethyl acetate=15:1)

EXAMPLE 3

6-(benzyloxy)-1-methyl-3,4-dihydronaphthalene-2-carbaldehyde

To phosphorus oxychloride (26.7 g), N,N-dimethylformamide (60 mL) was dropped at 0° C., followed by stirring for 20 minutes. Then, a solution of the compound (24.8 g) prepared in Example 2 in methylene chloride (60 mL) was slowly dropped thereto, followed by stirring at room temperature for 90 minutes. The reaction mixture was cooled to 0° C., poured into ice and then allowed to stand for a while. Next, the resultant was extracted with a mixed solvent of hexane-ethyl acetate (1:2). The organic layer was successively washed with water and a brine, dried and concentrated. The obtained solid was washed with tert-butyl methyl ether, to thereby obtain the title compound (19.9 g) having the following physical properties.
TLC: Rf 0.50 (hexane:ethyl acetate=3:1)

EXAMPLE 4

6-hydroxy-1-methyl-3,4-dihydronaphthalene-2-carbaldehyde

To thioanisole (35 mL), trifluoroacetic acid (140 mL) was added at 0° C. Then, the compound (9.17 g) prepared in Example 3 was added in portions thereto, followed by stirring at room temperature for 4 hours. The reaction mixture was poured into ice, followed by adding a 5 mol/L aqueous sodium hydroxide solution. After washing with tert-butyl methyl ether, 1 mol/L hydrochloric acid was added to the aqueous layer, followed by extracting with ethyl acetate. The organic layer was dried and concentrated. The obtained residue was purified by silica gel column chromatography (hexane:ethyl acetate=5:1 to 2:1), to thereby obtain the title compound (6.03 g) having the following physical properties.
TLC: Rf 0.26 (hexane:ethyl acetate=3:1)

EXAMPLE 5

6-[3-(4-fluorophenyl)propoxy]-1-methyl-3,4-dihydronaphthalene-2-carbaldehyde The procedure of Example 1 was similarly performed while using the compound prepared in Example 4 as a substitute for 6-hydroxy-3,4-dihydronaphthalen-1(2H)-one while using 1-bromo-3-(4-fluorophenyl)propane as a substitute for benzyl bromide, to thereby obtain the title compound having the following physical properties.
TLC: Rf 0.40 (hexane:ethyl acetate=3:1);
$^1$H-NMR (CDCl$_3$): δ 10.32 (s, 1H), 7.48 (d, J=8.50 Hz, 1H), 7.16 (dd, J=8.50, 5.50 Hz, 2H), 6.97 (t, J=8.50 Hz, 2H), 6.78 (dd, J=8.50, 2.50 Hz, 1H), 6.73 (d, J=2.50 Hz, 1H), 3.99 (t, J=6.00 Hz, 2H), 2.79 (t, J=7.50 Hz, 2H), 2.69-2.75 (m, 2H), 2.47-2.56 (m, 5H), 2.04-2.14 (m, 2H).

EXAMPLE 6 methyl 1-({6-[3-(4-fluorophenyl)propoxy]-1-methyl-3,4-dihydro-2-naphthalenyl}methyl)-3-azetidinecarboxylate

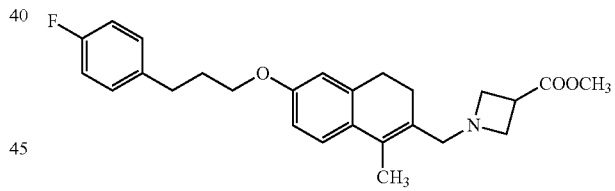

To a tetrahydrofuran (50 mL) solution of the compound (5.04 g) prepared in Example 5, triethylamine (4.33 mL), methyl azetidine-3-carboxylate hydrochloride (4.71 g, which was prepared in Example 38 described below), and triacetoxy sodium borohydride (9.88 g) were successively added under ice cooling. The reaction mixture was stirred at room temperature for 2.5 hours. Water was added to the reaction mixture under ice cooling. The resultant mixture was concentrated, and the obtained solution was extracted with ethyl acetate. The extract was successively washed with a saturated aqueous sodium hydrogen carbonate solution, water, and brine. The resultant was dried over anhydrous sodium sulfate, and concentrated. The obtained residue was purified by silica gel column chromatography (hexane:ethyl acetate=2:1 to 1:1 to 1:6), to thereby obtain the title compound (6.12 g) having the following physical properties. TLC: Rf 0.52 (hexane: ethyl acetate=1:3);
$^1$H-NMR (CDCl$_3$): δ 7.11-7.21 (m, 3H), 6.92-7.01 (m, 2H), 6.66-6.74 (m, 2H), 3.94 (t, J=6.13 Hz, 2H), 3.70 (s, 3H), 3.50-3.58 (m, 2H), 3.23-3.40 (m, 5H), 2.78 (t, J=7.50 Hz, 2H), 2.62-2.72 (m, 2H), 2.22-2.31 (m, 2H), 2.09 (s, 3H), 2.00-2.13 (m, 2H).

EXAMPLES 6-1 to 6-10

The procedure of Example 6 was similarly performed while using a corresponding aldehyde as a substitute for the compound prepared in Example 5. Thus, the compound having the following physical properties was each obtained.

EXAMPLE 6-1 methyl 1-({6-[3-(4-chlorophenyl)propoxy]-1-methyl-3,4-dihydro-2-naphthalenyl}methyl)-3-azetidinecarboxylate TLC: Rf 0.34 (hexane:ethyl acetate=1:3);
$^1$H-NMR (CDCl$_3$): δ 7.09-7.28 (m, 5H), 6.62-6.75 (m, 2H), 3.94 (t, J=6.13 Hz, 2H), 3.71 (s, 3H), 3.50-3.60 (m, 2H), 3.24-3.41 (m, 5H), 2.78 (t, J=7.55 Hz, 2H), 2.63-2.72 (m, 2H), 2.22-2.32 (m, 2H), 2.09 (s, 3H), 2.00-2.12 (m, 2H).

EXAMPLE 6-2 methyl 1-({6-[2-(4-isopropylphenyl)propoxy]-1-methyl-3,4-dihydro-2-naphthalenyl}methyl)-3-azetidinecarboxylate TLC: Rf 0.89 (chloroform:methanol=9:1);
$^1$H-NMR (CDCl$_3$): δ 7.12-7.24 (m, 5H), 6.63-6.76 (m, 2H), 4.04-4.12 (m, 1H), 3.91 (t, J=9.00 Hz, 1H), 3.70 (s, 3H), 3.48-3.61 (m, 2H), 3.09-3.43 (m, 6H), 2.82-2.94 (m, 1H), 2.66 (t, J=9.00 Hz, 2H), 2.17-2.30 (m, 2H), 2.08 (s, 3H), 1.40 (d, J=6.95 Hz, 3H), 1.25 (d, J=6.95 Hz, 6H).

EXAMPLE 6-3 methyl 1-[(6-{[(2R)-3-(4-fluorophenyl)-2-methylpropyl]oxy}-1-methyl-3,4-dihydro-2-naphthalenyl)methyl]-3-azetidinecarboxylate TLC: Rf 0.46 (chloroform:methanol=20:1);
$^1$H-NMR (CDCl$_3$): δ 7.06-7.23 (m, 3H), 6.89-7.02 (m, 2H), 6.63-6.75 (m, 2H), 3.76 (d, J=5.9 Hz, 2H), 3.71 (s, 2H), 3.51-3.59 (m, 2H), 3.22-3.41 (m, 6H), 2.84 (dd, J=13.5, 6.4 Hz, 1H), 2.67 (t, J=7.3 Hz, 2H), 2.52 (dd, J=13.5, 7.9 Hz, 1H), 2.12-2.31 (m, 3H), 2.09 (s, 3H), 1.00 (d, J=6.8 Hz, 3H).

EXAMPLE 6-4 methyl 1-[(6-{[(2S)-3-(4-fluorophenyl)-2-methylpropyl]oxy}-1-methyl-3,4-dihydro-2-naphthalenyl)methyl]-3-azetidinecarboxylate TLC: Rf 0.36 (hexane:ethyl acetate=1:1);
$^1$H-NMR (CDCl$_3$): δ 7.18 (d, J=8.40 Hz, 1H), 7.08-7.16 (m, 2H), 6.91-7.01 (m, 2H), 6.64-6.74 (m, 2H), 3.76 (d, J=5.85 Hz, 2H), 3.71 (s, 3H), 3.43-3.61 (m, 2H), 3.23-3.41 (m, 5H), 2.84 (dd, J=13.45, 6.50 Hz, 1H), 2.61-2.75 (m, 2H), 2.52 (dd, J=13.45, 7.68 Hz, 1H), 2.12-2.33 (m, 3H), 2.09 (s, 3H), 1.00 (d, J=6.7 Hz, 3H).

EXAMPLE 6-5 methyl 1-({1-Chloro-6-[3-(4-fluorophenyl)propoxy]-3,4-dihydro-2-naphthalenyl}methyl)-3-azetidinecarboxylate TLC: Rf 0.83 (chloroform:methanol=9:1);
$^1$H-NMR (CDCl$_3$): δ 7.51 (d, J=8.60 Hz, 1H), 7.11-7.19 (m, 2H), 6.91-7.02 (m, 2H), 6.73 (dd, J=8.60, 2.56 Hz, 1H), 6.66 (d, J=2.56 Hz, 1H), 3.95 (t, J=6.22 Hz, 2H), 3.71 (s, 3H), 3.57 (t, J=7.14 Hz, 2H), 3.28-3.47 (m, 5H), 2.78 (t, J=7.20 Hz, 2H), 2.75 (t, J=7.20 Hz, 2H), 2.43 (t, J=7.50 Hz, 2H), 1.99-2.13 (m, 2H).

EXAMPLE 6-6 methyl 1-[(6-{[1-(4-fluorobenzyl)cyclopropyl]methoxy}-1-methyl-3,4-dihydro-2-naphthalenyl)methyl]-3-azetidinecarboxylate TLC: Rf 0.73 (chloroform:methanol=9:1).

EXAMPLE 6-7 methyl 1-{[6-[3-(4-fluorophenyl)propoxy]-3-(trifluoromethyl)-1-benzothien-2-yl]methyl}-3-azetidinecarboxylate TLC: Rf 0.54 (hexane:ethyl acetate=3:1);
$^1$H-NMR (CDCl$_3$): δ 7.70-7.80 (m, 1H), 7.11-7.29 (m, 3H), 6.92-7.09 (m, 3H), 3.95-4.07 (m, 4H), 3.66-3.77 (m, 5H), 3.34-3.51 (m, 3H), 2.81 (t, J=7.5 Hz, 2H), 2.04-2.19 (m, 2H).

EXAMPLE 6-8 methyl 1-[(6-{[(2S)-3-(2,4-difluorophenyl)-2-methylpropyl]oxy}-1-methyl-3,4-dihydro-2-naphthalenyl)methyl]-3-azetidinecarboxylate TLC: Rf 0.20 (hexane:ethyl acetate=1:2);
$^1$H-NMR (CDCl$_3$): δ 7.18 (d, J=8.50 Hz, 1H), 7.08-7.16 (m, 1H), 6.74-6.82 (m, 2H), 6.66-6.72 (m, 2H), 3.78 (d, J=6.00 Hz, 2H), 3.71 (s, 3H), 3.50-3.58 (m, 2H), 3.25-3.37 (m, 5H), 2.85 (dd, J=14.00, 6.50 Hz, 1H), 2.64-2.71 (m, 2H), 2.57 (dd, J=14.00, 7.50 Hz, 1H), 2.17-2.31 (m, 3H), 2.08 (s, 3H), 1.01 (d, J=6.50 Hz, 3H).

EXAMPLE 6-9 methyl 1-[(6-{[(2S)-3-(4-chloro-2-fluorophenyl)-2-methylpropyl]oxy}-1-methyl-3,4-dihydro-2-naphthalenyl)methyl]-3-azetidinecarboxylate TLC: Rf 0.20 (hexane:ethyl acetate=1:2);
$^1$H-NMR (CDCl$_3$): δ 7.18 (d, J=8.50 Hz, 1H), 7.01-7.14 (m, 3H), 6.65-6.72 (m, 2H), 3.78 (d, J=6.00 Hz, 2H), 3.71 (s, 3H), 3.51-3.58 (m, 2H), 3.24-3.40 (m, 5H), 2.85 (dd, J=14.00, 6.50 Hz, 1H), 2.64-2.71 (m, 2H), 2.58 (dd, J=14.00, 8.00 Hz, 1H), 2.19-2.31 (m, 3H), 2.09 (s, 3H), 1.01 (d, J=6.50 Hz, 3H).

EXAMPLE 6-10 methyl 1-[(6-{[(2S)-3-(4-chlorophenyl)-2-methylpropyl]oxy}-1-methyl-3,4-dihydro-2-naphthalenyl)methyl]-3-azetidinecarboxylate TLC: Rf 0.33 (chloroform:methanol=20:1);
$^1$H-NMR (CDCl$_3$): δ 7.23 (d, J=8.4 Hz, 2H), 7.18 (d, J=8.4 Hz, 1H), 7.10 (d, J=8.4 Hz, 2H), 6.64-6.72 (m, 2H), 3.75 (d, J=5.9 Hz, 2H), 3.70 (s, 2H), 3.50-3.59 (m, 2H), 3.23-3.41 (m, 6H), 2.85 (dd, J=13.5, 6.5 Hz, 1H), 2.67 (t, J=7.1 Hz, 2H), 2.52 (dd, J=13.5, 7.8 Hz, 1H), 2.13-2.32 (m, 3H), 2.09 (s, 3H), 0.99 (d, J=6.8 Hz, 3H).

EXAMPLE 7

1-({6-[3-(4-fluorophenyl)propoxy]-1-methyl-3,4-dihydro-2-naphthalenyl}methyl)-3-azetidinecarboxylic acid

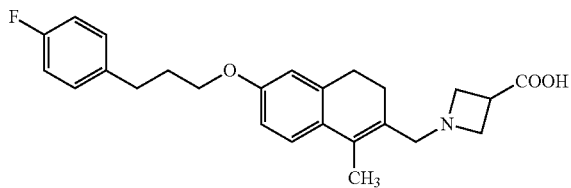 [SMILES: CC1=C(CN2CC(C(=O)O)C2)CCc2cc(OCCCc3ccc(F)cc3)ccc21]

To a methanol (120 mL) solution of the compound (6.02 g) prepared in Example 6, 1 mol/L aqueous sodium hydroxide (40 mL) was added dropwise under ice cooling. The reaction mixture was stirred for 3 hours under ice cooling. To the mixture, 1 mol/L hydrochloric acid (40 mL) was added. The generated insoluble matter was filtered, washed with water, and dried. The obtained solid was recrystallized from water-tetrahydrofuran, to thereby obtain the title compound (5.55 g) having the following physical properties.

Melting point: 154.0-155.3° C.;
TLC: Rf 0.35 (chloroform:methanol:aqueous ammonia=80:20:4);
$^1$H-NMR (CD$_3$OD): δ 7.31 (d, J=8.60 Hz, 1H), 7.15-7.25 (m, 2H), 6.92-7.02 (m, 2H), 6.75 (dd, J=8.60, 2.56 Hz, 1H), 6.71 (d, J=2.56 Hz, 1H), 4.10-4.26 (m, 4H), 4.07 (s, 2H), 3.95 (t, J=6.13 Hz, 2H), 3.34-3.48 (m, 1H), 2.66-2.82 (m, 4H), 2.20-2.28 (m, 2H), 2.20 (s, 3H), 1.98-2.10 (m, 2H).

EXAMPLES 7-1 to 7-10

The procedure similar to that of Example 7 was carried out using the compounds prepared in Examples 6-1 to 6-10 in place of the compound prepared in Example 6. As required, the resultant was converted into a corresponding salt, to thereby obtain the title compounds each having the following physical properties.

EXAMPLE 7-1

1-({6-[3-(4-chlorophenyl)propoxy]-1-methyl-3,4-dihydro-2-naphthalenyl}methyl)-3-azetidinecarboxylic acid

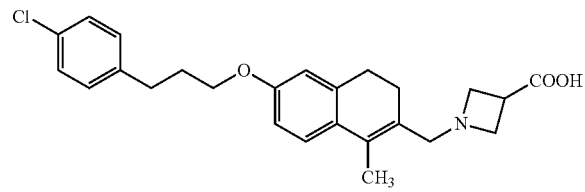 [SMILES: CC1=C(CN2CC(C(=O)O)C2)CCc2cc(OCCCc3ccc(Cl)cc3)ccc21]

Melting point: 165.4-166.9° C.;
TLC: Rf 0.32 (chloroform:methanol:aqueous ammonia=80:20:4);
$^1$H-NMR (CD$_3$OD): δ 7.31 (d, J=8.60 Hz, 1H), 7.16-7.28 (m, 4H), 6.75 (dd, J=8.60, 2.74 Hz, 1H), 6.70 (d, J=2.74 Hz, 1H), 4.09-4.24 (m, 4H), 4.07 (s, 2H), 3.96 (t, J=6.22 Hz, 2H), 3.34-3.47 (m, 1H), 2.67-2.82 (m, 4H), 2.17-2.28 (m, 5H), 1.99-2.11 (m, 2H).

EXAMPLE 7-2

1-({6-[2-(4-isopropylphenyl)propoxy]-1-methyl-3,4-dihydro-2-naphthalenyl}methyl)-3-azetidinecarboxylic acid hydrochloride TLC: Rf 0.11 (1-butanol:acetic acid:water=20:4:1);
$^1$H-NMR (CD$_3$OD): δ 7.31 (d, J=8.60 Hz, 1H), 7.12-7.23 (m, 4H), 6.75 (dd, J=8.60, 2.65 Hz, 1H), 6.70 (d, J=2.65 Hz, 1H), 4.20-4.41 (m, 4H), 4.15 (s, 2H), 4.07 (dd, J=9.30, 6.30 Hz, 1H), 3.98 (dd, J=9.30, 7.50 Hz, 1H), 3.60-3.76 (m, 1H), 3.10-3.20 (m, 1H), 2.79-2.92 (m, 1H), 2.67-2.76 (m, 2H), 2.21 (s, 3H), 2.17-2.27 (m, 2H), 1.36 (d, J=6.95 Hz, 3H), 1.23 (d, J=6.95 Hz, 6H).

EXAMPLE 7-3

1-[(6-{[(2R)-3-(4-fluorophenyl)-2-methylpropyl]oxy}-1-methyl-3,4-dihydro-2-naphthalenyl)methyl]-3-azetidinecarboxylic acid

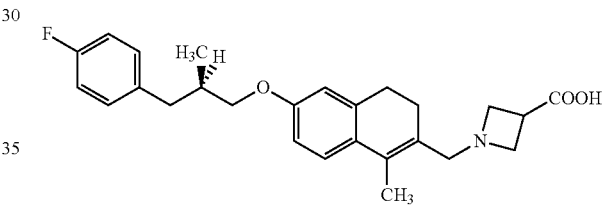

TLC: Rf 0.40 (chloroform:methaol:aqueous ammonia=80:20:4);
$^1$H-NMR (CD$_3$OD): δ 7.30 (d, J=8.42 Hz, 1H), 7.09-7.23 (m, 2H), 6.87-7.03 (m, 2H), 6.74 (dd, J=8.42, 2.56 Hz, 1H), 6.69 (d, J=2.56 Hz, 1H), 4.12-4.27 (m, 4H), 4.09 (s, 2H), 3.78 (d, J=6.04 Hz, 2H), 3.35-3.47 (m, 1H), 2.83 (dd, J=13.45, 6.50 Hz, 1H), 2.67-2.75 (m, 2H), 2.54 (dd, J=13.45, 7.78 Hz, 1H), 2.20 (s, 3H), 2.09-2.29 (m, 3H), 0.99 (d, J=6.77 Hz, 3H).

EXAMPLE 7-4

1-[(6-{[(2S)-3-(4-fluorophenyl)-2-methylpropyl]oxy}-1-methyl-3,4-dihydro-2-naphthalenyl)methyl]-3-azetidinecarboxylic acid

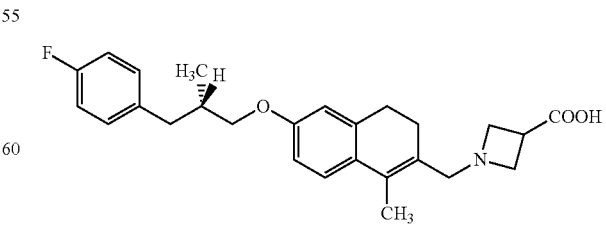

Melting point: 142.5-143.6° C.;
TLC: Rf 0.24 (chloroform:methaol:aqueous ammonia=5:1:0.1);

¹H-NMR (CD₃OD): δ 7.30 (d, J=8.42 Hz, 1H), 7.09-7.23 (m, 2H), 6.87-7.03 (m, 2H), 6.74 (dd, J=8.42, 2.56 Hz, 1H), 6.69 (d, J=2.56 Hz, 1H), 4.12-4.27 (m, 4H), 4.09 (s, 2H), 3.78 (d, J=6.04 Hz, 2H), 3.35-3.47 (m, 1H), 2.83 (dd, J=13.45, 6.50 Hz, 1H), 2.67-2.75 (m, 2H), 2.54 (dd, J=13.45, 7.78 Hz, 1H), 2.20 (s, 3H), 2.09-2.29 (m, 3H), 0.99 (d, J=6.77 Hz, 3H).

EXAMPLE 7-5

1-({1-chloro-6-[3-(4-fluorophenyl)propoxy]-3,4-dihydro-2-naphthalenyl}methyl)-3-azetidinecarboxylic acid TLC: Rf 0.12 (chloroform:methaol:aqueous ammonia=5:1:0.1);

¹H-NMR (CD₃OD): δ 7.55 (d, J=8.60 Hz, 1H), 7.10-7.26 (m, 2H), 6.92-7.05 (m, 2H), 6.80 (dd, J=8.60, 2.38 Hz, 1H), 6.76 (d, J=2.38 Hz, 1H), 4.22 (d, J=8.40 Hz, 4H), 4.17 (s, 2H), 3.97 (t, J=6.13 Hz, 2H), 3.36-3.49 (m, 1H), 2.70-2.89 (m, 4H), 2.41-2.49 (m, 2H), 1.97-2.11 (m, 2H).

EXAMPLE 7-6

1-[(6-{[1-(4-fluorobenzyl)cyclopropyl]methoxy}-1-methyl-3,4-dihydro-2-naphthalenyl)methyl]-3-azetidinecarboxylic acid TLC: Rf 0.14 (chloroform:methaol:aqueous ammonia=5:1:0.1);

¹H-NMR (CD₃OD): δ 7.29 (d, J=8.60 Hz, 1H), 7.13-7.22 (m, 2H), 6.88-6.98 (m, 2H), 6.65-6.73 (m, 2H), 4.10-4.26 (m, 4H), 4.07 (s, 2H), 3.61 (s, 2H), 3.36-3.47 (m, 1H), 2.78 (s, 2H), 2.66-2.75 (m, 2H), 2.14-2.28 (m, 5H), 0.52-0.68 (m, 4H).

EXAMPLE 7-7

1-{[6-[3-(4-fluorophenyl)propoxy]-3-(trifluoromethyl)-1-benzothien-2-yl]methyl}-3-azetidinecarboxylic acid TLC: Rf 0.32 (chloroform:methaol:aqueous ammonia=80:20:4);

¹H-NMR (CD₃OD): δ 7.71 (dd, J=9.0, 1.4 Hz, 1H), 7.39 (d, J=2.4 Hz, 1H), 7.22 (dd, J=8.8, 5.3 Hz, 2H), 7.05 (dd, J=9.0, 2.4 Hz, 1H), 6.98 (t, J=8.8 Hz, 2H), 4.09 (d, J=2.0 Hz, 2H), 4.02 (t, J=6.2 Hz, 2H), 3.72 (t, J=8.2 Hz, 2H), 3.50 (t, J=8.2 Hz, 2H), 3.23-3.35 (m, 1H), 2.81 (t, J=7.3 Hz, 2H), 2.01-2.15 (m, 2H).

EXAMPLE 7-8

1-[(6-{[(2S)-3-(2,4-difluorophenyl)-2-methylpropyl]oxy}-1-methyl-3,4-dihydro-2-naphthalenyl)methyl]-3-azetidinecarboxylic acid

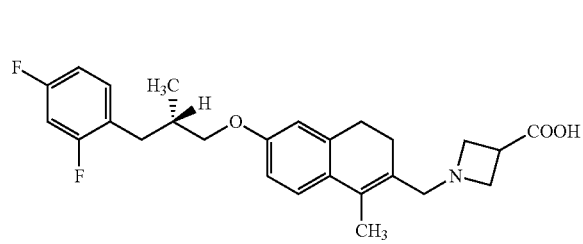 [SMILES: CC1=C(CN2CC(C(=O)O)C2)CCc2cc(OC[C@@H](C)Cc3ccc(F)cc3F)ccc21]

TLC: Rf 0.20 (chloroform:methanol:aqueous ammonia=80:20:4);

[α]$_D^{25}$:+30.6° (c 0.10; chloroform-ethanol, 1:1);

¹H-NMR (CDCl₃+CD₃OD): δ 7.26 (d, J=8.50 Hz, 1H), 7.09-7.18 (m, 1H), 6.75-6.83 (m, 2H), 6.73 (dd, J=8.50, 2.50 Hz, 1H), 6.68 (d, J=2.50 Hz, 1H), 4.31 (dd, J=10.00, 5.00 Hz, 2H), 4.00 (t, J=10.00 Hz, 2H), 3.94 (s, 2H), 3.80 (d, J=6.00 Hz, 2H), 3.20-3.32 (m, 1H), 2.85 (dd, J=14.00, 6.50 Hz, 1H), 2.69-2.77 (m, 2H), 2.58 (dd, J=14.00, 7.50 Hz, 1H), 2.20-2.35 (m, 3H), 2.18 (s, 3H), 1.02 (d, J=6.50 Hz, 3H).

EXAMPLE 7-9

1-[(6-{[(2S)-3-(4-chloro-2-fluorophenyl)-2-methylpropyl]oxy}-1-methyl-3,4-dihydro-2-naphthalenyl)methyl]-3-azetidinecarboxylic acid

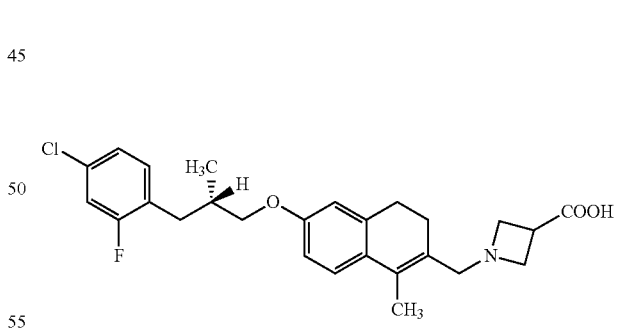

TLC: Rf 0.20 (chloroform:methanol:aqueous ammonia=80:20:4);

[α]$_D^{25}$: +64.1°(c 0.10; chloroform-ethanol, 1:1);

¹H-NMR (CDCl₃+CD₃OD): δ 7.26 (d, J=8.50 Hz, 1H), 7.03-7.15 (m, 3H), 6.72 (dd, J=8.50, 2.50 Hz, 1H), 6.67 (d, J=2.50 Hz, 1H), 4.25-4.35 (m, 2H), 3.99 (t, J=10.00 Hz, 2H), 3.93 (s, 2H), 3.80 (d, J=6.00 Hz, 2H), 3.22-3.32 (m, 1H), 2.86 (dd, J=14.00, 6.50 Hz, 1H), 2.69-2.77 (m, 2H), 2.59 (dd, J=14.00, 7.50 Hz, 1H), 2.21-2.36 (m, 3H), 2.18 (s, 3H), 1.03 (d, J=6.50 Hz, 3H).

EXAMPLE 7-10

1-[(6-{[(2S)-3-(4-chlorophenyl)-2-methylpropyl]oxy}-1-methyl-3,4-dihydro-2-naphthalenyl)methyl]-3-azetidinecarboxylic acid

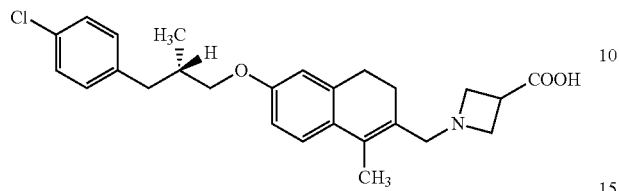

Melting point: 148.6-148.9° C.;
$[\alpha]_D^{25}$: +43.2° (c 0.50, ethanol);
TLC: Rf 0.24 (chloroform:methanol:aqueous ammonia=80:20:4);
$^1$H-NMR (CD$_3$OD): δ 7.31 (d, J=8.6 Hz, 1H), 7.24 (d, J=8.6 Hz, 2H), 7.15 (d, J=8.6 Hz, 2H), 6.66-6.78 (m, 2H), 4.12-4.28 (m, 4H), 4.10 (s, 2H), 3.78 (d, J=5.9 Hz, 2H), 3.33-3.50 (m, 1H), 2.84 (dd, J=13.5, 6.5 Hz, 1H), 2.65-2.77 (m, 2H), 2.55 (dd, J=13.5, 7.8 Hz, 1H), 2.12-2.31 (m, 6H), 1.00 (d, J=6.8 Hz, 3H).

EXAMPLE 8

1-({6-[3-(4-chlorophenyl)propoxy]-3,4-dihydro-2-naphthalenyl}methyl)-3-azetidinecarboxylic acid

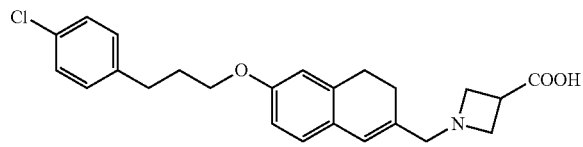 [SMILES: O=C(O)C1CN(CC2=Cc3ccc(OCCCc4ccc(Cl)cc4)cc3CC2)C1]

Azetidine-3-carboxylic acid (46 mg) and sodium hydroxide (18 mg) were dissolved in methanol (4 mL). To this solution, trimethoxymethane (0.050 mL) and a tetrahydrofuran (1 mL)-methanol (1 mL) mixed solution of 6-[3-(4-chlorophenyl)propoxy]-3,4-dihydronaphthalene-2-carboaldehyde (100 mg) were successively added under ice cooling. The reaction mixture was stirred for 3.5 hours under ice cooling. To the reaction mixture, sodium borohydride (17 mg) was added under ice cooling. The reaction mixture was stirred under ice cooling for 20 minutes. Thereafter, 4 mol/L hydrogen chloride/ethyl acetate solution was added until it was neutral, and concentrated. The obtained residue was purified by flash silica gel column chromatography (chloroform:methanol:aqueous ammonia=80:10:1 to 80:20:4), to thereby obtain the title compound (79 mg) having the following physical properties.

TLC: Rf 0.21 (chloroform:methanol:aqueous ammonia=80:20:4);
$^1$H-NMR (CD$_3$OD): δ 7.25 (d, J=8.50 Hz, 2H), 7.19 (d, J=8.50 Hz, 2H), 7.02 (d, J=9.00 Hz, 1H), 6.68-6.72 (m, 2H), 6.60 (s, 1H), 4.11-4.25 (m, 4H), 3.94 (t, J=6.00 Hz, 2H), 3.89 (s, 2H), 3.35-3.48 (m, 1H), 2.73-2.86 (m, 4H), 2.22-2.30 (m, 2H), 1.98-2.10 (m, 2H).

EXAMPLES 8-1 to 8-5

The procedure similar to that of Example 8 was carried out using a corresponding aldehyde compound in place of 6-[3-(4-chlorophenyl)propoxy]-1-methyl-3,4-dihydronaphthalene-2-carboaldehyde. As required, the resultant was converted into a corresponding salt, to thereby obtain the title compounds each having the following physical properties.

EXAMPLE 8-1

1-({6-[4-(4-chlorophenyl)butoxy]-1-methyl-3,4-dihydro-2-naphthalenyl}methyl)-3-azetidinecarboxylic acid (Free Form)
TLC: Rf 0.29 (chloroform:methanol:aqueous ammonia=80:20:4);
$^1$H-NMR (CD$_3$OD): δ 7.30 (d, J=8.50 Hz, 1H), 7.24 (d, J=8.50 Hz, 2H), 7.17 (d, J=8.50 Hz, 2H), 6.74 (dd, J=8.50, 2.50 Hz, 1H), 6.70 (d, J=2.50 Hz, 1H), 4.09-4.22 (m, 4H), 4.06 (s, 2H), 3.95-4.02 (m, 2H), 3.34-3.45 (m, 1H), 2.63-2.76 (m, 4H), 2.18-2.28 (m, 5H), 1.74-1.81 (m, 4H).
(Hydrochloride)
TLC: Rf 0.29 (chloroform:methanol:aqueous ammonia=80:20:4);
$^1$H-NMR (CD$_3$OD): δ 7.32 (d, J=8.50 Hz, 1H), 7.25 (d, J=8.50 Hz, 2H), 7.18 (d, J=8.50 Hz, 2H), 6.75 (dd, J=8.50, 2.50 Hz, 1H), 6.71 (d, J=2.50 Hz, 1H), 4.19-4.45 (m, 4H), 4.16 (s, 2H), 3.95-4.02 (m, 2H), 3.64-3.78 (m, 1H), 2.62-2.76 (m, 4H), 2.19-2.28 (m, 5H), 1.74-1.81 (m, 4H).

EXAMPLE 8-2

1-({6-[3-(4-chlorophenyl)-2,2-dimethylpropoxy]-1-methyl-3,4-dihydro-2-naphthalenyl}methyl)-3-azetidinecarboxylic acid hydrochloride TLC: Rf 0.16 (1-butanol:acetic acid:water=20:4:1);
$^1$H-NMR (CD$_3$OD): δ 7.35 (d, J=8.42 Hz, 1H), 7.16-7.22 (m, 2H), 7.07-7.11 (m, 2H), 6.74-6.82 (m, 2H), 4.19-4.49 (m, 4H), 4.17 (s, 2H), 3.63-3.79 (m, 1H), 3.53 (s, 2H), 2.71 (s, 2H), 2.68-2.79 (m, 2H), 2.23 (s, 3H), 2.18-2.31 (m, 2H), 1.01 (s, 6H).

EXAMPLE 8-3

1-[(6-{[1-(4-chlorobenzyl)cyclopropyl]methoxy}-1-methyl-3,4-dihydro-2-naphthalenyl)methyl]-3-azetidinecarboxylic acid hydrochloride TLC: Rf 0.14 (1-butanol:acetic acid:water=20:4:1);
$^1$H-NMR (CD$_3$OD): δ 7.31 (d, J=8.60 Hz, 1H), 7.14-7.24 (m, 4H), 6.71 (dd, J=8.60, 2.40 Hz, 1H), 6.67 (d, J=2.40 Hz, 1H), 4.18-4.43 (m, 4H), 4.16 (s, 2H), 3.66-3.78 (m, 1H), 3.61 (s, 2H), 2.78 (s, 2H), 2.67-2.76 (m, 2H), 2.21 (s, 3H), 2.17-2.30 (m, 2H), 0.54-0.69 (m, 4H).

EXAMPLE 8-4

1-[(6-{[(2E)-3-(4-chlorophenyl)-2-propenyl]oxy}-1-methyl-3,4-dihydro-2-naphthalenyl)methyl]-3-azetidinecarboxylic acid hydrochloride TLC: Rf 0.17 (chloroform:methanol:aqueous ammonia=80:20:4);
$^1$H-NMR (CD$_3$OD): δ 7.41 (d, J=8.50 Hz, 2H), 7.35 (d, J=8.50 Hz, 1H), 7.31 (d, J=8.50 Hz, 2H), 6.84 (dd, J=8.50, 2.50 Hz, 1H), 6.80 (d, J=2.50 Hz, 1H), 6.72 (dt, J=16.00, 1.50 Hz, 1H), 6.46 (dt, J=16.00, 5.50 Hz, 1H), 4.71 (dd, J=5.50, 1.50 Hz, 2H), 4.18-4.47 (m, 4H), 4.16 (s, 2H), 3.65-3.78 (m, 1H), 2.72-2.78 (m, 2H), 2.21-2.29 (m, 5H).

EXAMPLE 8-5

1-({6-[4-(4-fluorophenyl)butoxy]-1-methyl-3,4-dihydro-2-naphthalenyl}methyl)-3-azetidinecarboxylic acid hydrochloride TLC: Rf 0.23 (chloroform:methanol:aqueous ammonia=80:20:4);

$^1$H-NMR (CD$_3$OD): δ 7.31 (d, J=8.50 Hz, 1H), 7.19 (dd, J=8.50, 5.50 Hz, 2H), 6.96 (t, J=8.50 Hz, 2H), 6.75 (dd, J=8.50, 2.50 Hz, 1H), 6.71 (d, J=2.50 Hz, 1H), 4.20-4.45 (m, 4H), 4.15 (s, 2H), 3.95-4.02 (m, 2H), 3.63-3.78 (m, 1H), 2.62-2.77 (m, 4H), 2.18-2.30 (m, 5H), 1.72-1.82 (m, 4H).

EXAMPLE 9 tert-butyl 4-(4,4,5,5-tetramethyl-1,3,2-dioxaborolan-2-yl)-3,6-dihydro-1(2H)-pyridine carboxylate Using tert-butyl 4-oxopiperidine-1-carboxylate, 1,1,1-trifluoro-N-phenyl-N—[(trifluoromethyl)sulfonyl]methanesulfonamide, and 4,4,4',4',5,5,5',5'-octamethyl-2,2'-bi-1,3,2-dioxaborane, the similar procedure as described in Tetrahedron Letters, 2000, 41, 3705-3708 was carried out, to thereby obtain the title compound having the following physical properties.

TLC: Rf 0.63 (hexane:ethyl acetate=3:1);

$^1$H-NMR (CDCl$_3$): δ 6.25-6.70 (m, 1H), 3.86-4.02 (m, 2H), 3.44 (t, J=5.58 Hz, 2H), 2.12-2.34 (m, 2H), 1.42-1.49 (m, 9H), 1.26 (s, 12H).

EXAMPLE 10 tert-butyl 4-[2-methyl-4-(3-phenylpropoxy)phenyl]-3,6-dihydro-1(2H)-pyridinecalboxylate To an anhydrous N,N dimethylformamide (10 mL) solution of 1-bromo-2-methyl-4-(3-phenylpropoxy)benzene (641 mg), the compound (620 mg) prepared in Example 9, potassium carbonate (829 mg), and dichloro[(diphenylphosphino)ferrocene]palladium (II) (88 mg) were successively added. The reaction mixture was stirred at 80° C. for 3 hours. To the reaction mixture, saturated aqueous ammonium chloride solution (20 mL) and tert-butyl methyl ether (30 mL) were added. The organic layer was washed with brine, dried over anhydrous sodium sulfate, and concentrated. The obtained residue was purified by flash column chromatography (hexane:ethyl acetate=20:1 to 1:1), to thereby obtain the title compound (180 mg) having the following physical properties.

TLC: Rf 0.50 (hexane:ethyl acetate=5:1);

$^1$H-NMR (CDCl$_3$): δ 7.24-7.38 (m, 2H), 7.15-7.25 (m, 3H), 6.98 (d, J=8.23 Hz, 1H), 6.72 (d, J=2.56 Hz, 1H), 6.68 (dd, J=8.23, 2.56 Hz, 1H), 5.41-5.60 (m, 1H), 3.98-4.06 (m, 2H), 3.95 (t, J=6.31 Hz, 2H), 3.60 (t, J=5.67 Hz, 2H), 2.74-2.87 (m, 2H), 2.27-2.39 (m, 2H), 2.25 (s, 3H), 2.02-2.17 (m, 2H), 1.50 (s, 9H).

EXAMPLE 11

4-[2-methyl-4-(3-phenylpropoxy)phenyl]-1,2,3,6-tetrahydropyridine hydrochloride

To a methylene chloride (0.5 mL) solution of the compound (180 mg) prepared in Example 10, 4 mol/L hydrogen chloride/1,4-dioxane solution (2.0 mL) was added at room temperature. The reaction solution was stirred at room temperature for 1 hour. The mixture was concentrated. To the obtained residue, diisopropyl ether was added and dried, to thereby obtain the title compound (140 mg) having the following physical properties.

TLC: Rf 0.28 (chloroform:methanol:aqueous ammonia=8:1:0.1);

$^1$H-NMR (CD$_3$OD): δ 7.08-7.32 (m, 5H), 7.00 (d, J=8.23 Hz, 1H), 6.74 (d, J=2.20 Hz, 1H), 6.70 (dd, J=8.23, 2.20 Hz, 1H), 5.54-5.62 (m, 1H), 3.93 (t, J=6.31 Hz, 2H), 3.72-3.84 (m, 2H), 3.34-3.49 (m, 2H), 2.73-2.83 (m, 2H), 2.46-2.64 (m, 2H), 2.27 (s, 3H), 1.96-2.13 (m, 2H).

EXAMPLE 12 tert-butyl 3-[4-[2-methyl-4-(3-phenylpropoxy)phenyl]-3,6-dihydro-1(2H)-pyridinyl]propanoate To a methanol (2 mL) solution of the compound (100 mg) prepared in Example 11, tert-butyl acrylate (0.13 mL) and N,N-diisopropyl ethylamine (0.105 mL) were successively added at room temperature. The reaction mixture was stirred at room temperature for 20 hours. The mixture was concentrated. The obtained residue was purified by flash column chromatography (hexane:ethyl acetate:triethylamine=20:1:0 to 67:33:1), to thereby obtain the title compound (116 mg) having the following physical properties.

TLC: Rf 0.78 (hexane:ethyl acetate:triethylamine=1:1:0.5);

$^1$H-NMR (CDCl$_3$): δ 7.24-7.34 (m, 2H), 7.13-7.24 (m, 3H), 7.00 (d, J=8.23 Hz, 1H), 6.69-6.73 (m, 1H), 6.63-6.69 (m, 1H), 5.44-5.54 (m, 1H), 3.94 (t, J=6.31 Hz, 2H), 3.08-3.17 (m, 2H), 2.74-2.85 (m, 4H), 2.69 (t, J=5.58 Hz, 2H), 2.50 (t, J=7.50 Hz, 2H), 2.29-2.41 (m, 2H), 2.26 (s, 3H), 2.04-2.15 (m, 2H), 1.46 (s, 9H).

EXAMPLE 13

3-[4-[2-methyl-4-(3-phenylpropoxy)phenyl]-3,6-dihydro-1(2H)-pyridinyl]propanoic acid trifluoroacetate

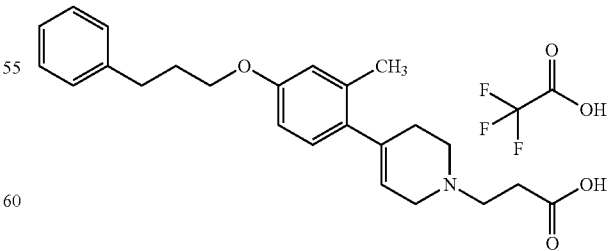

Trifluoroacetic acid (1.0 mL) was added to a methylene chloride (0.5 mL) solution of the compound (116 mg) prepared in Example 12 at room temperature. The reaction solution was stirred at room temperature for 2 hours. The mixture was concentrated. The obtained residue was dissolved in a water-acetonitrile mixed solution. The solution was freeze-dried, to thereby obtain the title compound (100 mg) having the following physical properties.

TLC: Rf 0.44 (chloroform:methanol:aqueous ammonia=8:2:0.4);
$^1$H-NMR (d$_6$-DMSO): δ 7.11-7.36 (m, 5H), 7.01 (d, J=8.23 Hz, 1H), 6.75-6.78 (m, 1H), 6.70-6.75 (m, 1H), 5.48-5.56 (m, 1H), 3.98 (t, J=6.31 Hz, 2H), 3.81-3.90 (m, 2H), 3.40-3.52 (m, 4H), 2.82 (t, J=7.32 Hz, 2H), 2.71-2.78 (m, 2H), 2.52-2.63 (m, 2H), 2.25 (s, 3H), 1.95-2.11 (m, 2H).

EXAMPLES 13-1 to 13-4

The procedure of Example 12 to 13 was similarly performed while using a corresponding amine compound as a substitute for the compound prepared in Example 11. Thus, the compound having the following physical properties was each obtained.

EXAMPLE 13-1

3-[4-[3-(3-phenylpropoxy)phenyl]-3,6-dihydro-1(2H)-pyridinyl]propanoic acid trifluoroacetate TLC: Rf 0.44 (chloroform:methanol:aqueous ammonia=8:2:0.4);
$^1$H-NMR (d$_6$-DMSO): δ 7.11-7.35 (m, 6H), 7.00-7.08 (m, 1H), 6.95-6.99 (m, 1H), 6.83-6.93 (m, 1H), 6.07-6.17 (m, 1H), 4.03 (t, J=6.40 Hz, 2H), 3.84-3.95 (m, 2H), 3.36-3.53 (m, 4H), 2.69-2.87 (m, 6H), 1.98-2.13 (m, 2H).

EXAMPLE 13-2

3-[6-(3-phenylpropoxy)-3',6'-dihydro-3,4'-bipyridine-1'(2'H)-yl]propanoic acid bistrifluoroacetate TLC: Rf 0.44 (chloroform:methanol:aqueous ammonia=8:2:0.4);
$^1$H-NMR (d$_6$-DMSO): δ 8.24 (d, J=2.56 Hz, 1H), 7.80 (dd, J=8.69, 2.56 Hz, 1H), 7.11-7.34 (m, 5H), 6.80 (d, J=8.69 Hz, 1H), 6.04-6.15 (m, 1H), 4.31 (t, J=6.59 Hz, 2H), 3.87-3.98 (m, 2H), 3.47-3.54 (m, 2H), 3.44 (t, J=7.32 Hz, 2H), 2.61-2.88 (m, 6H), 1.98-2.13 (m, 2H).

EXAMPLE 13-3

3-[4-[1-(4-phenylbutyl)-1H-pyrazol-4-yl]-3,6-dihydro-1(2H)-pyridinyl]propanoic acid bistrifluoroacetate TLC: Rf 0.44 (chloroform:methanol:aqueous ammonia=8:2:0.4);
$^1$H-NMR (d$_6$-DMSO): δ 7.79 (s, 1H), 7.59 (s, 1H), 7.20-7.32 (m, 2H), 7.08-7.20 (m, 3H), 5.83-5.94 (m, 1H), 4.10 (t, J=6.86 Hz, 2H), 3.78-3.89 (m, 2H), 3.36-3.54 (m, 4H), 2.79 (t, J=7.32 Hz, 2H), 2.54-2.70 (m, 4H), 1.72-1.89 (m, 2H), 1.50-1.66 (m, 2H).

EXAMPLE 13-4

3-[6-[5-(4-isobutylphenyl)-1,2,4-oxadiazol-3-yl]-3,4-dihydro-2(1H)-isoquinolinyl]propanoic acid trifluoroacetate TLC: Rf 0.19 (chloroform:methanol:aqueous ammonia=8:2:0.4);
$^1$H-NMR (CD$_3$OD): δ 8.12 (d, J=8.23 Hz, 2H), 8.00-8.10 (m, 2H), 7.35-7.50 (m, 3H), 4.58 (s, 2H), 3.65-3.77 (m, 2H), 3.60 (t, J=6.86 Hz, 2H), 3.29-3.39 (m, 2H), 2.94 (t, J=6.86 Hz, 2H), 2.61 (d, J=6.95 Hz, 2H), 1.84-2.06 (m, 1H), 0.95 (d, J=6.59 Hz, 6H).

EXAMPLE 14

7-(benzyloxy)-2,3,4,9-tetrahydro-1H-β-carboline

37% formalin aqueous solution (0.18 mL) was added to methanol-tetrahydrofuran mixed:solution (1:1, 10 mL) of {2-[6-(benzyloxy-1H-indol-3-yl]ethyl}amine (520 mg) under ice cooling. After the reaction solution was stirred for 2 hours, phosphate buffer (pH6.8) (1.0 mL) was added thereto. Then, the reaction solution was stirred for 16 hours. The reaction mixture was filtered, washed by water-methanol mixture solution, to thereby obtain the title compound (300 mg) having the following properties.

TLC: Rf 0.64 (chloroform:methanol:aqueous ammonia=8:2:0.4);
$^1$H-NMR (d$_6$-DMSO): δ 10.48 (s, 1H), 7.42-7.52 (m, 2H), 7.33-7.41 (m, 2H), 7.26-7.34 (m, 1H), 7.22 (d, J=8.42 Hz, 1H), 6.86 (d, J=2.38 Hz, 1H), 6.67 (dd, J=8.42, 2.38 Hz, 1H), 5.08 (s, 2H), 3.66 (s, 2H), 3.33-3.40 (m, 1H), 2.79-2.93 (m, 2H), 2.57-2.70 (m, 2H).

EXAMPLE 15 tert-butyl 7-(benzyloxy)-2-(3-tert-butoxy-3-oxopropyl)-1,2,3,4-tetrahydro-9H-β-carboline-9-carboxylate The procedure similar to that of Example 12 was carried out using the compound prepared in Example 14 in place of the compound prepared in Example 11. The obtained compound was protected using di-tert-butyl dicarbonate, to thereby obtain the title compound having the following physical properties.

TLC: Rf 0.45 (hexane:ethyl acetate=3:1);
$^1$H-NMR (CDCl$_3$): δ 7.80-7.86 (m, 1H), 7.43-7.50 (m, 2H), 7.30-7.42 (m, 3H), 7.27 (d, J=8.42 Hz, 1H), 6.93 (dd, J=8.42, 2.38 Hz, 1H), 5.12 (s, 2H), 3.92 (s, 2H), 2.93 (t, J=7.50 Hz, 2H), 2.79-2.87 (m, 2H), 2.64-2.74 (m, 2H), 2.54 (t, J=7.50 Hz, 2H), 1.65 (s, 9H), 1.45 (s, 9H).

EXAMPLE 16 tert-butyl 2-(3-tert-butoxy-3-oxopropyl)-7-hydroxy-1,2,3,4-tetrahydro-9H-β-carboline-9-carboxylate ASCA-II catalyst (4.5% palladium-0.5% platinum/carbon) (140 mg) was added to a methanol-ethyl acetate mixed solution (4:1, 5 mL) of the compound (290 mg) prepared in Example 15 at room temperature under an argon gas atmosphere. The reaction mixture was stirred under a hydrogen gas atmosphere for 3 hours. The mixture was replaced with an argon gas atmosphere. The mixture was filtered using Celite (trade name), and the filtrate was concentrated. The obtained residue was purified by silica gel column chromatography (hexane:ethyl acetate=1:1), to thereby obtain the title compound (203 mg) having the following physical properties.

TLC: Rf 0.24 (hexane:ethyl acetate=3:1)
$^1$H-NMR (CDCl$_3$): δ 7.54-7.68 (m, 1H), 7.20 (d, J=8.42 Hz, 1H), 6.76 (dd, J=8.42, 2.29 Hz, 1H), 4.54-5.36 (m, 1H), 3.90 (s, 2H), 2.87-3.03 (m, 2H), 2.77-2.88 (m, 2H), 2.60-2.77 (m, 2H), 2.45-2.58 (m, 2H), 1.66 (s, 9H), 1.45 (s, 9H).

EXAMPLE 17 tert-butyl 2-(3-tert-butoxy-3-oxopropyl)-7-(3-phenylpropoxy)-1,2,3,4-tetrahydro-9H-β-carboline-9-carboxylate To an anhydrous tetrahydrofuran (2.0 mL) solution of the compound (112 mg) prepared in Example 16, 3-phenylpropan-1-ol (0.074 mL), 1,1'-azobis(N,N'-dimethylformamide) (93 mg), and triphenyl phosphine (141 mg) were successively added under an argon gas atmosphere. The reaction solution was stirred at room temperature for 48 hours. To the reaction solution, tert-butyl methyl ether (3 mL) was added, the generated insoluble matter was filtered, and the filtrate was concentrated. The obtained residue was purified by silica gel column chromatography (hexane:ethyl acetate=5:1), to thereby obtain the title compound (84 mg) having the following physical properties.

TLC: Rf 0.71 (hexane:ethyl acetate=1:1);
$^1$H-NMR (CDCl$_3$): δ 7.66-7.76 (m, 1H), 7.15-7.35 (m, 6H), 6.86 (dd, J=8.42, 2.20Hz, 1H), 4.02 (t, J=6.31 Hz, 2H), 3.91 (s, 2H), 2.93 (t, J=7.50Hz, 2H), 2.78-2.89 (m, 4H), 2.64-2.75 (m, 2H), 2.54 (t, J=7.50Hz, 2H), 2.05-2.20 (m, 2H), 1.65 (s, 9H), 1.45 (s, 9H).

EXAMPLE 18

3-[7-(3-phenylpropoxy)-1,3,4,9-tetrahydro-2H-β-carbolin-2-yl]propanoic acid trifluoroacetate

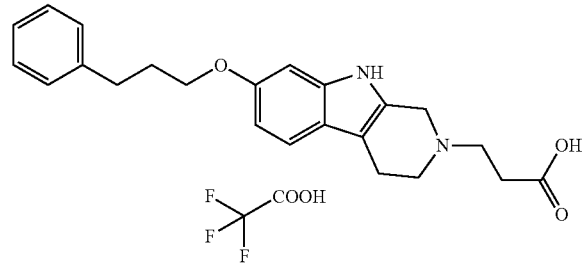

The procedure of Example 13 was similarly performed while using the compound prepared in Example 17 as a substitute for the compound prepared in Example 12. Thus, the compound having the following physical properties was obtained.

TLC: Rf 0.12 (chloroform:methanol:aqueous ammonia=8:2:0.4);
$^1$H-NMR (CD$_3$OD): δ 7.34 (d, J=8.60Hz, 1H), 7.07-7.29 (m, 5H), 6.86 (d, J=2.20Hz, 1H), 6.74 (dd, J=8.60, 2.20Hz, 1H), 4.53 (s, 2H), 3.97 (t, J=6.22 Hz, 2H), 3.67-3.78 (m, 2H), 3.63 (t, J=6.95 Hz, 2H), 3.03-3.19 (m, 2H), 2.94 (t, J=6.95 Hz, 2H), 2.75-2.87 (m, 2H), 2.00-2.16 (m, 2H).

EXAMPLE 18-1

3-{7-[3-(4-chlorophenyl)propoxy]-1,3,4,9-tetrahydro-2H-β-carbolin-2-yl}propanoic acid The procedures similar to that of Examples 17 and 18 were carried out using 3-(4-chlorophenyl)propan-1-ol in place of 3-phenylpropan-1-ol. As required, the resultants were converted into hydrochloride, to thereby obtain the title compounds each having the following physical properties.
(Trifluoroacetate)
TLC: Rf 0.11 (chloroform:methanol:aqueous ammonia=8:2:0.4);
$^1$H-NMR (CD$_3$OD): δ 7.35 (d, J=8.60Hz, 1H), 7.25 (d, J=8.79 Hz, 2H), 7.19 (d, J=8.79 Hz, 2H), 6.85 (d, J=2.01 Hz, 1H), 6.74 (dd, J=8.60, 2.01 Hz, 1H), 4.53 (s, 2H), 3.96 (t, J=6.13 Hz, 2H), 3.67-3.80 (m, 2H), 3.63 (t, J=6.95 Hz, 2H), 3.02-3.16 (m, 2H), 2.94 (t, J=6.95 Hz, 2H), 2.74-2.86 (m, 2H), 1.98-2.19 (m, 2H).
(Hydrochloride)
TLC: Rf 0.11 (chloroform:methanol:aqueous ammonia=8:2:0.4);
$^1$H-NMR (CD$_3$OD): δ 7.34 (d, J=8.78 Hz, 1H), 7.25 (d, J=8.78 Hz, 2H), 7.19 (d, J=8.78 Hz, 2H), 6.85 (d, J=2.20 Hz, 1H), 6.73 (dd, J=8.78, 2.20 Hz, 1H), 4.40-4.65 (m, 2H), 3.96 (t, J=6.13 Hz, 2H), 3.57-3.78 (m, 4H), 3.05-3.16 (m, 2H), 2.94 (t, J=7.04 Hz, 2H), 2.75-2.86 (m, 2H), 1.97-2.17 (m, 2H).

EXAMPLE 19

3-[6-(3-phenylpropoxy)-1,3,4,9-tetrahydro-2H-β-carbolin-2-yl]propanoic acid

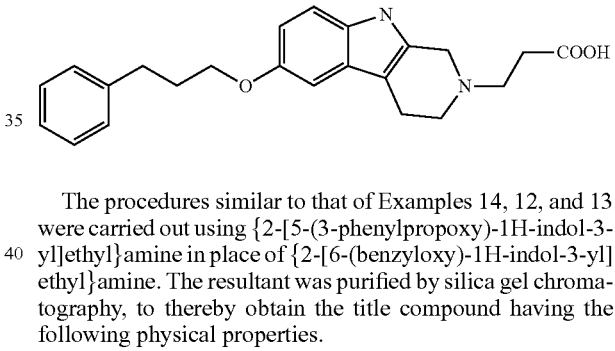

The procedures similar to that of Examples 14, 12, and 13 were carried out using {2-[5-(3-phenylpropoxy)-1H-indol-3-yl]ethyl}amine in place of {2-[6-(benzyloxy)-1H-indol-3-yl]ethyl}amine. The resultant was purified by silica gel chromatography, to thereby obtain the title compound having the following physical properties.

TLC: Rf 0.16 (chloroform:methanol:aqueous ammonia=8:2:0.4);
$^1$H-NMR (CD$_3$OD): δ 6.99-7.28 (m, 6H), 6.83 (d, J=2.29 Hz, 1H), 6.72 (dd, J=8.69, 2.29 Hz, 1H), 4.33 (s, 2H), 3.88 (t, J=6.04 Hz, 2H), 3.51 (t, J=6.04 Hz, 2H), 3.36 (t, J=6.77 Hz, 2H), 2.95 (t, J=6.04 Hz, 2H), 2.67-2.77 (m, 2H), 2.57 (t, J=6.77 Hz, 2H), 1.90-2.06 (m, 2H).

EXAMPLE 20

N'-hydroxy-4-(hydroxymethyl)benzenecarboxylmidamide

A methanol (50 mL) solution of hydroxylamine hydrochloride (5.2 g), 4-(hydroxymethyl)benzonitrile (5.0 g), and sodium hydrogen carbonate (12.6 g) was refluxed under heating for 20 hours. The reaction solution was cooled at room temperature, and then filtered through Celite (trade name). The filtrate was concentrated, to thereby obtain the title compound having the following physical properties. The obtained compound was used for the next reaction without further purification.

TLC: Rf 0.21 (chloroform:methanol:aqueous ammonia=8:1:0.1);

$^1$H-NMR (CDCl$_3$): δ 7.61 (d, J=8.10 Hz, 2H), 7.37 (d, J=8.10 Hz, 2H), 4.61 (s, 2H).

EXAMPLE 21

{4-[5-(4-isobutylphenyl)-1,2,4-oxadiazol-3-yl]phenyl}methanol

The compound prepared in Example 20 was dissolved in N,N-dimethylformamide (60 mL). To this solution, 4-isobutylbenzoic acid (6.7 g), 1-ethyl-3-(3-dimethylaminopropyl)carbodiimide hydrochloride (7.28 g), and 1-hydroxybenzotriazole monohydrate (5.1 g) were added at room temperature. The reaction solution was stirred at room temperature for 30 minutes, and stirred at 140° C. for 2 hours. The reaction mixture was added with water (50 mL), and extracted with an ethyl acetate-hexane (10:1) mixed solution. The extract was successively washed with 0.5 mol/L hydrochloric acid, saturated sodium hydrogen carbonate solution, and water. The resultant was dried over anhydrous sodium sulfate, and concentrated. The obtained residue was purified by silica gel column chromatography (hexane to hexane:ethyl acetate=1:1), to thereby obtain the title compound (4.14 g) having the following physical properties.

TLC: Rf 0.54 (hexane:ethyl acetate=1:1);
$^1$H-NMR (CD$_3$OD): δ 8.13 (d, J=8.60 Hz, 2H), 8.11 (d, J=8.42 Hz, 2H), 7.53 (d, J=8.60 Hz, 2H), 7.41 (d, J=8.42 Hz, 2H), 4.69 (s, 2H), 2.61 (d, J=7.14 Hz, 2H), 1.86-2.04 (m, 1H), 0.94 (d, J=6.59 Hz, 6H).

EXAMPLE 22

4-[5-(4-isobutylphenyl)-1,2,4-oxadiazol-3-yl]benzaldehyde

Dimethyl sulfoxide (2.13 mL) was added to a methylene chloride (40 mL) solution of oxalyl chloride (1.74 mL) at −78° C. under an argon gas atmosphere. After stirring the reaction mixture at −78° C. for 10 minutes, the compound (2.14 g) prepared in Example 21 and N,N-diisopropylethylamine (14.6 mL) were added at −78° C. The reaction mixture was stirred at room temperature for 3 hours. The mixture was concentrated, and the obtained residue was diluted with ethyl acetate. The obtained solution was successively washed with 0.5 mol/L potassium hydrogen sulfate solution, 1 mol/L hydrochloric acid, saturated sodium hydrogen carbonate solution, and water. The resultant was dried over anhydrous sodium sulfate, and concentrated. The obtained residue was purified by silica gel column chromatography (hexane:ethyl acetate=5:1), to thereby obtain the title compound (1.4 g) having the following physical properties.

TLC: Rf 0.61 (hexane:ethyl acetate=3:1);
$^1$H-NMR (CDCl$_3$): δ 10.11 (s, 1H), 8.36 (d, J=8.23 Hz, 2H), 8.13 (d, J=8.42 Hz, 2H), 8.03 (d, J=8.42 Hz, 2H), 7.34 (d, J=8.23 Hz, 2H), 2.59 (d, J=7.32 Hz, 2H), 1.82-2.07 (m, 1H), 0.94 (d, J=6.59 Hz, 6H).

EXAMPLE 23

2-({4-[5-(4-isobutylphenyl)-1,2,4-oxadiazol-3-yl]benzyl}amino)ethanol

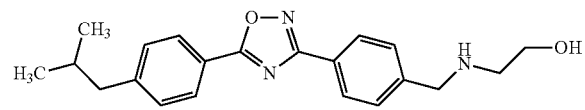 [SMILES: CC(C)Cc1ccc(-c2nc(-c3ccc(CNCCO)cc3)no2)cc1]

To a 5% acetic acid containing 1,2-dichloroethane solution (1.0 mL) of the compound (100 mg) prepared in Example 22, 2-aminoethanol (0.030 mL) and sodium triacetoxyborohydride (138 mg) were added. The reaction mixture was stirred for 18 hours. The mixture was concentrated. The obtained residue was diluted with ethyl acetate, and successively washed with saturated sodium hydrogen carbonate solution and water. The resultant was dried over anhydrous magnesium sulfate, and concentrated. The obtained residue was purified by silica gel column chromatography (chloroform:methanol:aqueous ammonia=160:10:1), to thereby obtain the title compound (75 mg) having the following physical properties.

TLC: Rf 0.48 (chloroform:methanol:aqueous ammonia=8:1:0.1);
$^1$H-NMR (CD$_3$OD): δ 8.12-8.16 (m, 4H), 7.58 (d, J=8.23 Hz, 2H), 7.41 (d, J=8.23 Hz, 2H), 4.02 (s, 2H), 3.73 (t, J=5.50 Hz, 2H), 2.88 (t, J=5.50 Hz, 2H), 2.60 (d, J=7.32 Hz, 2H), 1.91-2.04 (m, 1H), 0.94 (d, J=6.59 Hz, 6H).

EXAMPLE 24 tert-butyl 3-(3-oxo-1-piperidinyl)propanoate

The procedure of Example 12 to 22 was similarly performed while using piperidin-3-ol as a substitute for the compound prepared in Example 11. Thus, the compound having the following physical properties was obtained.

TLC: Rf 0.71 (chloroform:methanol:aqueous ammonia=8:1:0.1);
$^1$H-NMR (CDCl$_3$): δ 3.02 (s, 2H), 2.73 (t, J=7.14 Hz, 2H), 2.64-2.70 (m, 2H), 2.40 (t, J=7.14 Hz, 2H), 2.35 (t, J=6.77 Hz, 2H), 1.87-2.01 (m, 2H), 1.44 (s, 9H).

EXAMPLE 25 tert-butyl 3-{3-[4-(3-phenylpropoxy)benzylidene]-1-piperidinyl}propanoate (Mixture of E and Z isomers)

Sodium hydride (60% in-oil dispersion, 800 mg) was added at room temperature to dimethyl sulfoxide (20 mL) under an argon gas atmosphere. The reaction mixture was stirred at 60° C. for 3 hours. The reaction mixture was cooled at room temperature. From the total obtained solution, 1.3 mL was added at room temperature to a dimethyl sulfoxide solution (2.0 mL) of triphenyl[4-(4-phenylbutyl)benzyl]phosphonium bromide salt (830 mg). The reaction mixture was stirred at room temperature for 30 minutes, and added with a dimethyl sulfoxide (2.0 mL) solution of the compound (830 mg) prepared in Example 24. The reaction mixture was stirred at 50° C. for 18 hours. The mixture was added with water (10 mL), and extracted with diethyl ether. The extract was washed with water, dried over anhydrous sodium sulfate, and concentrated. The obtained residue was purified by silica gel column chromatography (hexane:ethyl acetate=3:1), to thereby obtain the title compound (112 mg) having the following physical properties.

TLC: Rf 0.44 (hexane:ethyl acetate=1:1);
$^1$H-NMR (CDCl$_3$): δ 7.16-7.35 (m, 5H), 7.04-7.16 (m, 2H), 6.84 (d, J=7.87 Hz, 2H), 6.24-6.34 (m, 1H), 3.89-4.03 (m, 2H), 2.98-3.21 (m, 2H), 2.76-2.89 (m, 2H), 2.60-2.75 (m, 2H), 2.51-2.62 (m, 2H), 2.44-2.52 (m, 1H), 2.31-2.44 (m, 2H), 2.20-2.31 (m, 1H), 2.03-2.16 (m, 2H), 1.66-1.82 (m, 1H), 1.51-1.67 (m, 1H), 1.36-1.49 (m, 9H).

EXAMPLES 26-1 to 26-16

The procedure of Example 6 was similarly performed while using a corresponding aldehyde compound as a substitute for the compound prepared in Example 5. Thus, the compound having the following physical properties was each obtained.

EXAMPLE 26-1 methyl 1-[(6-{[(2E)-3-(4-fluorophenyl)-2-methyl-propan-2-enyl]oxy}-1-methyl-3,4-dihydronaphthalen-2-yl)methyl]azetidine-3-carboxylate TLC: Rf 0.27 (hexane:ethyl acetate=1:3);
$^1$H-NMR (CDCl$_3$): δ 7.17-7.30 (m, 3H), 6.98-7.07 (m, 2H), 6.74-6.82 (m, 2H), 6.58 (s, 1H), 4.55 (s, 2H), 3.71 (s, 3H), 3.50-3.61 (m, 2H), 3.25-3.41 (m, 5H), 2.64-2.74 (m, 2H), 2.22-2.32 (m, 2H), 2.09 (s, 3H), 1.94 (d, J=1.46 Hz, 3H).

EXAMPLE 26-2 methyl 1-[(6-{[(2S)-2-(4-fluorobenzyl)butyl]oxy}-1-methyl-3,4-dihydronaphthalen-2-yl)methyl]azetidine-3-carboxylate

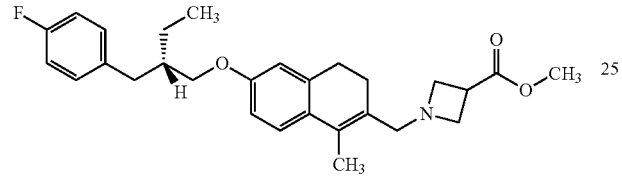

TLC: Rf 0.34 (chloroform:methanol=9:1);
$^1$H-NMR (CDCl$_3$): δ 7.20 (d, J=8.42 Hz, 1H), 7.06-7.16 (m, 2H), 6.86-7.01 (m, 2H), 6.51-6.77 (m, 2H), 3.88-4.05 (m, 2H), 3.78 (d, J=4.94 Hz, 2H), 3.74 (s, 3H), 3.52-3.62 (m, 5H), 2.64-2.80 (m, 4H), 2.26-2.36 (m, 2H), 2.13 (s, 3H), 1.89-2.01 (m, 1H), 1.39-1.56 (m, 2H), 0.97 (t, J=7.20 Hz, 3H).

EXAMPLE 26-3 methyl 1-[(6-{[(2R)-2-(4-fluorobenzyl)-3-methylbutyl]oxy}-1-methyl-3,4-dihydronaphthalen-2-yl)methyl]azetidine-3-carboxylate

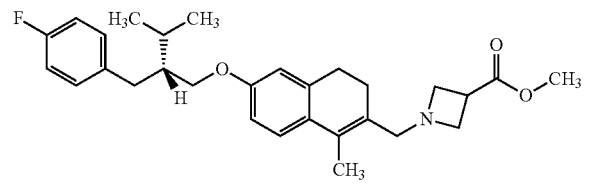 [SMILES: COC(=O)C1CN(CC2=C(C)c3ccc(OC[C@@H](Cc4ccc(F)cc4)C(C)C)cc3CC2)C1]

TLC: Rf 0.34 (chloroform:methanol=9:1);
$^1$H-NMR (CDCl$_3$): δ 7.07-7.21 (m, 3H), 6.80-7.02 (m, 2H), 6.49-6.72 (m, 2H), 3.80 (d, J=5.12 Hz, 2H), 3.71 (s, 3H), 3.58-3.68 (m, 2H), 3.22-3.49 (m, 5H), 2.57-2.83 (m, 4H), 2.18-2.34 (m, 2H), 2.08 (s, 3H), 1.79-1.99 (m, 2H), 0.97-1.03 (m, 6H).

EXAMPLE 26-4

1-chloro-6-{[(2S)-3-(4-fluorophenyl)-2-methylpropyl]oxy}-3,4-dihydronaphthalene-2-carbaldehyde TLC: Rf 0.60 (hexane:ethyl acetate=10:1);
$^1$H-NMR (CDCl$_3$): δ 10.33 (s, 1H), 7.79 (d, J=8.78 Hz, 1H), 7.06-7.17 (m, 2H), 6.89-7.04 (m, 2H), 6.80 (dd, J=8.78, 2.56 Hz, 1H), 6.72 (d, J=2.56 Hz, 1H), 3.81 (d, J=5.85 Hz, 2H), 2.75-2.89 (m, 3H), 2.47-2.68 (m, 3H), 2.10-2.32 (m, 1H), 1.03 (d, J=6.77 Hz, 3H).

EXAMPLE 26-5 methyl 1-[(6-{[(2S)-3-(4-fluorophenyl)-2-methylpropyl]oxy}-4,4-dimethyl-3,4-dihydronaphthalen-2-yl)methyl]azetidine-3-carboxylate TLC: Rf 0.45 (chloroform:methanol=20:1);
$^1$H-NMR (CDCl$_3$): δ 7.08-7.18 (m, 2H), 6.89-7.02 (m, 3H), 6.83 (d, J=2.2 Hz, 1H), 6.62 (dd, J=8.2, 2.2 Hz, 1H), 6.28 (s, 1H), 3.76 (d, J=5.9 Hz, 2H), 3.71 (s, 2H), 3.56 (t, J=6.2 Hz, 2H), 3.23-3.43 (m, 3H), 3.13 (s, 2H), 2.86 (dd, J=13.4, 6.0 Hz, 1H), 2.52 (dd, J=13.4, 7.7 Hz, 1H), 2.07-2.26 (m, 4H), 1.22 (s, 6H), 1.00 (d, J=6.8 Hz, 3H).

EXAMPLE 26-6 methyl 1-({6-[3-(4-fluorophenyl)propoxy]-1-benzothien-2-yl}methyl)azetidine-3-carboxylate TLC: Rf 0.45 (chloroform:methanol=20:1);
$^1$H-NMR (CDCl$_3$): δ 7.56 (d, J=8.8 Hz, 1H), 7.23 (d, J=2.4 Hz, 1H), 7.16 (dd, J=8.6, 5.5 Hz, 2H), 6.88-7.06 (m, 4H), 3.99 (t, J=6.2 Hz, 2H), 3.83 (s, 2H), 3.71 (s, 3H), 3.55-3.67 (m, 2H), 3.29-3.45 (m, 3H), 2.80 (t, J=7.3 Hz, 2H), 2.02-2.18 (m, 2H).

EXAMPLE 26-7 methyl 1-{[1-chloro-6-(3-cyclohexylpropoxy)-3,4-dihydronaphthalen-2-yl]methyl}azetidine-3-carboxylate TLC: Rf 0.40 (chloroform:methanol=20:1);
$^1$H-NMR (CDCl$_3$): δ 7.51 (d, J=8.6 Hz, 1H), 6.74 (dd, J=8.6, 2.7 Hz, 1H), 6.67 (d, J=2.7 Hz, 1H), 3.95 (t, J=6.7 Hz, 2H), 3.71 (s, 3H), 3.57 (t, J=7.0 Hz, 2H), 3.27-3.49 (m, 5H), 2.76 (t, J=7.1 Hz, 2H), 2.43 (t, J=7.1 Hz, 2H), 1.60-1.88 (m, 7H), 1.09-1.39 (m, 6H), 0.82-1.01 (m, 2H).

EXAMPLE 26-8 methyl 1-({1-chloro-6-[3-(4-chlorophenyl)propoxy]-3,4-dihydronaphthalen-2-yl}methyl)azetidine-3-carboxylate TLC: Rf 0.36 (chloroform:methanol=20:1);
$^1$H-NMR (CDCl$_3$): δ 7.51 (d, J=8.6 Hz, 1H), 7.25 (d, J=8.2 Hz, 2H), 7.13 (d, J=8.2 Hz, 2H), 6.73 (dd, J=8.6, 2.7 Hz, 1H), 6.66 (d, J=2.7 Hz, 1H), 3.94 (t, J=6.1 Hz, 2H), 3.71 (s, 3H), 3.56 (t, J=6.5 Hz, 2H), 3.28-3.47 (m, 5H), 2.70-2.83 (m, 4H), 2.43 (t, J=8.4 Hz, 2H), 2.00-2.13 (m, 2H).

EXAMPLE 26-9 methyl 1-[(1-chloro-6-{[(2S)-3-(4-chlorophenyl)-2-methylpropyl]oxy}-3,4-dihydronaphthalen-2-yl)methyl]azetidine-3-carboxylate

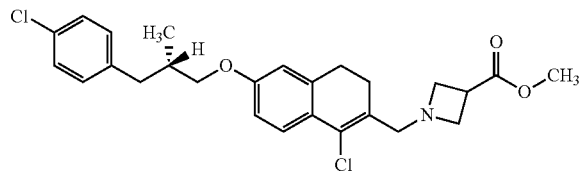 [SMILES: COC(=O)C1CN(CC2=C(Cl)c3ccc(OC[C@@H](C)Cc4ccc(Cl)cc4)cc3CC2)C1]

TLC: Rf 0.45 (chloroform:methanol=20:1);
¹H-NMR (CDCl₃): δ 7.51 (d, J=8.6 Hz, 1H), 7.24 (d, J=8.4 Hz, 2H), 7.10 (d, J=8.4 Hz, 2H), 6.72 (dd, J=8.6, 2.7 Hz, 1H), 6.65 (d, J=2.7 Hz, 1H), 3.76 (d, J=5.9 Hz, 2H), 3.71 (s, 2H), 3.57 (t, J=7.2 Hz, 2H), 3.28-3.49 (m, 6H), 2.84 (dd, J=13.5, 6.3 Hz, 1H), 2.75 (t, J=7.5 Hz, 2H), 2.52 (dd, J=13.5, 7.7 Hz, 1H), 2.43 (t, J=7.5 Hz, 2H), 2.13-2.28 (m, 1H), 1.00 (d, J=6.8 Hz, 3H).

EXAMPLE 26-10 methyl 1-({6-[2-(4-fluorophenoxy)ethoxy]-1-methyl-3,4-dihydronaphthalen-2-yl}methyl)azetidine-3-carboxylate TLC: Rf 0.15 (hexane:ethyl acetate=1:5);
¹H-NMR (CDCl₃): δ 7.19 (d, J=8.42 Hz, 1H), 6.84-7.01 (m, 4H), 6.70-6.79 (m, 2H), 4.23-4.34 (m, 4H), 3.70 (s, 3H), 3.50-3.59 (m, 2H), 3.25-3.40 (m, 5H), 2.62-2.73 (m, 2H), 2.22-2.31 (m, 2H), 2.09 (s, 3H).

EXAMPLE 26-11 methyl 1-({6-[2-(4-fluorophenoxy)propoxy]-1-methyl-3,4-dihydronaphthalen-2-yl}methyl)azetidine-3-carboxylate TLC: Rf 0.45 (hexane:ethyl acetate=1:6);
¹H-NMR (CDCl₃): δ 7.19 (d, J=8.42 Hz, 1H), 6.87-7.01 (m, 4H), 6.67-6.75 (m, 2H), 4.56-4.69 (m, 1H), 4.14 (dd, J=9.79, 5.67 Hz, 1H), 3.99 (dd, J=9.79, 5.03 Hz, 1H), 3.70 (s, 3H), 3.49-3.59 (m, 2H), 3.24-3.40 (m, 5H), 2.62-2.72 (m, 2H), 2.21-2.31 (m, 2H), 2.08 (s, 3H), 1.42 (d, J=6.40 Hz, 3H).

EXAMPLE 26-12 methyl 1-({6-[(4-isobutyl-1,3-oxazol-2-yl)methoxy]-1-methyl-3,4-dihydronaphthalen-2-yl}methyl)azetidine-3-carboxylate TLC: Rf 0.12 (hexane:ethyl acetate=1:2);
¹H-NMR (CDCl₃): δ 7.39 (t, J=1.00 Hz, 1H), 7.18 (d, J=8.50 Hz, 1H), 6.83 (dd, J=8.50, 2.50 Hz, 1H), 6.79 (d, J=2.50 Hz, 1H), 5.09 (s, 2H), 3.70 (s, 3H), 3.51-3.57 (m, 2H), 3.25-3.37 (m, 5H), 2.64-2.71 (m, 2H), 2.39 (dd, J=7.00, 1.00 Hz, 2H), 2.22-2.30 (m, 2H), 2.08 (s, 3H), 1.91-2.03 (m, 1H), 0.93 (d, J=6.50 Hz, 6H).

EXAMPLE 26-13 methyl 1-({6-[3-(4-methoxyphenyl)propoxy]-1-methyl-3,4-dihydronaphthalen-2-yl}methyl)azetidine-3-carboxylate TLC: Rf 0.42 (chloroform:methanol=20:1);
¹H-NMR (CDCl₃): δ 7.18 (d, J=8.2 Hz, 1H), 7.12 (d, J=8.6 Hz, 2H), 6.83 (d, J=8.6 Hz, 2H), 6.66-6.74 (m, 2H), 3.94 (t, J=6.2 Hz, 2H), 3.79 (s, 3H), 3.70 (s, 2H), 3.50-3.58 (m, 2H), 3.22-3.40 (m, 6H), 2.75 (t, J=7.5 Hz, 2H), 2.67 (t, J=7.3 Hz, 2H), 2.26 (t, J=7.5 Hz, 2H), 1.99-2.13 (m, 5H).

EXAMPLE 26-14 methyl 1-({6-[3-(4-fluorophenoxy)propoxy]-1-methyl-3,4-dihydronaphthalen-2-yl}methyl)azetidine-3-carboxylate TLC: Rf 0.31 (hexane:ethyl acetate=1:5);
¹H-NMR (CDCl₃): δ 7.19 (d, J=8.42 Hz, 1H), 6.91-7.00 (m, 2H), 6.80-6.87 (m, 2H), 6.73 (dd, J=8.42, 2.74 Hz, 1H), 6.69 (d, J=2.74 Hz, 1H), 4.07-4.19 (m, 4H), 3.70 (s, 3H), 3.50-3.59 (m, 2H), 3.24-3.41 (m, 5H), 2.62-2.71 (m, 2H), 2.18-2.31 (m, 4H), 2.08 (s, 3H).

EXAMPLE 26-15 methyl 1-({6-[3-{[tert-butyl(dimethyl)silyl]oxy}-2-(4-fluorobenzyl)propoxy]-1-methyl-3,4-dihydronaphthalen-2-yl}methyl)azetidine-3-carboxylate TLC: Rf 0.50 (chloroform:methanol=9:1);
¹H-NMR (CDCl₃): δ 7.08-7.19 (m, 3H), 6.89-6.98 (m, 2H), 6.61-6.71 (m, 2H), 3.87 (dd, J=5.67, 2.20 Hz, 2H), 3.70 (s, 3H), 3.59-3.68 (m, 2H), 3.50-3.58 (m, 2H), 3.27 (s, 5H), 2.73 (d, J=7.68 Hz, 2H), 2.62-2.70 (m, 2H), 2.11-2.30 (m, 3H), 2.08 (s, 3H), 0.89 (s, 9H), 0.01 (s, 6H).

EXAMPLE 26-16 methyl1-[(2E)-3-(4-{[(2S)-3-(4-chlorophenyl)-2-methylpropyl]oxy}phenyl)but-2-enyl]azetidine-3-carboxylate TLC: Rf 0.18 (hexane:ethyl acetate=1:3);
¹H-NMR (CDCl₃): δ 7.30 (d, J=9.00 Hz, 2H), 7.24 (d, J=8.50 Hz, 2H), 7.10 (d, J=8.50 Hz, 2H), 6.82 (d, J=9.00 Hz, 2H), 5.63 (tq, J=7.00, 1.00 Hz, 1H), 3.75 (d, J=6.00 Hz, 2H), 3.72 (s, 3H), 3.54-3.60 (m, 2H), 3.30-3.37 (m, 3H), 3.26 (d, J=7.00 Hz, 2H), 2.84 (dd, J=13.50, 6.50 Hz, 1H), 2.52 (dd, J=13.50, 7.50 Hz, 1H), 2.15-2.26 (m, 1H), 2.04 (d, J=1.00 Hz, 3H), 1.00 (d, J=7.00 Hz, 3H).

EXAMPLES 27-1 to 27-16

The procedure of Example 7 was similarly performed while using each of the compounds prepared in Examples 26-1 to 26-16 as a substitute for the compound prepared in Example 6. Thus, compounds each having the following physical properties was obtained.

EXAMPLE 27-1

1-[(6-{[(2E)-3-(4-fluorophenyl)-2-methylpropan-2-enyl]oxy}-1-methyl-3,4-dihydronaphthalen-2-yl)methyl]azetidine-3-carboxylic acid TLC: Rf 0.23 (chloroform:methanol:aqueous ammonia=80:20:4);
¹H-NMR (CDCl₃): δ 7.13-7.24 (m, 3H), 6.88-6.98 (m, 2H), 6.74 (dd, J=8.40, 2.54 Hz, 1H), 6.68 (d, J=2.54 Hz, 1H), 6.50 (s, 1H), 4.49 (s, 2H), 4.10-4.21 (m, 2H), 3.95-4.07 (m, 2H), 3.92 (s, 2H), 3.16-3.30 (m, 1H), 2.62-2.71 (m, 2H), 2.15-2.25 (m, 2H), 2.12 (s, 3H), 1.86 (d, J=1.10 Hz, 3H).

EXAMPLE 27-2

1-[(6-{[(2S)-2-(4-fluorobenzyl)butyl]oxy}-1-methyl-3,4-dihydronaphthalen-2-yl)methyl]azetidine-3-carboxylic acid

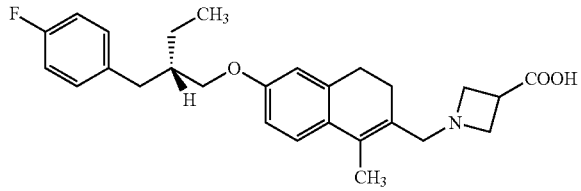 [SMILES: CC[C@@H](COc1ccc2c(c1)CCC(CN1CC(C(=O)O)C1)=C2C)Cc1ccc(F)cc1]

TLC: Rf 0.13 (1-butanol:acetic acid:water=20:4:1);
$^1$H-NMR (CD$_3$OD): δ 7.29 (d, J=8.60 Hz, 1H), 7.10-7.19 (m, 2H), 6.90-7.01 (m, 2H), 6.72 (dd, J=8.60, 2.56 Hz, 1H), 6.67 (d, J=2.56 Hz, 1H), 4.09-4.25 (m, 4H), 4.06 (s, 2H), 3.80 (d, J=5.12 Hz, 2H), 3.34-3.48 (m, 1H), 2.64-2.78 (m, 4H), 2.20 (s, 3H), 2.15-2.32 (m, 2H), 1.83-2.03 (m, 1H), 1.37-1.58 (m, 2H), 0.98 (t, J=7.50 Hz, 3H)

EXAMPLE 27-3

1-[(6-{[(2R)-2-(4-fluorobenzyl)-3-methylbutyl]oxy}-1-methyl-3,4-dihydronaphthalen-2-yl)methyl]azetidine-3-carboxylic acid

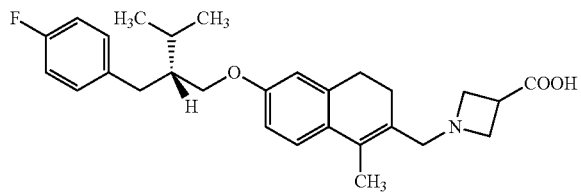 [SMILES: CC1=C(CN2CC(C(=O)O)C2)CCc2cc(OC[C@@H](Cc3ccc(F)cc3)C(C)C)ccc21]

TLC: Rf 0.13 (1-butanol:acetic acid:water=20:4:1);
$^1$H-NMR (CD$_3$OD): δ 7.28 (d, J=8.42 Hz, 1H), 7.11-7.22 (m, 2H), 6.88-7.03 (m, 2H), 6.68 (dd, J=8.42, 2.56 Hz, 1H), 6.62 (d, J=2.56 Hz, 1H), 4.08-4.23 (m, 4H), 4.06 (s, 2H), 3.78-3.89 (m, 2H), 3.30-3.48 (m, 1H), 2.61-2.83 (m, 4H), 2.19 (s, 3H), 2.16-2.27 (m, 2H), 1.80-1.97 (m, 2H), 1.03 (d, J=6.30 Hz, 3H), 1.01 (d, J=6.60 Hz, 3H).

EXAMPLE 27-4

1-[(1-chloro-6-{[(2S)-3-(4-fluorophenyl)-2-methylpropyl]oxy}-3,4-dihydronaphthalen-2-yl)methyl]azetidine-3-carboxylic acid

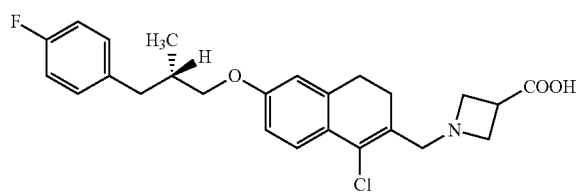 [SMILES: C[C@H](COc1ccc2c(c1)CCC(CN1CC(C(=O)O)C1)=C2Cl)Cc1ccc(F)cc1]

TLC: Rf 0.16 (1-butanol:acetic acid:water=20:4:1);
$^1$H-NMR (CD$_3$OD): δ 7.55 (d, J=8.60 Hz, 1H), 7.10-7.25 (m, 2H), 6.90-7.03 (m, 2H), 6.80 (dd, J=8.60, 2.38 Hz, 1H), 6.75 (d, J=2.38 Hz, 1H), 4.19-4.27 (m, 4H), 4.17 (s, 2H), 3.75-3.86 (m, 2H), 3.36-3.49 (m, 1H), 2.77-2.90 (m, 3H), 2.55 (dd, J=13.36, 7.68 Hz, 1H), 2.40-2.50 (m, 2H), 2.09-2.27 (m, 1H), 1.01 (d, J=6.77 Hz, 3H).

EXAMPLE 27-5

1-[(6-{[(2S)-3-(4-fluorophenyl)-2-methylpropyl]oxy}-4,4-dimethyl-3,4-dihydronaphthalen-2-yl)methyl]azetidine-3-carboxylic acid TLC: Rf 0.27 (chloroform:methanol:aqueous ammonia=80:20:4);
$^1$H-NMR (CD$_3$OD): δ 7.17 (dd, J=8.4, 5.5 Hz, 2H), 7.05 (d, J=8.2 Hz, 1H), 6.97 (t, J=8.4 Hz, 2H), 6.84 (d, J=2.2 Hz, 1H), 6.68 (dd, J=8.2, 2.2 Hz, 1H), 6.60 (s, 1H), 4.08-4.27 (m, 4H), 3.88 (s, 2H), 3.79 (d, J=5.7 Hz, 2H), 3.34-3.50 (m, 1H), 2.84 (dd, J=13.5, 6.6 Hz, 1H), 2.55 (dd, J=13.5, 7.8 Hz, 1H), 2.08-2.27 (m, 3H), 1.23 (s, 6H), 1.00 (d, J=6.8 Hz, 3H).

EXAMPLE 27-6

1-({6-[3-(4-fluorophenyl)propoxy]-1-benzothien-2-yl}methyl)azetidine-3-carboxylic acid TLC: Rf 0.23 (chloroform:methanol:aqueous ammonia=80:20:4);
$^1$H-NMR (CD$_3$OD): δ 7.70 (d, J=8.8 Hz, 1H), 7.39 (s, 1H), 7.37 (d, J=2.2 Hz, 1H), 7.21 (dd, J=8.8, 5.5 Hz, 2H), 6.92-7.06 (m, 3H), 4.51 (s, 2H), 4.10-4.18 (m, 4H), 4.01 (t, J=6.2 Hz, 2H), 3.32-3.47 (m, 1H), 2.80 (t, J=7.5 Hz, 2H), 2.01-2.15 (m, 2H).

EXAMPLE 27-7

1-{[1-chloro-6-(3-cyclohexylpropoxy)-3,4-dihydronaphthalen-2-yl]methyl}azetidine-3-carboxylic acid TLC: Rf 0.24 (chloroform:methanol:aqueous ammonia=80:20:4);
$^1$H-NMR (CD$_3$OD): δ 7.55 (d, J=8.4 Hz, 1H), 6.73-6.84 (m, 2H), 4.24 (d, J=8.1 Hz, 4H), 4.18 (s, 2H), 3.97 (t, J=6.5 Hz, 2H), 3.34-3.53 (m, 1H), 2.84 (t, J=7.5 Hz, 2H), 2.45 (t, J=7.5 Hz, 2H), 1.60-1.84 (m, 7H), 1.13-1.41 (m, 6H), 0.83-1.02 (m, 2H).

EXAMPLE 27-8

1-({1-chloro-6-[3-(4-chlorophenyl)propoxy]-3,4-dihydronaphthalen-2-yl}methyl)azetidine-3-carboxylic acid TLC: Rf 0.24 (chloroform:methanol:aqueous ammonia=80:20:4);
$^1$H-NMR (CD$_3$OD): δ 7.55 (d, J=8.6 Hz, 1H), 7.25 (d, J=8.6 Hz, 2H), 7.18 (d, J=8.6 Hz, 2H), 6.80 (dd, J=8.6, 2.7 Hz, 1H), 6.75 (d, J=2.7 Hz, 1H), 4.23 (d, J=8.2 Hz, 4H), 4.17 (s, 2H), 3.97 (t, J=6.2 Hz, 2H), 3.35-3.51 (m, 1H), 2.72-2.88 (m, 4H), 2.40-2.51 (m, 2H), 1.96-2.17 (m, 2H).

EXAMPLE 27-9

1-[(1-chloro-6-{[(2S)-3-(4-chlorophenyl)-2-methyl-propyl]oxy}-3,4-dihydronaphthalen-2-yl)methyl]azetidine-3-carboxylic acid

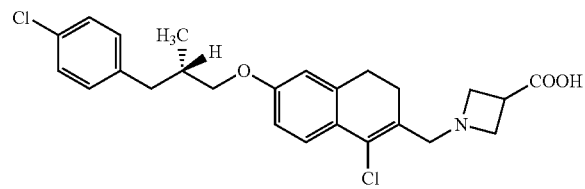 [SMILES: C[C@H](COc1ccc2c(c1)CCC(CN1CC(C(=O)O)C1)=C2Cl)Cc1ccc(Cl)cc1]

TLC: Rf 0.20 (chloroform:methanol:aqueous ammonia=80:20:4);
$^1$H-NMR (CD$_3$OD): δ 7.55 (d, J=8.4 Hz, 1H), 7.25 (d, J=8.4 Hz, 2H), 7.15 (d, J=8.4 Hz, 2H), 6.79 (dd, J=8.4, 2.6 Hz, 1H), 6.74 (d, J=2.6 Hz, 1H), 4.17-4.23 (m, 4H), 4.14 (s, 2H), 3.81 (d, J=5.9 Hz, 2H), 3.34-3.49 (m, 1H), 2.77-2.89 (m, 3H), 2.55 (dd, J=13.4, 7.9 Hz, 1H), 2.40-2.50 (m, 2H), 2.12-2.28 (m, 1H), 1.01 (d, J=6.8 Hz, 3H).

EXAMPLE 27-10

1-({6-[2-(4-fluorophenoxy)ethoxy]-1-methyl-3,4-dihydronaphthalen-2-yl}methyl)azetidine-3-carboxylic acid TLC: Rf 0.29 (chloroform:methanol:aqueous ammonia=80:20:4);
$^1$H-NMR (CD$_3$OD): δ 7.34 (d, J=8.60 Hz, 1H), 6.90-7.05 (m, 4H), 6.83 (dd, J=8.60, 2.74 Hz, 1H), 6.79 (d, J=2.74 Hz, 1H), 4.13-4.37 (m, 8H), 4.10 (s, 2H), 3.34-3.49 (m, 1H), 2.68-2.80 (m, 2H), 2.21 (s, 3H), 2.19-2.30 (m, 2H).

EXAMPLE 27-11

1-({6-[2-(4-fluorophenoxy)propoxy]-1-methyl-3,4-dihydronaphthalen-2-yl}methyl)azetidine-3-carboxylic acid TLC: Rf 0.31 (chloroform:methanol:aqueous ammonia=80:20:4);
$^1$H-NMR (CD$_3$OD): δ 7.32 (d, J=8.60 Hz, 1H), 6.91-7.03 (m, 4H), 6.78 (d, J=8.60, 2.74 Hz, 1H), 6.73 (d, J=2.74 Hz, 1H), 4.61-4.75 (m, 1H), 4.00-4.30 (m, 8H), 3.34-3.49 (m, 1H), 2.65-2.78 (m, 2H), 2.18-2.30 (m, 2H), 2.20 (s, 3H), 1.37 (d, J=6.40 Hz, 3H).

EXAMPLE 27-12

1-({6-[(4-isobutyl-1,3-oxazol-2-yl)methoxy]-1-methyl-3,4-dihydronaphthalen-2-yl}methyl)azetidine-3-carboxylic acid TLC: Rf 0.14 (chloroform:methanol:aqueous ammonia=80:20:4);
$^1$H-NMR (CD$_3$OD): δ 7.65 (t, J=1.00 Hz, 1H), 7.33 (d, J=8.50 Hz, 1H), 6.86 (dd, J=8.50, 2.50 Hz, 1H), 6.82 (d, J=2.50 Hz, 1H), 5.12 (s, 2H), 4.09-4.23 (m, 4H), 4.06 (s, 2H), 3.35-3.47 (m, 1H), 2.69-2.77 (m, 2H), 2.39 (dd, J=7.00, 1.00 Hz, 2H), 2.18-2.29 (m, 5H), 1.89-2.02 (m, 1H), 0.92 (d, J=6.50 Hz, 6H).

EXAMPLE 27-13

1-({6-[3-(4-methoxyphenyl)propoxy]-1-methyl-3,4-dihydronaphthalen-2-yl}methyl)azetidine-3-carboxylic acid TLC: Rf 0.25 (chloroform:methanol:aqueous ammonia=80:20:4);
$^1$H-NMR (CD$_3$OD): δ 7.30 (d, J=8.6 Hz, 1H), 7.10 (d, J=8.8 Hz, 2H), 6.81 (d, J=8.8 Hz, 2H), 6.74 (dd, J=8.6, 2.7 Hz, 1H), 6.70 (d, J=2.7 Hz, 1H), 4.04-4.21 (m, 4H), 4.02 (s, 2H), 3.94 (t, J=6.3 Hz, 2H), 3.74 (s, 3H), 3.32-3.47 (m, 1H), 2.65-2.78 (m, 4H), 2.20-2.28 (m, 2H), 2.19 (s, 3H), 1.95-2.08 (m, 2H).

EXAMPLE 27-14

1-({6-[3-(4-fluorophenoxy)propoxy]-1-methyl-3,4-dihydronaphthalen-2-yl}methyl)azetidine-3-carboxylic acid TLC: Rf 0.28 (chloroform:methanol:aqueous ammonia=80:20:4);
$^1$H-NMR (CD$_3$OD): δ 7.31 (d, J=8.60 Hz, 1H), 6.85-7.02 (m, 4H), 6.79 (dd, J=8.60, 2.56 Hz, 1H), 6.74 (d, J=2.56 Hz, 1H), 4.06-4.27 (m, 10H), 3.34-3.48 (m, 1H), 2.65-2.76 (m, 2H), 2.20 (s, 3H), 2.14-2.29 (m, 4H).

EXAMPLE 27-15

1-({6-[2-(4-fluorobenzyl)-3-hydroxypropoxy]-1-methyl-3,4-dihydronaphthalen-2-yl}methyl)azetidine-3-carboxylic acid TLC: Rf 0.17 (1-butanol:acetic acid:water=20:4:1);
$^1$H-NMR (CD$_3$OD): δ 7.30 (d, J=8.60 Hz, 1H), 7.15-7.24 (m, 2H), 6.91-7.04 (m, 2H), 6.74 (dd, J=8.60, 2.38 Hz, 1H), 6.70 (d, J=2.38 Hz, 1H), 4.09-4.26 (m, 4H), 4.07 (s, 2H), 3.91 (d, J=5.31 Hz, 2H), 3.63 (d, J=5.85 Hz, 2H), 3.34-3.52 (m, 1H), 2.65-2.79 (m, 4H), 2.20 (s, 3H), 2.13-2.28 (m, 3H).

EXAMPLE 27-16

1-[(2E)-3-(4-{[(2S)-3-(4-chlorophenyl)-2-methyl-propyl]oxy}phenyl)but-2-enyl]azetidine-3-carboxylic acid

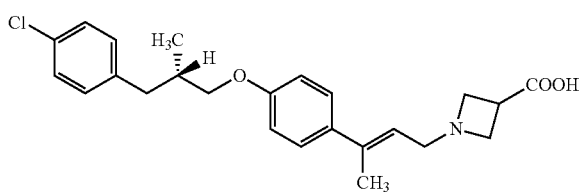 [SMILES: C/C(=C\CN1CC(C(=O)O)C1)c1ccc(OC[C@@H](C)Cc2ccc(Cl)cc2)cc1]

TLC: Rf 0.22 (chloroform:methanol:aqueous ammonia=80:20:4);
$^1$H-NMR (CD$_3$OD): δ 7.38 (d, J=8.50 Hz, 2H), 7.24 (d, J=8.50 Hz, 2H), 7.15 (d, J=8.50 Hz, 2H), 6.87 (d, J=8.50 Hz, 2H), 5.64 (tq, J=7.50, 1.50 Hz, 1H), 4.10-4.26 (m, 4H), 3.98 (d, J=7.50 Hz, 2H), 3.79 (d, J=6.00 Hz, 2H), 3.35-3.43 (m, 1H), 2.85 (dd, J=13.50, 6.50 Hz, 1H), 2.55 (dd, J=13.50, 7.50 Hz, 1H), 2.13-2.25 (m, 4H), 1.01 (d, J=7.00 Hz, 3H).

EXAMPLE 28

1-((2E)-3-{4-[3-(4-chlorophenyl)propoxy]phenyl}but-2-enyl)azetidine-3-carboxylic acid The procedure of Example 8 was similarly performed while using a corresponding aldehyde compound as a substitute for 6-[3-(4-chlorophenyl)propoxy]-1-methyl-3,4-dihydronaphthalene-2-carboaldehyde. Thus, the title compound having the following physical properties was obtained.
TLC: Rf 0.18 (chloroform:methanol:aqueous ammonia=80:20:4);
$^1$H-NMR (CDCl$_3$+CD$_3$OD): δ 7.34 (d, J=9.00 Hz, 2H), 7.25 (d, J=8.50 Hz, 2H), 7.15 (d, J=8.50 Hz, 2H), 6.87 (d, J=9.00 Hz, 2H), 5.60-5.67 (m, 1H), 4.23 (dd, J=10.00, 6.00 Hz, 2H), 4.05 (t, J=10.00 Hz, 2H), 3.96 (t, J=6.00 Hz, 2H), 3.85-3.91 (m, 2H), 3.24-3.33 (m, 1H), 2.79 (t, J=7.50 Hz, 2H), 2.15 (d, J=1.00 Hz, 3H), 2.04-2.14 (m, 2H).

EXAMPLES 29-1 to 29-5

The procedure of each of Examples 12 and 13 was similarly performed while using a corresponding amine compound as a substitute for the compound prepared in Example 11. Thus, compounds each having the following physical properties was obtained.

EXAMPLE 29-1

3-[4-{4-[3-(4-chlorophenyl)propoxy]phenyl}-3,6-dihydropyridin-1(2H)-yl]propanoic acid trifluoroacetate TLC: Rf 0.28 (chloroform:methanol:aqueous ammonia=80:20:4);
$^1$H-NMR (CD$_3$OD): δ 7.40 (d, J=8.97 Hz, 2H), 7.25 (d, J=8.60 Hz, 2H), 7.19 (d, J=8.60 Hz, 2H), 6.90 (d, J=8.97 Hz, 2H), 5.97-6.08 (m, 1H), 3.90-4.01 (m, 4H), 3.55-3.63 (m, 2H), 3.51 (t, J=6.59 Hz, 2H), 2.82-2.93 (m, 4H), 2.74-2.83 (m, 2H), 1.95-2.15 (m, 2H).

EXAMPLE 29-2

3-[4-(4-{[(2S)-3-(4-chlorophenyl)-2-methylpropyl]oxy}phenyl)-3,6-dihydropyridin-1(2H)-yl]propanoic acid trifluoroacetate TLC: Rf 0.24 (chloroform:methanol:aqueous ammonia=80:20:4);
$^1$H-NMR (CD$_3$OD): δ 7.40 (d, J=8.97 Hz, 2H), 7.24 (d, J=8.41 Hz, 2H), 7.15 (d, J=8.41 Hz, 2H), 6.89 (d, J=8.97 Hz, 2H), 5.94-6.11 (m, 1H), 3.86-4.00 (m, 2H), 3.79 (d, J=5.85 Hz, 2H), 3.45-3.64 (m, 4H), 2.79-2.93 (m, 5H), 2.44-2.66 (m, 1H), 2.10-2.33 (m, 1H), 1.01 (d, J=6.77 Hz, 3H).

EXAMPLE 29-3

3-{7-[(5-phenylpentyl)oxy]-1,3,4,5-tetrahydro-2H-2-benzoazepin-2-yl}propanoic acid trifluoroacetate TLC: Rf 0.38 (chloroform:methanol:aqueous ammonia=80:20:4);
$^1$H-NMR (CD$_3$OD): δ 7.30 (d, J=8.23 Hz, 1H), 7.19-7.27 (m, 2H), 7.07-7.19 (m, 3H), 6.83 (d, J=2.56 Hz, 1H), 6.79 (dd, J=8.23, 2.56 Hz, 1H), 4.42-4.52 (m, 2H), 3.97 (t, J=6.40 Hz, 2H), 3.41-3.69 (m, 2H), 3.14-3.39 (m, 2H), 2.93-3.06 (m, 2H), 2.82 (t, J=6.95 Hz, 2H), 2.55-2.70 (m, 2H), 1.86-2.19 (m, 2H), 1.74-1.85 (m, 2H), 1.61-1.73 (m, 2H), 1.42-1.57 (m, 2H).

EXAMPLE 29-4

3-{7-[3-(4-chlorophenyl)propoxy]-9-methyl-1,3,4,9-tetrahydro-2H-β-carbolin-2-yl}propanoic acid trifluoroacetate TLC: Rf 0.27 (chloroform:methanol:aqueous ammonia=80:20:4);
$^1$H-NMR (CD$_3$OD): δ 7.37 (d, J=8.42 Hz, 1H), 7.25 (d, J=8.78 Hz, 2H), 7.20 (d, J=8.78 Hz, 2H), 6.87 (d, J=2.01 Hz, 1H), 6.76 (dd, J=8.42, 2.01 Hz, 1H), 4.55-4.69 (m, 2H), 4.01 (t, J=6.13 Hz, 2H), 3.62 (s, 3H), 3.57-3.76 (m, 4H), 3.06-3.17 (m, 2H), 2.98 (t, J=7.14 Hz, 2H), 2.77-2.89 (m, 2H), 2.00-2.17 (m, 2H).

EXAMPLE 29-5

3-{5-[(5-phenylpentyl)oxy]-1,3-dihydro-2H-isoindol-2-yl}propanoic acid trifluoroacetate TLC: Rf 0.21 (chloroform:methanol:aqueous ammonia=80:20:4);
$^1$H-NMR (CD$_3$OD): δ 7.19-7.31 (m, 3H), 7.07-7.19 (m, 3H), 6.86-6.98 (m, 2H), 4.51-4.79 (m, 4H), 3.97 (t, J=6.31 Hz, 2H), 3.69 (t, J=6.86 Hz, 2H), 2.88 (t, J=6.86 Hz, 2H), 2.56-2.69 (m, 2H), 1.74-1.88 (m, 2H), 1.60-1.74 (m, 2H), 1.42-1.57 (m, 2H).

EXAMPLE 30 methyl N-[(6-{[(2S)-3-(4-chlorophenyl)-2-methylpropyl]oxy}-1-methyl-3,4-dihydronaphthalen-2-yl)methyl]-β-alaninate

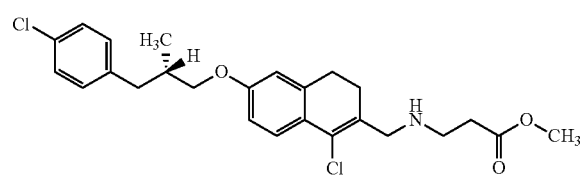 [SMILES: COC(=O)CCNCC1=C(Cl)c2ccc(OC[C@@H](C)Cc3ccc(Cl)cc3)cc2CC1]

The procedure of Example 6 was similarly performed while using 6-{[(2S)-3-(4-chlorophenyl)-2-methylpropyl]oxy}-1-methyl-3,4-dihydronaphthalene-2-carbaldehyde as a substitute for the compound prepared in Example 5 and using methyl-β-alaninate as a substitute for methyl azetidine-3-carboxylate hydrochloride. Thus, the title compound having the following physical properties was obtained.
TLC: Rf 0.62 (chloroform:methanol:aqueous ammonia=80:10:1).

EXAMPLE 31

N-[(6-{[(2S)-3-(4-chlorophenyl)-2-methylpropyl]oxy}-1-methyl-3,4-dihydronaphthalen-2-yl)methyl]-β-alanine The procedure of Example 7 was similarly performed while using the compound prepared in Example 30 as a substitute for the compound prepared in Example 6. Thus, the compound having the following physical properties was obtained.

TLC: Rf 0.27 (chloroform:methanol:aqueous ammonia=80:20:4);
$^1$H-NMR (CD$_3$OD): δ 7.28 (d, J=8.6 Hz, 1H), 7.24 (d, J=8.6 Hz, 2H), 7.15 (d, J=8.6 Hz, 2H), 6.73 (dd, J=8.6, 2.8 Hz, 1H), 6.69 (d, J=2.8 Hz, 1H), 3.88 (s, 2H), 3.78 (d, J=5.9 Hz, 2H), 3.18 (t, J=6.3 Hz, 2H), 2.84 (dd, J=13.4, 6.4 Hz, 1H), 2.75 (t, J=7.3 Hz, 2H), 2.47-2.60 (m, 3H), 2.33 (t, J=7.3 Hz, 2H), 2.11-2.25 (m, 4H), 1.00 (d, J=6.8 Hz, 3H).

EXAMPLE 32

1-(methoxymethoxy)-3-propylbenzene

Methoxymethyl chloride (8.4 mL) and potassium carbonate (30 g) were added to an N,N-dimethylformamide (150 mL) solution of 3-propylphenol (10 g) at room temperature, followed by stirring at 50° C. for one day. The reaction solution was poured into ice water. The insoluble matter was filtered off, and extracted with a hexane-ethyl acetate (1:1) mixed solvent. The organic layer was successively washed with water and brine. The resultant was dried over magnesium sulfate, and concentrated. The obtained residue was purified by silica gel column chromatography (hexane only to hexane:ethyl acetate=10:1), to thereby obtain the title compound (8.0 g) having the following physical properties.

TLC: Rf 0.64 (hexane:ethyl acetate=10:1);
$^1$H-NMR (CDCl$_3$): δ 7.18 (dd, J=8.50, 7.50 Hz, 1H), 6.80-6.88 (m, 3H), 5.16 (s, 2H), 3.48 (s, 3H), 2.56 (t, J=7.50 Hz, 2H), 1.56-1.71 (m, 2H), 0.94 (t, J=7.50 Hz, 3H).

EXAMPLE 33

2-(methoxymethoxy)-4-propylbenzaldehyde

Tert-butyllithium (1.56 mol/L pentane solution, 33.9 mL) was added to a hexane (100 mL) solution of the compound (7.95 g) prepared in Example 32 at 0° C., followed by stirring for 30 minutes. N,N-dimethylformamide (5.12 mL) was added dropwise thereto. The reaction solution was added with a saturated ammonium chloride solution, and extracted with ethyl acetate. The organic layer was washed with brine, dried over sodium sulfate, and concentrated. The obtained residue was purified by silica gel column chromatography (hexane:ethyl acetate=14:1 to 10:1), to thereby obtain the title compound (4.94 g) having the following physical properties.

TLC: Rf 0.27 (hexane:ethyl acetate=10:1);
$^1$H-NMR (CDCl$_3$): δ 10.44 (s, 1H), 7.76 (d, J=7.9 Hz, 1H), 7.01 (s, 1H), 6.91 (d, J=7.9 Hz, 1H), 5.30 (s, 2H), 3.53 (s, 3H), 2.62 (t, J=7.5 Hz, 2H), 1.58-1.75 (m, 2H), 0.96 (t, J=7.3 Hz, 3H).

EXAMPLE 34

2-hydroxy-4-propylbenzaldehyde

A 4 mol/L hydrogen chloride/1,4-dioxane solution (50 mL) was added to a 1,4-dioxane (10 mL) solution of the compound (4.50 g) prepared in Example 33, followed by stirring at room temperature for 1 hour. The reaction solution was concentrated, to thereby obtain the title compound (3.48 g) having the following physical properties.

TLC: Rf 0.57 (hexane:ethyl acetate=10:1);
$^1$H-NMR (CDCl$_3$): δ 11.04 (s, 1H), 9.83 (s, 1H), 7.45 (d, J=7.9 Hz, 1H), 6.83 (d, J=7.9 Hz, 1H), 6.81 (s, 1H), 2.61 (t, J=7.5 Hz, 2H), 1.58-1.74 (m, 2H), 0.95 (t, J=7.3 Hz, 3H).

EXAMPLE 35

2-methoxy-4-propylbenzaldehyde

Potassium carbonate (3.79 g) and methyl iodide (1.71 mL) were added to an N,N-dimethylformamide (40 mL) solution of the compound (3.00 g) prepared in Example 34 at room temperature, followed by stirring at 40° C. for 2 hours. The reaction solution was added with water, and extracted with a hexane-ethyl acetate (3:1) mixed solvent. The organic layer was washed with brine, dried over sodium sulfate, and concentrated, to thereby obtain the title compound (8.0 g) having the following physical properties.

TLC: Rf 0.40 (hexane:ethyl acetate=10:1);
$^1$H-NMR (CDCl$_3$): δ 10.41 (s, 1H), 7.75 (d, J=7.9 Hz, 1H), 6.86 (d, J=7.9 Hz, 1H), 6.78 (s, 1H), 3.93 (s, 3H), 2.63 (t, J=7.5 Hz, 2H), 1.59-1.77 (m, 2H), 0.97 (t, J=7.3 Hz, 3H).

EXAMPLE 36

1-(hydroxymethyl)-2-methoxy-4-propylbenzene

Sodium borohydride (958 mg) was added to a methanol (40 mL) solution of the compound (3.02 g) prepared in Example 35 at 0° C., followed by stirring at room temperature for 1 hour. The reaction solution was concentrated, added with water, and extracted with ethyl acetate. The organic layer was dried over sodium sulfate, and concentrated. The obtained residue was purified by silica gel column chromatography (hexane:ethyl acetate=6:1 to 3:1), to thereby obtain the title compound (2.87 g) having the following physical properties.

TLC: Rf 0.31 (hexane:ethyl acetate=3:1);
$^1$H-NMR (CDCl$_3$): δ 7.16 (d, J=7.5 Hz, 1H), 6.76 (d, J=7.5 Hz, 1H), 6.71 (s, 1H), 4.65 (s, 2H), 3.87 (s, 3H), 2.58 (t, J=7.5 Hz, 2H), 1.57-1.72 (m, 2H), 0.95 (t, J=7.3 Hz, 3H).

EXAMPLE 37

1-({6-[(2-methoxy-4-propylbenzyl)oxy]-1-methyl-3,4-dihydro-2-naphthalenyl}methyl)-3-azetidinecarboxylic acid

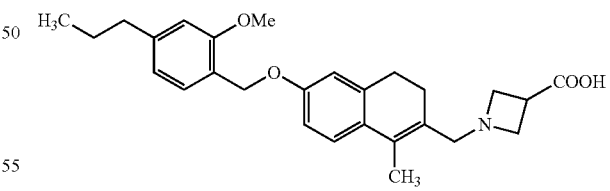

The procedures similar to that of Examples 5, 6, and 7 were performed while using 1-(bromomethyl)-2-methoxy-4-propylbenzene (which was prepared by adding phosphorus tribromide to the compound prepared in Example 36 in diethyl ether at 0° C., and reacting the mixture at room temperature for 1 hour) as a substitute for 1-bromo-3-(4-fluorophenyl) propane, to thereby obtain the title compound having the following physical properties.

$^1$H-NMR (CD$_3$OD): δ 7.31 (d, J=8.4 Hz, 1H), 7.25 (d, J=7.7 Hz, 1H), 6.73-6.86 (m, 4H), 5.04 (s, 2H), 4.12-4.29 (m,

4H), 4.10 (s, 2H), 3.84 (s, 3H), 3.34-3.50 (m, 1H), 2.72 (t, J=7.0 Hz, 2H), 2.59 (t, J=7.3 Hz, 2H), 2.15-2.31 (m, 5H), 1.57-1.74 (m, 2H), 0.94 (t, J=7.4 Hz, 3H); amorphous.

EXAMPLES 37-1 to 37-16

Example 37 was similarly performed while using a corresponding phenol compound as a substitute for a compound prepared in Example 4 and using a corresponding alcohol compound as a substitute for a compound prepared in Example 36, to thereby obtain the title compound having the following physical properties.

EXAMPLE 37-1

1-({6-[(4-isobutyl-2-methoxybenzyl)oxy]-1-methyl-3,4-dihydro-2-naphthalenyl}methyl)-3-azetidinecarboxylic acid

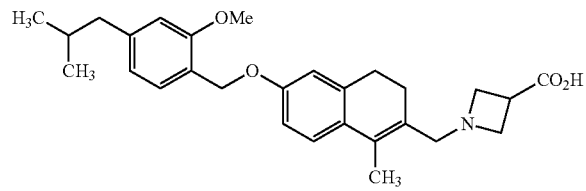 [SMILES: COc1cc(CC(C)C)ccc1COc1ccc2c(c1)CCC(CN1CC(C(=O)O)C1)=C2C]

TLC: Rf 0.23 (chloroform:methanol:aqueous ammonia=80:20:4);

$^1$H-NMR (CD$_3$OD): δ 7.32 (d, J=8.60 Hz, 1H), 7.26 (d, J=7.68 Hz, 1H), 6.83 (dd, J=8.60, 2.74 Hz, 1H), 6.77-6.80 (m, 2H), 6.71-6.75 (m, 1H), 5.04 (s, 2H), 4.11-4.27 (m, 4H), 4.09 (s, 2H), 3.84 (s, 3H), 3.34-3.48 (m, 1H), 2.67-2.77 (m, 2H), 2.48 (d, J=7.32 Hz, 2H), 2.20 (s, 3H), 2.18-2.28 (m, 2H), 1.81-1.95 (m, 1H), 0.91 (d, J=6.77 Hz, 6H).

EXAMPLE 37-2

1-({6-[(4-isobutyl-3-methoxybenzyl)oxy]-1-methyl-3,4-dihydro-2-naphthalenyl}methyl)-3-azetidinecarboxylic acid

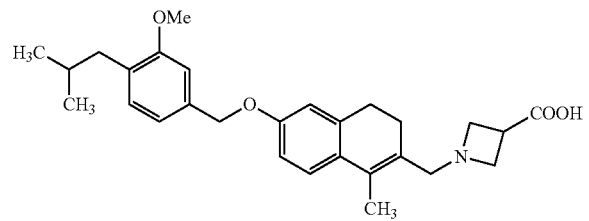 [SMILES: COc1cc(COc2ccc3c(c2)CCC(CN2CC(C(=O)O)C2)=C3C)ccc1CC(C)C]

TLC: Rf 0.17 (chloroform:methanol:aqueous ammonia=80:20:4);

$^1$H-NMR (CD$_3$OD): δ 7.32 (d, J=8.50 Hz, 1H), 7.05 (d, J=7.50 Hz, 1H), 6.98 (d, J=1.50 Hz, 1H), 6.90 (dd, J=7.50, 1.50 Hz, 1H), 6.85 (dd, J=8.50, 2.50 Hz, 1H), 6.81 (d, J=2.50 Hz, 1H), 5.04 (s, 2H), 4.12-4.26 (m, 4H), 4.08 (s, 2H), 3.80 (s, 3H), 3.34-3.47 (m, 1H), 2.69-2.77 (m, 2H), 2.46 (d, J=7.00 Hz, 2H), 2.19-2.29 (m, 5H), 1.81-1.95 (m, 1H), 0.86 (d, J=7.00 Hz, 6H).

EXAMPLE 37-3

1-({6-[(2-ethoxy-4-isobutylbenzyl)oxy]-1-methyl-3,4-dihydro-2-naphthalenyl}methyl)-3-azetidinecarboxylic acid

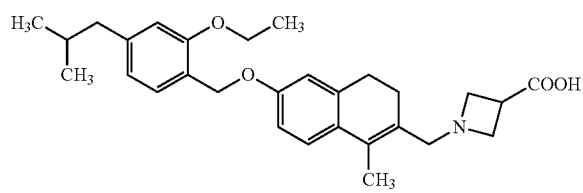 [SMILES: CCOc1cc(CC(C)C)ccc1COc1ccc2c(c1)CCC(CN1CC(C(=O)O)C1)=C2C]

TLC: Rf 0.32 (chloroform:methanol:aqueous ammonia=80:20:4);

$^1$H-NMR (CD$_3$OD): δ 7.32 (d, J=8.6 Hz, 1H), 7.25 (d, J=7.5 Hz, 1H), 6.68-6.88 (m, 4H), 5.06 (s, 2H), 4.12-4.30 (m, 4H), 4.03-4.14 (m, 4H), 3.36-3.50 (m, 1H), 2.72 (t, J=6.6 Hz, 2H), 2.46 (d, J=7.1 Hz, 2H), 2.16-2.30 (m, 5H), 1.78-1.96 (m, 1H), 1.38 (t, J=7.0 Hz, 3H), 0.90 (d, J=6.6 Hz, 6H).

EXAMPLE 37-4

1-[(6-{[4-isopropoxy-2-(trifluoromethyl)benzyl]oxy}-1-methyl-3,4-dihydro-2-naphthalenyl)methyl]-3-azetidinecarboxylic acid

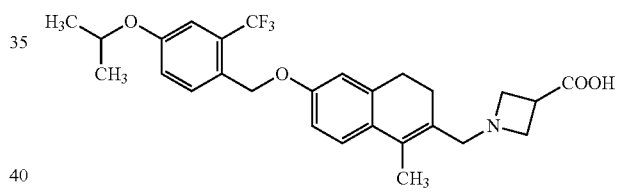

TLC: Rf 0.23 (chloroform:methanol:aqueous ammonia=80:20:4);

$^1$H-NMR (CD$_3$OD): δ 7.58 (d, J=8.50 Hz, 1H), 7.33 (d, J=8.50 Hz, 1H), 7.19 (d, J=2.50 Hz, 1H), 7.17 (dd, J=8.50, 2.50 Hz, 1H), 6.81 (dd, J=8.50, 2.50 Hz, 1H), 6.78 (d, J=2.50 Hz, 1H), 5.14 (s, 2H), 4.62-4.73 (m, 1H), 4.08-4.24 (m, 4H), 4.06 (s, 2H), 3.35-3.47 (m, 1H), 2.70-2.77 (m, 2H), 2.19-2.28 (m, 5H), 1.33 (d, J=6.00 Hz, 6H).

EXAMPLE 37-5

1-[(6-{[2,4-bis(trifluoromethyl)benzyl]oxy}-1-methyl-3,4-dihydro-2-naphthalenyl)methyl]-3-azetidinecarboxylic acid

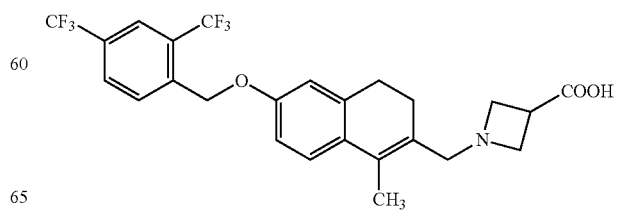

¹H-NMR (CD₃OD): δ 7.96-8.03 (m, 3H), 7.36 (d, J=8.50 Hz, 1H), 6.82-6.88 (m, 2H), 5.35 (s, 2H), 4.12-4.27 (m, 4H), 4.09 (s, 2H), 3.37-3.49 (m, 1H), 2.70-2.79 (m, 2H), 2.19-2.30 (m, 5H); amorphous.

EXAMPLE 37-6

1-({1-chloro-6-[(2-methoxy-4-propylbenzyl)oxy]-3,4-dihydro-2-naphthalenyl}methyl)-3-azetidinecarboxylic acid

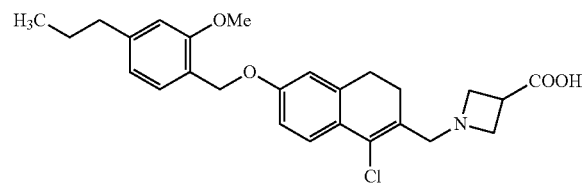 [SMILES: CCCc1ccc(COc2ccc3c(c2)CCC(CN2CC(C(=O)O)C2)=C3Cl)c(OC)c1]

TLC: Rf 0.29 (chloroform:methanol:aqueous ammonia=80:20:4);

¹H-NMR (CD₃OD): δ 7.55 (d, J=8.6 Hz, 1H), 7.24 (d, J=7.7 Hz, 1H), 6.86 (dd, J=8.6, 2.6 Hz, 1H), 6.80-6.84 (m, 2H), 6.76 (d, J=7.7 Hz, 1H), 5.06 (s, 2H), 4.23 (d, J=8.2 Hz, 4H), 4.18 (s, 2H), 3.84 (s, 3H), 3.35-3.51 (m, 1H), 2.83 (t, J=7.3 Hz, 2H), 2.59 (t, J=7.3 Hz, 2H), 2.45 (t, J=7.3 Hz, 2H), 1.56-1.74 (m, 2H), 0.94 (t, J=7.3 Hz, 3H);

Crystal;

Melting point 157.9-158.0° C.

EXAMPLE 37-7

1-({1-chloro-6-[(4-isobutyl-2-methoxybenzyl)oxy]-3,4-dihydro-2-naphthalenyl}methyl)-3-azetidinecarboxylic acid

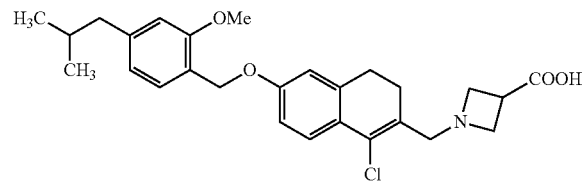 [SMILES: COc1cc(CC(C)C)ccc1COc1ccc2c(c1)CCC(CN1CC(C(=O)O)C1)=C2Cl]

TLC: Rf 0.32 (chloroform:methanol:aqueous ammonia=80:20:4);

¹H-NMR (CD₃OD): δ 7.56 (d, J=8.6 Hz, 1H), 7.25 (d, J=7.5 Hz, 1H), 6.88 (dd, J=8.6, 2.6 Hz, 1H), 6.84 (d, J=2.6 Hz, 1H), 6.79 (d, J=1.3 Hz, 1H), 6.74 (dd, J=7.5, 1.3 Hz, 1H), 5.07 (s, 2H), 4.24 (d, J=8.2 Hz, 4H), 4.19 (s, 2H), 3.84 (s, 3H), 3.37-3.50 (m, 1H), 2.84 (t, J=7.7 Hz, 2H), 2.41-2.52 (m, 4H), 1.80-1.97 (m, 1H), 0.91 (d, J=6.8 Hz, 6H); amorphous.

EXAMPLE 37-8

1-[(1-chloro-6-{[(2S)-3-(2,4-difluorophenyl)-2-methylpropyl]oxy}-3,4-dihydro-2-naphthalenyl)methyl]-3-azetidinecarboxylic acid

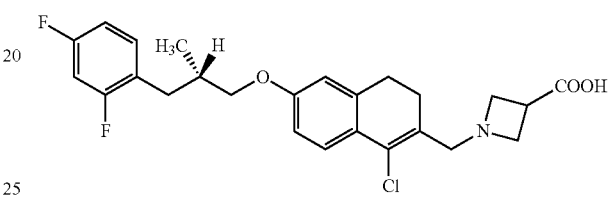

TLC: Rf 0.24 (chloroform:methanol:aqueous ammonia=80:20:4);

¹H-NMR (CD₃OD): δ 7.53 (d, J=8.6 Hz, 1H), 7.15-7.31 (m, 1H), 6.81-6.94 (m, 2H), 6.71-6.81 (m, 2H), 3.97-4.18 (m, 6H), 3.83 (d, J=5.9 Hz, 2H), 3.31-3.46 (m, 1H), 2.76-2.92 (m, 3H), 2.59 (dd, J=14.1, 7.9 Hz, 1H), 2.44 (t, J=8.6 Hz, 2H), 2.15-2.31 (m, 1H), 1.01 (d, J=6.8 Hz, 3H).

EXAMPLE 37-9

1-[(6-{[4-ethoxy-2-(trifluoromethyl)benzyl]oxy}-1-methyl-3,4-dihydro-2-naphthalenyl)methyl]-3-azetidinecarboxylic acid

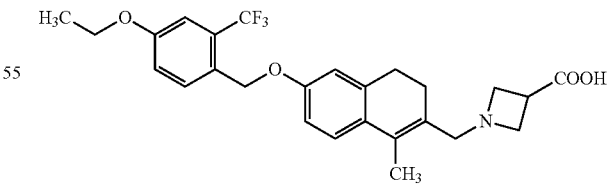

TLC: Rf 0.33 (chloroform:methanol:aqueous ammonia=80:20:4);

¹H-NMR (CD₃OD): δ 7.59 (d, J=8.80 Hz, 1H) 7.34 (d, J=8.60 Hz, 1H) 7.21 (d, J=2.60 Hz, 1H) 7.15 (dd, J=8.60, 2.60 Hz, 1H) 6.74-6.87 (m, 2H) 5.14 (s, 2H) 4.11-4.31 (m, 4H)

4.02-4.15 (m, 4H) 3.34-3.50 (m, 1H) 2.73 (t, J=6.80 Hz, 2H) 2.14-2.32 (m, 5H) 1.40 (t, J=7.00 Hz, 3H).

EXAMPLE 37-10

1-({6-[(4-ethyl-2-methoxybenzyl)oxy]-1-methyl-3,4-dihydro-2-naphthalenyl}methyl)-3-azetidinecarboxylic acid

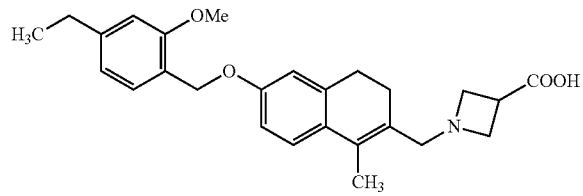 [SMILES: CCc1ccc(COc2ccc3c(c2)CCC(CN2CC(C(=O)O)C2)=C3C)c(OC)c1]

TLC: Rf 0.28 (chloroform:methanol:aqueous ammonia=80:20:4);

$^1$H-NMR (CD$_3$OD): δ 7.30 (d, J=8.50 Hz, 1H), 7.25 (d, J=7.50 Hz, 1H), 6.74-6.85 (m, 4H), 5.04 (s, 2H), 4.08-4.24 (m, 4H), 4.06 (s, 2H), 3.85 (s, 3H), 3.35-3.46 (m, 1H), 2.60-2.76 (m, 4H), 2.18-2.28 (m, 5H), 1.24 (t, J=7.50 Hz, 3H).

EXAMPLE 37-11

1-({6-[(2-methoxy-4-propylbenzyl)oxy]-1,5-dimethyl-3,4-dihydro-2-naphthalenyl}methyl)-3-azetidinecarboxylic acid

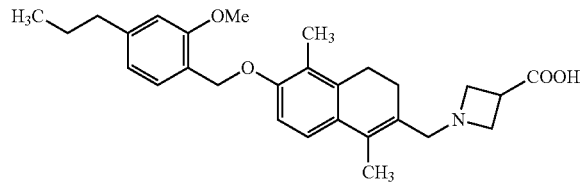 [SMILES: CCCc1ccc(COc2ccc3c(c2C)CCC(CN2CC(C(=O)O)C2)=C3C)c(OC)c1]

TLC: Rf 0.19 (chloroform:methanol:aqueous ammonia=80:20:4);

$^1$H-NMR (CD$_3$OD): δ 7.27 (d, J=7.50 Hz, 1H), 7.21 (d, J=8.50 Hz, 1H), 6.80-6.85 (m, 2H), 6.76 (dd, J=7.50, 1.00 Hz, 1H), 5.05 (s, 2H), 4.10-4.25 (m, 4H), 4.07 (s, 2H), 3.85 (s, 3H), 3.35-3.46 (m, 1H), 2.70-2.77 (m, 2H), 2.56-2.63 (m, 2H), 2.17-2.27 (m, 8H), 1.59-1.72 (m, 2H), 0.95 (t, J=7.50 Hz, 3H).

EXAMPLE 37-12

1-({6-[(2-difluoromethoxy-4-propylbenzyl)oxy]-1-methyl-3,4-dihydro-2-naphthalenyl}methyl)-3-azetidinecarboxylic acid

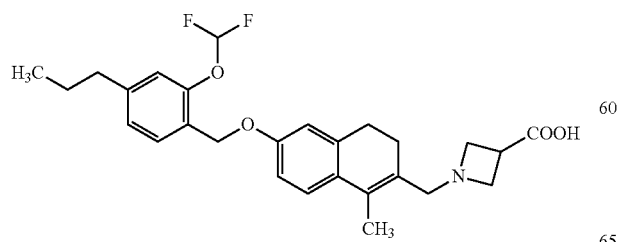

TLC: Rf 0.15 (chloroform:methanol:aqueous ammonia=80:20:4);

$^1$H-NMR (CD$_3$OD): δ 7.42 (d, J=7.50 Hz, 1H), 7.33 (d, J=8.50 Hz, 1H), 7.01-7.11 (m, 2H), 6.82 (t, J=74.00 Hz, 1H), 6.79-6.86 (m, 2H), 5.08 (s, 2H), 4.10-4.25 (m, 4H), 4.08 (s, 2H), 3.35-3.49 (m, 1H), 2.69-2.77 (m, 2H), 2.61 (t, J=7.50 Hz, 2H), 2.19-2.28 (m, 5H), 1.58-1.72 (m, 2H), 0.94 (t, J=7.50 Hz, 3H).

EXAMPLE 37-13

1-[(6-{[2,4-bis(trifluoromethyl)benzyl]oxy}-1-chloro-3,4-dihydro-2-naphthalenyl)methyl]-3-azetidinecarboxylic acid

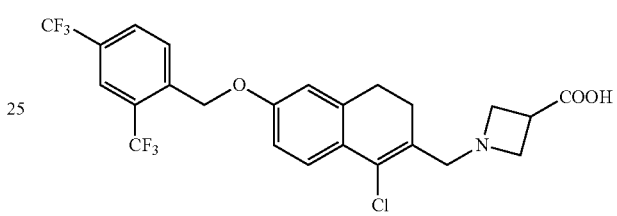

TLC: Rf 0.35 (chloroform:methanol:aqueous ammonia=80:20:4);

$^1$H-NMR (CD$_3$OD): δ 7.92-8.08 (m, 3H), 7.61 (d, J=8.60 Hz, 1H), 6.86-6.96 (m, 2H), 5.37 (s, 2H), 4.07-4.25 (m, 6H), 3.36-3.49 (m, 1H), 2.79-2.92 (m, 2H), 2.40-2.52 (m, 2H); crystal.

EXAMPLE 37-14

1-[(6-{[2-(difluoromethoxy)-4-propylbenzyl]oxy}-1,5-dimethyl-3,4-dihydro-2-naphthalenyl)methyl]-3-azetidinecarboxylic acid

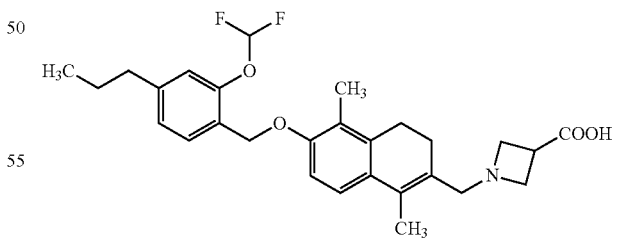

TLC: Rf 0.24 (chloroform:methanol:aqueous ammonia=80:20:4);

$^1$H-NMR (CD$_3$OD): δ 7.43 (d, J=7.50 Hz, 1H), 7.23 (d, J=8.50 Hz, 1H), 7.08 (d, J=7.50 Hz, 1H), 7.02 (s, 1H), 6.85 (d, J=8.50 Hz, 1H), 6.82 (t, J=74.00 Hz, 1H), 5.09 (s, 2H), 4.10-4.25 (m, 4H), 4.08 (s, 2H), 3.34-3.47 (m, 1H), 2.70-2.77 (m,

2H), 2.58-2.66 (m, 2H), 2.17-2.28 (m, 8H), 1.59-1.72 (m, 2H), 0.95 (t, J=7.50 Hz, 3H); crystal.

EXAMPLE 37-15

1-[(6-{[4-ethoxy-3-(trifluoromethyl)benzyl]oxy}-1-methyl-3,4-dihydro-2-naphthalenyl)methyl]-3-azetidinecarboxylic acid

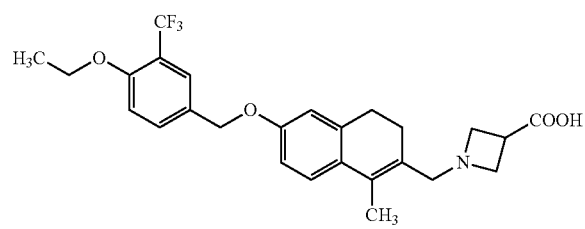 [SMILES: CCOc1ccc(COc2ccc3c(c2)CCC(CN2CC(C(=O)O)C2)=C3C)cc1C(F)(F)F]

TLC: Rf 0.20 (chloroform:methanol:aqueous ammonia=80:20:4);
$^1$H-NMR (CD$_3$OD): δ 7.58-7.64 (m, 2H), 7.33 (d, J=8.50 Hz, 1H), 7.15 (d, J=8.00 Hz, 1H), 6.85 (dd, J=8.50, 2.50 Hz, 1H), 6.81 (d, J=2.50 Hz, 1H), 5.05 (s, 2H), 4.11-4.25 (m, 6H), 4.08 (s, 2H), 3.35-3.48 (m, 1H), 2.69-2.77 (m, 2H), 2.18-2.27 (m, 5H), 1.41 (t, J=7.00 Hz, 3H); crystal.

EXAMPLE 37-16

1-({6-[(2-methoxy-6-propyl-3-pyridinyl)methoxy]-1,5-dimethyl-3,4-dihydro-2-naphthalenyl}methyl)-3-azetidinecarboxylic acid

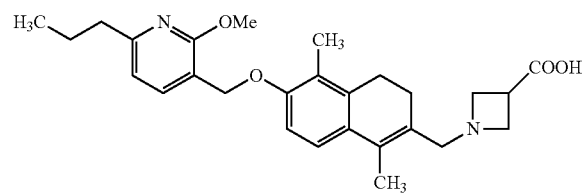 [SMILES: CCCc1ccc(COc2ccc3c(c2C)CCC(CN2CC(C(=O)O)C2)=C3C)c(OC)n1]

TLC: Rf 0.40 (chloroform:methanol:aqueous ammonia=80:20:4);
$^1$H-NMR (CD$_3$OD): δ 7.62 (d, J=7.32 Hz, 1H), 7.22 (d, J=8.78 Hz, 1H), 6.82 (d, J=8.78 Hz, 1H), 6.77 (d, J=7.32 Hz, 1H), 5.00 (s, 2H), 4.08-4.24 (m, 4H), 4.05 (s, 2H), 3.96 (s, 3H), 3.34-3.48 (m, 1H), 2.69-2.77 (m, 2H), 2.61-2.69 (m, 2H), 2.14-2.29 (m, 8H), 1.64-1.85 (m, 2H), 0.95 (t, J=7.41 Hz, 3H); crystal.

EXAMPLE 38 methyl azetidine-3-carboxylate hydrochloride

Methanol (70 mL) was added dropwise under stirring at 0° C. to thionyl chloride (23.4 mL), and azetidine-3-carboxylic acid (CAS No. 36476-78-5, 25 g) was added, followed by stirring at room temperature for 2 hours. The reaction solution was concentrated, to thereby obtain the title compound (36 g) having the following physical properties.
TLC: Rf 0.68 (chloroform:methanol:aqueous ammonia=20:5:1);
$^1$H-NMR (CD$_3$OD): δ 4.18-4.33 (m, 4H), 3.72-3.81 (m, 4H).

EXAMPLE 38-1 ethyl azetidine-3-carboxylate hydrochloride

The procedure of Example 38 was performed while using an ethanol as a substitute for methanol. Thus, the title compound having the following physical properties was obtained.
TLC: Rf 0.20 (chloroform:methanol:aqueous ammonia=20:5:1);
$^1$H-NMR (DMSO-d$_6$): δ 9.19-9.59 (m, 1H), 9.01-9.26 (m, 1H), 4.13 (q, J=7.1 Hz, 2H), 3.95-4.15 (m, 4H), 3.60-3.76 (m, 1H), 1.20 (t, J=7.1 Hz, 3H).

EXAMPLE 39 ethyl 1-benzylazetidine-3-carboxylate

Tetraethylammonium acetate tetrahydrate (9.42 g) was added to a 1,3-dimethyl-3,4,5,6-tetrahydro-2(1H)-pyrimidinone (DMPU, 40 mL) solution of diethyl 1-benzylazetidine-3,3-dicarboxylate (7.00 g, which was prepared according to the method described in Synthetic Communications, volume 33, No. 19, page 3347, 2003), followed by stirring at 130° C. for 12 hours. The reaction solution was added with water, and extracted with an ethyl acetate-hexane (1:1) mixed solvent. The organic layer was washed with water, hexane was added, and extracted with 0.5 mol/L hydrochloric acid. The aqueous layer was washed with tert-butyl methyl ether, and the pH was adjusted to 8 using a 5 mol/L aqueous sodium hydroxide solution, followed by further extraction with ethyl acetate. The organic layer was washed with brine, dried over sodium sulfate, and concentrated, to thereby obtain the title compound (3.21 g) having the following physical properties.
TLC: Rf 0.54 (hexane:ethyl acetate=1:2);
$^1$H-NMR (CDCl$_3$): δ 7.11-7.41 (m, 5H), 4.15 (q, J=7.1 Hz, 2H), 3.60 (s, 2H), 3.46-3.58 (m, 2H), 3.23-3.41 (m, 3H), 1.26 (t, J=7.1 Hz, 3H).

EXAMPLE 40 ethyl azetidine-3-carboxylate hydrochloride 4N hydrogen chloride/dioxane solution (4.6 mL) was added to a 1,4-dioxane (5 mL) solution of the compound (2.00 g) prepared in Example 39. The mixture was stirred for a while, and concentrated. The resultant was added with ethanol (30 mL) and 20% palladium hydroxide/carbon (about 50% wet, 200 mg), followed by stirring at 70° C. for 7 hours under a hydrogen atmosphere. The reaction solution was filtered, and the filtrate was concentrated, to thereby obtain the title compound (1.60 g) having the following physical properties.
TLC: Rf 0.14 (chloroform:methanol:aqueous ammonia=80:10:1).

EXAMPLE 41

2-methoxy-4-propylphenol

Palladium-carbon (5 mass %, 54 mg) was added to a 2-propanol (2.5 mL) solution of eugenol (CAS No. 97-53-0, 500 mg) under an argon atmosphere. The resultant mixture was vigorously stirred at an external temperature of 50° C. under a hydrogen flow for about 4.5 hours. The reaction solution was filtered through Celite, and the filtrate was concentrated, to thereby obtain the title compound (447 mg) having the following physical properties.

TLC: Rf 0.55 (hexane:ethyl acetate=6:1).

EXAMPLE 42

2-methoxy-4-propylphenyl trifluoromethanesulfonate

Pyridine (63.3 mL) was added to an acetonitrile (450 mL) solution of the compound (100.0 g) prepared in Example 41. The reaction solution was cooled to an internal temperature of −4° C., and trifluoromethanesulfonic anhydride (108.6 mL) was slowly added dropwise, followed by stirring at an internal temperature of about 0 to 10° C. for about 30 minutes. The reaction solution was added with 0.5 mol/L hydrochloric acid (400 mL), and extracted with toluene. The organic layer was successively washed with water and brine, dried, and concentrated, to thereby obtain the title compound (178.7 g) having the following physical properties.

TLC: Rf 0.63 (hexane:ethyl acetate=6:1);
$^1$H-NMR (CDCl$_3$): δ 7.10 (d, J=8.4 Hz, 1H), 6.83 (d, J=2.00 Hz, 1H), 6.76 (dd, J=8.40, 2.00 Hz, 1H), 3.90 (s, 3H), 2.59 (t, J=7.60 Hz, 2H), 1.59-1.73 (m, 2H), 0.96 (t, J=7.20 Hz, 3H).

EXAMPLE 43 methyl 2-methoxy-4-propylbenzoate

To a dimethyl sulfoxide (20 mL)-methanol (15 mL) mixed solution of the compound (5.00 g) prepared in Example 42, triethylamine (4.70 mL), 1,3-bis(diphenylphosphino)propane (DPPP, 346 mg), and palladium acetate (94 mg) were added, followed by vigorously stirring at an internal temperature of about 70° C. under a carbon monooxide atmosphere for about 2.5 hours. The reaction solution was cooled, and diluted with methyl tert-butyl ether (20 mL), and added with a 3.5% aqueous sodium bicarbonate solution (67.5 mL), thiocyanuric acid (201 mg), and activated carbon (500 mg), followed by vigorously stirring at room temperature for about 30 minutes. The precipitate was filtered. The organic layer was successively washed with water and brine, dried, and concentrated, to thereby obtain the title compound (3.10 g) having the following physical properties.

TLC: Rf 0.50 (hexane:ethyl acetate=2:1);
$^1$H-NMR (CDCl$_3$): δ 7.73 (d, J=8.00 Hz, 1H), 6.77-6.82 (m, 2H), 3.90 (s, 3H), 3.87 (s, 3H), 2.61 (t, J=7.50 Hz, 2H), 1.59-1.73 (m, 2H), 0.95 (t, J=7.50 Hz, 3H).

EXAMPLE 44

(2-methoxy-4-propylphenyl)methanol

Red-Al/toluene solution (66.5% content, 2.05 g) was slowly added to a tetrahydrofuran (3 mL) solution of the compound (1.00 g) prepared in Example 43 at an internal temperature of 5° C., followed by stirring at an internal temperature of about 35° C. for about 2.5 hours. Methanol (0.5 mL) was added to the reaction solution at an internal temperature of 9° C. to stop the reaction. The reaction solution was poured into a 50% aqueous potassium sodium tartrate tetrahydrate solution, and extracted with ethyl acetate. The organic layer was successively washed with water and brine, dried, and concentrated, to thereby obtain the title compound (0.91 g) having the following physical properties.

TLC: Rf 0.43 (hexane:ethyl acetate=2:1);
$^1$H-NMR (CDCl$_3$): δ 7.16 (d, J=7.50 Hz, 1H), 6.76 (dd, J=7.50, 1.50 Hz, 1H), 6.71 (d, J=1.50 Hz, 1H), 4.65 (s, 2H), 3.86 (s, 3H), 2.58 (t, J=7.50 Hz, 2H), 2.20 (s, 1H), 1.58-1.72 (m, 2H), 0.95 (t, J=7.50 Hz, 3H).

EXAMPLE 45

1-(chloromethyl)-2-methoxy-4-propylbenzene

Pyridine (79 mL) was added to a dimethoxyethane (640 mL) solution of the compound (160 g) prepared in Example 44. Thionyl chloride (71.3 mL) was slowly added dropwise under stirring, followed by further stirring for 30 minutes. The reaction solution was cooled, added with ice water, and extracted with methyl tert-butyl ether. The organic layer was successively washed with an aqueous saturated sodium hydrogen carbonate solution and brine, dried, and concentrated, to thereby obtain the title compound (169 g) having the following physical properties.

TLC: Rf 0.65 (hexane:ethyl acetate=10:1);
$^1$H-NMR (CDCl$_3$): δ 7.24 (d, J=7.50 Hz, 1H), 6.76 (dd, J=7.50, 1.50 Hz, 1H), 6.71 (d, J=1.50 Hz, 1H), 4.64 (s, 2H), 3.87 (s, 3H), 2.53-2.64 (m, 2H), 1.57-1.72 (m, 2H), 0.95 (t, J=7.50 Hz, 3H).

EXAMPLE 46

6-[(2-methoxy-4-propylbenzyl)oxy]-1-methyl-3,4-dihydro-2-naphthalenecarboaldehyde Potassium phosphate (189 g) was added to an N,N-dimethylacetamide (584 mL) solution of the compound (146 g) prepared in Example 4 and the compound (162 g) prepared in Example 45, followed by stirring at 60° C. for 2 hours. The reaction solution was cooled, and added with water. The precipitate was filtered and dried. The obtained crude (263 g) was recrystallized from ethyl acetate (520 mL)-heptane (2600 mL) mixed solvent, to thereby obtain the title compound (213 g) having the following physical properties.

TLC: Rf 0.25 (hexane:ethyl acetate=6:1);
$^1$H-NMR (CDCl$_3$): δ 10.30 (s, 1H), 7.46 (d, J=8.50 Hz, 1H), 7.31 (d, J=7.50 Hz, 1H), 6.89 (dd, J=8.50, 2.50 Hz, 1H), 6.84 (d, J=2.50 Hz, 1H), 6.79 (dd, J=7.50, 1.50 Hz, 1H), 6.73 (d, J=1.50 Hz, 1H), 5.10 (s, 2H), 3.86 (s, 3H), 2.68-2.76 (m, 2H), 2.56-2.63 (m, 2H), 2.47-2.54 (m, 5H), 1.58-1.73 (m, 2H), 0.96 (t, J=7.50 Hz, 3H).

EXAMPLE 46-1

6-{[2,4-bis(trifluoromethyl)benzyl]oxy}-1-methyl-3,4-dihydro-2-naphthalenecarboaldehyde The procedure of Example 46 was similarly performed while using 2,4-bis (trifluoromethyl)benzyl chloride (CAS No. 195136-46-0) as a substitute for the compound prepared in Example 45. Thus, the title compound having the following physical properties was obtained.

TLC: Rf 0.27 (hexane:ethyl acetate=5:1);
$^1$H-NMR (CDCl$_3$): δ 10.33 (s, 1H), 7.96 (s, 1H), 7.92 (d, J=9.00 Hz, 1H), 7.85 (d, J=9.00 Hz, 1H), 7.50 (d, J=8.50 Hz, 1H), 6.82-6.88 (m, 2H), 5.36 (s, 2H), 2.71-2.78 (m, 2H), 2.48-2.55 (m, 5H).

EXAMPLE 47 ethyl 1-({6-[(2-methoxy-4-propylbenzyl)oxy]-1-methyl-3,4-dihydro-2-naphthalenyl}methyl)-3-azetidinecarboxylate Triethylamine (95.5 mL) and sodium triacetoxyborohydride (145 g) were added at 0° C. to a tetrahydrofuran (800 mL) solution of the compound (200 g) prepared in Example 46, followed by stirring for 10 minutes. An acetonitrile (400 mL) solution of the compound (113 g) prepared in Example 38-1 was added dropwise to the resultant mixture, followed by stirring at 30 to 40° C. for 1.5 hours. The reaction solution was added with an aqueous sodium carbonate solution, and extracted with ethyl acetate. The organic layer was washed with an aqueous sodium carbonate solution, dried, and concentrated, to thereby obtain the title compound (281 g) having the following physical properties.

TLC: Rf 0.31 (hexane:ethyl acetate=1:1);
$^1$H-NMR (CDCl$_3$): δ 7.33 (d, J=7.50 Hz, 1H), 7.19 (d, J=8.50 Hz, 1H), 6.76-6.84 (m, 3H), 6.72 (s, 1H), 5.06 (s, 2H), 4.16 (q, J=7.00 Hz, 2H), 3.85 (s, 3H), 3.52-3.60 (m, 2H), 3.25-3.38 (m, 5H), 2.64-2.72 (m, 2H), 2.55-2.63 (m, 2H), 2.22-2.30 (m, 2H), 2.09 (s, 3H), 1.58-1.72 (m, 2H), 1.26 (t, J=7.00 Hz, 3H), 0.95 (t, J=7.00 Hz, 3H).

EXAMPLE 47-1 ethyl 1-[(6-{[2,4-bis(trifluoromethyl)benzyl]oxy}-1-methyl-3,4-dihydro-2-naphthalenyl)methyl]-3-azetidinecarboxylate The procedure of Example 47 was similarly performed while using the compound prepared in Example 46-1 as a substitute for the compound prepared in Example 46. Thus, the title compound having the following physical properties was obtained.

TLC: Rf 0.13 (hexane:ethyl acetate=2:1);
$^1$H-NMR (CDCl$_3$): δ 7.91-7.97 (m, 2H), 7.83 (d, J=8.00 Hz, 1H), 7.20 (d, J=8.50 Hz, 1H), 6.73-6.79 (m, 2H), 5.32 (s, 2H), 4.16 (q, J=7.00 Hz, 2H), 3.51-3.61 (m, 2H), 3.23-3.37 (m, 5H), 2.65-2.73 (m, 2H), 2.22-2.33 (m, 2H), 2.09 (s, 3H), 1.26 (t, J=7.00 Hz, 3H).

EXAMPLE 48

1-({6-[(2-methoxy-4-propylbenzyl)oxy]-1-methyl-3,4-dihydro-2-naphthalenyl}methyl)-3-azetidinecarboxylic acid An aqueous (135 mL) solution of sodium hydroxide (28 g) was added to a methanol (1320 mL) solution of the compound (262 g) prepared in Example 47, followed by stirring at 40° C. for 2 hours. The reaction solution was added with 5 mol/L hydrochloric acid (135 mL) and water (1050 mL), and the precipitate was filtered. The obtained precipitate was washed with a methanol-water (1:1) mixed solvent (470 mL), and dried. The obtained powder was suspended in acetone (2.0 L), followed by stirring at 60° C. for 2 hours. The reaction solution was cooled. The precipitate was filtered and washed with acetone (390 mL), to thereby obtain the title compound (191 g) having the following physical properties.

Melting point 158-163° C.;
TLC: Rf 0.20 (chloroform:methanol:aqueous ammonia=20:5:1);
$^1$H-NMR (CD$_3$OD): δ 7.31 (d, J=8.50 Hz, 1H), 7.25 (d, J=7.50 Hz, 1H), 6.82 (m, 2H), 6.77 (m, 2H), 5.04 (s, 2H), 4.18 (m, 4H), 4.08 (s, 2H), 3.85 (s, 3H), 3.41 (m, 1H), 2.72 (t, J=8.06 Hz, 2H), 2.59 (t, J=7.50 Hz, 2H), 2.23 (m, 5H), 1.65 (m, 2H), 0.94 (t, J=7.50 Hz, 3H);
IR(KBr): 3418, 2957, 2931, 2820, 1605, 1500, 1382, 1250, 993, 489 cm$^{-1}$;
Powder X-ray diffraction spectrum: The measurement results are shown in Table 1 and the chart is shown in FIG. 1.

TABLE 1

| d value (Angstrom) | Diffraction angle (2θ, °) | Relative intensity (%) |
|---|---|---|
| d = 10.48375 | 8.427 | 67.8 |
| d = 9.48985 | 9.312 | 24.9 |
| d = 8.47631 | 10.428 | 19.9 |
| d = 7.47227 | 11.834 | 48.0 |
| d = 6.99142 | 12.651 | 76.4 |
| d = 5.85132 | 15.129 | 10.1 |
| d = 5.27542 | 16.792 | 65.6 |
| d = 4.98672 | 17.772 | 49.7 |
| d = 4.84775 | 18.286 | 100.0 |
| d = 4.72367 | 18.771 | 34.0 |
| d = 4.60305 | 19.267 | 19.1 |
| d = 4.45544 | 19.912 | 37.8 |
| d = 4.19597 | 21.157 | 74.6 |
| d = 4.12497 | 21.525 | 34.5 |
| d = 3.99689 | 22.224 | 34.2 |
| d = 3.91138 | 22.716 | 27.2 |
| d = 3.79347 | 23.432 | 65.7 |
| d = 3.71787 | 23.915 | 42.7 |
| d = 3.50995 | 25.355 | 28.2 |
| d = 3.37123 | 26.417 | 16.4 |
| d = 3.29393 | 27.048 | 22.0 |

Differential scanning calorimetry (DSC, heating rate: 5° C./min): An endothermic peak near 170° C. was confirmed. The chart is shown in FIG. 2.

EXAMPLE 48-1

1-[(6-{[2,4-bis(trifluoromethyl)benzyl]oxy}-1-methyl-3,4-dihydro-2-naphthalenyl)methyl]-3-azetidinecarboxylic acid The procedure of Example 48 was similarly performed while using the compound prepared in Example 47-1 as a substitute for the compound prepared in Example 47. Thus, the title compound having the following physical properties was obtained.

Melting point 155-165° C.;
TLC: Rf 0.18 (chloroform:methanol:aqueous ammonia=20:5:1);
$^1$H-NMR (CD$_3$OD): δ 7.89-8.02 (m, 3H), 7.33 (d, J=8.43 Hz, 1H), 6.77-6.86 (m, 2H), 5.32 (s, 2H), 4.13-4.29 (m, 4H), 4.09 (s, 2H), 3.33-3.49 (m, 1H), 2.68-2.79 (m, 2H), 2.17-2.33 (m, 5H);
Powder X-ray diffraction spectrum: The measurement results are shown in Table 2 and the chart is shown in FIG. 3.

TABLE 2

| d value (Angstrom) | Diffraction angle (2θ, °) | Relative intensity (%) |
|---|---|---|
| 10.47991 | 8.430 | 13.7 |
| 8.42050 | 10.497 | 11.1 |
| 7.36612 | 12.005 | 22.3 |
| 6.68490 | 13.233 | 17.2 |
| 5.68958 | 15.562 | 13.7 |
| 5.41787 | 16.347 | 64.1 |
| 5.25255 | 16.866 | 13.6 |
| 5.02870 | 17.622 | 31.6 |

TABLE 2-continued

| d value (Angstrom) | Diffraction angle (2θ, °) | Relative intensity (%) |
|---|---|---|
| 4.83075 | 18.350 | 100.0 |
| 4.75633 | 18.640 | 43.4 |
| 4.56545 | 19.427 | 44.9 |
| 4.49335 | 19.742 | 29.9 |
| 4.37825 | 20.266 | 27.6 |
| 4.21626 | 21.053 | 29.1 |
| 4.16364 | 21.322 | 20.9 |
| 4.01449 | 22.124 | 44.6 |
| 3.93543 | 22.575 | 17.4 |
| 3.83216 | 23.191 | 34.6 |
| 3.77205 | 23.566 | 46.3 |
| 3.69712 | 24.051 | 31.4 |
| 3.58866 | 24.789 | 35.6 |

Differential scanning calorimetry (DSC, heating rate: 10° C./min): An endothermic peak near 172° C. was confirmed. The chart is shown in FIG. 4.

EXAMPLE 49

1-({6-[(2-methoxy-4-propylbenzyl)oxy]-1-methyl-3,4-dihydro-2-naphthalenyl}methyl)-3-azetidinecarboxylic acid monohydrate A methanol (150 mL)-water (15 mL) mixed solvent was added to the compound (3.10 g) prepared in Example 48. The resultant mixture was heated to 60° C. to be completely dissolved. The resultant solution was added with water (210 mL), and left to stand at 0° C. for 1 hour. The precipitate was filtered. The obtained precipitate was washed with a methanol-water (2:3) mixed solvent and dried, to thereby obtain the title compound (A-type crystal) (2.89 g) having the following physical properties.

TLC: Rf 0.20 (chloroform:methanol:aqueous ammonia=20:5:1);

$^1$H-NMR (CD$_3$OD): δ 7.30 (d, J=8.6 Hz, 1H), 7.24 (d, J=7.7 Hz, 1H), 6.70-6.87 (m, 4H), 5.04 (s, 2H), 4.12-4.28 (m, 4H), 4.09 (s, 2H), 3.84 (s, 3H), 3.34-3.50 (m, 1H), 2.72 (t, J=6.8 Hz, 2H), 2.59 (t, J=7.3 Hz, 2H), 2.16-2.30 (m, 5H), 1.57-1.74 (m, 2H), 0.94 (t, J=7.3 Hz, 3H);

Powder X-ray diffraction spectrum: The measurement results are shown in Table 3 and the chart is shown in FIG. 5.

TABLE 3

| d value (Angstrom) | Diffraction angle (2θ, °) | Relative intensity (%) |
|---|---|---|
| d = 9.97990 | 8.854 | 100.0 |
| d = 7.93331 | 11.144 | 18.9 |
| d = 7.68139 | 11.511 | 24.0 |
| d = 7.28869 | 12.133 | 13.4 |
| d = 6.66106 | 13.281 | 64.6 |
| d = 6.32713 | 13.986 | 28.7 |
| d = 6.10808 | 14.490 | 12.0 |
| d = 5.80013 | 15.264 | 6.1 |
| d = 5.08879 | 17.413 | 61.6 |
| d = 4.77069 | 18.584 | 22.7 |
| d = 4.73380 | 18.730 | 19.6 |
| d = 4.59884 | 19.285 | 14.2 |
| d = 4.46361 | 19.875 | 21.8 |
| d = 4.23432 | 20.963 | 19.2 |
| d = 3.99706 | 22.223 | 52.3 |
| d = 3.95885 | 22.440 | 42.5 |
| d = 3.72944 | 23.840 | 22.2 |
| d = 3.70683 | 23.988 | 24.2 |
| d = 3.57303 | 24.900 | 24.0 |
| d = 3.54316 | 25.113 | 29.1 |

Differential scanning calorimetry (DSC, heating rate: 5° C./min): Endothermic peaks near 123° C. and near 168° C. were confirmed. The chart is shown in FIG. 6.

A methyl ethyl ketone-water (10:1) mixed solution (3.75 mL) was added under heating at 70° C. to the title compound (A-type crystal) (500 mg) prepared in this example. After the mixture was completely dissolved, the resultant solution was left to stand at room temperature overnight, and subsequently left to stand at a low temperature (about 5° C.) for 2 days. The obtained solid was collected by a filter, dried at 40° C. under reduced pressure (about 6 mmHg) for 4 hours, to thereby obtain a white solid of the title compound (B-type crystal) (305 mg) having the following physical properties.

Powder X-ray diffraction spectrum: The measurement results are shown in Table 4 and the chart is shown in FIG. 7.

TABLE 4

| d value (Angstrom) | Diffraction angle (2θ, °) | Relative intensity (%) |
|---|---|---|
| d = 9.73547 | 9.076 | 77.1 |
| d = 7.87100 | 11.233 | 31.7 |
| d = 7.58344 | 11.660 | 29.3 |
| d = 6.83790 | 12.936 | 71.2 |
| d = 6.49668 | 13.619 | 59.4 |
| d = 6.18156 | 14.317 | 13.9 |
| d = 5.60660 | 15.794 | 20.6 |
| d = 5.24141 | 16.902 | 71.3 |
| d = 5.10255 | 17.366 | 86.8 |
| d = 4.90216 | 18.081 | 49.1 |
| d = 4.71929 | 18.788 | 27.4 |
| d = 4.43114 | 20.022 | 87.8 |
| d = 4.14036 | 21.444 | 30.5 |
| d = 4.10430 | 21.635 | 30.2 |
| d = 3.96738 | 22.391 | 100.0 |
| d = 3.90770 | 22.738 | 61.3 |
| d = 3.79457 | 23.425 | 32.7 |
| d = 3.71500 | 23.934 | 41.6 |
| d = 3.62279 | 24.553 | 31.4 |
| d = 3.50981 | 25.356 | 28.3 |
| d = 3.05410 | 29.218 | 28.8 |

Differential scanning calorimetry (DSC, heating rate: 5° C./min): Endothermic peaks near 115° C. and near 167° C. were confirmed. The chart is shown in FIG. 8.

EXAMPLE 49-1

1-[(6-{[2,4-bis(trifluoromethyl)benzyl]oxy}-1-methyl-3,4-dihydro-2-naphthalenyl)methyl]-3-azetidinecarboxylic acid monohydrate The procedure of Example 49 was similarly performed while using the compound prepared in Example 48-1 as a substitute for the compound prepared in Example 48. Thus, the title compound having the following physical properties was obtained.

TLC: Rf 0.18 (chloroform:methanol:aqueous ammonia=20:5:1);

$^1$H-NMR (CD$_3$OD): δ 7.91-8.03 (m, 3H), 7.35 (d, J=8.60 Hz, 1H), 6.79-6.88 (m, 2H), 5.34 (s, 2H), 4.13-4.29 (m, 4H), 4.10 (s, 2H), 3.33-3.49 (m, 1H), 2.68-2.78 (m, 2H), 2.17-2.33 (m, 5H);

Powder X-ray diffraction spectrum: The measurement results are shown in Table 5 and the chart is shown in FIG. 9.

TABLE 5

| d value (Angstrom) | Diffraction angle (2θ, °) | Relative intensity (%) |
|---|---|---|
| 11.56944 | 7.635 | 76.2 |
| 7.75051 | 11.407 | 38.0 |
| 7.43156 | 11.899 | 59.1 |
| 6.95904 | 12.710 | 49.7 |
| 6.69471 | 13.214 | 20.1 |
| 6.49820 | 13.615 | 38.1 |
| 6.04854 | 14.633 | 14.3 |
| 5.80619 | 15.247 | 25.5 |
| 5.28185 | 16.771 | 36.8 |
| 5.13914 | 17.241 | 50.6 |
| 4.89009 | 18.126 | 20.7 |
| 4.66002 | 19.029 | 100.0 |
| 4.44685 | 19.950 | 75.8 |
| 4.37032 | 20.303 | 36.3 |
| 4.26592 | 20.805 | 96.7 |
| 4.17962 | 21.240 | 18.8 |
| 4.05539 | 21.899 | 13.6 |
| 3.87521 | 22.930 | 64.0 |
| 3.78047 | 23.513 | 85.5 |
| 3.64590 | 24.394 | 23.1 |

Differential scanning calorimetry (DSC, heating rate: 10° C./min): The chart is shown in FIG. 10.

EXAMPLE 50

1-({6-[(2-methoxy-4-propylbenzyl)oxy]-1-methyl-3,4-dihydro-2-naphthalenyl}methyl)-3-azetidinecarboxylic acid hydrochloride 0.1 mol/L hydrochloric acid (5.54 mL) was gradually added to a methanol (8 mL)-water (2 mL) mixed solution of the compound (201 mg) prepared in Example 48 under ice bath. The solution was freeze-dried, to thereby obtain the title compound (218 mg) having the following physical properties.

TLC: Rf 0.20 (chloroform:methanol:aqueous ammonia=20:5:1);
$^1$H-NMR (CDCl$_3$): δ 7.17-7.48 (m, 2H), 6.63-6.92 (m, 4H), 5.05 (s, 2H), 3.23-4.71 (m, 12H), 2.65-2.82 (m, 2H), 2.57 (t, J=7.41 Hz, 2H), 2.31-2.45 (m, 2H), 2.18 (s, 3H), 1.50-1.79 (m, 2H), 0.95 (t, J=7.32 Hz, 3H).

EXAMPLE 50-1

1-[(6-{[2,4-bis(trifluoromethyl)benzyl]oxy}-1-methyl-3,4-dihydro-2-naphthalenyl)methyl]-3-azetidinecarboxylic acid hydrochloride The procedure of Example 50 was similarly performed while using the compound prepared in Example 48-1 as a substitute for the compound prepared in Example 48. Thus, the compound having the following physical properties was obtained.

TLC: Rf 0.18 (chloroform:methanol:aqueous ammonia=20:5:1);
$^1$H-NMR (CD$_3$OD): δ 7.87-8.09 (m, 3H), 7.37 (d, J=8.05 Hz, 1H), 6.76-6.95 (m, 2H), 5.35 (s, 2H), 4.21-4.50 (m, 4H), 4.16 (s, 2H), 3.57-3.82 (m, 1H), 2.58-2.83 (m, 2H), 2.15-2.38 (m, 5H).

EXAMPLE 51 sodium 1-({6-[(2-methoxy-4-propylbenzyl)oxy]-1-methyl-3,4-dihydro-2-naphthalenyl}methyl)-3-azetidinecarboxylate To the compound (200 mg) prepared in Example 48, 0.1 mol/L aqueous sodium hydroxide solution (4.56 mL) was added, and the solution was freeze-dried. The obtained residue was dissolved in water and freeze-dried again, to thereby obtain the title compound (209 mg) having the following physical properties.

TLC: Rf 0.20 (chloroform:methanol:aqueous ammonia=20:5:1);
$^1$H-NMR (CDCl$_3$): δ 7.21-7.30 (m, 2H), 6.99-7.15 (m, 1H), 6.59-6.78 (m, 3H), 4.95 (s, 2H), 3.74 (s, 3H), 3.33-3.49 (m, 2H), 3.07-3.30 (m, 5H), 2.45-2.70 (m, 4H), 2.06-2.20 (m, 2H), 1.95 (s, 3H), 1.51-1.68 (m, 2H), 0.92 (t, J=7.23 Hz, 3H).

Examples 51-2 to 51-5

The procedure similar to that of Example 51 was carried out using an aqueous potassium hydroxide solution or an aqueous calcium hydroxide solution in place of an aqueous sodium hydroxide solution and using the compound prepared in Example 48-1 in place of the compound prepared in Example 48, to thereby obtain the respective compounds having the following physical properties.

EXAMPLE 51-2 potassium 1-({6-[(2-methoxy-4-propylbenzyl)oxy]-1-methyl-3,4-dihydro-2-naphthalenyl}methyl)-3-azetidinecarboxylate TLC: Rf 0.20 (chloroform:methanol:aqueous ammonia=20:5:1);
$^1$H-NMR (CDCl$_3$): δ 7.21-7.37 (m, 2H), 7.06 (d, J=9.15 Hz, 1H), 6.50-6.87 (m, 3H), 4.94 (s, 2H), 3.73 (s, 3H), 3.30-3.47 (m, 2H), 3.03-3.26 (m, 4H), 2.82-2.99 (m, 1H), 2.41-2.68 (m, 4H), 2.06-2.20 (m, 2H), 1.95 (s, 3H), 1.46-1.71 (m, 2H), 0.91 (t, J=7.32 Hz, 3H).

EXAMPLE 51-3

1-({6-[(2-methoxy-4-propylbenzyl) oxy]-1-methyl-3,4-dihydro-2-naphthalenyl}methyl)-3-azetidinecarboxylic acid hemicalcium salt TLC: Rf 0.20 (chloroform:methanol:aqueous ammonia=20:5:1);
$^1$H-NMR (CDCl$_3$): δ 7.17-7.40 (m, 2H), 6.67-6.90 (m, 4H), 5.05 (s, 2H), 3.94-4.42 (m, 4H), 3.90 (s, 2H), 3.83 (s, 3H), 3.27-3.56 (m, 1H), 2.69 (t, J=7.3 Hz, 2H), 2.52-2.62 (m, 2H), 2.28-2.41 (m, 2H), 2.16 (s, 3H), 1.54-1.72 (m, 2H), 0.95 (t, J=7.3 Hz, 3H).

EXAMPLE 51-4 sodium 1-[(6-{[2,4-bis(trifluoromethyl)benzyl]oxy}-1-methyl-3,4-dihydro-2-naphthalenyl)methyl]-3-azetidinecarboxylate TLC: Rf 0.18 (chloroform:methanol:aqueous ammonia=20:5:1);
$^1$H-NMR (CD$_3$OD): δ 7.89-8.10 (m, 3H), 7.18-7.36 (m, 1H), 6.73-6.85 (m, 2H), 5.33 (s, 2H), 3.51-3.73 (m, 2H), 3.35-3.48 (m, 4H), 3.17-3.26 (m, 1H), 2.56-2.78 (m, 2H), 2.17-2.34 (m, 2H), 2.10 (s, 3H).

EXAMPLE 51-5 potassium 1-[(6-{[2,4-bis(trifluoromethyl)benzyl]oxy}-1-methyl-3,4-dihydro-2-naphthalenyl)methyl]-3-azetidinecarboxylate TLC: Rf 0.18 (chloroform:methanol:aqueous ammonia=20:5:1);
$^1$H-NMR (CD$_3$OD): δ 7.84-8.12 (m, 3H), 7.16-7.38 (m, 1H), 6.65-6.87 (m, 2H), 5.33 (s, 2H), 3.55-3.70 (m, 2H), 3.35-3.50 (m, 4H), 3.13-3.27 (m, 1H), 2.62-2.77 (m, 2H), 2.18-2.30 (m, 2H), 2.10 (s, 3H).

EXAMPLE 52 ethyl 1-({6-[(2-methoxy-4-propylbenzyl)oxy]-1-methyl-3,4-dihydro-2-naphthalenyl}methyl)-3-azetidinecalboxylate 1-oxide M-chloroperbenzoic acid (57.3 mg) was added under ice bath to a dichloromethane (2 mL) solution of the compound (100 mg) prepared in Example 47, followed by stirring for 30 minutes. A saturated aqueous sodium thiosulfate solution, saturated aqueous sodium hydrogen carbonate solution, and dichloromethane were added to the reaction solution. The organic layer was washed with brine, dried, and concentrated. The obtained amorphous (128 mg) was purified by silica gel column chromatography (ethyl acetate: methanol=4:1 to dichloromethane:methanol=10:1) to thereby individually isolate the title compounds each having the following physical properties.
Less polar compound
TLC: Rf 0.26 (ethyl acetate:methanol=4:1);
$^1$H-NMR (CDCl$_3$): δ 7.24-7.38 (m, 2H), 6.65-6.92 (m, 4H), 5.08 (s, 2H), 4.42-4.69 (m, 2H), 4.27-4.40 (m, 2H), 4.22 (q, J=7.2 Hz, 2H), 3.86 (s, 3H), 3.48 (s, 2H), 3.18-3.34 (m, 1H), 2.51-2.85 (m, 6H), 2.20 (s, 3H), 1.58-1.74 (m, 2H), 1.28 (t, J=7.2 Hz, 3H), 0.96 (t, J=7.3 Hz, 3H). More polar compound
TLC: Rf 0.13 (ethyl acetate:methanol=4:1);
$^1$H-NMR (CDCl$_3$): δ 7.19-7.39 (m, 2H), 6.60-6.98 (m, 4H), 5.08 (s, 2H), 4.49-4.67 (m, 2H), 4.03-4.26 (m, 6H), 3.81-3.98 (m, 4H), 2.47-2.95 (m, 6H), 2.18 (s, 3H), 1.55-1.74 (m, 2H), 1.26 (t, J=7.4 Hz, 3H), 0.96 (t, J=7.2 Hz, 3H).

EXAMPLE 53

1-({6-[(2-methoxy-4-propylbenzyl)oxy]-1-methyl-3,4-dihydro-2-naphthalenyl}methyl)-3-azetidinecarboxylic acid 1-oxide A 5 mol/L aqueous sodium hydroxide (700 μL) solution was added under ice bath to a tetrahydrofuran-methanol (1:1) mixed solution (2.8 mL) of the compound (Less polar compound, 43 mg) prepared in Example 52, followed by stirring for 30 minutes. The reaction solution was concentrated, and purified by silica gel column chromatography (dichloromethane:methanol:aqueous ammonia=20:5:1), to thereby obtain the title compound (27 mg) having the following physical properties.
Less polar compound
TLC: Rf 0.32 (chloroform:methanol:aqueous ammonia=20:5:1);
$^1$H-NMR (CDCl$_3$): δ 7.20-7.37 (m, 2H), 6.65-6.92 (m, 4H), 5.05 (s, 2H), 4.82-5.00 (m, 2H), 4.40-4.59 (m, 2H), 4.27 (s, 2H), 3.83 (s, 3H), 3.27-3.42 (m, 1H), 2.63-2.78 (m, 2H), 2.53-2.63 (m, 2H), 2.36-2.53 (m, 2H), 2.17 (s, 3H), 1.53-1.75 (m, 2H), 0.90-0.99 (m, 3H).
The compound (more polar compound) prepared in Example 52 was subjected to the same procedure as described above, to thereby obtain the title compound having the following physical properties.
More polar compound
TLC: Rf 0.30 (chloroform:methanol:aqueous ammonia=20:5:1);
$^1$H-NMR (CDCl$_3$): δ 7.21-7.35 (m, 2H), 6.66-6.90 (m, 4H), 5.04 (s, 2H), 4.49-4.77 (m, 6H), 3.82 (s, 3H), 3.52-3.69 (m, 1H), 2.37-2.77 (m, 6H), 2.22 (s, 3H), 1.52-1.75 (m, 2H), 0.94 (t, J=7.2 Hz, 3H).

EXAMPLE 54 rel-1-({{(1R,2R)-6-[(2-methoxy-4-propylbenzyl)oxy]-1-methyl-1,2,3,4-tetrahydro-2-naphthalenyl}methyl)-3-azetidinecarboxylic acid (cis isomer, RS Configuration is Not Determined Yet)

10% palladium-carbon (wet, 10 mg) was added to a methanol-ethyl acetate-tetrahydrofuran
(2:1:1) solution (8.0 mL) of the compound (100 mg) prepared in Example 48, followed by stirring at room temperature under a hydrogen flow for 12 hours. The reaction solution was filtered through Celite (trade name), and concentrated. The obtained residue was purified by silica gel column chromatography (chloroform:methanol:aqueous ammonia=80:10:1 to 20:5:1), to thereby obtain the title compound (45 mg) having the following physical properties.
TLC: Rf 0.43 (chloroform:methanol:aqueous ammonia=20:5:1);
$^1$H-NMR (CD$_3$OD): δ 7.24 (d, J=7.68 Hz, 1H), 7.00 (d, J=8.60 Hz, 1H), 6.80 (s, 1H), 6.69-6.78 (m, 2H), 6.63-6.69 (m, 1H), 4.98 (s, 2H), 4.12-4.30 (m, 4H), 3.83 (s, 3H), 3.33-3.50 (m, 1H), 3.23-3.29 (m, 1H), 3.16 (dd, J=12.81, 8.23 Hz, 1H), 2.75-2.96 (m, 3H), 2.51-2.63 (m, 2H), 1.95-2.18 (m, 1H), 1.55-1.81 (m, 4H), 1.09 (d, J=7.14 Hz, 3H), 0.94 (t, J=7.32 Hz, 3H).

EXAMPLE 55

1-{[6-hydroxy-7-(2-methoxy-4-propylbenzyl)-1-methyl-3,4-dihydro-2-naphthalenyl]methyl}-3-azetidinecarboxylic acid (Compound 55(a)) and 1-{[6-hydroxy-5-(2-methoxy-4-propylbenzyl)-1-methyl-3,4-dihydro-2-naphthalenyl]methyl}-3-azetidinecarboxylic acid (Compound 55(b))

The 1st liquid (200 mL) as specified in the disintegration test of the Japanese Pharmacopoeia 14th edition was added to the compound (200 mg) prepared in Example 48, followed by stirring at 37° C. for one day. The reaction solution was cooled to 0° C., and adjusted to pH 4 to 5 using an aqueous sodium hydroxide solution. The precipitate was filtered. The obtained precipitate was purified by silica gel column chromatography (chloroform:methanol:aqueous ammonia=80:10:1 to 20:5:1), to thereby obtain the title compound 55(a) (60 mg) and the title compound 55(b) (9 mg) having the following physical properties.
Compound 55 (a):
TLC: Rf 0.22 (chloroform:methanol:aqueous ammonia=20:5:1);
$^1$H-NMR (CD$_3$OD): δ 6.98 (s, 1H), 6.90 (d, J=7.50 Hz, 1H), 6.75 (d, J=1.46 Hz, 1H), 6.64 (dd, J=7.50, 1.46 Hz, 1H), 6.57 (s, 1H), 4.08-4.24 (m, 4H), 4.02 (s, 2H), 3.82 (s, 2H), 3.80 (s, 3H), 3.32-3.45 (m, 1H), 2.59-2.69 (m, 2H), 2.49-2.59 (m, 2H), 2.15-2.24 (m, 2H), 2.05 (s, 3H), 1.55-1.69 (m, 2H), 0.92 (t, J=7.32 Hz, 3H).
Compound 55 (b):
TLC: Rf 0.22 (chloroform:methanol:aqueous ammonia=20:5:1);
$^1$H-NMR (CD$_3$OD): δ 7.20 (d, J=8.45 Hz, 1H), 6.72-6.75 (m, 1H), 6.73 (d, J=8.45 Hz, 1H), 6.48-6.56 (m, 2H), 4.04-4.24 (m, 4H), 4.03 (s, 2H), 3.92 (s, 2H), 3.87 (s, 3H), 3.30-3.45 (m, 1H), 2.42-2.57 (m, 4H), 2.19 (s, 3H), 2.00-2.13 (m, 2H), 1.52-1.68 (m, 2H), 0.91 (t, J=7.41 Hz, 3H).

Examples 56-1 to 56-9

The procedures similar to that of Examples 5 and 6, and as required, the procedure of Example 7, were carried out using a corresponding benzyl bromide compound in place of 1-bromo-3-(4-fluorophenyl)propane and using a corresponding azetidine compound in place of methyl azetidine-3-carboxylate hydrochloride, to thereby obtain the title compounds each having the following physical properties.

EXAMPLE 56-1

1-({6-[(4-isobutyl-2-methoxybenzyl)oxy]-1-methyl-3,4-dihydro-2-naphthalenyl}methyl)-3-azetidinecarboxamide TLC: Rf 0.38 (chloroform:methanol:aqueous ammonia=280:30:1);
$^1$H-NMR (CD$_3$OD): δ 7.25 (d, J=7.50 Hz, 1H), 7.19 (d, J=8.42 Hz, 1H), 6.68-6.81 (m, 4H), 5.02 (s, 2H), 3.84 (s, 3H), 3.48-3.58 (m, 2H), 3.31-3.41 (m, 5H), 2.58-2.72 (m, 2H), 2.48 (d, J=7.14 Hz, 2H), 2.16-2.30 (m, 2H), 2.10 (s, 3H), 1.78-1.98 (m, 1H), 0.91 (d, J=6.59 Hz, 6H).

EXAMPLE 56-2

1-({6-[(4-isobutyl-2-methoxybenzyl)oxy]-1-methyl-3,4-dihydro-2-naphthalenyl}methyl)-N-methyl-3-azetidinecarboxamide TLC: Rf 0.47 (chloroform:methanol:aqueous ammonia=280:30:1);
$^1$H-NMR (CD$_3$OD): δ 7.26 (d, J=7.68 Hz, 1H), 7.20 (d, J=8.23 Hz, 1H), 6.68-6.82 (m, 4H), 5.02 (s, 2H), 3.84 (s, 3H), 3.46-3.60 (m, 2H), 3.19-3.41 (m, 5H), 2.72 (s, 3H), 2.60-2.70 (m, 2H), 2.48 (d, J=7.32 Hz, 2H), 2.15-2.30 (m, 2H), 2.11 (s, 3H), 1.81-1.96 (m, 1H), 0.91 (d, J=6.59 Hz, 6H).

EXAMPLE 56-3

N-hydroxy-1-({6-[(4-isobutyl-2-methoxybenzyl)oxy]-1-methyl-3,4-dihydro-2-naphthalenyl}methyl)-3-azetidinecarboxamide TLC: Rf 0.20 (chloroform:methanol:aqueous ammonia=80:10:1);
$^1$H-NMR (CD$_3$OD): δ 7.26 (d, J=7.68 Hz, 1H), 7.20 (d, J=8.42 Hz, 1H), 6.66-6.83 (m, 4H), 5.02 (s, 2H), 3.84 (s, 3H), 3.46-3.57 (m, 2H), 3.34-3.44 (m, 4H), 3.10-3.26 (m, 1H), 2.59-2.71 (m, 2H), 2.47 (d, J=7.32 Hz, 2H), 2.14-2.30 (m, 2H), 2.10 (s, 3H), 1.80-1.96 (m, 1H), 0.91 (d, J=6.59 Hz, 6H).

EXAMPLE 56-4

1-({6-[(2-methoxy-4-propylbenzyl)oxy]-1-methyl-2-naphthyl}methyl)-3-azetidinecarboxylic acid TLC: Rf 0.21 (chloroform:methanol:aqueous ammonia=20:5:1);
$^1$H-NMR (CD$_3$OD:CDCl$_3$=3.6:1): δ 8.03 (d, J=10.06 Hz, 1H), 7.66 (d, J=8.60 Hz, 1H), 7.24-7.39 (m, 4H), 6.73-6.82 (m, 2H), 5.17 (s, 2H), 4.56 (s, 2H), 4.11-4.25 (m, 4H), 3.87 (s, 3H), 3.31-3.46 (m, 1H), 2.72 (s, 3H), 2.58 (t, J=7.70 Hz, 2H), 1.58-1.72 (m, 2H), 0.94 (t, J=7.32 Hz, 3H).

EXAMPLE 56-5

1-[(6-{[2,4-bis(trifluoromethyl)benzyl]oxy}-1-methyl-2-naphthyl)methyl]-3-azetidinecarboxylic acid TLC: Rf 0.31 (chloroform:methanol:aqueous ammonia=20:5:1);
$^1$H-NMR (CD$_3$OD): δ 8.14 (d, J=9.15 Hz, 1H), 7.96-8.10 (m, 3H), 7.72 (d, J=8.60 Hz, 1H), 7.43 (d, J=8.60 Hz, 1H), 7.31-7.39 (m, 2H), 5.48 (s, 2H), 4.60 (s, 2H), 4.14-4.25 (m, 4H), 3.33-3.48 (m, 1H), 2.75 (s, 3H).

Example 56-6

1-[(6-{[4-(2-hydroxypropyl)-2-methoxybenzyl]oxy}-1-methyl-3,4-dihydro-2-naphthalenyl)methyl]-3-azetidinecarboxylic acid TLC: Rf 0.25 (chloroform:methanol:aqueous ammonia=20:5:1);
$^1$H-NMR (CD$_3$OD): δ 7.33 (d, J=8.50 Hz, 1H), 7.28 (d, J=7.50 Hz, 1H), 6.87 (d, J=1.50 Hz, 1H), 6.77-6.85 (m, 3H), 5.05 (s, 2H), 4.13-4.25 (m, 4H), 4.09 (s, 2H), 3.91-4.01 (m, 1H), 3.86 (s, 3H), 3.36-3.47 (m, 1H), 2.63-2.82 (m, 4H), 2.18-2.28 (m, 5H), 1.15 (d, J=6.00 Hz, 3H).

EXAMPLE 56-7

1-[(6-{[4-(1-hydroxypropyl)-2-methoxybenzyl]oxy}-1-methyl-3,4-dihydro-2-naphthalenyl)methyl]-3-azetidinecarboxylic acid TLC: Rf 0.14 (chloroform:methanol:aqueous ammonia=20:5:1);
$^1$H-NMR (CD$_3$OD): δ 7.26-7.35 (m, 2H), 7.00 (d, J=1.28 Hz, 1H), 6.89 (dd, J=7.78, 1.28 Hz, 1H), 6.82 (dd, J=8.41, 2.74 Hz, 1H), 6.78 (d, J=2.74 Hz, 1H), 5.06 (s, 2H), 4.52 (t, J=6.50 Hz, 1H), 4.09-4.26 (m, 4H), 4.06 (s, 2H), 3.87 (s, 3H), 3.33-3.49 (m, 1H), 2.65-2.76 (m, 2H), 2.16-2.29 (m, 5H), 1.64-1.83 (m, 2H), 0.90 (t, J=7.41 Hz, 3H).

EXAMPLE 56-8

1-({6-[(5-hydroxy-2-methoxy-4-propylbenzyl)oxy]-1-methyl-3,4-dihydro-2-naphthalenyl}methyl)-3-azetidinecarboxylic acid TLC: Rf 0.24 (chloroform:methanol:aqueous ammonia=20:5:1).

EXAMPLE 56-9

1-({6-[(3-hydroxy-2-methoxy-4-propylbenzyl)oxy]-1-methyl-3,4-dihydro-2-naphthalenyl}methyl)-3-azetidinecarboxylic acid

EXAMPLES 57-1 to 57-87

The procedures similar to that of Examples 5, 6, and 7 were carried out using a corresponding halide in place of 1-bromo-3-(4-fluorophenyl)propane, to thereby obtain the title compounds each having the following physical properties.

EXAMPLE 57-1

1-{[6-(2-hydroxy-3-phenylpropoxy)-1-methyl-3,4-dihydro-2-naphthalenyl]methyl}-3-azetidinecarboxylic acid TLC: Rf 0.13 (butanol:acetic acid:water=20:4:1);
$^1$H-NMR (CD$_3$OD): δ 7.31 (d, J=8.42 Hz, 1H), 7.08-7.28 (m, 5H), 6.76 (dd, J=8.42, 2.70 Hz, 1H), 6.72 (d, J=2.70 Hz, 1H), 4.08-4.24 (m, 5H), 4.07 (s, 2H), 3.93 (dd, J=9.60, 3.90 Hz, 1H), 3.85 (dd, J=9.60, 5.70 Hz, 1H), 3.35-3.47 (m, 1H), 2.96 (dd, J=13.50, 6.30 Hz, 1H), 2.85 (dd, J=13.50, 7.20 Hz, 1H), 2.67-2.75 (m, 2H), 2.20 (s, 3H), 2.17-2.28 (m, 2H).

EXAMPLE 57-2

1-({6-[3-(4-fluorophenyl)-2-methoxypropoxy]-1-methyl-3,4-dihydro-2-naphthalenyl}methyl)-3-azetidinecarboxylic acid TLC: Rf 0.15 (butanol:acetic acid:water=20:4:1);
$^1$H-NMR (CD$_3$OD): δ 7.32 (d, J=8.60 Hz, 1H), 7.19-7.29 (m, 2H), 6.92-7.05 (m, 2H), 6.76 (dd, J=8.60, 2.56 Hz, 1H), 6.71 (d, J=2.56 Hz, 1H), 4.12-4.27 (m, 4H), 4.10 (s, 2H), 3.99 (dd, J=9.90, 3.90 Hz, 1H), 3.89 (dd, J=9.90, 5.10 Hz, 1H), 3.67-3.79 (m, 1H), 3.40 (s, 3H), 3.37-3.48 (m, 1H), 2.83-3.00 (m, 2H), 2.65-2.76 (m, 2H), 2.20 (s, 3H), 2.14-2.28 (m, 2H).

EXAMPLE 57-3

1-({1-chloro-6-[(4-isobutylbenzyl)oxy]-3,4-dihydro-2-naphthalenyl}methyl)-3-azetidinecarboxylic acid TLC: Rf 0.24 (chloroform:methanol:aqueous ammonia=20:5:1);
$^1$H-NMR (CD$_3$OD): δ 7.57 (d, J=8.4 Hz, 1H), 7.32 (d, J=8.1 Hz, 2H), 7.15 (d, J=8.1 Hz, 2H), 6.90 (dd, J=8.4, 2.6 Hz, 1H), 6.86 (d, J=2.6 Hz, 1H), 5.06 (s, 2H), 4.23 (d, J=8.1 Hz, 4H), 4.18 (s, 2H), 3.36-3.51 (m, 1H), 2.84 (t, J=7.2 Hz, 2H), 2.41-2.51 (m, 4H), 1.77-1.94 (m, 1H), 0.89 (d, J=6.6 Hz, 6H).

EXAMPLE 57-4

1-[(2Z)-3-chloro-3-(4-{[(2S)-3-(4-fluorophenyl)-2-methylpropyl]oxy}phenyl)-2-propenyl]-3-azetidinecarboxylic acid TLC: Rf 0.22 (butanol:acetic acid:water=20:4:1);
$^1$H-NMR (CDCl$_3$): δ 7.54 (d, J=9.00 Hz, 2H), 7.04-7.15 (m, 2H), 6.95 (t, J=8.69 Hz, 2H), 6.85 (d, J=9.00 Hz, 2H), 6.15 (t, J=6.86 Hz, 1H), 4.16-4.32 (m, 2H), 3.89-4.05 (m, 4H), 3.78 (d, J=5.85 Hz, 2H), 3.18-3.35 (m, 1H), 2.82 (dd, J=13.50, 6.60 Hz, 1H), 2.54 (dd, J=13.50, 7.80 Hz, 1H), 2.08-2.30 (m, 1H), 1.01 (d, J=6.77 Hz, 3H).

EXAMPLE 57-5

1-({6-[2-(4-fluorobenzyl)-3-methoxypropoxy]-1-methyl-3,4-dihydro-2-naphthalenyl}methyl)-3-azetidinecarboxylic acid TLC: Rf 0.15 (butanol:acetic acid:water=20:4:1);
$^1$H-NMR (CD$_3$OD): δ 7.26 (d, J=8.42 Hz, 1H), 7.14-7.22 (m, 2H), 6.91-7.04 (m, 2H), 6.72 (dd, J=8.42, 2.56 Hz, 1H), 6.67 (d, J=2.56 Hz, 1H), 3.75-4.02 (m, 7H), 3.41 (d, J=5.85 Hz, 2H), 3.25-3.38 (m, 5H), 2.76 (d, J=7.68 Hz, 2H), 2.63-2.72 (m, 2H), 2.18-2.31 (m, 3H), 2.16 (s, 3H).

EXAMPLE 57-6

1-({6-[(3-isobutylbenzyl)oxy]-1-methyl-3,4-dihydro-2-naphthalenyl}methyl)-3-azetidinecarboxylic acid TLC: Rf 0.29 (chloroform:methanol:aqueous ammonia=20:5:1);
$^1$H-NMR (CD$_3$OD): δ 7.31 (d, J=8.60 Hz, 1H), 7.18-7.30 (m, 3H), 7.06-7.11 (m, 1H), 6.84 (dd, J=8.60, 2.74 Hz, 1H), 6.79 (d, J=2.74 Hz, 1H), 5.05 (s, 2H), 4.12-4.27 (m, 4H), 4.09 (s, 2H), 3.34-3.47 (m, 1H), 2.66-2.76 (m, 2H), 2.47 (d, J=7.32 Hz, 2H), 2.18-2.28 (m, 5H), 1.77-1.92 (m, 1H), 0.88 (d, J=6.59 Hz, 6H).

EXAMPLE 57-7

1-[(2E)-3-(4-{[(2S)-3-(4-chlorophenyl)-2-methylpropyl]oxy}-2-methylphenyl)-2-butenyl]-3-azetidinecarboxylic acid TLC: Rf 0.18 (chloroform:methanol:aqueous ammonia=20:5:1);
$^1$H-NMR (CD$_3$OD): δ 7.25 (d, J=8.50 Hz, 2H), 7.15 (d, J=8.50 Hz, 2H), 6.96 (d, J=8.00 Hz, 1H), 6.65-6.72 (m, 2H), 5.23 (t, J=7.00 Hz, 1H), 4.15-4.26 (m, 4H), 3.97 (d, J=7.00 Hz, 2H), 3.75 (d, J=5.50 Hz, 2H), 3.37-3.44 (m, 1H), 2.82 (dd, J=13.50, 6.50 Hz, 1H), 2.55 (dd, J=13.50, 7.50 Hz, 1H), 2.23 (s, 3H), 2.13-2.22 (m, 1H), 2.06 (s, 3H), 1.00 (d, J=7.00 Hz, 3H).

EXAMPLE 57-8

1-[(1-chloro-6-{[(2S)-3-(4-chloro-2-fluorophenyl)-2-methylpropyl]oxy}-3,4-dihydro-2-naphthalenyl)methyl]-3-azetidinecarboxylic acid TLC: Rf 0.24 (chloroform:methanol:aqueous ammonia=20:5:1);
$^1$H-NMR (CD$_3$OD): δ 7.51 (d, J=8.60 Hz, 1H), 7.21 (t, J=8.20 Hz, 1H), 7.06-7.17 (m, 2H), 6.76 (dd, J=8.60, 2.70 Hz, 1H), 6.71 (d, J=2.70 Hz, 1H), 3.87-3.97 (m, 2H), 3.75-3.87 (m, 6H), 3.24-3.41 (m, 1H), 2.87 (dd, J=12.40, 5.30 Hz, 1H), 2.79 (t, J=7.10 Hz, 2H), 2.60 (dd, J=12.40, 8.00 Hz, 1H), 2.43 (t, J=7.10 Hz, 2H), 2.16-2.30 (m, 1H), 1.01 (d, J=6.80 Hz, 3H).

EXAMPLE 57-9

1-({6-[3-(4-chlorophenyl)-3-hydroxypropoxy]-1-methyl-3,4-dihydro-2-naphthalenyl}methyl)-3-azetidinecarboxylic acid TLC: Rf 0.20 (chloroform:methanol:aqueous ammonia=20:5:1);
$^1$H-NMR (CD$_3$OD): δ 7.26-7.39 (m, 5H), 6.75 (dd, J=8.50, 2.70 Hz, 1H), 6.70 (d, J=2.70 Hz, 1H), 4.83-4.92 (m, 1H), 4.07-4.25 (m, 5H), 4.04 (s, 2H), 3.89-4.01 (m, 1H), 3.33-3.47 (m, 1H), 2.71 (t, J=7.00 Hz, 2H), 2.00-2.29 (m, 7H).

EXAMPLE 57-10

1-[(2Z)-3-chloro-3-(4-{[(2S)-3-(4-fluorophenyl)-2-methylpropyl]oxy}-2-methylphenyl)-2-propenyl]-3-azetidinecarboxylic acid TLC: Rf 0.24 (butanol:acetic acid:water=20:4:1);
$^1$H-NMR (CD$_3$OD): δ 7.12-7.21 (m, 3H), 6.89-7.03 (m, 2H), 6.67-6.78 (m, 2H), 5.79 (t, J=6.90 Hz, 1H), 4.16-4.32 (m, 4H), 4.09 (d, J=6.90 Hz, 2H), 3.70-3.85 (m, 2H), 3.34-3.51 (m, 1H), 2.82 (dd, J=13.54, 6.40 Hz, 1H), 2.54 (dd, J=13.54, 7.68 Hz, 1H), 2.33 (s, 3H), 2.10-2.25 (m, 1H), 1.00 (d, J=6.77 Hz, 3H).

EXAMPLE 57-11

1-({6-[3-(4-chlorophenyl)-3-methoxypropoxy]-1-methyl-3,4-dihydro-2-naphthalenyl}methyl)-3-azetidinecarboxylic acid TLC: Rf 0.22 (chloroform:methanol:aqueous ammonia=20:5:1);
$^1$H-NMR (CD$_3$OD): δ 7.24-7.41 (m, 5H), 6.74 (dd, J=8.6, 2.6 Hz, 1H), 6.69 (d, J=2.6 Hz, 1H), 4.42 (dd, J=7.9, 5.3 Hz, 1H), 4.06-4.23 (m, 5H), 4.03 (s, 2H), 3.85-3.96 (m, 1H), 3.35-3.46 (m, 1H), 3.19 (s, 3H), 2.71 (t, J=7.3 Hz, 2H), 2.10-2.29 (m, 5H), 1.92-2.07 (m, 2H).

EXAMPLE 57-12

1-({1-chloro-6-[(3-isobutylbenzyl)oxy]-3,4-dihydro-2-naphthalenyl}methyl)-3-azetidinecarboxylic acid TLC: Rf 0.22 (chloroform:methanol:aqueous ammonia=20:5:1);
$^1$H-NMR (CD$_3$OD): δ 7.56 (d, J=8.6 Hz, 1H), 7.18-7.31 (m, 3H), 7.07-7.13 (m, 1H), 6.83-6.92 (m, 2H), 5.08 (s, 2H), 4.21 (d, J=7.7 Hz, 4H), 4.16 (s, 2H), 3.35-3.50 (m, 1H), 2.83 (t, J=7.0 Hz, 2H), 2.41-2.52 (m, 4H), 1.78-1.93 (m, 1H), 0.88 (d, J=6.6 Hz, 6H).

EXAMPLE 57-13

1-({6-[3-(4,4-difluorocyclohexyl)propoxy]-1-methyl-3,4-dihydro-2-naphthalenyl}methyl)-3-azetidinecarboxylic acid TLC: Rf 0.28 (chloroform:methanol:aqueous ammonia=20:5:1);
$^1$H-NMR (CD$_3$OD): δ 7.29 (d, J=8.4 Hz, 1H), 6.75 (dd, J=8.4, 2.8 Hz, 1H), 6.70 (d, J=2.8 Hz, 1H), 4.03-4.22 (m, 4H), 4.00 (s, 2H), 3.96 (t, J=6.4 Hz, 2H), 3.32-3.46 (m, 1H), 2.71 (t, J=7.1 Hz, 2H), 2.23 (t, J=7.1 Hz, 2H), 2.18 (s, 3H), 1.91-2.09 (m, 2H), 1.58-1.88 (m, 7H), 1.33-1.49 (m, 2H), 1.14-1.31 (m, 2H).

EXAMPLE 57-14 sodium 1-({6-[(6-isobutyl-3-pyridinyl)methoxy]-1-methyl-3,4-dihydro-2-naphthalenyl}methyl)-3-azetidinecarboxylate TLC: Rf 0.15 (butanol:acetic acid:water=20:4:1);
$^1$H-NMR (CD$_3$OD): δ 8.49 (d, J=1.46 Hz, 1H), 7.82 (dd, J=8.05, 1.46 Hz, 1H), 7.29 (d, J=8.05 Hz, 1H), 7.21 (d, J=8.23 Hz, 1H), 6.72-6.86 (m, 2H), 5.09 (s, 2H), 3.54 (t, J=7.59 Hz, 2H), 3.14-3.39 (m, 3H), 2.55-2.73 (m, 5H), 2.17-2.29 (m, 2H), 2.09 (s, 3H), 1.96-2.15 (m, 2H), 0.93 (d, J=6.59 Hz, 6H).

EXAMPLE 57-15

1-({6-[(2-fluoro-4-isobutylbenzyl)oxy]-1-methyl-3,4-dihydro-2-naphthalenyl}methyl)-3-azetidinecarboxylic acid TLC: Rf 0.31 (chloroform:methanol:aqueous ammonia=20:5:1);
$^1$H-NMR (CD$_3$OD): δ 7.31-7.42 (m, 2H), 6.90-7.01 (m, 2H), 6.86 (dd, J=8.50, 2.50 Hz, 1H), 6.81 (d, J=2.50 Hz, 1H), 5.09 (s, 2H), 4.11-4.24 (m, 4H), 4.08 (s, 2H), 3.35-3.47 (m, 1H), 2.69-2.77 (m, 2H), 2.49 (d, J=7.00 Hz, 2H), 2.19-2.28 (m, 5H), 1.79-1.94 (m, 1H), 0.90 (d, J=6.50 Hz, 6H).

EXAMPLE 57-16

1-({6-[(5-isobutyl-2-methoxybenzyl) oxy]-1-methyl-3,4-dihydro-2-naphthalenyl}methyl)-3-azetidinecarboxylic acid TLC: Rf 0.19 (chloroform:methanol:aqueous ammonia=20:5:1);
$^1$H-NMR (CD$_3$OD): δ 7.30 (d, J=8.50 Hz, 1H), 7.14 (d, J=2.00 Hz, 1H), 7.05 (dd, J=8.50, 2.00 Hz, 1H), 6.89 (d, J=8.50 Hz, 1H), 6.82 (dd, J=8.50, 2.50 Hz, 1H), 6.78 (d, J=2.50 Hz, 1H), 5.07 (s, 2H), 4.11-4.23 (m, 4H), 4.06 (s, 2H), 3.84 (s, 3H), 3.36-3.45 (m, 1H), 2.66-2.76 (m, 2H), 2.39 (d, J=7.00 Hz, 2H), 2.18-2.28 (m, 5H), 1.70-1.84 (m, 1H), 0.85 (d, J=6.50 Hz, 6H).

EXAMPLE 57-17

1-({6-[(2,4-dimethoxybenzyl) oxy]-1-methyl-3,4-dihydro-2-naphthalenyl}methyl)-3-azetidinecarboxylic acid TLC: Rf 0.25 (chloroform:methanol:aqueous ammonia=20:5:1);
$^1$H-NMR (CD$_3$OD): δ 7.31 (d, J=8.4 Hz, 1H), 7.26 (d, J=8.2 Hz, 1H), 6.82 (dd, J=8.4, 2.6 Hz, 1H), 6.77 (d, J=2.6 Hz, 1H), 6.56 (d, J=2.4 Hz, 1H), 6.50 (dd, J=8.2, 2.4 Hz, 1H), 4.99 (s, 2H), 4.10-4.27 (m, 4H), 4.09 (s, 2H), 3.83 (s, 3H), 3.79 (s, 3H), 3.34-3.48 (m, 1H), 2.72 (t, J=6.0 Hz, 2H), 2.17-2.30 (m, 5H).

EXAMPLE 57-18

1-[(6-{[4-(benzyloxy)-2-methoxybenzyl]oxy}-1-methyl-3,4-dihydro-2-naphthalenyl)methyl]-3-azetidinecarboxylic acid TLC: Rf 0.25 (chloroform:methanol:aqueous ammonia=20:5:1);
$^1$H-NMR (CD$_3$OD): δ 7.23-7.48 (m, 7H), 6.82 (dd, J=8.4, 2.9 Hz, 1H), 6.77 (d, J=2.9 Hz, 1H), 6.64 (d, J=2.0 Hz, 1H), 6.58 (dd, J=8.3, 2.0 Hz, 1H), 5.09 (s, 2H), 5.00 (s, 2H), 4.10-4.29 (m, 4H), 4.09 (s, 2H), 3.82 (s, 3H), 3.33-3.50 (m, 1H), 2.72 (t, J=5.7 Hz, 2H), 2.17-2.29 (m, 5H).

EXAMPLE 57-19

1-({6-[(3-isobutyl-2-methoxybenzyl) oxy]-1-methyl-3,4-dihydro-2-naphthalenyl}methyl)-3-azetidinecarboxylic acid TLC: Rf 0.21 (chloroform:methanol:aqueous ammonia=20:5:1);
$^1$H-NMR (CD$_3$OD): δ 7.32 (d, J=8.50 Hz, 1H), 7.28 (dd, J=7.50, 2.00 Hz, 1H), 7.15 (dd, J=7.50, 2.00 Hz, 1H), 7.04 (t, J=7.50 Hz, 1H), 6.85 (dd, J=8.50, 2.50 Hz, 1H), 6.80 (d, J=2.50 Hz, 1H), 5.10 (s, 2H), 4.10-4.24 (m, 4H), 4.07 (s, 2H), 3.76 (s, 3H), 3.34-3.48 (m, 1H), 2.68-2.76 (m, 2H), 2.54 (d, J=7.00 Hz, 2H), 2.19-2.28 (m, 5H), 1.87-2.02 (m, 1H), 0.91 (d, J=6.50 Hz, 6H).

Example 57-20

1-({6-[(4-isobutyl-2-methylbenzyl)oxy]-1-methyl-3,4-dihydro-2-naphthalenyl}methyl)-3-azetidinecarboxylic acid TLC: Rf 0.21 (chloroform:methanol:aqueous ammonia=20:5:1);
$^{1}$H-NMR (CD$_{3}$OD): δ 7.31 (d, J=8.50 Hz, 1H), 7.25 (d, J=7.50 Hz, 1H), 6.99 (s, 1H), 6.95 (d, J=7.50 Hz, 1H), 6.85 (dd, J=8.50, 2.50 Hz, 1H), 6.80 (d, J=2.50 Hz, 1H), 5.02 (s, 2H), 4.01-4.18 (m, 4H), 3.99 (s, 2H), 3.34-3.45 (m, 1H), 2.69-2.77 (m, 2H), 2.44 (d, J=7.00 Hz, 2H), 2.33 (s, 3H), 2.18-2.29 (m, 5H), 1.77-1.93 (m, 1H), 0.90 (d, J=6.50 Hz, 6H).

EXAMPLE 57-21

1-({6-[(4-butyl-2-methoxybenzyl)oxy]-1-methyl-3,4-dihydro-2-naphthalenyl}methyl)-3-azetidinecarboxylic acid TLC: Rf 0.36 (chloroform:methanol:aqueous ammonia=20:5:1);
$^{1}$H-NMR (CD$_{3}$OD): δ 7.31 (d, J=8.6 Hz, 1H), 7.25 (d, J=7.5 Hz, 1H), 6.72-6.86 (m, 4H), 5.04 (s, 2H), 4.12-4.29 (m, 4H), 4.10 (s, 2H), 3.84 (s, 3H), 3.34-3.49 (m, 1H), 2.72 (t, J=6.8 Hz, 2H), 2.61 (t, J=7.7 Hz, 2H), 2.15-2.31 (m, 5H), 1.54-1.67 (m, 2H), 1.30-1.44 (m, 2H), 0.94 (t, J=7.3 Hz, 3H).

EXAMPLE 57-22

1-[(6-{[4-(2,2-dimethylpropyl)-2-methoxybenzyl]oxy}-1-methyl-3,4-dihydro-2-naphthalenyl)methyl]-3-azetidinecarboxylic acid TLC: Rf 0.36 (chloroform:methanol:aqueous ammonia=20:5:1);
$^{1}$H-NMR (CD$_{3}$OD): δ 7.32 (d, J=8.6 Hz, 1H), 7.26 (d, J=7.5 Hz, 1H), 6.68-6.88 (m, 4H), 5.05 (s, 2H), 4.12-4.28 (m, 4H), 4.10 (s, 2H), 3.84 (s, 3H), 3.33-3.51 (m, 1H), 2.68-2.78 (m, 2H), 2.51 (s, 2H), 2.16-2.30 (m, 5H), 0.92 (s, 9H).

EXAMPLE 57-23

1-({6-[(4-isopropoxy-2-methoxybenzyl)oxy]-1-methyl-3,4-dihydro-2-naphthalenyl}methyl)-3-azetidinecarboxylic acid TLC: Rf 0.36 (chloroform:methanol:aqueous ammonia=20:5:1);
$^{1}$H-NMR (CD$_{3}$OD): δ 7.31 (d, J=8.6 Hz, 1H), 7.23 (d, J=8.4 Hz, 1H), 6.82 (dd, J=8.6, 2.7 Hz, 1H), 6.77 (d, J=2.7 Hz, 1H), 6.52 (d, J=2.4 Hz, 1H), 6.48 (dd, J=8.4, 2.4 Hz, 1H), 4.98 (s, 2H), 4.53-4.66 (m, 1H), 4.12-4.29 (m, 4H), 4.10 (s, 2H), 3.81 (s, 3H), 3.34-3.50 (m, 1H), 2.72 (t, J=7.0 Hz, 2H), 2.16-2.30 (m, 5H), 1.30 (d, J=6.0 Hz, 6H).

EXAMPLE 57-24

1-({6-[(4-cyclohexyl-2-methoxybenzyl)oxy]-1-methyl-3,4-dihydro-2-naphthalenyl}methyl)-3-azetidinecarboxylic acid TLC: Rf 0.32 (chloroform:methanol:aqueous ammonia=20:5:1);
$^{1}$H-NMR (CD$_{3}$OD): δ 7.32 (d, J=8.4 Hz, 1H), 7.26 (d, J=7.7 Hz, 1H), 6.73-6.88 (m, 4H), 5.04 (s, 2H), 4.12-4.30 (m, 4H), 4.11 (s, 2H), 3.85 (s, 3H), 3.36-3.51 (m, 1H), 2.72 (t, J=7.0 Hz, 2H), 2.40-2.62 (m, 1H), 2.15-2.30 (m, 5H), 1.69-1.93 (m, 5H), 1.22-1.56 (m, 5H).

EXAMPLE 57-25

1-({6-[(4-isobutyl-2-isopropoxybenzyl)oxy]-1-methyl-3,4-dihydro-2-naphthalenyl}methyl)-3-azetidinecarboxylic acid TLC: Rf 0.32 (chloroform:methanol:aqueous ammonia=20:5:1);
$^{1}$H-NMR (CD$_{3}$OD): δ 7.31 (d, J=8.4 Hz, 1H), 7.25 (d, J=7.7 Hz, 1H), 6.67-6.88 (m, 4H), 5.03 (s, 2H), 4.57-4.70 (m, 1H), 4.12-4.29 (m, 4H), 4.10 (s, 2H), 3.35-3.50 (m, 1H), 2.72 (t, J=6.8 Hz, 2H), 2.45 (d, J=7.3 Hz, 2H), 2.16-2.30 (m, 5H), 1.77-1.95 (m, 1H), 1.31 (d, J=5.9 Hz, 6H), 0.90 (d, J=6.8 Hz, 6H).

EXAMPLE 57-26

1-[(6-{[4-isobutyl-2-(trifluoromethyl)benzyl]oxy}-1-methyl-3,4-dihydro-2-naphthalenyl)methyl]-3-azetidinecarboxylic acid TLC: Rf 0.17 (chloroform:methanol:aqueous ammonia=20:5:1);
$^{1}$H-NMR (CD$_{3}$OD): δ 7.62 (d, J=8.00 Hz, 1H), 7.51 (s, 1H), 7.42 (d, J=8.00 Hz, 1H), 7.34 (d, J=8.50 Hz, 1H), 6.78-6.85 (m, 2H), 5.21 (s, 2H), 4.11-4.25 (m, 4H), 4.09 (s, 2H), 3.35-3.49 (m, 1H), 2.69-2.77 (m, 2H), 2.57 (d, J=7.00 Hz, 2H), 2.19-2.27 (m, 5H), 1.84-1.97 (m, 1H), 0.91 (d, J=6.50 Hz, 6H).

EXAMPLE 57-27

1-({6-[(2-chloro-4-isobutylbenzyl)oxy]-1-methyl-3,4-dihydro-2-naphthalenyl}methyl)-3-azetidinecarboxylic acid TLC: Rf 0.23 (chloroform:methanol:aqueous ammonia=20:5:1);
$^{1}$H-NMR (CD$_{3}$OD): δ 7.43 (d, J=8.00 Hz, 1H), 7.34 (d, J=8.50 Hz, 1H), 7.23 (d, J=1.50 Hz, 1H), 7.11 (dd, J=8.00, 1.50 Hz, 1H), 6.85 (dd, J=8.50, 2.50 Hz, 1H), 6.81 (d, J=2.50 Hz, 1H), 5.13 (s, 2H), 4.10-4.24 (m, 4H), 4.08 (s, 2H), 3.36-3.47 (m, 1H), 2.70-2.78 (m, 2H), 2.48 (d, J=7.00 Hz, 2H), 2.19-2.28 (m, 5H), 1.81-1.92 (m, 1H), 0.90 (d, J=6.50 Hz, 6H).

EXAMPLE 57-28

1-({6-[(2-methoxy-4-{[(1S)-1-methylpropyl]oxy}benzyl)oxy]-1-methyl-3,4-dihydro-2-naphthalenyl}methyl)-3-azetidinecarboxylic acid TLC: Rf 0.32 (chloroform:methanol:aqueous ammonia=20:5:1);
$^{1}$H-NMR (CD$_{3}$OD): δ 7.31 (d, J=8.6 Hz, 1H), 7.23 (d, J=8.4 Hz, 1H), 6.82 (dd, J=8.4, 2.7 Hz, 1H), 6.77 (d, J=2.7 Hz, 1H), 6.53 (d, J=2.2 Hz, 1H), 6.48 (dd, J=8.6, 2.2 Hz, 1H), 4.99 (s, 2H), 4.29-4.45 (m, 1H), 4.11-4.28 (m, 4H), 4.09 (s, 2H), 3.82 (s, 3H), 3.33-3.51 (m, 1H), 2.72 (t, J=6.8 Hz, 2H), 2.16-2.29 (m, 5H), 1.54-1.79 (m, 2H), 1.26 (d, J=6.0 Hz, 3H), 0.98 (t, J=7.5 Hz, 3H).

EXAMPLE 57-29

1-({6-[(2-methoxy-4-{[(1R)-1-methylpropyl]oxy}benzyl)oxy]-1-methyl-3,4-dihydro-2-naphthalenyl}methyl)-3-azetidinecarboxylic acid TLC: Rf 0.32 (chloroform:methanol:aqueous ammonia=20:5:1);
$^1$H-NMR (CD$_3$OD): δ 7.31 (d, J=8.6 Hz, 1H), 7.23 (d, J=8.4 Hz, 1H), 6.82 (dd, J=8.4, 2.7 Hz, 1H), 6.77 (d, J=2.7 Hz, 1H), 6.53 (d, J=2.2 Hz, 1H), 6.48 (dd, J=8.6, 2.2 Hz, 1H), 4.99 (s, 2H), 4.29-4.45 (m, 1H), 4.11-4.28 (m, 4H), 4.09 (s, 2H), 3.82 (s, 3H), 3.33-3.51 (m, 1H), 2.72 (t, J=6.8 Hz, 2H), 2.16-2.29 (m, 5H), 1.54-1.79 (m, 2H), 1.26 (d, J=6.0 Hz, 3H), 0.98 (t, J=7.5 Hz, 3H).

EXAMPLE 57-30

1-({6-[(3-isobutyl-5-methoxybenzyl) oxy]-1-methyl-3,4-dihydro-2-naphthalenyl}methyl)-3-azetidinecarboxylic acid TLC: Rf 0.20 (chloroform:methanol:aqueous ammonia=20:5:1);
$^1$H-NMR (CD$_3$OD): δ 7.31 (d, J=8.50 Hz, 1H), 6.78-6.86 (m, 4H), 6.62-6.66 (m, 1H), 5.03 (s, 2H), 4.10-4.26 (m, 4H), 4.07 (s, 2H), 3.77 (s, 3H), 3.36-3.47 (m, 1H), 2.68-2.76 (m, 2H), 2.44 (d, J=7.00 Hz, 2H), 2.18-2.27 (m, 5H), 1.79-1.91 (m, 1H), 0.88 (d, J=6.50 Hz, 6H).

EXAMPLE 57-31

1-({6-[(3-isobutyl-4-methoxybenzyl)oxy]-1-methyl-3,4-dihydro-2-naphthalenyl}methyl)-3-azetidinecarboxylic acid TLC: Rf 0.20 (chloroform:methanol:aqueous ammonia=20:5:1);
$^1$H-NMR (CD$_3$OD): δ 7.30 (d, J=8.50 Hz, 1H), 7.22 (dd, J=8.00, 2.00 Hz, 1H), 7.12 (d, J=2.00 Hz, 1H), 6.90 (d, J=8.00 Hz, 1H), 6.83 (dd, J=8.50, 2.50 Hz, 1H), 6.78 (d, J=2.50 Hz, 1H), 4.98 (s, 2H), 4.07-4.22 (m, 4H), 4.05 (s, 2H), 3.80 (s, 3H), 3.35-3.46 (m, 1H), 2.66-2.76 (m, 2H), 2.46 (d, J=7.00 Hz, 2H), 2.18-2.27 (m, 5H), 1.81-1.96 (m, 1H), 0.86 (d, J=6.50 Hz, 6H).

EXAMPLE 57-32

1-[(1-methyl-6-{[4-propoxy-2-(trifluoromethyl)benzyl]oxy}-3,4-dihydro-2-naphthalenyl)methyl]-3-azetidinecarboxylic acid TLC: Rf 0.33 (chloroform:methanol:aqueous ammonia=20:5:1);
$^1$H-NMR (CD$_3$OD): δ 7.60 (d, J=8.80 Hz, 1H), 7.34 (d, J=8.60 Hz, 1H), 7.22 (d, J=2.60 Hz, 1H), 7.15 (dd, J=8.60, 2.60 Hz, 1H), 6.74-6.87 (m, 2H), 5.14 (s, 2H), 4.12-4.29 (m, 4H), 4.10 (s, 2H), 3.99 (t, J=6.50 Hz, 2H), 3.34-3.49 (m, 1H), 2.73 (t, J=7.00 Hz, 2H), 2.16-2.30 (m, 5H), 1.74-1.89 (m, 2H), 1.05 (t, J=7.40 Hz, 3H).

EXAMPLE 57-33

1-[(6-{[4-butoxy-2-(trifluoromethyl)benzyl]oxy}-1-methyl-3,4-dihydro-2-naphthalenyl)methyl]-3-azetidinecarboxylic acid TLC: Rf 0.33 (chloroform:methanol:aqueous ammonia=20:5:1);
$^1$H-NMR (CD$_3$OD): δ 7.59 (d, J=8.60 Hz, 1H), 7.34 (d, J=8.60 Hz, 1H), 7.21 (d, J=2.60 Hz, 1H), 7.15 (dd, J=8.60, 2.60 Hz, 1H), 6.75-6.86 (m, 2H), 5.14 (s, 2H), 4.12-4.29 (m, 4H), 4.11 (s, 2H), 4.04 (t, J=6.40 Hz, 2H), 3.36-3.50 (m, 1H), 2.73 (t, J=7.00 Hz, 2H), 2.16-2.31 (m, 5H), 1.70-1.85 (m, 2H), 1.44-1.60 (m, 2H), 0.99 (t, J=7.40 Hz, 3H).

EXAMPLE 57-34

1-[(6-{[4-(cyclobutyloxy)-2-(trifluoromethyl)benzyl]oxy}-1-methyl-3,4-dihydro-2-naphthalenyl)methyl]-3-azetidinecarboxylic acid TLC: Rf 0.33 (chloroform:methanol:aqueous ammonia=20:5:1);
$^1$H-NMR (CD$_3$OD): δ 7.58 (d, J=8.40 Hz, 1H), 7.34 (d, J=8.40 Hz, 1H), 7.13 (d, J=2.70 Hz, 1H), 7.06 (dd, J=8.40, 2.70 Hz, 1H), 6.74-6.86 (m, 2H), 5.14 (s, 2H), 4.68-4.81 (m, 1H), 4.11-4.31 (m, 4H), 4.11 (s, 2H), 3.33-3.51 (m, 1H), 2.73 (t, J=7.10 Hz, 2H), 2.39-2.57 (m, 2H), 2.04-2.32 (m, 7H), 1.65-1.97 (m, 2H).

EXAMPLE 57-35

1-[(6-{[4-(cyclopentyloxy)-2-(trifluoromethyl)benzyl]oxy}-1-methyl-3,4-dihydro-2-naphthalenyl)methyl]-3-azetidinecarboxylic acid TLC: Rf 0.33 (chloroform:methanol:aqueous ammonia=20:5:1);
$^1$H-NMR (CD$_3$OD): δ 7.58 (d, J=8.40 Hz, 1H), 7.34 (d, J=8.60 Hz, 1H), 7.18 (d, J=2.70 Hz, 1H), 7.13 (dd, J=8.60, 2.70 Hz, 1H), 6.74-6.87 (m, 2H), 5.14 (s, 2H) 4.80-4.94 (m, 1H), 4.12-4.30 (m, 4H), 4.11 (s, 2H), 3.35-3.50 (m, 1H), 2.73 (t, J=7.30 Hz, 2H), 2.16-2.32 (m, 5H), 1.56-2.07 (m, 8H).

EXAMPLE 57-36

1-[(6-{[4-isobutoxy-2-(trifluoromethyl)benzyl]oxy}-1-methyl-3,4-dihydro-2-naphthalenyl)methyl]-3-azetidinecarboxylic acid TLC: Rf 0.33 (chloroform:methanol:aqueous ammonia=20:5:1);
$^1$H-NMR (CD$_3$OD): δ 7.60 (d, J=9.00 Hz, 1H), 7.34 (d, J=8.40 Hz, 1H), 7.22 (d, J=2.60 Hz, 1H), 7.15 (dd, J=8.40, 2.60 Hz, 1H), 6.73-6.88 (m, 2H), 5.14 (s, 2H), 4.10-4.30 (m, 4H), 4.10 (s, 2H), 3.80 (d, J=6.40 Hz, 2H), 3.33-3.50 (m, 1H), 2.73 (t, J=7.30 Hz, 2H), 2.16-2.32 (m, 5H), 1.99-2.16 (m, 1H), 1.04 (d, J=6.60 Hz, 6H).

EXAMPLE 57-37

1-({6-[(2-chloro-4-propylbenzyl)oxy]-1-methyl-3,4-dihydro-2-naphthalenyl}methyl)-3-azetidinecarboxylic acid TLC: Rf 0.15 (chloroform:methanol:aqueous ammonia=20:5:1);
$^1$H-NMR (CD$_3$OD): δ 7.43 (d, J=8.00 Hz, 1H), 7.34 (d, J=8.50 Hz, 1H), 7.26 (d, J=1.50 Hz, 1H), 7.14 (dd, J=8.00, 1.50 Hz, 1H), 6.85 (dd, J=8.50, 2.50 Hz, 1H), 6.81 (d, J=2.50 Hz, 1H), 5.13 (s, 2H), 4.11-4.26 (m, 4H), 4.08 (s, 2H), 3.36-3.50 (m, 1H), 2.69-2.78 (m, 2H), 2.59 (t, J=7.50 Hz, 2H), 2.18-2.28 (m, 5H), 1.56-1.74 (m, 2H), 0.94 (t, J=7.50 Hz, 3H).

EXAMPLE 57-38

1-[(1-methyl-6-{[4-(trifluoromethyl)benzyl]oxy}-3,4-dihydro-2-naphthalenyl)methyl]-3-azetidinecarboxylic acid TLC: Rf 0.14 (chloroform:methanol:aqueous ammonia=20:5:1);
$^1$H-NMR (CD$_3$OD): δ 7.66 (d, J=8.50 Hz, 2H), 7.64 (d, J=8.50 Hz, 2H), 7.32 (d, J=8.50 Hz, 1H), 6.82-6.89 (m, 2H), 5.19 (s, 2H), 4.10-4.25 (m, 4H), 4.07 (s, 2H), 3.35-3.47 (m, 1H), 2.69-2.78 (m, 2H), 2.18-2.28 (m, 5H).

EXAMPLE 57-39

1-({6-[(2,4-dimethylbenzyl)oxy]-1-methyl-3,4-dihydro-2-naphthalenyl}methyl)-3-azetidinecarboxylic acid TLC: Rf 0.15 (chloroform:methanol:aqueous ammonia=20:5:1);
$^1$H-NMR (CD$_3$OD): δ 7.33 (d, J=8.50 Hz, 1H), 7.23 (d, J=7.50 Hz, 1H), 7.03 (s, 1H), 6.98 (d, J=7.50 Hz, 1H), 6.85 (dd, J=8.50, 2.50 Hz, 1H), 6.80 (d, J=2.50 Hz, 1H), 5.02 (s, 2H), 4.12-4.25 (m, 4H), 4.08 (s, 2H), 3.36-3.47 (m, 1H), 2.70-2.78 (m, 2H), 2.31 (s, 3H), 2.29 (s, 3H), 2.19-2.28 (m, 5H).

EXAMPLE 57-40

1-[(6-{[2-fluoro-4-(trifluoromethyl)benzyl]oxy}-1-methyl-3,4-dihydro-2-naphthalenyl)methyl]-3-azetidinecarboxylic acid TLC: Rf 0.15 (chloroform:methanol:aqueous ammonia=20:5:1);
$^1$H-NMR (CD$_3$OD): δ 7.74 (dd, J=7.50, 7.50 Hz, 1H), 7.46-7.55 (m, 2H), 7.35 (d, J=8.50 Hz, 1H), 6.88 (dd, J=8.50, 2.50 Hz, 1H), 6.84 (d, J=2.50 Hz, 1H), 5.22 (s, 2H), 4.11-4.25 (m, 4H), 4.08 (s, 2H), 3.36-3.48 (m, 1H), 2.71-2.78 (m, 2H), 2.19-2.30 (m, 5H).

EXAMPLE 57-41

1-({6-[(2-isobutyl-6-methoxy-4-pyridinyl)methoxy]-1-methyl-3,4-dihydro-2-naphthalenyl}methyl)-3-azetidinecarboxylic acid TLC: Rf 0.24 (chloroform:methanol:aqueous ammonia=20:5:1);
$^1$H-NMR (CD$_3$OD): δ 7.31 (d, J=8.50 Hz, 1H), 6.78-6.85 (m, 3H), 6.63 (s, 1H), 5.07 (s, 2H), 4.10-4.25 (m, 4H), 4.07 (s, 2H), 3.87 (s, 3H), 3.35-3.48 (m, 1H), 2.67-2.77 (m, 2H), 2.53 (d, J=7.00 Hz, 2H), 2.18-2.28 (m, 5H), 2.03-2.15 (m, 1H), 0.90 (d, J=6.50 Hz, 6H).

EXAMPLE 57-42

1-({6-[(5-chloro-6-isobutyl-3-pyridinyl)methoxy]-1-methyl-3,4-dihydro-2-naphthalenyl}methyl)-3-azetidinecarboxylic acid TLC: Rf 0.24 (chloroform:methanol:aqueous ammonia=20:5:1);
$^1$H-NMR (CD$_3$OD): δ 8.46 (d, J=2.00 Hz, 1H), 7.90 (d, J=2.00 Hz, 1H), 7.34 (d, J=8.50 Hz, 1H), 6.82-6.91 (m, 2H), 5.13 (s, 2H), 4.11-4.25 (m, 4H), 4.08 (s, 2H), 3.37-3.46 (m, 1H), 2.83 (d, J=7.50 Hz, 2H), 2.71-2.78 (m, 2H), 2.11-2.29 (m, 6H), 0.95 (d, J=6.50 Hz, 6H).

EXAMPLE 57-43

1-({6-[(2-fluoro-4-isopropoxybenzyl)oxy]-1-methyl-3,4-dihydro-2-naphthalenyl}methyl)-3-azetidinecarboxylic acid TLC: Rf 0.28 (chloroform:methanol:aqueous ammonia=20:5:1);
$^1$H-NMR (CD$_3$OD): δ 7.28-7.42 (m, 2H), 6.85 (dd, J=8.5, 2.7 Hz, 1H), 6.79 (d, J=2.7 Hz, 1H), 6.64-6.76 (m, 2H), 5.02 (s, 2H), 4.53-4.67 (m, 1H), 4.11-4.27 (m, 4H), 4.09 (s, 2H), 3.33-3.50 (m, 1H), 2.73 (t, J=7.0 Hz, 2H), 2.16-2.30 (m, 5H), 1.30 (d, J=6.0 Hz, 6H).

EXAMPLE 57-44

1-({6-[(4-isopropyl-2-methoxybenzyl)oxy]-1-methyl-3,4-dihydro-2-naphthalenyl}methyl)-3-azetidinecarboxylic acid TLC: Rf 0.18 (chloroform:methanol:aqueous ammonia=20:5:1);
$^1$H-NMR (CD$_3$OD): δ 7.23-7.33 (m, 2H), 6.74-6.88 (m, 4H), 5.03 (s, 2H), 4.10-4.24 (m, 4H), 4.06 (s, 2H), 3.85 (s, 3H), 3.35-3.47 (m, 1H), 2.82-2.96 (m, 1H), 2.65-2.77 (m, 2H), 2.13-2.32 (m, 5H), 1.25 (d, J=6.95 Hz, 6H).

EXAMPLE 57-45

1-({6-[(2-cyano-4-isopropoxybenzyl)oxy]-1-methyl-3,4-dihydro-2-naphthalenyl}methyl)-3-azetidinecarboxylic acid TLC: Rf 0.21 (chloroform:methanol:aqueous ammonia=20:5:1);
$^1$H-NMR (CD$_3$OD): δ 7.54 (d, J=8.6 Hz, 1H), 7.34 (d, J=8.6 Hz, 1H), 7.28 (d, J=2.7 Hz, 1H), 7.20 (dd, J=8.6, 2.7 Hz, 1H), 6.87 (dd, J=8.6, 2.6 Hz, 1H), 6.83 (d, J=2.6 Hz, 1H), 5.14 (s, 2H), 4.58-4.74 (m, 1H), 4.09-4.26 (m, 4H), 4.08 (s, 2H), 3.33-3.48 (m, 1H), 2.74 (t, J=7.0 Hz, 2H), 2.17-2.31 (m, 5H), 1.33 (d, J=6.0 Hz, 6H).

EXAMPLE 57-46

1-[(6-{[(2S)-3-(4-chlorophenyl)-2-methylpropyl]oxy}-1,5-dimethyl-3,4-dihydro-2-naphthalenyl)methyl]-3-azetidinecarboxylic acid TLC: Rf 0.19 (chloroform:methanol:aqueous ammonia=20:5:1);
$^1$H-NMR (CD$_3$OD): δ 7.18-7.26 (m, 3H), 7.15 (d, J=8.50 Hz, 2H), 6.70 (d, J=8.50 Hz, 1H), 4.10-4.25 (m, 4H), 4.08 (s, 2H), 3.79 (d, J=5.50 Hz, 2H), 3.35-3.45 (m, 1H), 2.88 (dd, J=13.00, 6.50 Hz, 1H), 2.70-2.77 (m, 2H), 2.60 (dd, J=13.00, 7.50 Hz, 1H), 2.18-2.28 (m, 9H), 1.05 (d, J=7.00 Hz, 3H).

EXAMPLE 57-47

1-[(6-{[4-isobutyl-2-(methylsulfonyl)benzyl]oxy}-1-methyl-3,4-dihydro-2-naphthalenyl)methyl]-3-azetidinecarboxylic acid TLC: Rf 0.25 (chloroform:methanol:aqueous ammonia=20:5:1);

¹H-NMR (CD₃OD): δ 7.87 (d, J=1.80 Hz, 1H), 7.66 (d, J=7.90 Hz, 1H), 7.52 (dd, J=7.90, 1.80 Hz, 1H), 7.36 (d, J=8.40 Hz, 1H), 6.81-6.94 (m, 2H), 5.48 (s, 2H), 4.11-4.27 (m, 4H), 4.09 (s, 2H), 3.34-3.50 (m, 1H), 3.20 (s, 3H), 2.75 (t, J=7.10 Hz, 2H), 2.61 (d, J=7.10 Hz, 2H), 2.17-2.31 (m, 5H), 1.84-1.99 (m, 1H), 0.93 (d, J=6.60 Hz, 6H).

EXAMPLE 57-48

1-[(6-{[4-isopropoxy-2-(methylsulfonyl)benzyl]oxy}-1-methyl-3,4-dihydro-2-naphthalenyl)methyl]-3-azetidinecarboxylic acid TLC: Rf 0.25 (chloroform:methanol:aqueous ammonia=20:5:1);
¹H-NMR (CD₃OD): δ 7.62 (d, J=8.40 Hz, 1H), 7.56 (d, J=2.60 Hz, 1H), 7.36 (d, J=8.40 Hz, 1H), 7.23 (dd, J=8.40, 2.60 Hz, 1H), 6.88 (dd, J=8.40, 2.40 Hz, 1H), 6.84 (d, J=2.40 Hz, 1H), 5.41 (s, 2H), 4.64-4.78 (m, 1H), 4.09-4.26 (m, 4H), 4.07 (s, 2H), 3.33-3.49 (m, 1H), 3.20 (s, 3H), 2.74 (t, J=8.20 Hz, 2H), 2.17-2.30 (m, 5H), 1.35 (d, J=6.00 Hz, 6H).

EXAMPLE 57-49

1-[(6-{[3-fluoro-5-(trifluoromethyl)benzyl]oxy}-1-methyl-3,4-dihydro-2-naphthalenyl)methyl]-3-azetidinecarboxylic acid TLC: Rf 0.25 (chloroform:methanol:aqueous ammonia=20:5:1);
¹H-NMR (CD₃OD): δ 7.60 (s, 1H), 7.49 (d, J=9.70 Hz, 1H), 7.30-7.43 (m, 2H), 6.80-6.93 (m, 2H), 5.19 (s, 2H), 4.10-4.26 (m, 4H), 4.09 (s, 2H), 3.33-3.49 (m, 1H), 2.74 (t, J=8.10 Hz, 2H), 2.14-2.31 (m, 5H).

EXAMPLE 57-50

1-[(6-{[4-fluoro-2-(trifluoromethyl)benzyl]oxy}-1-methyl-3,4-dihydro-2-naphthalenyl)methyl]-3-azetidinecarboxylic acid TLC: Rf 0.25 (chloroform:methanol:aqueous ammonia=20:5:1);
¹H-NMR (CD₃OD): δ 7.71-7.83 (m, 1H), 7.52 (dd, J=9.20, 2.70 Hz, 1H), 7.30-7.46 (m, 2H), 6.76-6.88 (m, 2H), 5.22 (s, 2H), 4.09-4.26 (m, 4H), 4.08 (s, 2H), 3.33-3.48 (m, 1H), 2.74 (t, J=6.60 Hz, 2H), 2.15-2.30 (m, 5H).

EXAMPLE 57-51

1-({6-[(3-fluoro-4-isopropoxybenzyl)oxy]-1-methyl-3,4-dihydro-2-naphthalenyl}methyl)-3-azetidinecarboxylic acid TLC: Rf 0.19 (chloroform:methanol:aqueous ammonia=20:5:1);
¹H-NMR (CD₃OD): δ 7.31 (d, J=8.60 Hz, 1H), 7.10-7.20 (m, 2H), 7.05 (t, J=8.32 Hz, 1H), 6.76-6.87 (m, 2H), 5.00 (s, 2H), 4.50-4.64 (m, 1H), 4.09-4.27 (m, 4H), 4.07 (s, 2H), 3.33-3.49 (m, 1H), 2.67-2.78 (m, 2H), 2.19-2.28 (m, 2H), 2.20 (s, 3H), 1.32 (d, J=6.04 Hz, 6H).

EXAMPLE 57-52

1-[(6-{[4-isopropoxy-3-(trifluoromethyl)benzyl]oxy}-1-methyl-3,4-dihydro-2-naphthalenyl)methyl]-3-azetidinecarboxylic acid TLC: Rf 0.21 (chloroform:methanol:aqueous ammonia=20:5:1);
¹H-NMR (CD₃OD): δ 7.53-7.66 (m, 2H), 7.32 (d, J=8.60 Hz, 1H), 7.17 (d, J=8.60 Hz, 1H), 6.78-6.88 (m, 2H), 5.04 (s, 2H), 4.66-4.80 (m, 1H), 4.08-4.27 (m, 4H), 4.07 (s, 2H), 3.34-3.51 (m, 1H), 2.66-2.79 (m, 2H), 2.20 (s, 3H), 2.18-2.29 (m, 2H), 1.34 (d, J=6.04 Hz, 6H).

EXAMPLE 57-53

1-({6-[(2-methoxy-4-propylbenzyl)oxy]-1,7-dimethyl-3,4-dihydro-2-naphthalenyl}methyl)-3-azetidinecarboxylic acid TLC: Rf 0.20 (chloroform:methanol:aqueous ammonia=20:5:1);
¹H-NMR (CD₃OD): δ 7.28 (d, J=7.50 Hz, 1H), 7.18 (s, 1H), 6.82 (d, J=1.50 Hz, 1H), 6.75-6.79 (m, 2H), 5.06 (s, 2H), 4.10-4.25 (m, 4H), 4.07 (s, 2H), 3.85 (s, 3H), 3.35-3.47 (m, 1H), 2.66-2.73 (m, 2H), 2.59 (t, J=7.50 Hz, 2H), 2.18-2.26 (m, 8H), 1.59-1.72 (m, 2H), 0.95 (t, J=7.50 Hz, 3H).

EXAMPLE 57-54

1-[(6-{[(2S)-3-(4-chlorophenyl)-2-methylpropyl]oxy}-1,7-dimethyl-3,4-dihydro-2-naphthalenyl)methyl]-3-azetidinecarboxylic acid TLC: Rf 0.20 (chloroform:methanol:aqueous ammonia=20:5:1);
¹H-NMR (CD₃OD): δ 7.25 (d, J=8.00 Hz, 2H), 7.14-7.18 (m, 3H), 6.60 (s, 1H), 4.10-4.24 (m, 4H), 4.07 (s, 2H), 3.80 (m, 2H), 3.35-3.47 (m, 1H), 2.86 (dd, J=13.50, 6.50 Hz, 1H), 2.64-2.72 (m, 2H), 2.59 (dd, J=13.50, 7.50 Hz, 1H), 2.18-2.26 (m, 9H), 1.05 (d, J=7.00 Hz, 3H).

EXAMPLE 57-55

1-[(6-{[(2S)-3-(4-chlorophenyl)-2-methylpropyl]oxy}-5-methoxy-1-methyl-3,4-dihydro-2-naphthalenyl)methyl]-3-azetidinecarboxylic acid TLC: Rf 0.25 (chloroform:methanol:aqueous ammonia=20:5:1);
¹H-NMR (CD₃OD): δ 7.25 (d, J=8.2 Hz, 2H), 7.18 (d, J=8.2 Hz, 2H), 7.13 (d, J=8.6 Hz, 1H), 6.80 (d, J=8.6 Hz, 1H), 4.12-4.29 (m, 4H), 4.11 (s, 2H), 3.70-3.89 (m, 5H), 3.34-3.51 (m, 1H), 2.90 (dd, J=14.3, 6.6 Hz, 1H), 2.72-2.84 (m, 2H), 2.58 (dd, J=14.3, 7.5 Hz, 1H), 2.12-2.30 (m, 6H), 1.05 (d, J=6.6 Hz, 3H).

EXAMPLE 57-56

1-[(6-{[(2S)-3-(4-chlorophenyl)-2-methylpropyl]oxy}-7-methoxy-1-methyl-3,4-dihydro-2-naphthalenyl)methyl]-3-azetidinecarboxylic acid TLC: Rf 0.25 (chloroform:methanol:aqueous ammonia=20:5:1);
¹H-NMR (CD₃OD): δ 7.24 (d, J=8.60 Hz, 2H), 7.17 (d, J=8.60 Hz, 2H), 7.00 (s, 1H), 6.69 (s, 1H), 4.12-4.28 (m, 4H), 4.10 (s, 2H), 3.85 (s, 3H), 3.81 (d, J=5.90 Hz, 2H), 3.34-3.50 (m, 1H), 2.87 (dd, J=13.40, 6.80 Hz, 1H), 2.60-2.70 (m, 2H), 2.55 (dd, J=13.40, 7.70 Hz, 1H), 2.14-2.29 (m, 6H), 1.01 (d, J=6.80 Hz, 3H).

EXAMPLE 57-57

1-({5-methoxy-6-[(2-methoxy-4-propylbenzyl)oxy]-1-methyl-3,4-dihydro-2-naphthalenyl}methyl)-3-azetidinecarboxylic acid TLC: Rf 0.25 (chloroform:methanol:aqueous ammonia=20:5:1);
$^1$H-NMR (CD$_3$OD): δ 7.30 (d, J=7.70 Hz, 1H), 7.13 (d, J=8.60 Hz, 1H), 6.92 (d, J=8.60 Hz, 1H), 6.83 (d, J=1.30 Hz, 1H), 6.77 (dd, J=7.70, 1.30 Hz, 1H), 5.09 (s, 2H), 4.13-4.28 (m, 4H), 4.10 (s, 2H), 3.84 (s, 3H), 3.77 (s, 3H), 3.34-3.49 (m, 1H), 2.72-2.85 (m, 2H), 2.59 (t, J=7.30 Hz, 2H), 2.11-2.27 (m, 5H), 1.57-1.74 (m, 2H), 0.94 (t, J=7.30 Hz, 3H).

Example 57-58

1-({7-methoxy-6-[(2-methoxy-4-propylbenzyl)oxy]-1-methyl-3,4-dihydro-2-naphthalenyl}methyl)-3-azetidinecarboxylic acid TLC: Rf 0.25 (chloroform:methanol:aqueous ammonia=20:5:1);
$^1$H-NMR (CD$_3$OD): δ 7.27 (d, J=8.10 Hz, 1H), 6.99 (s, 1H), 6.79-6.84 (m, 2H), 6.76 (dd, J=8.10, 1.60 Hz, 1H), 5.08 (s, 2H), 4.06-4.23 (m, 4H), 4.04 (s, 2H), 3.84 (s, 3H), 3.83 (s, 3H), 3.33-3.45 (m, 1H), 2.53-2.70 (m, 4H), 2.15-2.26 (m, 5H), 1.59-1.71 (m, 2H), 0.94 (t, J=7.40 Hz, 3H).

EXAMPLE 57-59

1-({6-[(4-sec-butyl-2-methoxybenzyl)oxy]-1-methyl-3,4-dihydro-2-naphthalenyl}methyl)-3-azetidinecarboxylic acid TLC: Rf 0.24 (chloroform:methanol:aqueous ammonia=20:5:1);
$^1$H-NMR (CD$_3$OD): δ 7.22-7.35 (m, 2H), 6.72-6.87 (m, 4H), 5.04 (s, 2H), 4.10-4.25 (m, 4H), 4.07 (s, 2H), 3.85 (s, 3H), 3.35-3.47 (m, 1H), 2.66-2.78 (m, 2H), 2.54-2.64 (m, 1H), 2.14-2.31 (m, 5H), 1.53-1.69 (m, 2H), 1.23 (d, J=6.95 Hz, 3H), 0.82 (t, J=7.32 Hz, 3H).

EXAMPLE 57-60

1-({1-chloro-6-[(4-ethyl-2-methoxybenzyl)oxy]-3,4-dihydro-2-naphthalenyl}methyl)-3-azetidinecarboxylic acid TLC: Rf 0.25 (chloroform:methanol:aqueous ammonia=20:5:1);
$^1$H-NMR (CD$_3$OD): δ 7.55 (d, J=8.60 Hz, 1H), 7.25 (d, J=7.70 Hz, 1H), 6.81-6.90 (m, 3H), 6.78 (dd, J=7.70, 1.60 Hz, 1H), 5.06 (s, 2H), 4.23 (d, J=8.20 Hz, 4H), 4.17 (s, 2H), 3.85 (s, 3H), 3.36-3.50 (m, 1H), 2.83 (t, J=7.50 Hz, 2H), 2.64 (q, J=7.50 Hz, 2H), 2.45 (t, J=7.50 Hz, 2H), 1.23 (t, J=7.50 Hz, 3H).

EXAMPLE 57-61

1-[(1-chloro-6-{[4-ethoxy-2-(trifluoromethyl)benzyl]oxy}-3,4-dihydro-2-naphthalenyl)methyl]-3-azetidinecarboxylic acid TLC: Rf 0.25 (chloroform:methanol:aqueous ammonia=20:5:1);
$^1$H-NMR (CD$_3$OD): δ 7.59 (d, J=8.60 Hz, 1H), 7.58 (d, J=8.60 Hz, 1H), 7.22 (d, J=2.60 Hz, 1H), 7.16 (dd, J=8.60, 2.60 Hz, 1H), 6.87 (dd, J=8.60, 2.60 Hz, 1H), 6.82-6.85 (m, 1H), 5.16 (s, 2H), 4.23 (d, J=8.10 Hz, 4H), 4.17 (s, 2H), 4.10 (q, J=7.00 Hz, 2H), 3.36-3.50 (m, 1H), 2.85 (t, J=7.10 Hz, 2H), 2.46 (t, J=7.10 Hz, 2H), 1.41 (t, J=7.00 Hz, 3H).

EXAMPLE 57-62

1-[(1-chloro-6-{[4-isopropoxy-2-(trifluoromethyl)benzyl]oxy}-3,4-dihydro-2-naphthalenyl)methyl]-3-azetidinecarboxylic acid TLC: Rf 0.25 (chloroform:methanol:aqueous ammonia=20:5:1);
$^1$H-NMR (CD$_3$OD): δ 7.52-7.64 (m, 2H), 7.19 (d, J=2.6 Hz, 1H), 7.15 (dd, J=8.6, 2.6 Hz, 1H), 6.88 (dd, J=8.2, 2.6 Hz, 1H), 6.82-6.85 (m, 1H), 5.16 (s, 2H), 4.61-4.75 (m, 1H), 4.23 (d, J=8.4 Hz, 4H), 4.18 (s, 2H), 3.36-3.51 (m, 1H), 2.85 (t, J=7.0 Hz, 2H), 2.46 (t, J=7.0 Hz, 2H), 1.33 (d, J=6.0 Hz, 6H).

EXAMPLE 57-63

1-({6-[(2-methoxy-4-methylbenzyl)oxy]-1-methyl-3,4-dihydro-2-naphthalenyl}methyl)-3-azetidinecarboxylic acid TLC: Rf 0.19 (chloroform:methanol:aqueous ammonia=20:5:1);
$^1$H-NMR (CD$_3$OD): δ 7.31 (d, J=8.42 Hz, 1H), 7.23 (d, J=7.50 Hz, 1H), 6.69-6.88 (m, 4H), 5.03 (s, 2H), 4.10-4.26 (m, 4H), 4.07 (s, 2H), 3.84 (s, 3H), 3.33-3.49 (m, 1H), 2.64-2.79 (m, 2H), 2.33 (s, 3H), 2.15-2.29 (m, 5H).

EXAMPLE 57-64

1-({6-[(4-chloro-2-methoxybenzyl)oxy]-1-methyl-3,4-dihydro-2-naphthalenyl}methyl)-3-azetidinecarboxylic acid TLC: Rf 0.19 (chloroform:methanol:aqueous ammonia=20:5:1);
$^1$H-NMR (CD$_3$OD): δ 7.28-7.38 (m, 2H), 7.03 (d, J=1.65 Hz, 1H), 6.95 (dd, J=8.14, 1.65 Hz, 1H), 6.76-6.85 (m, 2H), 5.05 (s, 2H), 4.09-4.24 (m, 4H), 4.06 (s, 2H), 3.87 (s, 3H), 3.35-3.49 (m, 1H), 2.64-2.78 (m, 2H), 2.14-2.31 (m, 5H).

EXAMPLE 57-65

1-({6-[(2-methoxybenzyl)oxy]-1-methyl-3,4-dihydro-2-naphthalenyl}methyl)-3-azetidinecarboxylic acid TLC: Rf 0.20 (chloroform:methanol:aqueous ammonia=20:5:1);
$^1$H-NMR (CD$_3$OD): δ 7.21-7.43 (m, 3H), 6.97-7.03 (m, 1H), 6.88-6.96 (m, 1H), 6.77-6.88 (m, 2H), 5.09 (s, 2H), 4.08-4.26 (m, 4H), 4.05 (s, 2H), 3.86 (s, 3H), 3.35-3.49 (m, 1H), 2.64-2.82 (m, 2H), 2.12-2.31 (m, 5H).

EXAMPLE 57-66

1-{[6-(benzyloxy)-1-methyl-3,4-dihydro-2-naphthalenyl]methyl}-3-azetidinecarboxylic acid TLC: Rf 0.20 (chloroform:methanol:aqueous ammonia=20:5:1);

¹H-NMR (CD₃OD): δ 7.22-7.46 (m, 6H), 6.85 (dd, J=8.72, 2.74 Hz, 1H), 6.81 (d, J=2.74 Hz, 1H), 5.08 (s, 2H), 4.12-4.30 (m, 4H), 4.09 (s, 2H), 3.33-3.51 (m, 1H), 2.66-2.80 (m, 2H), 2.17-2.31 (m, 5H).

EXAMPLE 57-67

1-({6-[(2-methoxy-6-propyl-3-pyridinyl)methoxy]-1-methyl-3,4-dihydro-2-naphthalenyl}methyl)-3-azetidinecarboxylic acid TLC: Rf 0.19 (chloroform:methanol:aqueous ammonia=20:5:1);
¹H-NMR (CD₃OD): δ 7.61 (d, J=7.50 Hz, 1H), 7.32 (d, J=8.60 Hz, 1H), 6.73-6.87 (m, 3H), 5.01 (s, 2H), 4.10-4.29 (m, 4H), 4.08 (s, 2H), 3.96 (s, 3H), 3.34-3.49 (m, 1H), 2.57-2.81 (m, 4H), 2.15-2.31 (m, 5H), 1.67-1.82 (m, 2H), 0.95 (t, J=7.41 Hz, 3H).

EXAMPLE 57-68

1-[(6-{[6-isobutyl-4-(trifluoromethyl)-3-pyridinyl]methoxy}-1-methyl-3,4-dihydro-2-naphthalenyl)methyl]-3-azetidinecarboxylic acid TLC: Rf 0.21 (chloroform:methanol:aqueous ammonia=20:5:1);
¹H-NMR (CD₃OD): δ 8.80 (s, 1H), 7.60 (s, 1H), 7.37 (d, J=8.42 Hz, 1H), 6.81-6.91 (m, 2H), 5.26 (s, 2H), 4.14-4.29 (m, 4H), 4.11 (s, 2H), 3.34-3.51 (m, 1H), 2.77 (d, J=7.32 Hz, 2H), 2.71-2.80 (m, 2H), 2.22 (s, 3H), 2.19-2.30 (m, 2H), 2.04-2.18 (m, 1H), 0.94 (d, J=6.59 Hz, 6H).

EXAMPLE 57-69

1-({6-[(4-chloro-6-isobutyl-3-pyridinyl)methoxy]-1-methyl-3,4-dihydro-2-naphthalenyl}methyl)-3-azetidinecarboxylic acid TLC: Rf 0.21 (chloroform:methanol:aqueous ammonia=20:5:1);
¹H-NMR (CD₃OD): δ 8.55 (s, 1H), 7.42 (s, 1H), 7.36 (d, J=8.42 Hz, 1H), 6.89 (dd, J=8.42, 2.56 Hz, 1H), 6.85 (d, J=2.56 Hz, 1H), 5.20 (s, 2H), 4.12-4.28 (m, 4H), 4.10 (s, 2H), 3.33-3.50 (m, 1H), 2.70-2.79 (m, 2H), 2.66 (d, J=7.32 Hz, 2H), 2.21 (s, 3H), 2.18-2.30 (m, 2H), 2.00-2.13 (m, 1H), 0.93 (d, J=6.77 Hz, 6H).

EXAMPLE 57-70

1-[(6-{[2-methoxy-4-(trifluoromethyl)benzyl]oxy}-1-methyl-3,4-dihydro-2-naphthalenyl)methyl]-3-azetidinecarboxylic acid TLC: Rf 0.11 (chloroform:methanol:aqueous ammonia=20:5:1);
¹H-NMR (CD₃OD): δ 7.58 (d, J=7.50 Hz, 1H), 7.33 (d, J=8.23 Hz, 1H), 7.19-7.28 (m, 2H), 6.76-6.90 (m, 2H), 5.15 (s, 2H), 4.12-4.27 (m, 4H), 4.09 (s, 2H), 3.94 (s, 3H), 3.35-3.50 (m, 1H), 2.67-2.79 (m, 2H), 2.16-2.31 (m, 5H).

EXAMPLE 57-71

1-({6-[(5-chloro-2-methoxybenzyl)oxy]-1-methyl-3,4-dihydro-2-naphthalenyl}methyl)-3-azetidinecarboxylic acid TLC: Rf 0.13 (chloroform:methanol:aqueous ammonia=20:5:1);
¹H-NMR (CD₃OD): δ 7.29-7.38 (m, 2H), 7.26 (dd, J=8.78, 2.74 Hz, 1H), 6.98 (d, J=8.78 Hz, 1H), 6.78-6.86 (m, 2H), 5.07 (s, 2H), 4.13-4.29 (m, 4H), 4.10 (s, 2H), 3.87 (s, 3H), 3.36-3.52 (m, 1H), 2.66-2.81 (m, 2H), 2.16-2.31 (m, 5H).

EXAMPLE 57-72

1-({6-[(4-isobutyl-2-methoxybenzyl) oxy]-3,4-dihydro-2-naphthalenyl}methyl)-3-azetidinecarboxylic acid TLC: Rf 0.30 (chloroform:methanol:aqueous ammonia=20:5:1);
¹H-NMR (CD₃OD): δ 7.24 (d, J=7.70 Hz, 1H), 7.02 (d, J=9.00 Hz, 1H), 6.69-6.82 (m, 4H), 6.59 (s, 1H), 5.03 (s, 2H), 4.10-4.27 (m, 4H), 3.89 (s, 2H), 3.84 (s, 3H), 3.33-3.49 (m, 1H), 2.81 (t, J=8.10 Hz, 2H), 2.48 (d, J=7.10 Hz, 2H), 2.26 (t, J=8.10 Hz, 2H), 1.79-1.97 (m, 1H), 0.91 (d, J=6.80 Hz, 6H).

EXAMPLE 57-73

1-({6-[(2-methoxy-4-propylbenzyl) oxy]-3,4-dihydro-2-naphthalenyl}methyl)-3-azetidinecarboxylic acid TLC: Rf 0.30 (chloroform:methanol:aqueous ammonia=20:5:1);
¹H-NMR (CD₃OD): δ 7.24 (d, J=7.50 Hz, 1H), 7.01 (d, J=9.00 Hz, 1H), 6.71-6.85 (m, 4H), 6.59 (s, 1H), 5.02 (s, 2H), 4.10-4.27 (m, 4H), 3.89 (s, 2H), 3.84 (s, 3H), 3.33-3.50 (m, 1H), 2.81 (t, J=8.10 Hz, 2H), 2.59 (t, J=7.10 Hz, 2H), 2.26 (t, J=8.10 Hz, 2H), 1.56-1.74 (m, 2H), 0.94 (t, J=7.30 Hz, 3H).

EXAMPLE 57-74

1-({6-[(4-isobutyl-2-methoxybenzyl) oxy]-1,5-dimethyl-3,4-dihydro-2-naphthalenyl}methyl)-3-azetidinecarboxylic acid TLC: Rf 0.26 (chloroform:methanol:aqueous ammonia=20:5:1);
¹H-NMR (CD₃OD): δ 7.27 (d, J=7.50 Hz, 1H), 7.21 (d, J=8.50 Hz, 1H), 6.83 (d, J=8.50 Hz, 1H), 6.78 (d, J=1.50 Hz, 1H), 6.73 (dd, J=7.50, 1.50 Hz, 1H), 5.05 (s, 2H), 4.10-4.25 (m, 4H), 4.07 (s, 2H), 3.85 (s, 3H), 3.34-3.43 (m, 1H), 2.69-2.77 (m, 2H), 2.48 (d, J=7.00 Hz, 2H), 2.17-2.27 (m, 8H), 1.81-1.95 (m, 1H), 0.92 (d, J=6.50 Hz, 6H).

EXAMPLE 57-75

1-[(6-{[4-isopropoxy-3-(trifluoromethyl)benzyl]oxy}-1,5-dimethyl-3,4-dihydro-2-naphthalenyl)methyl]-3-azetidinecarboxylic acid TLC: Rf 0.20 (chloroform:methanol:aqueous ammonia=20:5:1);
¹H-NMR (CD₃OD): δ 7.58-7.65 (m, 2H), 7.24 (d, J=8.50 Hz, 1H), 7.18 (d, J=9.00 Hz, 1H), 6.87 (d, J=8.50 Hz, 1H), 5.06 (s, 2H), 4.68-4.81 (m, 1H), 4.11-4.24 (m, 4H), 4.09 (s, 2H), 3.36-3.47 (m, 1H), 2.68-2.78 (m, 2H), 2.17-2.27 (m, 8H), 1.34 (d, J=6.00 Hz, 6H).

EXAMPLE 57-76

1-[(1-methyl-6-{[4-(2,2,2-trifluoroethoxy)-3-(trifluoromethyl)benzyl]oxy}-3,4-dihydro-2-naphthalenyl)methyl]-3-azetidinecarboxylic acid TLC: Rf 0.35 (chloroform:methanol:aqueous ammonia=20:5:1);

¹H-NMR (CD₃OD): δ 7.62-7.74 (m, 2H), 7.33 (d, J=8.4 Hz, 1H), 7.25 (d, J=8.8 Hz, 1H), 6.79-6.90 (m, 2H), 5.09 (s, 2H), 4.66 (q, J=8.2 Hz, 2H), 4.13-4.29 (m, 4H), 4.10 (s, 2H), 3.35-3.51 (m, 1H), 2.74 (t, J=6.6 Hz, 2H), 2.15-2.30 (m, 5H).

EXAMPLE 57-77

1-[(1-methyl-6-{[4-{[(1S)-1-methylpropyl]oxy}-3-(trifluoromethyl)benzyl]oxy}-3,4-dihydro-2-naphthalenyl)methyl]-3-azetidinecarboxylic acid TLC: Rf 0.35 (chloroform:methanol:aqueous ammonia=20:5:1);
¹H-NMR (CD₃OD): δ 7.53-7.64 (m, 2H), 7.33 (d, J=8.4 Hz, 1H), 7.14 (d, J=8.4 Hz, 1H), 6.77-6.89 (m, 2H), 5.04 (s, 2H), 4.46-4.60 (m, 1H), 4.12-4.29 (m, 4H), 4.10 (s, 2H), 3.34-3.50 (m, 1H), 2.73 (t, J=8.1 Hz, 2H), 2.17-2.30 (m, 5H), 1.61-1.81 (m, 2H), 1.30 (d, J=6.0 Hz, 3H), 0.99 (t, J=7.5 Hz, 3H).

EXAMPLE 57-78

1-[(6-{[6-isopropoxy-4-(trifluoromethyl)-3-pyridinyl]methoxy}-1-methyl-3,4-dihydro-2-naphthalenyl)methyl]-3-azetidinecarboxylic acid TLC: Rf 0.24 (chloroform:methanol:aqueous ammonia=20:5:1);
¹H-NMR (CD₃OD): δ 8.39 (s, 1H), 7.35 (d, J=8.60 Hz, 1H), 7.01 (s, 1H), 6.85 (dd, J=8.60, 2.56 Hz, 1H), 6.80 (d, J=2.56 Hz, 1H), 5.28-5.42 (m, 1H), 5.13 (s, 2H), 4.13-4.29 (m, 4H), 4.10 (s, 2H), 3.34-3.50 (m, 1H), 2.70-2.80 (m, 2H), 2.20-2.30 (m, 2H), 2.22 (s, 3H), 1.35 (d, J=6.22 Hz, 6H).

EXAMPLE 57-79

1-({6-[(4-chloro-6-isopropoxy-3-pyridinyl)methoxy]-1-methyl-3,4-dihydro-2-nhthalenyl}methyl)-3-azetidinecarboxylic acid TLC: Rf 0.24 (chloroform:methanol:aqueous ammonia=20:5:1);
¹H-NMR (CD₃OD): δ 8.20 (s, 1H), 7.33 (d, J=8.42 Hz, 1H), 7.13 (s, 1H), 6.84 (dd, J=8.42, 2.56 Hz, 1H), 6.80 (d, J=2.56 Hz, 1H), 5.04 (s, 2H), 4.78-4.87 (m, 1H), 4.09-4.26 (m, 4H), 4.07 (s, 2H), 3.34-3.48 (m, 1H), 2.69-2.78 (m, 2H), 2.20 (s, 3H), 2.18-2.30 (m, 2H), 1.37 (d, J=6.04 Hz, 6H).

EXAMPLE 57-80

1-[(6-{[4-(2-hydroxy-2-methylpropyl)-2-methoxybenzyl]oxy}-1-methyl-3,4-dihydro-2-naphthalenyl)methyl]-3-azetidinecarboxylic acid TLC: Rf 0.25 (chloroform:methanol:aqueous ammonia=20:5:1);
¹H-NMR (CD₃OD): δ 7.31 (d, J=8.50 Hz, 1H), 7.27 (d, J=7.50 Hz, 1H), 6.89 (d, J=1.50 Hz, 1H), 6.77-6.85 (m, 3H), 5.06 (s, 2H), 4.11-4.25 (m, 4H), 4.08 (s, 2H), 3.86 (s, 3H), 3.35-3.46 (m, 1H), 2.68-2.77 (m, 4H), 2.19-2.28 (m, 5H), 1.18 (s, 6H).

EXAMPLE 57-81

1-({1-tert-butyl-6-[(2-methoxy-4-propylbenzyl)oxy]-3,4-dihydro-2-naphthalenyl}methyl)-3-azetidinecarboxylic acid TLC: Rf 0.27 (chloroform:methanol:aqueous ammonia=20:5:1);
¹H-NMR (CD₃OD): δ 7.35 (d, J=8.50 Hz, 1H), 7.26 (d, J=7.50 Hz, 1H), 6.82 (d, J=1.50 Hz, 1H), 6.73-6.79 (m, 3H), 5.03 (s, 2H), 4.29 (s, 2H), 4.03-4.23 (m, 4H), 3.85 (s, 3H), 3.33-3.43 (m, 1H), 2.55-2.63 (m, 2H), 2.46-2.53 (m, 2H), 1.89-1.96 (m, 2H), 1.58-1.73 (m, 2H), 1.45 (s, 9H), 0.94 (t, J=7.50 Hz, 3H).

EXAMPLE 57-82

1-[(1-methyl-6-{[4-(2,2,2-trifluoroethoxy)-2-(trifluoromethyl)benzyl]oxy}-3,4-dihydro-2-naphthalenyl)methyl]-3-azetidinecarboxylic acid TLC: Rf 0.24 (chloroform:methanol:aqueous ammonia=20:5:1);
¹H-NMR (CD₃OD): δ 7.69 (d, J=8.60 Hz, 1H), 7.32-7.38 (m, 2H), 7.28 (dd, J=8.42, 2.74 Hz, 1H), 6.82 (dd, J=8.60, 2.54 Hz, 1H), 6.79 (d, J=2.54 Hz, 1H), 5.19 (s, 2H), 4.64 (q, J=8.29 Hz, 2H), 4.10-4.27 (m, 4H), 4.10 (s, 2H), 3.34-3.50 (m, 1H), 2.68-2.79 (m, 2H), 2.19-2.29 (m, 2H), 2.21 (s, 3H).

EXAMPLE 57-83

1-({6-[(4-methoxy-6-propyl-3-pyridinyl)methoxy]-1-methyl-3,4-dihydro-2-naphthalenyl}methyl)-3-azetidinecarboxylic acid TLC: Rf 0.27 (chloroform:methanol:aqueous ammonia=20:5:1);
¹H-NMR (CD₃OD): δ 8.28 (s, 1H), 7.33 (d, J=8.60 Hz, 1H), 6.96 (s, 1H), 6.77-6.88 (m, 2H), 5.06 (s, 2H), 4.09-4.28 (m, 4H), 4.07 (s, 2H), 3.94 (s, 3H), 3.34-3.48 (m, 1H), 2.67-2.78 (m, 4H), 2.15-2.32 (m, 5H), 1.65-1.83 (m, 2H), 0.97 (t, J=7.32 Hz, 3H).

EXAMPLE 57-84

1-({5-iodo-6-[(2-methoxy-4-propylbenzyl)oxy]-1-methyl-3,4-dihydro-2-naphthalenyl}methyl)-3-azetidinecarboxylic acid TLC: Rf 0.38 (chloroform:methanol:aqueous ammonia=20:5:1);
¹H-NMR (CD₃OD): δ 7.44 (d, J=7.50 Hz, 1H), 7.37 (d, J=8.60 Hz, 1H), 6.86 (d, J=8.60 Hz, 1H), 6.74-6.83 (m, 2H), 5.14 (s, 2H), 4.12-4.27 (m, 4H), 4.10 (s, 2H), 3.86 (s, 3H), 3.36-3.49 (m, 1H), 2.87-2.99 (m, 2H), 2.53-2.65 (m, 2H), 2.13-2.33 (m, 5H), 1.55-1.73 (m, 2H), 0.95 (t, J=7.41 Hz, 3H).

EXAMPLE 57-85

1-[(6-{[2,4-bis(trifluoromethyl)benzyl]oxy}-5-iodo-1-methyl-3,4-dihydro-2-naphthalenyl)methyl]-3-azetidinecarboxylic acid TLC: Rf 0.28 (chloroform:methanol:aqueous ammonia=20:5:1);
¹H-NMR (CD₃OD): δ 8.24-8.30 (m, 1H), 8.00-8.06 (m, 2H), 7.44 (d, J=8.60 Hz, 1H), 6.88 (d, J=8.60 Hz, 1H), 5.44 (s, 2H), 4.15-4.32 (m, 4H), 4.14 (s, 2H), 3.36-3.50 (m, 1H), 2.90-3.01 (m, 2H), 2.23-2.33 (m, 2H), 2.22 (s, 3H).

EXAMPLE 57-86

1-{[1-ethyl-6-(4-phenylbutoxy)-3,4-dihydro-2-naphthalenyl]methyl}-3-azetidinecarboxylic acid TLC: Rf 0.29 (chloroform:methanol:aqueous ammonia=20:5:1);

$^1$H-NMR (CD$_3$OD): δ 7.30 (d, J=8.60 Hz, 1H), 7.08-7.27 (m, 5H), 6.74 (dd, J=8.60, 2.70 Hz, 1H), 6.70 (d, J=2.70 Hz, 1H), 4.09-4.26 (m, 4H), 4.05 (s, 2H), 3.92-4.01 (m, 2H), 3.34-3.47 (m, 1H), 2.60-2.77 (m, 6H), 2.15-2.24 (m, 2H), 1.72-1.81 (m, 4H), 1.09 (t, J=7.41 Hz, 3H).

EXAMPLE 57-87

1-({6-[3-(4-chlorophenyl)propoxy]-1-ethyl-3,4-dihydro-2-naphthalenyl}methyl)-3-azetidinecarboxylic acid TLC: Rf 0.30 (chloroform:methanol:aqueous ammonia=20:5:1);
$^1$H-NMR (CD$_3$OD): δ 7.29 (d, J=8.60 Hz, 1H), 7.19-7.26 (m, 2H), 7.13-7.19 (m, 2H), 6.73 (dd, J=8.60, 2.70 Hz, 1H), 6.69 (d, J=2.70 Hz, 1H), 4.07-4.24 (m, 4H), 4.02 (s, 2H), 3.93 (t, J=6.13 Hz, 2H), 3.33-3.46 (m, 1H), 2.63-2.79 (m, 6H), 2.15-2.26 (m, 2H), 1.95-2.08 (m, 2H), 1.09 (t, J=7.41 Hz, 3H).

BIOLOGICAL EXAMPLES

The pharmacological activities of the compounds of the present invention were confirmed by the following Biological Examples. All operations were carried out by conventional methods by preparing gene-highly expressing cells based on the fundamental genetic engineering techniques. Also, the measuring methods in the present invention for evaluating the compounds of the present invention are improved in measuring methods, measuring accuracy, and/or measuring sensitivity. The details are described below. The preparation of histological preparation was also carried out by conventional methods based on the fundamental genetic engineering techniques with an appropriate modification.

Biological Example 1

Measurement of Inhibitory Activity of the Compound of the Present Invention on Binding of [$^3$H]-PhS1P to EDG-6

[Experimental Method]
By using cell membrane fraction of an EDG-6-overexpressing Chinese Hamster Ovary (CHO) cell and 1 mg protein/mL of the membrane fraction, reaction was carried out in a 96-well assay plate. Into each well, 80 μL of a vehicle (DMSO) solution diluted with 2× Binding Buffer (100 mmol/L Tris pH 7.5, 200 mM NaCl, 30 mM NaF, 1% BSA) or a ligand solution having a two-fold higher concentration and 40 μL of 10 nmol/L [$^3$H]-PhS1P (5,5,6,6,-tetratritium phytosphingosine-1-phosphate, which was prepared in the following manner. A compound (anti-7: tert-butyl (4S)-4-[(1S,2R)-1-(benzyloxy)-2-hydroxyhexadec-3-yn-1-yl]-2,2-dimethyl-1,3-oxazolizine-3-carboxylate) prepared in accordance with the method described in the document (Tetrahedron Lett., 38(34), 6027-6030 (1997)) was reacted with benzyl bromide in tetrahydrofuran in the presence of potassium hexamethyldisilylamide, to thereby protect the hydroxy group. Then, it was treated in a hydrogen chloride/methanol solution to deblock the acetonide group. The compound thus obtained was reacted with N,N-diethyl-1,5-dihydro-2,4,3-benzodioxaphosphepin-3-amine in methylene chloride in the presence of tetrazole and then oxidized with m-chloroperbenzoic acid. Then, it was reacted in the presence of ASCA-2 catalyst (manufactured by N.E. CHEMCAT CORPORATION, 4.5% palladium-0.5% platinum catalyst carried on active carbon, see, Fine Chemical, Oct. 1, 2002, pages 5 to 14) in methanol under a tritium atmosphere. The obtained compound was treated with a 4 N hydrogen chloride/1,4-dioxane solution in methylene chloride to thereby obtain the desired compound) were added. Further, 40 μL of the membrane fraction solution was added and reacted at room temperature for 60 minutes. After the completion of the reaction, the reaction mixture was filtered by aspiration with a 96-well UNIFILTER, washed with 50 mL of a washing buffer (50 mmol/L Tris pH7.5, 0.5% BSA) thrice and dried at 60° C. for 45 minutes. Then, 50 μL/well of MicroScint 20 was added and the plate was covered with TopSeal-P. Next, the radioactivity was measured with TopCount (manufactured by Perkin Elmer Inc.).
[Results]
The compounds of the present invention showed inhibitory activities on the binding of [$^3$H]-PhS1P to EDG-6.

Biological Example 2

Counting the Number of Lymphocyte in Blood

[Experimental Method]
Test compounds were orally administered to male BALB/c mice or male Sprague-Dawley rats (Charles River Laboratories, Japan, Inc., 6-week-old at the time of use). 4 to 72 hours after the administration, the blood was collected from the aorta abdominalis under ether anesthesia. The number of the total leucocyte count, the lymphocyte count, the neutrophil count, the erythrocyte count, the platelet count in blood and the hematocrit value were measured with a multipurpose automatic blood cell counter (SF-3000, manufactured by Sysmex Corporation). Evaluation was made by setting the average blood cell count in a vehicle-administered group (vehicle group) as 100% and calculating the percentage of vehicle from the average blood cell count of each test compound-administered group. Based on the test compound doses and percentages of vehicle with the doses, the dose of the compound required for lowering the blood cell count to 50% was calculated as ED$_{50}$.
[Results]
The compounds of the present invention significantly lowered the number of lymphocyte in blood at an oral dose of 10 mg/kg. For example, ED$_{50}$ values after 24 hours after the administration of the compounds prepared in Example 27-7 and Example 37 were 1.6 mg/kg and 0.029 mg/kg, respectively.

Biological Example 3

Evaluation of an Agonistic Activity Against EDG of the Compound of the Present Invention by Monitoring Changes in Intracellular Calcium Ion [Ca$^{2+}$]$_i$ Concentration

[Experimental Method]
Human EDG-1, EDG-3, EDG-5, or EDG-8 gene overexpressing CHO cells were cultured in Ham's F12 medium (manufactured by GibcoBRL) containing 10% FBS (fetal bovine serum), penicillin/streptomycin, and blasticidin (5 μg/ml). The cultured cells were incubated in a 5 μM Fura2-AM solution (Ham's F12 medium containing 10% of FBS, 20 mM HEPES buffer (pH7.4), and 2.5 mM probenecid) at 37° C. for 60 minutes. After washing once with Hanks solution containing 20 mM HEPES buffer (pH7.4) and 2.5 mM probenecid, the plate was soaked in the same solution. Then, the plate was set on a fluorescent drug screening system (FDSS 6000; Hamamatsu Photonics K. K.) and the intracellular calcium ion concentration was measured without stimulation for 30 seconds. A test compound (final concentration: 1 nM to 10 µM, dimethylsulfoxide (DMSO) solution) was added and S1P (final concentration: 100 nM) was added 5 minutes thereafter. Then, the increase in the intracellular calcium ion concentration was measured before and after the addition of S1P at intervals of 3 seconds (excitation wavelength: 340 nm and 380 nm, fluorescence wavelength: 500 nm).

The agonistic activity of the compound against each EDG was determined by using the peak value due to S1P-stimulation in a well containing DMSO as a substitute for the evaluated compound as a control value (A), comparing the value before the addition of the evaluated compound with the increased value (B) in the fluorescent ratio after the addition, and calculating the increase ratio (%) in the intracellular calcium ion $[Ca^{2+}]_i$ concentration as: increase ratio (%)=(B/A)×100. Increase ratios of the compound at individual concentrations were determined and the $EC_{50}$ value was calculated.

[Results]

It was observed that the compounds of the present invention showed an agonistic activity against EDG-1. For example, $EC_{50}$ values of the compounds prepared in Examples 18, 13-4, 29-1, 27-7, 37, and 37-6 were 662 nmol/L, 41 nmol/L, 133 nmol/L, 0.7 nmol/L, 1.0 nmol/L, and 0.7 nmol/L, respectively.

Biological Example 4

Mouse Model of Dermatitis Caused by Continuous Application of Hapten

[Experimental Method]

A 1% (w/v) 4-ethoxymethylene-2-phenyl-2-oxazolin-5-one (hereinafter, abbreviated as "oxalon") solution was applied (20 µL) to an ear auricle (right, both faces) of mice (male BALB/c) to perform the primary sensitization. Seven days after the sensitization, a 1% (w/v) oxalon solution was applied (20 µL) to the ear auricle for elicitation (Day 0). The same procedure as the Day 0 was repeated on Days 2, 4, 6, 8, 10, 12, 14, and 16. A test compound was dissolved in a vehicle and was then orally administered or applied to both faces of the right ear (20 µL) before the application of oxalon. To the control group, only the vehicle was applied. Immediately before the administration of the test compound and 24 hours after the oxalon application, the thickness of the mouse ear auricle was measured with Dialthicknessgauge (OZAKI MFG. CO., LTD.) as an indication of the efficacy to the mouse model of dermatitis induced by the continuous application of hapten.

Biological Example 5

Adjuvant-induced Arthritis Model

[Experimental Method]

Evaluation was made using 7-week-old male or female Lewis rats. After measuring the volume of the left hind leg of the rats, a 500 µg/rat suspension of dry *Mycobacterium butyricum* cells (Difco), which was employed as an adjuvant, in liquid paraffin was subcutaneously injected into the right hind foot pad of each rat, thereby producing rats adjuvant-induced arthritis model. By comparing a test group, to which the test compound was orally administered, with a control group, to which the test compound was not administered, the therapeutic or preventive effects were measured.

Biological Example 6

Experimental-allergic-encephalomyelitis (EAE) Model (Case 1) Administration of the Compound of the Present Invention from the Day of Sensitization

[Experimental Method]

Killed *Mycobacterium tuberculosis* (*M. tuberculosis* H37 Ra, Difco, Cat No. 231141) was suspended in distilled water for injection to dissolve MBP (Myelin basic protein, SIGMA, Cat No. M-2295) (Killed Mycobacteriumtuberculosis: 1000 μg/mL, MBP: 60 μg/mL). This solution was mixed with an equivalent amount of FCA (Freund Complete Adjuvant, CHEMICON, Cat No. AR001) to thereby prepare an emulsion. Female LEW/CrlCrlj rats (Charles River Laboratories, Japan, Inc., 6-week-old at the time of purchase, 7-week-old at the time of sensitization) were antigen-sensitized by a single subcutaneous injection (0.1 mL/rat) of the emulsion in the right foot pad under slight ether anesthesia, thereby inducing the symptoms of experimental allergic encephalomyelitis. The day of sensitization was defined as Day 0.

The EAE symptoms of the rats were observed every day from Day 8 to Day 20, and were evaluated based on the following criteria: Tail relaxation: 1 point, Incomplete paralysis of hind legs: 1 point, Complete paralysis of hind legs: another 1 point, and Incontinentia: 1 point. The maximum score was 4 points. Death was 5 points.

Using a 0.5% MC solution (0.5 w/v % Methyl Cellulose 400cP Solution, Wako Pure Chemical Industries, Ltd., Cat No. 133-14255) as a vehicle, the test compound was forcibly administered orally in an amount of 5 mL/kg once a day from before the day of sensitization to Day 19. To a control group, the same amount of 0.5% MC solution was forcibly administered orally once a day for the same period. The body weight was measured every day from Day 0 and the dose was determined based on the body weight of each day.

[Results]

The efficacy of the test compound was evaluated by comparing the test group, to which the test compound was orally administered, with the control group, to which only the vehicle was orally administered. In this administration period, the compound prepared in Example 37 almost completely inhibited the development of symptoms at an oral dose of 0.1 mg/kg, and completely inhibited the development of symptoms at an oral dose of 0.3 mg/kg. The compound prepared in Example 37-5 almost completely inhibited the development of symptoms at an oral dose of 0.3 mg/kg.

(Case 2) Administration of the Compound of the Present Invention from Immediately Before Development of Symptoms

[Experimental Method]

Killed *Mycobacterium tuberculosis* (*M. tuberculosis* H37 Ra, Difco, Cat No. 231141) was suspended in distilled water for injection to dissolve MBP (Myelin basic protein, SIGMA, Cat No. M-2295) (Killed *Mycobacterium tuberculosis:* 1000 μg/mL, MBP: 60 μg/mL). This solution was mixed with an equivalent amount of FCA (Freund Complete Adjuvant, CHEMICON, Cat No. AR001) to thereby prepare an emulsion. Female LEW/CrlCrlj rats (Charles River Laboratories, Japan, Inc., 6-week-old at the time of purchase, 7-week-old at the time of sensitization) were antigen-sensitized by a single subcutaneous injection (0.1 mL/rat) of the emulsion in the right foot pad under slight ether anesthesia, thereby inducing the symptoms of experimental allergic encephalomyelitis. The day of sensitization was defined as Day 0.

The EAE symptoms of the rats were observed every day from Day 7 to Day 20, and evaluated based on the following criteria: Tail relaxation: 1 point, Incomplete paralysis of hind legs: 1 point, Complete paralysis of hind legs: another 1 point, and Incontinentia: 1 point. The maximum score was 4 points. Death was 5 points.

Using 0.5% MC solution (0.5 w/v % Methyl Cellulose 400cP Solution, Wako Pure Chemical Industries, Ltd., Cat No. 133-14255) as a vehicle, the test compound was forcibly administered orally in an amount of 5 mL/kg once a day from Day 9 before sensitization to Day 19. To a control group, the same amount of 0.5% MC solution was forcibly administered orally once a day for the same period. The body weight was measured every day from Day 9 and the dose was determined based on the body weight of each day.

[Results]

The efficacy of the test compound was evaluated by comparing the test group, to which the test compound was orally administered, with the control group, to which only the vehicle was orally administered. In this administration period, the compound prepared in Example 37 almost completely inhibited the development of symptoms at an oral dose of 0.3 mg/kg. It was confirmed that the compound prepared in Example 37-5 had the effect of inhibiting the development of symptoms at an oral dose of 0.3 mg/kg.

(Case 3) Administration of the Compound of the Present Invention after Development of Symptoms

[Experimental Method]

Killed *Mycobacterium tuberculosis* (*M. tuberculosis* H37 Ra, Difco, Cat No. 231141) was suspended in distilled water for injection to dissolve MBP (Myelin basic protein, SIGMA, Cat No. M-2295) (Killed *Mycobacterium tuberculosis*: 1000 µg/mL, MBP: 60 µg/mL). This solution was mixed with an equivalent amount of FCA (Freund Complete Adjuvant, CHEMICON, Cat No. AR001) to thereby prepare an emulsion. Female LEW/CrlCrlj rats (Charles River Laboratories, Japan, Inc., 6-week-old at the time of purchase, 7-week-old at the time of sensitization) were antigen-sensitized by a single subcutaneous injection (0.1 mL/rat) of the emulsion in the right foot pad under slight ether anesthesia, thereby inducing the symptoms of experimental allergic encephalomyelitis. The day of sensitization was defined as Day 0.

The EAE symptoms of the rats were observed every day from Day 10 to Day 20, and evaluated based on the following criteria: Tail relaxation: 1 point, Incomplete paralysis of hind legs: 1 point, Complete paralysis of hind legs: another 1 point, and Incontinentia: 1 point. The maximum score was 4 points. Death was 5 points.

Using 0.5% MC solution (0.5 w/v % Methyl Cellulose 400cP Solution, Wako Pure Chemical Industries, Ltd., Cat No. 133-14255) as a vehicle, the test compound was forcibly administered orally in an amount of 5 mL/kg once a day from Day 11 or Day 12 to Day 19 after all rats developed the EAE symotoms. To a control group, the same amount of 0.5% MC solution was forcibly administered orally once a day for the same period. The body weight was measured every day from Day 10 and the dose was determined based on the body weight of each day.

[Results]

The efficacy of the test compound was evaluated by comparing the test group, to which the test compound was orally administered, with the control group, to which only the vehicle was orally administered.

Biological Example 7

Evaluation of Cardiotoxicity (Bradycardia)

[Experimental Method]

A catheter was inserted into the jugular vein and carotid artery (or the femoral vein and femoral artery) of mammals (e.g., SD rat and a rabbit). The tip of the arterial cannula was connected to a pressure transducer (DX-100, manufactured by NIHON KOHDEN CORP.), thereby measuring blood pressure through a strain pressure amplifier (AP-641G, manufactured by NIHON KOHDEN CORP.) and measuring heart rate through an instantaneous heart rate measuring unit (AT-601G, manufactured by NIHON KOHDEN CORP.), respectively. Alternatively, heart rate was measured with an electrocardiogram. Under anesthesia or under awareness after arousal was induced, the test compound was administered intravenously or administered orally. Then, changes in blood pressure and heart rate were measured.

[Results]

The influence of the compound of the present invention on cardiotoxicity was slight. For example, when the compound prepared in Example 37 was intravenously administered to rabbits at a dose of 0.01 mg/kg, the heart rate of the rabbits decreased as low as 20% or lower.

When $ED_{50}$ values after 24 hours after the administration of the test compound at a dose determined by the method according to Biological Example 2 were defined as Cmg/kg and the dose determined by the method according to this biological example, at which the heart rate decreased by 20%, was defined as $D_A$mg/kg, the ratio ($D_A$/C) can be defined as a safety index (A) ($SI_A$: safety index A) of the compound.

Biological Example 8

Evaluation of Safety of the Compound of the Present Invention

[Experimental Method]

The compound of the present invention was forcibly administered orally, through a probe, into the stomach of SD rats (Crj:CD (SD) IGS, male, 6-week-old) once a day for a period of 4 days to 14 days. The rats were dissected the day after termination of the administration, and subjected to measurement of various organ weights, histopathological test, hematology test, and blood biochemical test.

[Results]

It was proved that the compound of the present invention is sufficiently safe.

When $ED_{50}$ values after 24 hours after the administration of the test compound at a dose determined by the method according to Biological Example 2 were defined as Cmg/kg and the dose determined by the method according to this biological example, at which the liver weight was significantly increased, was defined as $D_B$mg/kg, the ratio ($D_B$/C) can be defined as a safety index (B) ($SI_B$: safety index B) of the compound.

FORMULATION EXAMPLES

Formulation Examples which can be carried out in the present invention are shown below.

Formulation Example 1

1-{[1-chloro-6-(3-cyclohexylpropoxy)-3,4-dihydronaphthalen-2-yl]methyl}azetidine-3-carboxylic acid (100 g), calcium carboxymethylcellulose (disintegrant, 20.0 g), magnesium stearate (lubricant, 10.0 g) and microcrystalline cellulose (870 g) were mixed in a conventional manner, punched out to obtain 10,000 tablets each containing 10 mg of the active ingredient.

Formulation Example 2

1-{[1-chloro-6-(3-cyclohexylpropoxy)-3,4-dihydronaphthalen-2-yl]methyl}azetidine-3-carboxylic acid (100 g), mannitol (2 kg) and distilled water (50 L) were mixed in a conventional manner. Then the solution was filtered through a dustproofing filter, and then 5 ml aliquots were charged into ampoules, which were autoclaved to obtain 10,000 ampoules each containing 10 mg of the active ingredient.

[Industrial Applicability]

The compound of the present invention can be applied to the following pharmaceuticals.

The compound of the present invention has an ability to bind S1P receptor (in particular, EDG-1, EDG-6, and/or EDG-8). Accordingly, the compound is useful as a preventing and/or treating agent for mammals (for example, human, or non-human animals such as simian, ovine, bovine, equine, canine, feline, leporine, rat, and mouse), for: rejection to transplantation, transplanted organ abolition, graft-versus-host disease (e.g., acute graft-versus-host disease during bone-marrow transplantation and the like), autoimmune diseases (e.g., systemic lupus erythematosus, Behcet's syndrome, scleroderma, nephrotic syndrome, rheumatoid arthritis, ulcerative colitis, Crohn's disease, autoimmune hemolytic anemia, idiopathic thrombocytopenic purpura, myasthenia gravis, muscular dystrophy, and multiple sclerosis), allergic diseases (e.g., atopic dermatitis, pollen disease, food allergy, psora, and drug (e.g., anesthetic such as lidocaine) allergy), inflammatory diseases (e.g., varicose vein such as hemorrhoid, anal fissure, or anal fistula, dissecting aneurysm of the aorta or sepsis, angiitis, nephritis, pneumonia, and chronic active hepatitis), respiratory disease (e.g., pulmonary fibrosis, asthma, and interstitial pneumonia), metabolic disease and endocrine disease (e.g., diabetes type-I), circulatory system disease (e.g., ischemia reperfusion disorders, arteriosclerosis, arteriosclerosis obliterans, thromboangiitis obliterans, diabetic neuropathy, acute cardiac failure, and angina), various edematous disorders developed from blood hyperpermeability (e.g., myocardial infarction, cerebral infarction, DIC (disseminated intravascular coagulation), pleuritis, congestive heart failure, and multiple organ failure), traumatism (e.g., bedsore and burn), osteoporosis, chronic hepatitis, fibrosis such as liver fibrosis, chronic renal failure, renal glomerulus sclerosis, infection, ulcer, lymphoma, malignant tumor (e.g., cancer), leukemia, cerebral embolism, ischemic abnormality of various organs, shock with blood incompatibility during blood transfusion, genetic disease, neurodegenerating diseases (e.g., Parkinson's disease, parkinsonian syndrome, Alzheimer's disease, and amyotrophic lateral sclerosis), and the like.

Figure 1:
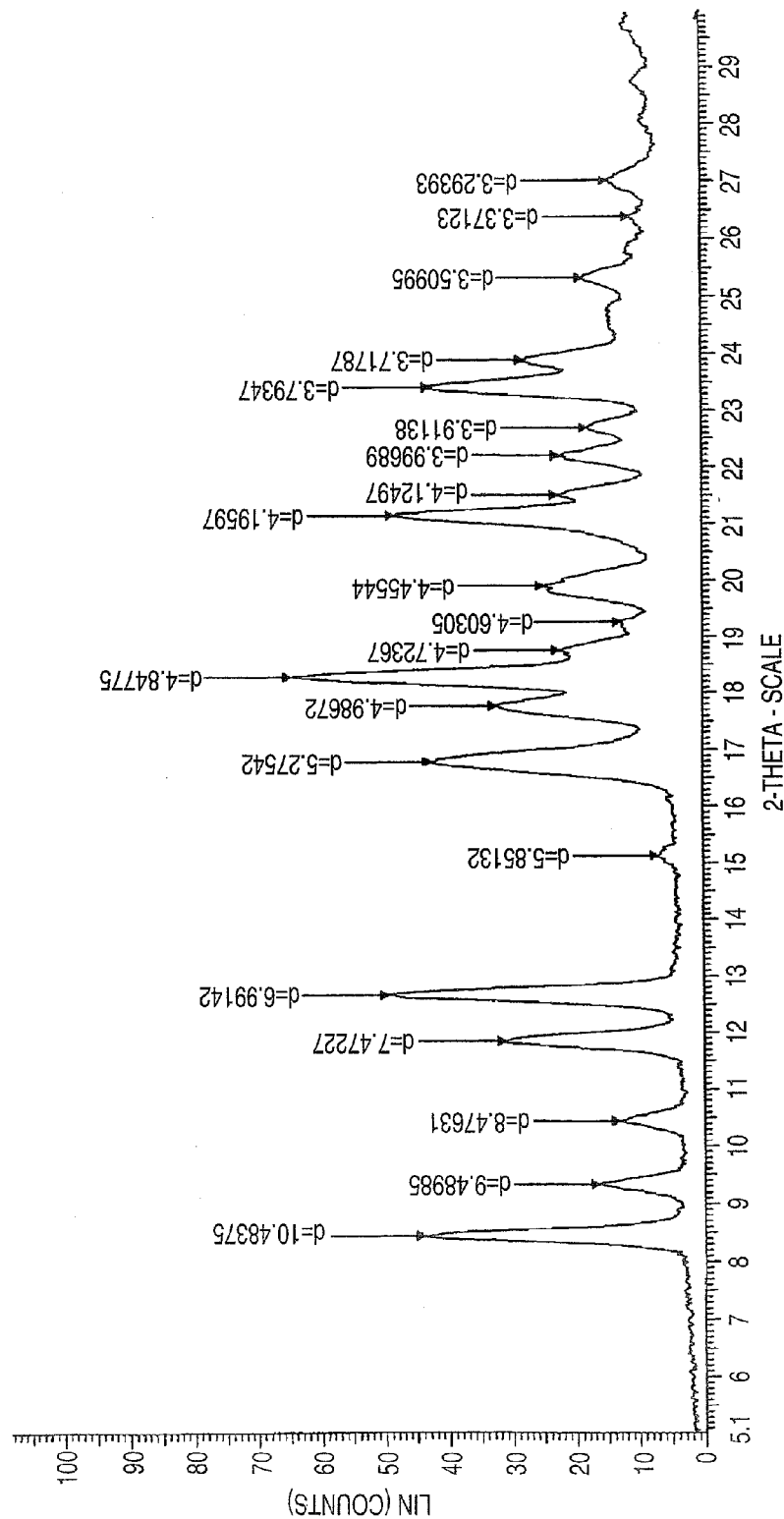
FIG. 1 is an X-ray powder diffractogram of a compound prepared in Example 48.
Figure 2:
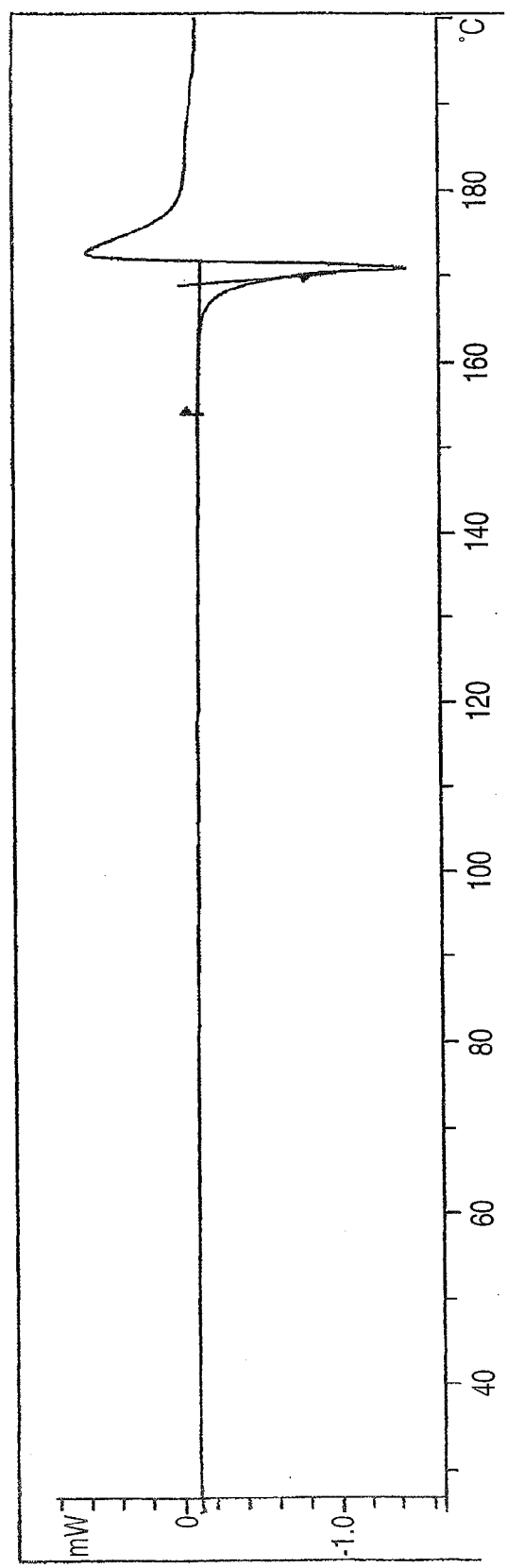
FIG. 2 is a differential scanning calorimetry (DSC) chart of the compound prepared in Example 48.
Figure 3:
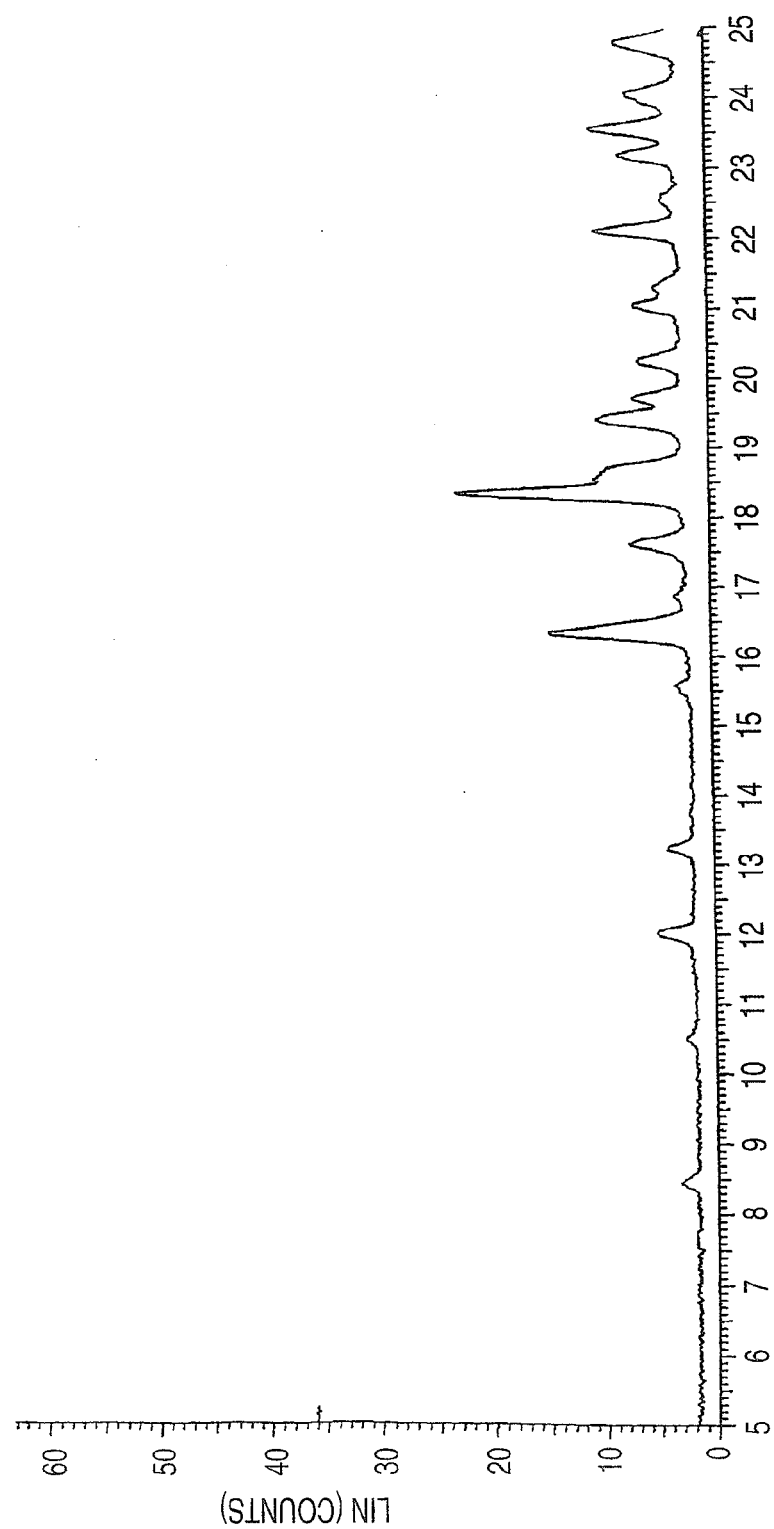
FIG. 3 is an X-ray powder diffractogram of a compound prepared in Example 48 (1).
Figure 4:
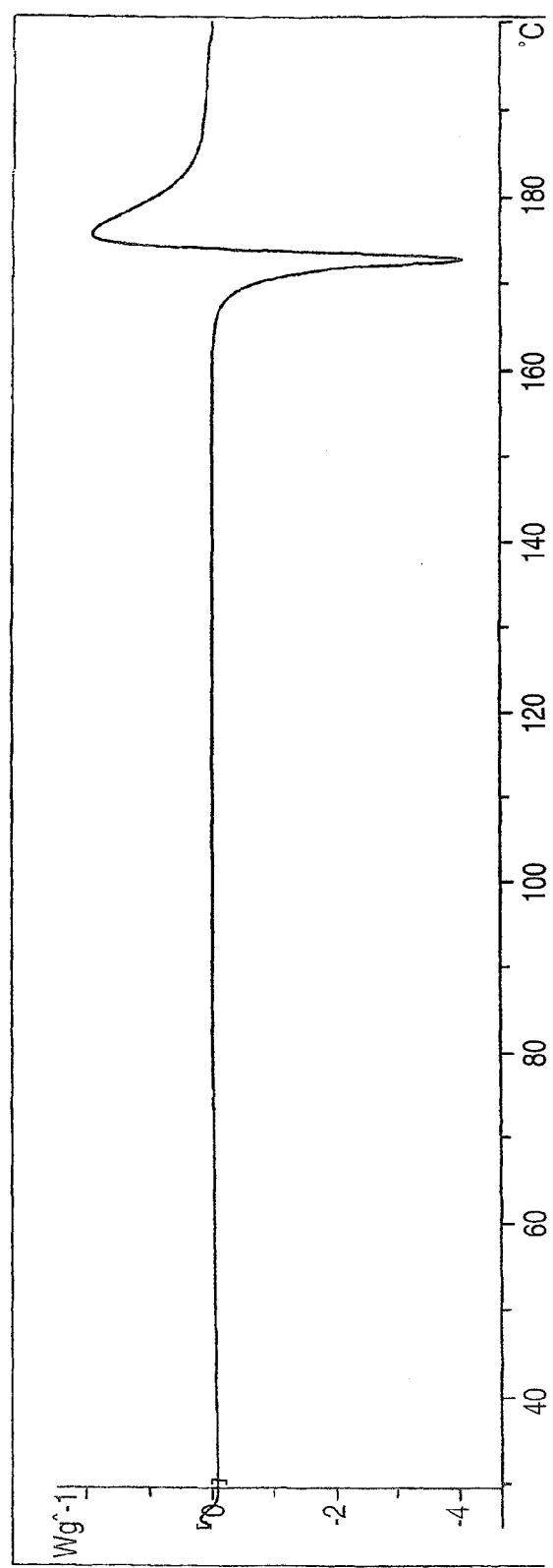
FIG. 4 is a differential scanning calorimetry (DSC) chart of the compound prepared in Example 48 (1).
Figure 5:
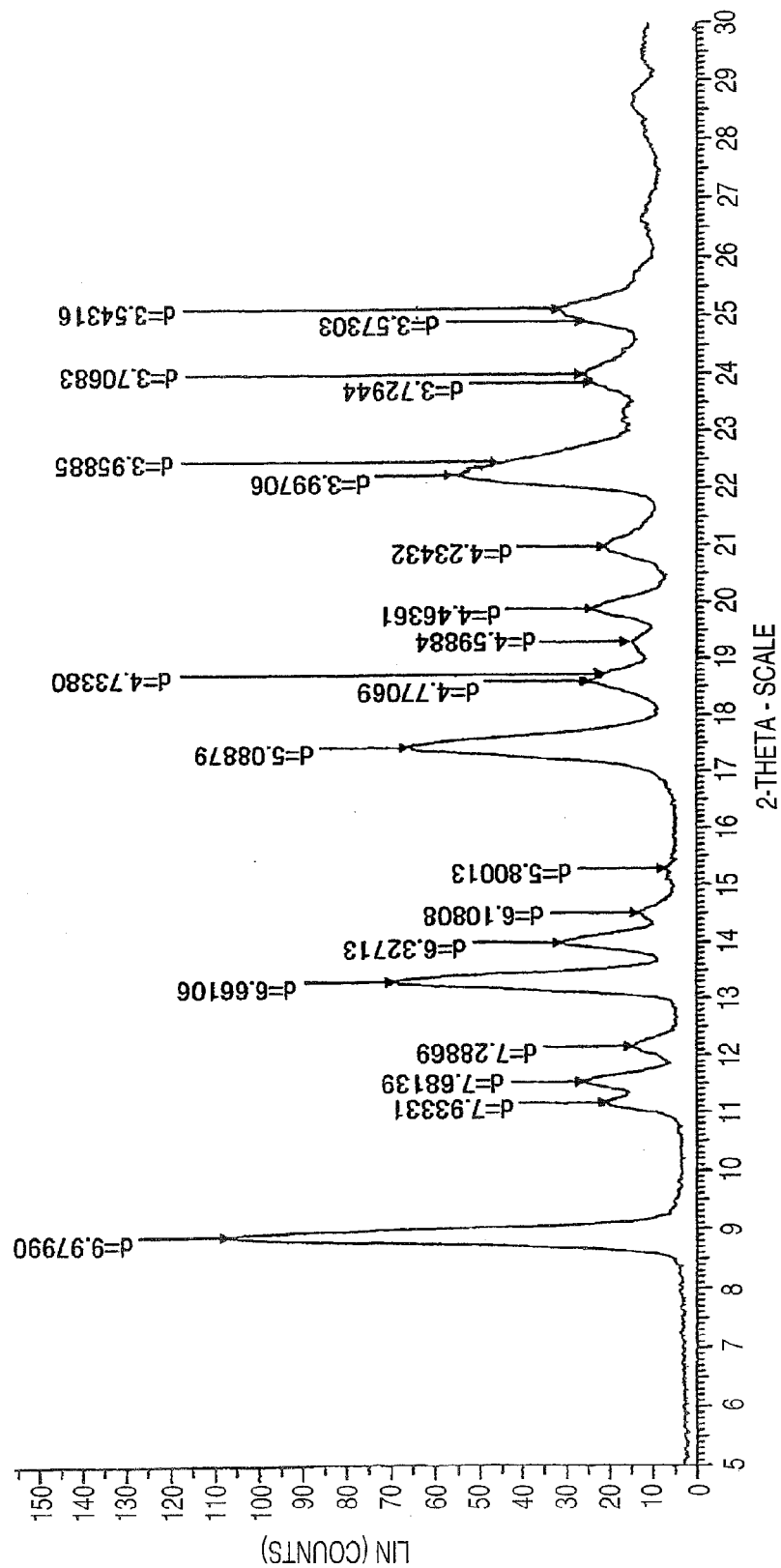
FIG. 5 is an X-ray powder diffractogram of a compound (A-type crystal) prepared in Example 49.
Figure 6:
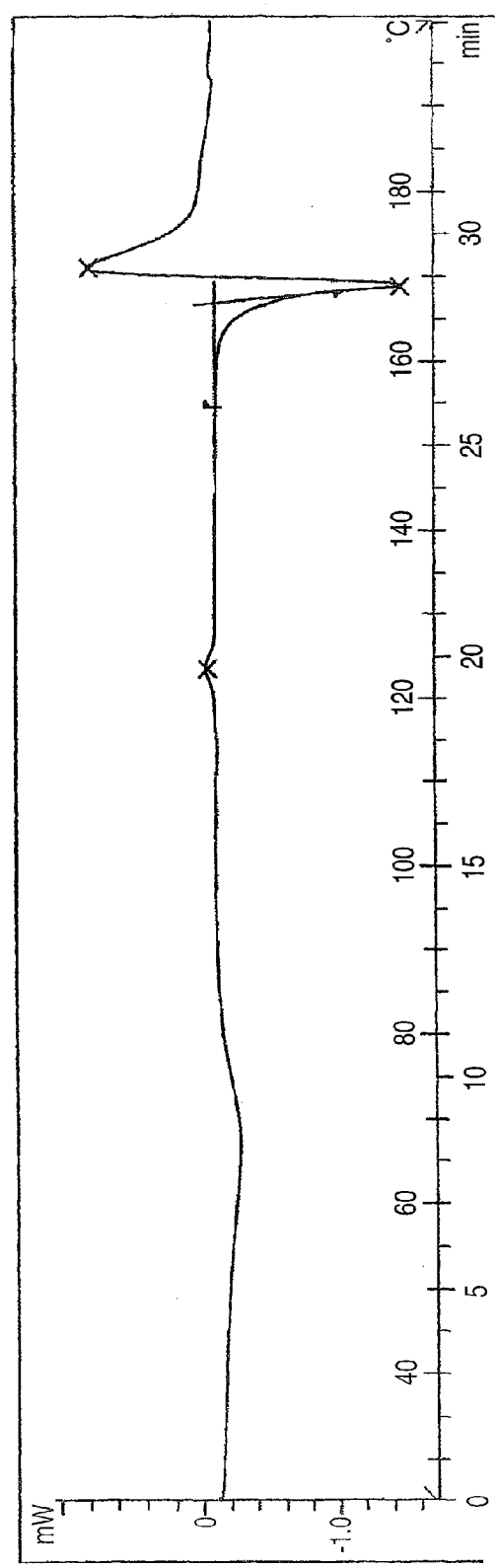
FIG. 6 is a differential scanning calorimetry (DSC) chart of the compound (A-type crystal) prepared in Example 49.
Figure 7:
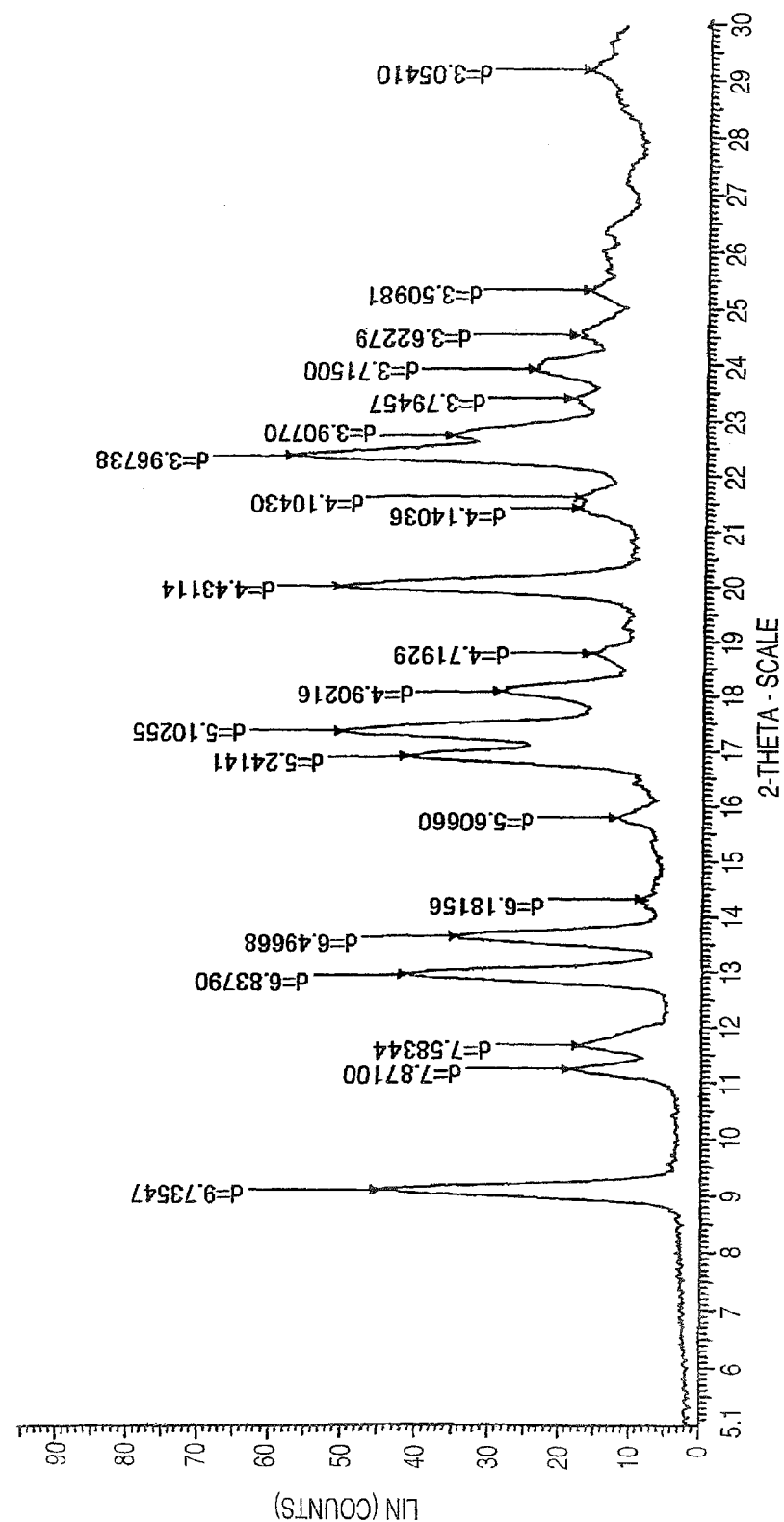
FIG. 7 is an X-ray powder diffractogram of a compound (B-type crystal) prepared in Example 49.
Figure 8:
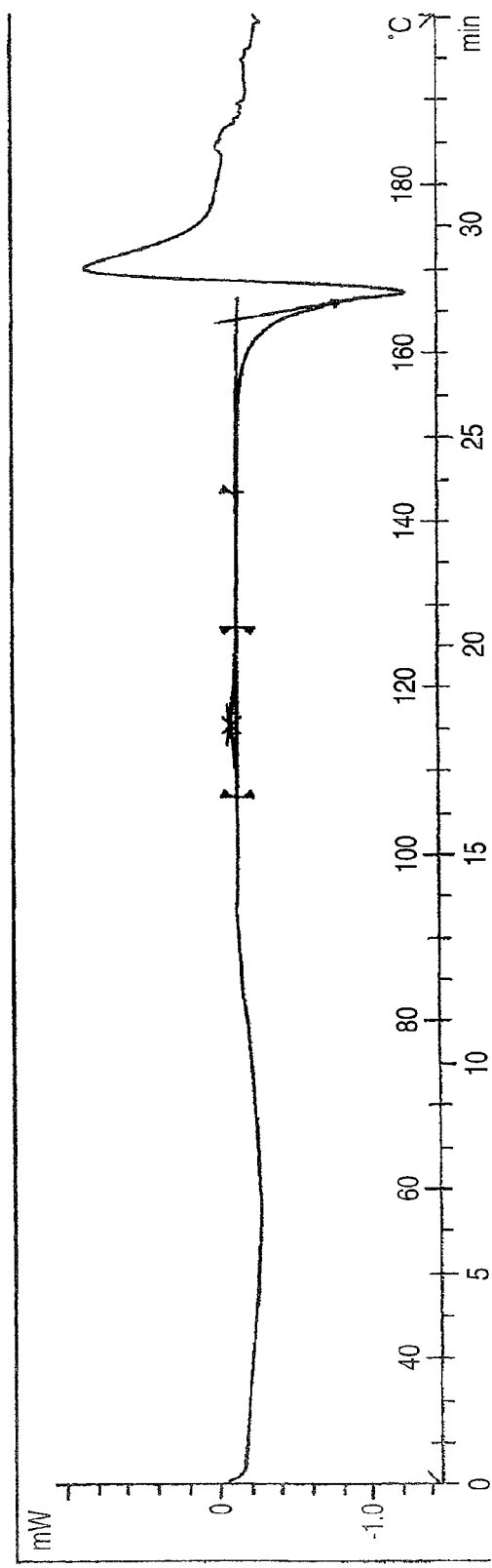
FIG. 8 is a differential scanning calorimetry (DSC) chart of the compound (B-type crystal) prepared in Example 49.
Figure 9:
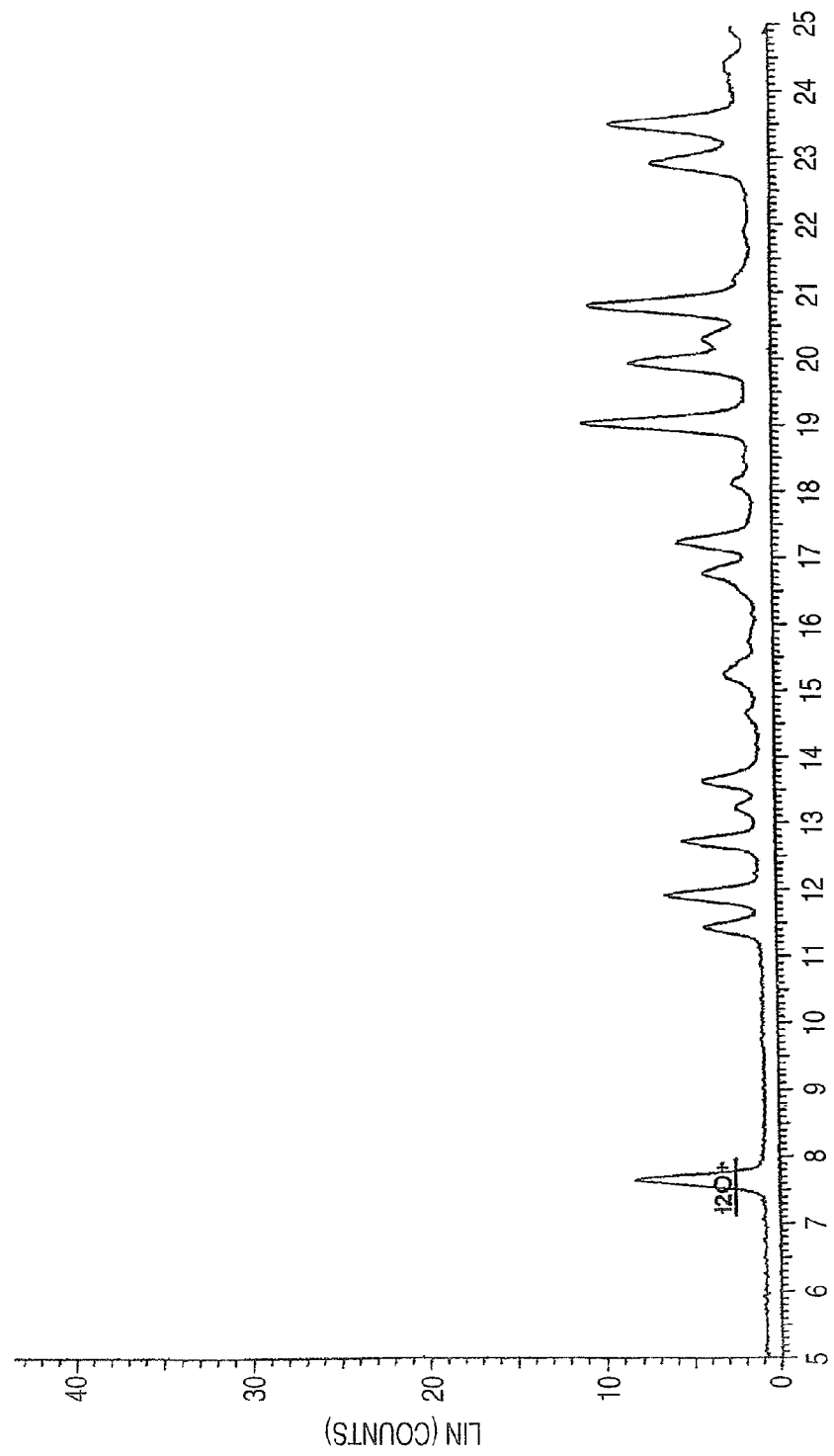
FIG. 9 is an X-ray powder diffractogram of a compound prepared in Example 49 (1).
Figure 10:
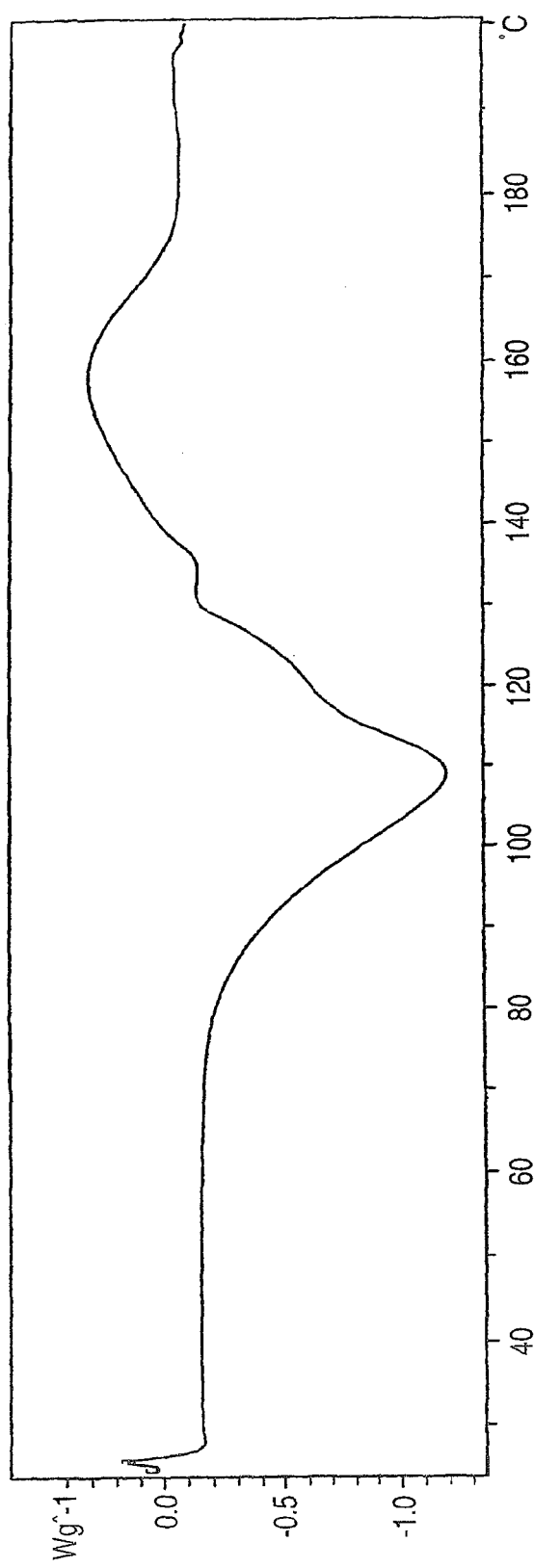
FIG. 10 is a differential scanning calorimetry (DSC) chart of the compound prepared in Example 49 (1).

The invention claimed is:

1. 1-[(6-{[2,4-bis(trifluoromethyl)benzyl]oxy}-1-methyl-3,4-dihydro-2-naphthalenyl)methyl]-3-azetidinecarboxylic acid, a salt thereof, an N-oxide form thereof, a solvate thereof or a prodrug thereof.

2. The compound according to claim 1, which is selected from the group consisting of
   (1) 1-[(6-{[2,4-bis (trifluoromethyl)benzyl] oxy } -1-methyl-3,4-dihydro-2-naphthalenyl)methyl]-3-azetidinecarboxylic acid,
   (2) ethyl 1-[(6-{[2,4-bis(trifluoromethyl)benzyl]oxy}-1-methyl-3,4-dihydro-2-naphthalenyl)methyl]-3-azetidinecarboxylate,
   (3) 1-[(6-{[2,4-bis (trifluoromethyl)benzyl] oxy } -1-methyl-3,4-dihydro-2-naphthalenyl)methyl]-3-azetidinecarboxylic acid monohydrate,
   (4) 1-[(6-{[2,4-bis (trifluoromethyl)benzyl] oxy } -1-methyl-3,4-dihydro-2-naphthalenyl)methyl]-3-azetidinecarboxylic acid hydrochloride,
   (5) sodium 1-[(6-{[2,4-bis (trifluoromethyl)benzyl] oxy } -1-methyl-3,4-dihydro-2-naphthalenyl)methyl]-3-azetidinecarboxylate, and
   (6) potassium 1-[(6-{[2,4-bis(trifluoromethyl)benzyl] oxy}-1-methyl-3,4-dihydro-2-naphthalenyl) methyl] -3-azetidinecarboxylate.

3. A compound which is 1-[(6-{[2,4-bis(trifluoromethyl) benzyl] oxy}-1-methyl-3,4-dihydro-2-naphthalenyl)methyl]-3-azetidinecarboxylic acid.

4. A pharmaceutical composition which comprises the compound according to claim 1, a salt thereof, an N-oxide form thereof, a solvate thereof or a prodrug thereof.

* * * * *